(12) United States Patent
Froelich et al.

(10) Patent No.: US 11,421,007 B2
(45) Date of Patent: Aug. 23, 2022

(54) ZINC FINGER PROTEIN COMPOSITIONS FOR MODULATION OF HUNTINGTIN (HTT)

(71) Applicants: Sangamo Therapeutics, Inc., Richmond, CA (US); CHDI Foundation, Inc., New York, NY (US)

(72) Inventors: Steven Froelich, Richmond, CA (US); Ignacio Munoz-Sanjuan, New York, NY (US); Edward J. Rebar, Richmond, CA (US); Bryan Zeitler, Richmond, CA (US); H. Steve Zhang, Richmond, CA (US)

(73) Assignees: Sangamo Therapeutics, Inc., Brisbane, CA (US); CHDI Foundation, Inc., New York, NY (US)

( * ) Notice: Subject to any disclaimer, the term of this patent is extended or adjusted under 35 U.S.C. 154(b) by 388 days.

(21) Appl. No.: 16/386,885

(22) Filed: Apr. 17, 2019

(65) Prior Publication Data

US 2019/0322711 A1    Oct. 24, 2019

Related U.S. Application Data

(60) Provisional application No. 62/659,552, filed on Apr. 18, 2018, provisional application No. 62/780,605, filed on Dec. 17, 2018.

(51) Int. Cl.

| | |
|---|---|
| *C12N 15/11* | (2006.01) |
| *C07K 14/47* | (2006.01) |
| *A61P 25/00* | (2006.01) |
| *C12N 7/00* | (2006.01) |
| *A61K 38/00* | (2006.01) |

(52) U.S. Cl.
CPC .......... *C07K 14/4702* (2013.01); *A61P 25/00* (2018.01); *C07K 14/4703* (2013.01); *C12N 7/00* (2013.01); *A61K 38/00* (2013.01); *C12N 2750/14143* (2013.01); *C12N 2750/14171* (2013.01)

(58) Field of Classification Search
CPC .......... A61K 38/00; C12N 15/11; C12N 9/22; A61P 25/14
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,067,317 B2 | 6/2006 | Rebar et al. | |
| 7,153,949 B2 | 12/2006 | Kim et al. | |
| 7,163,824 B2 | 1/2007 | Cox, III et al. | |
| 7,262,054 B2 | 8/2007 | Jamieson et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,329,986 B2 | 12/2012 | Butler et al. | |
| 8,399,218 B2 | 3/2013 | Gupta et al. | |
| 8,409,861 B2 | 4/2013 | Guschin et al. | |
| 8,563,314 B2 | 10/2013 | Gregory et al. | |
| 8,585,526 B2 | 11/2013 | Beutler et al. | |
| 8,623,618 B2 | 1/2014 | Doyon et al. | |
| 8,771,985 B2 | 7/2014 | Cui et al. | |
| 8,841,260 B2 | 9/2014 | Miller et al. | |
| 8,871,905 B2 | 10/2014 | Holmes et al. | |
| 8,895,264 B2 | 11/2014 | Cost et al. | |
| 8,936,936 B2 | 1/2015 | Holmes et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |

(Continued)

FOREIGN PATENT DOCUMENTS

| | | |
|---|---|---|
| GB | 2338237 A | 12/1999 |
| WO | 95/19431 A1 | 7/1995 |

(Continued)

OTHER PUBLICATIONS

Agustin-Pavon, et al., "Deimmunization for Gene Therapy: Host Matching of Synthetic Zinc Finger Constructs Enables Long-Term Mutant Huntingtin Repression in Mice," *Mol Neurodegener* 11:64 (2016).
Arber, "Organization and Function of Neuronal Circuits Controlling Movement," *EMBO Mol Med* 9(3):281-284 (2017).
Arteaga-Bracho, et al., "Postnatal and Adult Consequences of Loss of Huntingtin During Development: Implications for Huntington's Disease," *Neurobiol Dis* 96:144-155 (2016).
Banez-Coronel, et al., "Ran Translation in Huntington Disease," *Neuron* 88(4):667-677 (2015).
Beaumont, et al., "Phosphodiesterase 10A Inhibition Improves Cortico-Basal Ganglia Function in Huntington's Disease Models," *Neuron* 92(6):1220-1237 (2016).

(Continued)

*Primary Examiner* — Karen Cochrane Carlson
(74) *Attorney, Agent, or Firm* — Foley & Lardner LLP

(57) ABSTRACT

The present disclosure is in the field of modulation of Htt gene expression and HTT protein levels.

16 Claims, 66 Drawing Sheets

Specification includes a Sequence Listing.

(56) References Cited

U.S. PATENT DOCUMENTS

| | | | |
|---|---|---|---|
| 9,045,763 | B2 | 6/2015 | DeKelver et al. |
| 9,150,847 | B2 | 10/2015 | Rebar |
| 9,206,404 | B2 | 12/2015 | Cui et al. |
| 9,222,105 | B2 | 12/2015 | Cost et al. |
| 9,234,016 | B2 | 1/2016 | Gregory et al. |
| 9,394,545 | B2 | 7/2016 | Rebar |
| 9,499,597 | B2 | 11/2016 | Wang et al. |
| 9,873,894 | B2 | 1/2018 | Conway et al. |
| 9,943,565 | B2 | 4/2018 | Gregory et al. |
| 2002/0115215 | A1 | 8/2002 | Wolffe et al. |
| 2002/0160940 | A1 | 10/2002 | Case et al. |
| 2003/0082552 | A1 | 5/2003 | Wolffe et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0079475 | A1 | 4/2006 | Zhang et al. |
| 2006/0188987 | A1 | 8/2006 | Guschin et al. |
| 2007/0218528 | A1 | 9/2007 | Miller |
| 2009/0136465 | A1 | 5/2009 | Merenick et al. |
| 2011/0265198 | A1 | 10/2011 | Gregory et al. |
| 2013/0177960 | A1 | 7/2013 | Rebar |
| 2014/0335063 | A1 | 11/2014 | Cannon et al. |
| 2015/0255877 | A1 | 9/2015 | Liu et al. |
| 2015/0335708 | A1 | 11/2015 | Froelich et al. |
| 2016/0200781 | A1 | 7/2016 | Isalan et al. |
| 2017/0096460 | A1 | 4/2017 | Froelich et al. |

FOREIGN PATENT DOCUMENTS

| | | | |
|---|---|---|---|
| WO | 96/06166 | A1 | 2/1996 |
| WO | 98/37186 | A1 | 8/1998 |
| WO | 98/53057 | A1 | 11/1998 |
| WO | 98/53058 | A1 | 11/1998 |
| WO | 98/53059 | A1 | 11/1998 |
| WO | 98/53060 | A1 | 11/1998 |
| WO | 98/54311 | A1 | 12/1998 |
| WO | 00/27878 | A1 | 5/2000 |
| WO | 01/60970 | A2 | 8/2001 |
| WO | 01/83732 | A2 | 11/2001 |
| WO | 01/83793 | A2 | 11/2001 |
| WO | 01/88197 | A2 | 11/2001 |
| WO | 02/016536 | A1 | 2/2002 |
| WO | 02/044376 | A2 | 6/2002 |
| WO | 02/077227 | A2 | 10/2002 |
| WO | 02/099084 | A2 | 12/2002 |
| WO | 03/016496 | A2 | 2/2003 |
| WO | WO-2017/077329 | A2 | 5/2017 |
| WO | WO-2020/150338 | A1 | 7/2020 |

OTHER PUBLICATIONS

Bird, et al., "Methyiation-Induced Repression-Belts, Braces and Chromatin," *Cell* 99:451-454 (1999).

Boudreau, et al., "Nonallele-Specific Silencing of Mutant and Wild-Type Huntingtin Demonstrates Therapeutic Efficacy in Huntington's Disease Mice," *Mol Ther* 17(6):1053-1063 (2009).

Bradley, et al., "Derivation of Huntington's Disease-Affected Human Embryonic Siem Cell Lines," *Stem Cells Dev* 20(3):495-502 (2011).

Brasher, et al., "The Structure of Mouse HP1 Suggests a Unique Mode of Single Peptide Recognition by the Shadow Chromo Domain Dimer," *EMBO J* 19(7):1587-1597 (2000).

Brooks, et al., "Mouse Models of Huntington's Disease," *Curr Top Behav Neurosci* 22:101-133 (2015).

Capelli, et al., "Locomotor Speed Control Circuits in the Caudal Brainstem," *Nature* 551(7680):373-377 (2017).

Carroll, et al., "Potent and Selective Antisense Oligonucleotides Targeting Single-Nucleotide Polymorphisms in the Huntington Disease Gene / Allele-Specific Silencing of Mutant Huntingtin," *Mol Ther.* 19(12):2178-85 (2011).

Carty, et al., "Characterization of Htt Inclusion Size, Location, and Timing in the ZQ175 Mouse Model of Huntington's Disease: An in Vivo High-Content Imaging Study," *PLoS One* 10(4):e0123527 (2015).

Chern, et al., "The Regulator of MAT2 (ROM2) Protein Binds To Early Maturation Promoters and Represses PVALF-Activated Transcription," *Plant Cell* 8(2):305-321 (1996).

Cummings, et al., "Alterations in Cortical Excitation and Inhibition in Genetic Mouse Models of Huntington's Disease," *J. Neurosci* 29(33):10371-86 (2009).

Datson, et al., "The Expanded CAG Repeat in the Huntingtin Gene as Target for Therapeutic RNA Modulation Throughout the HD Mouse Brain," *PLoS One* 12(2):e0171127 (2017).

Davies, et al., "Polyalanine and Polyserine Frameshift Products in Huntington's Disease," *Journal of Medical Genetics* 43(11):893-896 (2006).

Di Prospero, et al., "Therapeutics Development for Triplet Repeat Expansion Diseases," *Nature Reviews Genetics* 6:756-765 (2005).

Dragatsis, et al., "Inactivation of HDH in the Brain and Testis Results in Progressive Neurodegeneration and Sterility in Mice," *Nat Genet* 26(3):300-306 (2000).

Dull, et al., "A Third-Generation Lentivirus Vector With a Conditional Packaging System." *Journal of Virology* 72(11):8463-8471 (1998).

Duyao, et al., "Inactivation of the Mouse Huntington's Disease Gene Homolog HDH," *Science* 269(5222):407-410 (1995).

Evers, et al., "Targeting Several CAG Expansion Diseases by a Single Antisense Oligonucleotide," *PLoS One* 6(9):e24308 (2011).

Fiszer, et al., "Inhibition of Mutant Huntingtin Expression by RNA Duplex Targeting Expanded CAG Repeats," *Nucleic Acids Res* 39(13):5578-5585 (2011).

Gagnon, et al., "Allele-Selective Inhibition of Mutant Huntingtin Expression With Antisense Oligonucleotides Targeting the Expanded CAG Repeat," *Biochemistry* 49(47):10166-10178 (2010).

Garriga-Canut, et al., "Synthetic Zinc Finger Repressors Reduce Mutant Huntingtin Expression in the Brain of R6/2 Mice," *Proc Nat Acad Sci USA* 109(45):e3136-45 (2012).

Gersbach, et al., "Activating Human Genes With Zinc Finger Proteins, Tales, and CRISPR/CAS9 for Gene Therapy and Regenerative Medicine," *Expert Opin Ther Targets* 18(8):835-839 (2014).

Graham, et al., "Cleavage at the CASPASE-6 Site is Required for Neuronal Dysfunction and Degeneration Due to Mutant Huntingtin," *Cell* 125:1179-1191 (2006).

Grondin, et al., "Six-Month Partial Suppression of Huntingtin is Well Tolerated in the Adult Rhesus Striatum," *Brain* 135(4):1197-1209 (2012).

Harper, et al., "RNA Interference Improves Motor and Neuropathological Abnormalities in a Huntington's Disease Mouse Model," *Proc Natl Acad Sci* 102(16):5820-5825 (2005).

Hauck, et al., "Generation and Characterization of Chimeric Recombinant AAV Vectors," *Mol Ther* 7(3):419-425 (2003).

Heikkinen, et al., "Characterization of Neurophysiological and Behavioral Changes, MRI Brain Volumetry and 1H MRS in ZQ175 Knock-In Mouse Model of Huntington's Disease," *PLoS One* 7(12):e50717 (2012).

Hinde, et al., "Spatiotemporal Regulation of Heterochromatin Protein 1-Alpha Oligomerization and Dynamics in Live Cells," *Sci Rep* 5:12001 (2015).

Hu, et al., "Allele-Specific Silencing of Mutant Huntingtin and Ataxin-3 Genes by Targeting Expanded CAG Repeats in MRNAS," *Nat Biotech* 27(5):478-484 (2009).

Iyengar, et al., "KAP1 Protein: An Enigmatic Master Regulator of the Genome," *J Biol Chem* 286(30):26267-26276 (2011).

Kay, et al., "Huntingtin Haplotypes Provide Prioritized Target Panels for Allele-Specific Silencing in Huntington Disease Patients of European Ancestry," *Mol Ther* 23(11):1759-1771 (2015).

Kells, et al., "AAV-Mediated Gene Delivery of BDNF or GDNF is Neuroprotective in a Model of Huntington Disease," *Molecular Therapy* 9(5):682-688 (2004).

Knoepfler, et al., "Sin Meets Nurd and Other Tails of Repression," *Cell* 99:447-450 (1999).

Kordasiewicz, et al., "Sustained Therapeutic Reversal of Huntington's Disease by Transient Repression of Huntingtin Synthesis," *Neuron* 74(6):1031-1044 (2012).

(56) References Cited

OTHER PUBLICATIONS

Landwehrmeyer, et al., "Data Analytics From Enroll-HD, a Global Clinical Research Platform for Huntington's Disease," *Movement Disorders Clinical Practice* 4(2):212-224 (2017).
Langer, et al., "Carbon-11 Epidepride: A Suitable Radioligand for PET Investigation of Striatal and Extrastriatal Dopamine D2 Receptors," *Nucl Med Biol* 26(5):509-18 (1999).
Latorra, et al., "Enhanced Allele-Specific PCR Discrimination in SNP Genotyping Using 3' Locked Nucleic Acid (LNA) Primers," *Hum Mutat* 22(1):79-85 (2003).
Lombardi, et al., "A Majority of Huntington's Disease Patients May be Treatable by Individualized Allele-Specific RNA Interference," *Exp Neurol* 217(2):312-319 (2009).
Lopes, et al., "Identification of Novel Genetic Causes of Rett Syndromelike Phenotypes," *J Med Genet* 53(3):190-199 (2016).
Lupo, et al., "Krab-Zinc Finger Proteins: A Repressor Family Displaying Multiple Biological Functions," *Curr Genomics* 14(4):268-278 (2013).
Lutz, et al., "Modulation of Thyroid Hormone Receptor Silencing Function by Co-Repressors and a Synergizing Transcription Factor," *Biochem Soc Trans* 28(4):386-389 (2000).
Mangiarini, et al., "Exon 1 of the HD Gene With an Expanded CAG Repeat is Sufficient to Cause a Progressive Neurological Phenotype in Transgenic Mice," *Cell* 87:493-506 (1996).
Marks, et al., "Long-Term Safety of Patients With Parkinson's Disease Receiving RAAV2-Neurturin (CERE-120) Gene Transfer," *Hum Gene Ther* 27(7):522-527 (2016).
Marti, "RNA Toxicity Induced By Expanded CAG Repeats in Huntington's Disease," *Brain Pathol* 26(6):779-786 (2016).
McBride, et al., "Preclinical Safety of RNAi-Mediated Htt Suppression in the Rhesus Macaque as a Potential Therapy for Huntington's Disease," *Mol Ther* 19(12):2152-2162 (2011).
Mele, et al., "Human Genomics. The Human Transcriptome Across Tissues and Individuals," *Science* 348(6235):660-665 (2015).
Menalled, et al., "Comprehensive Behavioral and Molecular Characterization of a New Knock-In Mouse Model of Huntington's Disease: ZQ175," *PLoS ONE* 7(12):e49838 (2012).
Minderer, et al., "Chronic Imaging of Cortical Sensory Map Dynamics Using a Genetically Encoded Calcium Indicator," *J Physiol* 590(1):99-107 (2012).
Mirny, "Nucleosome-Mediated Cooperativity Between Transcription Factors," *Proc Natl Acad Sci USA* 107(52):22534-22539 (2010).
Monod, et al., "On the Nature of Allosteric Transitions: A Plausible Model," *J Mol Biol* 12:88-118 (1965).
Morlan, et al., "Mutation Detection by Real-Time PCR: A Simple, Robust and Highly Selective Method," *PLOS ONE* 4(2):e4584 (2009).
Nagy, et al., "Performance Evaluation of the Small-Animal Nanoscan PET/MRI System," *J. Nucl Med* 54(10):1825-32 (2013).
Nasir, et al., "Targeted Disruption of the Huntington's Disease Gene Results in Embryonic Lethality and Behavioral and Morphological Changes in Heterozygotes," *Cell* 81(5):811-823 (1995).
Nekludova, et al., "Distinctive DNA Conformation With Enlarged Major Groove is Found in Zn-Finger-DNA and Other Protein-DNA Complexes," *Proc Natl Acad Sci USA* 91:6948-6952 (1994).
Niccolini, et al., "Striatal Molecular Alterations in HD Gene Carriers: A Systematic Review and Meta-Analysis of PET Studies," *J Neurol Neurosurg Psychiatry* 89(2):185-196 (2018).
Pavletich, et al., "Zing Finger-DNA Recognition: Crystal Structure of a ZIF268-DNA Complex at 2.1 Å," *Science* 252:809-817 (1991).
Peng, et al., "Biochemical Analysis of Thekruppel-Associated Box (KRAB) Transcriptional Repression Domain," *J Biol Chem* 275(24):18000-18010 (2000).
Pfister, et al., "Five SIRNAs Targeting Three SNPs May Provide Therapy for Three-Quarters of Huntington's Disease Patients," *Cur Biol* 19(9):774-778 (2009).
Reiter, et al., "Combinatorial Function of Transcription Factors and Cofactors," *Curr Opin Genet Dev* 43:73-81 (2017).

Robertson, et al., "DNMT1 Forms a Complex With RB, E2F1 and HDAC1 and Represses Transcription From E2F-Responsive Promoters," *Nature Genetics* 25:338-342 (2000).
Rodan, et al., "A Novel Neurodevelopmental Disorder Associated With Compound Heterozygous Variants in the Huntingtin Gene," *Eur J Hum Genet* 24(12):1833 (2016).
Ross, et al., "Huntington's Disease: From Molecular Pathogenesis to Clinical Treatment," *The Lancet. Neurology* 10(1):83-98 (2011).
Russell, et al., "The Phosphodiesterase 10 Positron Emission Tomography Tracer, [$^{18}$F]MNI-659, as a Novel Biomarker for Early Huntington Disease," *JAMA Neurology* 71(12): 1520-1528 (2014).
Sathasivam, et al., "Aberrant Splicing of HTT Generates the Pathogenic Exon 1 Protein in Huntington Disease," *Proc Natl Acad Sci USA* 110(6):2366-2370 (2013).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Southwell, et al., "In Vivo Evaluation of Candidate Allele-Specific Mutant Huntingtin Gene Silencing Antisense Oligonucleotides," *Mol Ther* 22(12):2093-106 (2014).
Stanek, et al., "Silencing Mutant Huntingtin by Adeno-Associated Virus-Mediated RNA Interference Ameliorates Disease Manifestations in the YAC128 Mouse Model of Huntington's Disease," *Human Gene Therapy* 25(5):461-474 (2014).
Stiles, et al., "Widespread Suppression of Huntingtin With Convection-Enhanced Delivery of SIRNA," *Exp Neurol* 233(1):463-471 (2012).
Swarts, et al., "DNA-Guided DNA Interference by a Prokaryotic Argonaute," *Nature* 507(7491):258-261 (2014).
Trettel, et al., "Dominant Phenotypes Produced by the HD Mutation In STHDH(Q111) Striatal Cells," *Human Molecular Genetics* 9(19):2799-2809 (2000).
Tyler, et al., "The "Dark Side" of Chromatin Remodeling: Repressive Effects on Transcription," *Cell* 99:443-446 (1999).
Walker, "Huntington's Disease," *Lancet* 369(9557):218-228 (2007).
Wang, et al., "Ablation of Huntingtin in Adult Neurons is Nondeleterious but Its Depletion in Young Mice Causes Acute Pancreatitis," *Proc Natl Acad Sci USA* 113(12):3359-3364 (2016).
Wild, et al., "Quantifying Mutant Huntingtin in Huntington's Disease CSF," *J Neurol Neurosurg Psychiatry* 85:e4 (2014).
Wilson, et al., "Loss of Extra-Striatal Phosphodiesterase 10A Expression in Early Premanifest Huntington's Disease Gene Carriers," *Journal of the Neurological Sciences* 368:243-248 (2016).
Wu, et al., "Functional Analysis of HD2 Histone Deacetylase Homologues in *Arabidopsis thaliana*," *The Plant Journal* 22(1):19-27 (2000).
Yamamoto, et al., "Reversal of Neuropathology and Motor Dysfunction in a Conditional Model of Huntington's Disease," *Cell* 101(1):57-66 (2000).
You, et al., "Design of LNA Probes That Improve Mismatch Discrimination," *Nucleic Acids Research* 34(8):e60 (2006).
Yu, et al., "An Engineered VEGF-Activating Zinc Finger Protein Transcription Factor Improves Blood Flow and Limb Salvage in Advanced-Age Mice," *FASEB J.* 20(3):479-481 (2006).
Yu, et al., "Single-Stranded RNAs Use RNAi to Potently and Allele-Selectively Inhibit Mutant Huntingtin Expression," *Cell* 150(5):895-908 (2012).
Zeitlin, et al., "Increased Apoptosis and Early Embryonic Lethality in Mice Nullizygous for the Huntington's Disease Gene Homologue," *Nat Genet* 11(2):155-163 (1995).
Zolotukhin, et al., "Recombinant Adeno-Associated Virus Purification Using Novel Methods Improves Infectious Titer and Yield," *Gene Ther.* 6(6):973-85 (1999).
Zuccato, et al., "Progressive Loss of BDNF in a Mouse Model of Huntington's Disease and Rescue by BDNF Delivery," *Pharmacological Research* 52(2):133-139 (2005).
Zuccato, et al., "Molecular Mechanisms and Potential Therapeutical Targets in Huntington's Disease," *Physiological Reviews* 90(3):905-981 (2010).
Zeitler, et al., Allele-selective transcriptional repression of mutant HTT for the treatment of Huntington's disease, Nature Medicine, 25(7):1131-1142 (2019).

| Regulated on Microarray by | Microarray Fold Repression 1 2 4 8 16 32 | | | Gene | CAG to TSS Distance (bp) | Total CAG# | Contig CAG# |
| --- | --- | --- | --- | --- | --- | --- | --- |
| | A | B | C | | | | |
| ZFP-A | ■ | □ | ■ | STC1 | 30 | 18 | 6 |
| | □ | □ | ■ | GLS | 36 | 15 | 15 |
| | ■ | □ | ■ | NAP1L3 | 393 | 19 | 6 |
| ZFP-B | □ | ■ | □ | IL17RA | 174 | 6 | 2 |
| | □ | ■ | ■ | SLC7A11 | 15 | 7 | 7 |
| | □ | ■ | ■ | MBD5 | 90 | 6 | 5 |
| ZFP-C | □ | □ | ■ | ATXN2 | -122 | 22 | 13 |
| | □ | □ | ■ | ORC4 | 80 | 19 | 5 |
| | ■ | ■ | ■ | THAP11 | 778 | 25 | 10 |
| No ZFP | □ | □ | □ | TBP | 7528 | 32 | 19 |
| | □ | □ | □ | DNM1 | -12502 | 24 | 6 |
| | □ | □ | □ | FBXO11 | 131 | 14 | 4 |
| | | | | HTT (CAG18) | 192 | 19 | 18 |
| | | | | HTT (CAG45) | 192 | 46 | 45 |

FIG. 11B

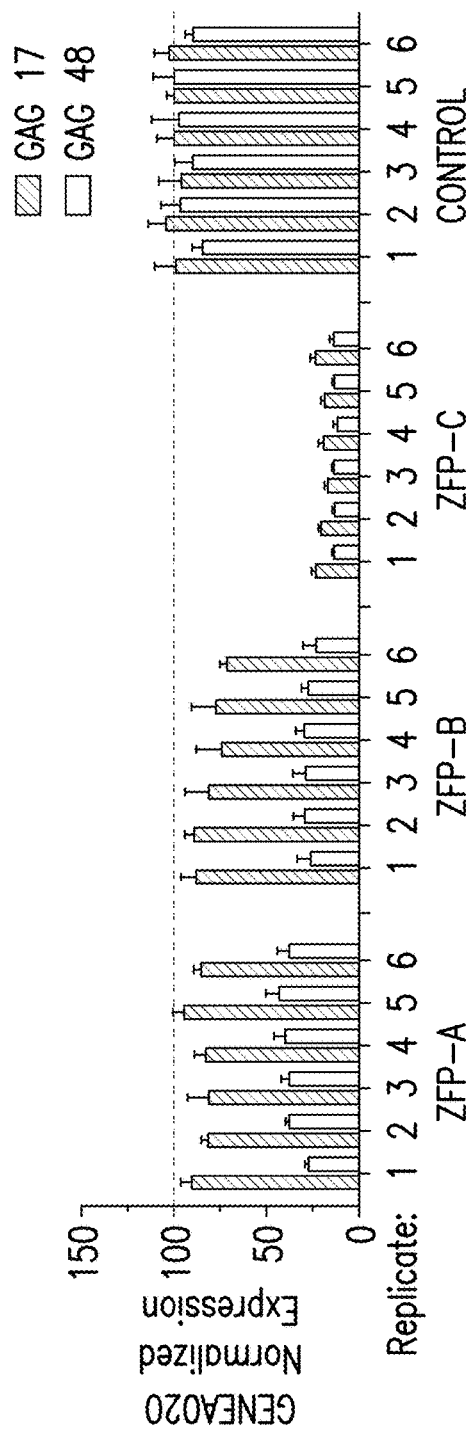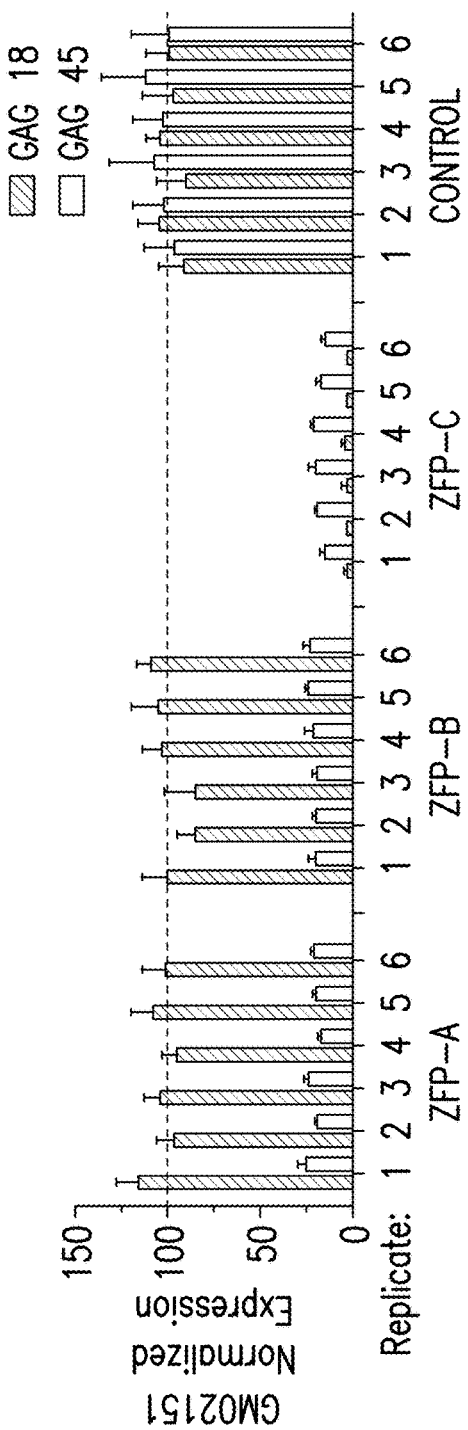

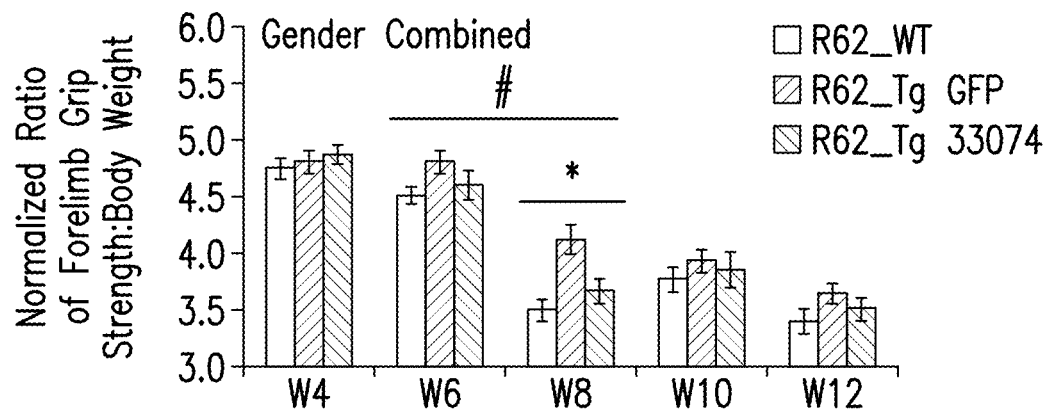
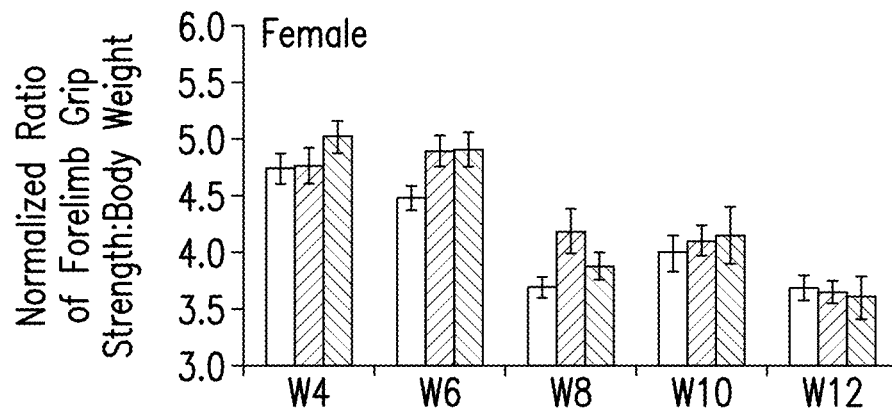
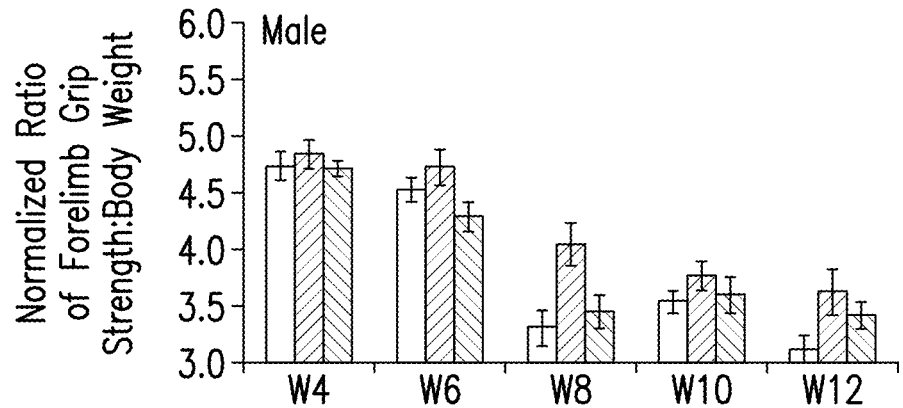
FIG. 13C

SEQUENCE LISTING

```
<160> NUMBER OF SEQ ID NOS: 93

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 1
gcagagctct ctggctaact agag                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggcaacta gaaggcacag                                               20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaacggtgc attggaacg                                                19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttcgaatcc caattctttg cc                                            22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
agcacgttgc ccaggaggtc ac                                            22

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgcaggctgc agggttac                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgcaccga ccgtgagt                                                18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cagctccctg tcccggcgg                                               19

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agtttggagg gtttctc                                                 17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtttggagg gtttctt                                                 17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agggtttctc cgctcagc                                                18

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcgactaaag caggatttca gg                                           22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
tctcctccac agagtttgtg a                                              21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccttctttct ggactaagaa gctg                                           24

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tccctcatcc actgtgt                                                   17

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ctcatctact gtgt                                                      14

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 17
cagcagnngc agcancagca g                                              21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggtccggc agaggaacc                                                 19

<210> SEQ ID NO 19
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttcacacggt ctttcttggt gg                                              22

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcccggctgt ggctga                                                     16

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcacacggt ctttcttggt gg                                              22

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caggtccggc agaggaacc                                                  19

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcccggctgt ggctga                                                     16

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttcacacggt ctttcttggt gg                                              22

<210> SEQ ID NO 25
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctggctggtg gagagagaaa tt                                              22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgtcgtcct tgtagtcaac tga                                             23

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Gly Glu Lys Pro Phe Gln
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Gly Ser Gln Lys Pro Phe Gln
1               5

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Pro Asn Pro His Arg Arg Thr Asp Pro Ser His Lys Pro Phe Gln
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ser Ser Asp Leu Ser Arg
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Trp Ser Thr Arg Lys Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Gly Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp Asn Leu Ser Glu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Arg Cys Asn Leu Arg Cys
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Ala Cys Cys Arg Tyr Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 36

Arg Leu Trp Asn Arg Lys Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Arg Ser Thr Arg Asn Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Thr Leu Ser Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Trp Thr Leu Val Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Ser Asp Leu Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Ala Val Leu Ser Glu
1               5

<210> SEQ ID NO 42
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 42

Arg Ser Asp Val Leu Ser Glu
1               5

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcagcagcag cagcagca                                                 18

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcagcagcag cagca                                                    15

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcagcagcag cagcagcag                                                19

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcagcagcag cagcag                                                   16

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcagcagcag cagcagcagc a                                             21

<210> SEQ ID NO 48
<211> LENGTH: 13
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 48
gcagcagcag cag                                                          13

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cagcagcagc agcagcag                                                     18

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cagcagcagc agcagcagca                                                   20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cagcagcagc agcagcagca g                                                 21

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cagcagcagc agcagca                                                      17

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cagcagcagc agca                                                         14

<210> SEQ ID NO 54
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 54
gctgctgctg ctgctgct                                                     18

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gctgctgctg ctgctgctg                                                    19

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gctgctgctg ctgct                                                        15

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gctgctgctg ctgctg                                                       16

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctgctgctgc tgctgctg                                                     18

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctgctgctgc tgctgctgct                                                   20

<210> SEQ ID NO 60
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 60
ctgctgctgc tgctgctgct g                                              21

<210> SEQ ID NO 61
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 gctgctgct                                                             9

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctgctgctgc tgct                                                      14

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctgctgctgc tgctg                                                     15

<210> SEQ ID NO 64
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Ala Pro Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Gln Ser Ser Asp Leu Ser Arg His Ile Arg Thr His Thr Gly Glu
        35                  40                  45

Lys Pro Phe Ala Cys Asp Ile Cys Gly Arg Lys Phe Ala Gln Trp Ser
    50                  55                  60

Thr Arg Lys Arg His Thr Lys Ile His Thr Gly Ser Gln Lys Pro Phe
65                  70                  75                  80

Gln Cys Arg Ile Cys Met Arg Asn Phe Ser Gln Ser Ser Asp Leu Ser
                85                  90                  95

Arg His Ile Arg Thr His Thr Gly Glu Lys Pro Phe Ala Cys Asp Ile
            100                 105                 110

Cys Gly Arg Lys Phe Ala Gln Trp Ser Thr Arg Lys Arg His Thr Lys
```

```
            115                 120                 125
Ile His Thr Gly Glu Lys Pro Phe Gln Cys Arg Ile Cys Met Arg Lys
        130                 135                 140

Phe Ala Gln Ser Gly Asp Leu Thr Arg His Thr Lys Ile His Leu Arg
145                 150                 155                 160

Gln Lys Asp Ala Ala Arg Gly Ser Gly Met Asp Ala Lys Ser Leu Thr
                165                 170                 175

Ala Trp Ser Arg Thr Leu Val Thr Phe Lys Asp Val Phe Val Asp Phe
            180                 185                 190

Thr Arg Glu Glu Trp Lys Leu Leu Asp Thr Ala Gln Gln Ile Val Tyr
        195                 200                 205

Arg Asn Val Met Leu Glu Asn Tyr Lys Asn Leu Val Ser Leu Gly Tyr
    210                 215                 220

Gln Leu Thr Lys Pro Asp Val Ile Leu Arg Leu Glu Lys Gly Glu Glu
225                 230                 235                 240

Pro Trp Leu Val Glu Arg Glu Ile His Gln Glu Thr His Pro Asp Ser
                245                 250                 255

Glu Thr Ala Phe Glu Ile Lys Ser Ser Val
            260                 265

<210> SEQ ID NO 65
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Asn Leu Ser Glu His Ile Arg Thr His Thr Gly Glu
        35                  40                  45

Lys Pro Phe Ala Cys Asp Ile Cys Gly Arg Lys Phe Ala Lys Arg Cys
    50                  55                  60

Asn Leu Arg Cys His Thr Lys Ile His Thr His Pro Arg Ala Pro Ile
65                  70                  75                  80

Pro Lys Pro Phe Gln Cys Arg Ile Cys Met Arg Asn Phe Ser Gln Ser
                85                  90                  95

Gly Asp Leu Thr Arg His Ile Arg Thr His Thr Gly Glu Lys Pro Phe
            100                 105                 110

Ala Cys Asp Ile Cys Gly Arg Lys Phe Ala Gln Ser Gly Asp Leu Thr
        115                 120                 125

Arg His Thr Lys Ile His Thr Pro Asn Pro His Arg Arg Thr Asp Pro
    130                 135                 140

Ser His Lys Pro Phe Gln Cys Arg Ile Cys Met Arg Asn Phe Ser Arg
145                 150                 155                 160

Ser Asp Asn Leu Ser Glu His Ile Arg Thr His Thr Gly Glu Lys Pro
                165                 170                 175

Phe Ala Cys Asp Ile Cys Gly Arg Lys Phe Ala Lys Arg Cys Asn Leu
            180                 185                 190

Arg Cys His Thr Lys Ile His Leu Arg Gln Lys Asp Ala Ala Arg Gly
        195                 200                 205
```

```
Ser Gly Met Asp Ala Lys Ser Leu Thr Ala Trp Ser Arg Thr Leu Val
    210                 215                 220

Thr Phe Lys Asp Val Phe Val Asp Phe Thr Arg Glu Glu Trp Lys Leu
225                 230                 235                 240

Leu Asp Thr Ala Gln Gln Ile Val Tyr Arg Asn Val Met Leu Glu Asn
                245                 250                 255

Tyr Lys Asn Leu Val Ser Leu Gly Tyr Gln Leu Thr Lys Pro Asp Val
            260                 265                 270

Ile Leu Arg Leu Glu Lys Gly Glu Pro Trp Leu Val Glu Arg Glu
                275                 280                 285

Ile His Gln Glu Thr His Pro Asp Ser Glu Thr Ala Phe Glu Ile Lys
    290                 295                 300

Ser Ser Val
305

<210> SEQ ID NO 66
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Ala Pro Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
                20                  25                  30

Ser Arg Ser Asp Asn Leu Ser Glu His Ile Arg Thr His Thr Gly Glu
            35                  40                  45

Lys Pro Phe Ala Cys Asp Ile Cys Gly Arg Lys Phe Ala Lys Arg Cys
        50                  55                  60

Asn Leu Arg Cys His Thr Lys Ile His Thr Gly Ser Gln Lys Pro Phe
65                  70                  75                  80

Gln Cys Arg Ile Cys Met Arg Asn Phe Ser Arg Ser Asp Asn Leu Ser
                85                  90                  95

Glu His Ile Arg Thr His Thr Gly Glu Lys Pro Phe Ala Cys Asp Ile
            100                 105                 110

Cys Gly Arg Lys Phe Ala Lys Arg Cys Asn Leu Arg Cys His Thr Lys
        115                 120                 125

Ile His Thr Gly Ser Gln Lys Pro Phe Gln Cys Arg Ile Cys Met Arg
    130                 135                 140

Asn Phe Ser Arg Ser Asp Asn Leu Ser Glu His Ile Arg Thr His Thr
145                 150                 155                 160

Gly Glu Lys Pro Phe Ala Cys Asp Ile Cys Gly Arg Lys Phe Ala Lys
                165                 170                 175

Arg Cys Asn Leu Arg Cys His Thr Lys Ile His Leu Arg Gln Lys Asp
            180                 185                 190

Ala Ala Arg Gly Ser Gly Met Asp Ala Lys Ser Leu Thr Ala Trp Ser
        195                 200                 205

Arg Thr Leu Val Thr Phe Lys Asp Val Phe Val Asp Phe Thr Arg Glu
    210                 215                 220

Glu Trp Lys Leu Leu Asp Thr Ala Gln Gln Ile Val Tyr Arg Asn Val
225                 230                 235                 240

Met Leu Glu Asn Tyr Lys Asn Leu Val Ser Leu Gly Tyr Gln Leu Thr
                245                 250                 255
```

```
Lys Pro Asp Val Ile Leu Arg Leu Glu Lys Gly Glu Pro Trp Leu
            260                 265                 270

Val Glu Arg Glu Ile His Gln Glu Thr His Pro Asp Ser Glu Thr Ala
        275                 280                 285

Phe Glu Ile Lys Ser Ser Val
        290                 295

<210> SEQ ID NO 67
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Ala Pro Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Asn Leu Ser Glu His Ile Arg Thr His Thr Gly Glu
        35                  40                  45

Lys Pro Phe Ala Cys Asp Ile Cys Gly Arg Lys Phe Ala Lys Arg Cys
    50                  55                  60

Asn Leu Arg Cys His Thr Lys Ile His Thr His Pro Arg Ala Pro Ile
65                  70                  75                  80

Pro Lys Pro Phe Gln Cys Arg Ile Cys Met Arg Asn Phe Ser Gln Ser
                85                  90                  95

Ser Asp Leu Ser Arg His Ile Arg Thr His Thr Gly Glu Lys Pro Phe
            100                 105                 110

Ala Cys Asp Ile Cys Gly Arg Lys Phe Ala Gln Trp Ser Thr Arg Lys
        115                 120                 125

Arg His Thr Lys Ile His Thr Gly Glu Lys Pro Phe Gln Cys Arg Ile
    130                 135                 140

Cys Met Arg Lys Phe Ala Gln Ser Gly Asp Leu Thr Arg His Thr Lys
145                 150                 155                 160

Ile His Leu Arg Gln Lys Asp Ala Ala Arg Gly Ser Gly Met Asp Ala
                165                 170                 175

Lys Ser Leu Thr Ala Trp Ser Arg Thr Leu Val Thr Phe Lys Asp Val
            180                 185                 190

Phe Val Asp Phe Thr Arg Glu Glu Trp Lys Leu Leu Asp Thr Ala Gln
        195                 200                 205

Gln Ile Val Tyr Arg Asn Val Met Leu Glu Asn Tyr Lys Asn Leu Val
    210                 215                 220

Ser Leu Gly Tyr Gln Leu Thr Lys Pro Asp Val Ile Leu Arg Leu Glu
225                 230                 235                 240

Lys Gly Glu Glu Pro Trp Leu Val Glu Arg Glu Ile His Gln Glu Thr
                245                 250                 255

His Pro Asp Ser Glu Thr Ala Phe Glu Ile Lys Ser Ser Val
            260                 265                 270

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 68
cagcagcagc agcagcagca                                                    20

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Thr Gly Leu Leu Asn Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ser Tyr Asn Leu Lys Thr
1               5

<210> SEQ ID NO 71
<211> LENGTH: 60
<212> TYPE: DNA
<213> ORGANISM: Homo sapiens
<220> FEATURE:
<221> NAME/KEY: misc_feature
<222> LOCATION: (1)..(60)
<223> OTHER INFORMATION: This sequence may encompass 15-20 "CAG" repeats

<400> SEQUENCE: 71
cagcagcagc agcagcagca gcagcagcag cagcagcagc agcagcagca gcagcagcag        60

<210> SEQ ID NO 72
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagcagcagc agcagcagca gcagcagcag cagcagcagc agcagcagca gcagcagcag        60
cagcagcagc agcagcagca gcagcagcag cagcagcagc agcagcagca gcagcagcag       120
cagcagcagc agcagcagca gcagcagcag                                        150

<210> SEQ ID NO 73
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
cagcagcagc agcagcagca gcagcagcag cagcagcagc agcagcagca gcagcagcag        60
cagcagcagc agcagcagca gcagcagcag cagcagcagc agcagcagca gcagcagcag       120

```
cagcagcagc agcagcagca gcagcagcag cagcagcagc agcagcagca gcagcagcag    180
cagcagcagc agcagcagca gcagcagcag cagcagcagc agcagcagca gcagcagcag    240
```

<210> SEQ ID NO 74
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc agcagcagca gcagcagcag    240
cagcagcagc agcagcagca gcagcagcag cagcagcagc agcagcagca gcagcagcag    300
cagcagcagc agcagcagca gcagcag                                       327
```

<210> SEQ ID NO 75
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc agcagcagca gcagcagcag    240
cagcagcagc agcagcagca gcagcagcag cagcagcagc agcagcagca gcagcagcag    300
cagcagcagc agcagcagca gcagcagcag cagcagcagc agcagcagca gcagcagcag    360
cagcagcagc agcagcagca gcagcagcag cagcagcagc agcagcagca gcagcagcag    420
cagcagcagc agcagcagca gcagcagcag cagcagcagc agcagcagca gcagcagcag    480
cagcagcagc agcagcagca gcagcagcag cagcagcagc agcagcagca gcagcagcag    540
```

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76

```
cagcagcagc agcagcagca gcagcagcag cagcagcagc agcagcagca g              51
```

<210> SEQ ID NO 77
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 77
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcag                                                             129

<210> SEQ ID NO 78
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcag                                            144

<210> SEQ ID NO 79
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cagcagcagc agcagcagca gcagcagcag cagcagcagc agcagcagca gcag            54

<210> SEQ ID NO 80
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcag                                                      135

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagcagcagc agcagcagca gcagcagcag cagcagcagc agcag                      45

<210> SEQ ID NO 82
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
```

```
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca g                                             201

<210> SEQ ID NO 83
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cagcagcagc agcagcagca gcagcagcag cagcagcagc agcagcagca gcagcagcag    60
cag                                                                  63

<210> SEQ ID NO 84
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
cagcagcagc agcagcagca gcagcagcag cagcagcagc agcagcagca gcagcagcag    60
cagcagcagc agcagcagca gcagcagcag cagcagcagc agcagcagca gcag         114

<210> SEQ ID NO 85
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag                                    210

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cagcagcagc ag                                                        12

<210> SEQ ID NO 87
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 87
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300
cagcagcagc agcagcagca gcagcagcag cag                                  333

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr His Pro Arg Ala Pro Ile Pro Lys Pro Phe Gln
1               5                   10

<210> SEQ ID NO 89
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(117)
<223> OTHER INFORMATION: This sequence may encompass 36-39 "CAG" repeats

<400> SEQUENCE: 89
cagcagcagc agcagcagca gcagcagcag cagcagcagc agcagcagca gcagcagcag      60
cagcagcagc agcagcagca gcagcagcag cagcagcagc agcagcagca gcagcag        117

<210> SEQ ID NO 90
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcagcagcag cagc                                                        14

<210> SEQ ID NO 91
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
cagcagcagc agcagcagca gcagcagcag cagcagcagc agcagcagca gcagcagcag      60
cagcagcagc agcagcagca gcagcagcag cagcagcagc agcagcagca gcagcagcag     120

<210> SEQ ID NO 92
<211> LENGTH: 57
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 92
cagcagcagc agcagcagca gcagcagcag cagcagcagc agcagcagca gcagcag          57

<210> SEQ ID NO 93
<211> LENGTH: 84
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
cagcagcagc agcagcagca gcagcagcag cagcagcagc agcagcagca gcagcagcag       60
cagcagcagc agcagcagca gcag                                              84
```

ZINC FINGER PROTEIN COMPOSITIONS FOR MODULATION OF HUNTINGTIN (HTT)

CROSS-REFERENCE TO RELATED APPLICATIONS

The present application claims the benefit of U.S. Provisional Application No. 62/659,552, filed Apr. 18, 2018, and U.S. Provisional Application No. 62/780,605, filed Dec. 17, 2018 the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 15, 2019, is named 8325-0173_SL.txt and is 34,376 bytes in size.

TECHNICAL FIELD

The present disclosure is in the field of diagnostics and therapeutics for Huntington's Disease.

BACKGROUND

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent.

Huntington's Disease is an example of a trinucleotide repeat expansion disorders were first characterized in the early 1990s (see Di Prospero and Fischbeck (2005) *Nature Reviews Genetics* 6:756-765). These disorders involve the localized expansion of unstable repeats of sets of three nucleotides and can result in loss of function of the gene in which the expanded repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from a doubling to a log order increase in the number of repeats. In HD, repeats are inserted within the N terminal coding region of the large cytosolic protein Huntingtin (Htt). Normal Htt alleles contain 15-20 CAG repeats (SEQ ID NO:71), while alleles containing 35 or more repeats can be considered potentially HD causing alleles and confer risk for developing the disease. Alleles containing 36-39 repeats (SEQ ID NO:89) are considered incompletely penetrant, and those individuals harboring those alleles may or may not develop the disease (or may develop symptoms later in life) while alleles containing 40 repeats or more are considered completely penetrant. In fact, no asymptomatic persons containing HD alleles with 40 or more repeats have been reported. Those individuals with juvenile onset HD (<21 years of age) are often found to have 60 or more CAG repeats. In addition to an increase in CAG repeats, it has also been shown that HD can involve+1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43:893-896).

In HD, the mutant Htt allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

Furthermore, trinucleotide expansion in Htt leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CA1 region of the hippocampus, the angular gyms in the parietal lobe, Purkinje cells of the cerebellum, lateral tuberal nuclei of the hypothalamus, and the centromedialparafascicular complex of the thalamus (Walker (2007) *Lancet* 369:218-228).

The role of the normal Htt protein is poorly understood, but it may be involved in neurogenesis, apoptotic cell death, and/or vesicle trafficking. In addition, there is evidence that wild-type Htt stimulates the production of brain-derived neurotrophic factor (BDNF), a pro-survival factor for the striatal neurons. It has been shown that progression of HD correlates with a decrease in BDNF expression in mouse models of HD (Zuccato et al. (2005) *Pharmacological Research* 52(2):133-139), and that delivery of either BDNF or glial cell line-derived neurotrophic factor (GDNF) via adeno-associated viral (AAV) vector-mediated gene delivery may protect straital neurons in mouse models of HD (Kells et al. (2004) *Molecular Therapy* 9(5):682-688).

A variety of mechanisms for HD pathogenesis have been investigated, including toxicity from the mutant HTT (mHTT) protein and loss of normal HTT protein (Ross & Tabrizi (2011) *The Lancet. Neurology* 10:83-98; Zuccato et al. (2010) *Physiological Reviews* 90:905-981). Results from multiple HD mouse models expressing mHtt suggest that it exerts its pathogenic activity primarily through gain-of-function toxicity (Brooks & Dunnett (2015) *Curr Top Behav Neurosci* 22:101-133). The finding that inactivating an inducible mHTT transgene results in disease reversal (Yamamoto et al. (2000) *Cell* 101:57-66) has led to the development of HTT-lowering agents as potential therapeutics. RNA interference (RNAi) and antisense oligonucleotides (ASO) targeting HTT mRNA have shown efficacy in a variety of HD preclinical models (Boudreau et al. (2009) *Mol Ther* 17:1053-1063; Harper et al. (2005) *Proc Natl Acad Sci* 102:5820-5825; Kordasiewicz et al. (2012) *Neuron* 74:1031-1044; Stanek et al. (2014) *Human Gene Ther.*

25(5):461). and a recent Phase 1/2a trial showed that multiple intrathecal administrations of an ASO lowered both normal and mutant HTT levels in participants' cerebrospinal fluid.

Diagnostic and treatment options for HD are currently very limited. In terms of diagnostics, altered (mutant) Htt (mHTT) levels are significantly associated with disease burden score, and soluble mHTT species increase in concentration with disease progression. However, low-abundance mHTT is difficult to quantify in the patient CNS, which limits both study of the role in the neuropathobiology of HD in vivo, and precludes the demonstration of target engagement by HTT-lowering drugs. See, e.g., Wild et al. (2014) *J Neurol Neurosurg Psychiatry* 85:e4.

With regard to treatment, some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of mutant HD Htt by caspase may play a role in the pathogenicity of the disease. Transgenic mice carrying caspase-6 resistant mutant Htt were found to maintain normal neuronal function and did not develop striatal neurodegeneration as compared to mice carrying a non-caspase resistant mutant Htt allele (see Graham et al. (2006) *Cell* 125:1179-1191). Molecules which target members of the apoptotic pathway have also been shown to have a slowing effect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant Htt to the NDMA receptor to prevent the exertion of toxic effects on the nerve cell. However, no statistically significant improvements were observed in neuron function in these trials. In addition, the Huntington Study Group conducted a randomized, double-blind study using Co-enzyme Q. Although a trend towards slower disease progression among patients that were treated with coenzyme Q10 was observed, there was no significant change in the rate of decline of total functional capacity. (Di Prospero and Fischbeck, ibid).

Recombinant transcription factors comprising the DNA binding domains from zinc finger proteins ("ZFPs") have the ability to regulate gene expression of endogenous genes, including Htt genes. See, e.g., U.S. Pat. Nos. 9,943,565; 9,499,597; 9,234,016; and 8,841,260 and U.S. Patent Publication Nos. 2015/0335708; 2017/0096460; and 20150255877. Clinical trials using these engineered transcription factors containing zinc finger proteins have shown that these novel transcription factors are capable of treating various conditions. (see, e.g., Yu et al. (2006) *FASEB J.* 20:479-481).

In addition, artificial nucleases comprising ZFPs have the ability to modify gene expression of endogenous genes via nuclease-mediated modification of the gene, including either homology directed repair (HDR), following non-homologous end joining (NHEJ) and/or by end capture during non-homologous end joining (NHEJ) driven processes. See, for example, U.S. Pat. Nos. 9,873,894; 9,394,545; 9,150, 847; 9,206,404; 9,222,105; 9,045,763; 9,005,973; 8,956, 828; 8,936,936; 8,945,868; 8,871,905; 8,586,526; 8,563, 314; 8,329,986; 8,399,218; 6,534,261; 6,599,692; 6,503, 717; 6,689,558; 7,067,317; 7,262,054; 7,888,121; 7,972, 854; 7,914,796; 7,951,925; 8,110,379; 8,409,861; 8,771, 985; 8,895,264; U.S. Patent Publication Nos. 2003/ 0232410; 2005/0208489; 2005/0026157; 2005/0064474; 2006/0063231; 2011/0265198; and 2013/0177960, the disclosures of which are incorporated by reference in their entireties for all purposes. Thus, these methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway.

However, there remains a need for methods for the diagnosis, study, treatment and/or prevention of Huntington's Disease, including detection of mHTT for monitoring disease progression, for increased understanding of the neuropathobiology of HD and to evaluate disease-modifying HD therapeutics.

SUMMARY

Disclosed herein are methods and compositions for diagnosing and/or treating Huntington's Disease. In particular, provided herein are zinc finger protein compositions that modulate Htt expression, including selective repression of a mutant Htt gene (mHtt) expression the toxic mutant HTT (mHTT) protein. The compositions and methods selectively repress >99% of HD-causing alleles over an 80-fold dose range, while preserving expression of >86% of wild type alleles found in the HD population. Expression of other CAG-containing genes is minimally affected, and artificial transcription factor repressors as described herein are active and well tolerated in HD neurons beyond 100 days in culture and at least 9 months or more in the mouse brain.

Thus, in one aspect, ZFP genetic modulators for Htt genes are described. In certain embodiments, the genetic modulator comprises an artificial ZFP transcription factor or zinc finger nuclease (ZFN) and functional domain (transcriptional activator, transcriptional repressor, nuclease domain, etc.) that modulate expression of an HD allele (e.g., Htt). In certain embodiments, the zinc finger proteins have the recognition helices shown any of the appended Tables or Figures. In certain embodiments, the ZFP-TFs are formulated into a pharmaceutical composition, for example, for administration to a subject.

In one aspect, the genetic modulators described herein are ZFP repressors (artificial transcription factors or nucleases that repress Htt expression). These ZFP repressors may bind to wild-type and/or mutant Htt alleles specifically. Certain repressors bind to both wild-type and mutant Htt genes; others bind to wild-type only and still others bind to mutant Htt genes only. In some embodiments, the artificial transcription factors form a stable complex of multimers of a given size, and thus are capable of preferentially interacting with a CAG tract above a certain minimum size, wherein that minimum size is greater than the length of a wild-type CAG tract.

In certain embodiments, the ZFP genetic modulators as described herein preferentially modify expression of a mutant Htt allele. In some embodiments, the ZFP genetic modulator (e.g., repressor) binds specifically to mutant Htt alleles wherein the expanded tract encodes poly-glutamine, while in other embodiments, the genetic modulator binds specifically to a mutant Htt allele wherein the expansion tract encodes poly-serine. Thus, in some embodiments, the ZFP genetic modulator modulates both the wild type and mutant forms of the Htt allele. In certain embodiments, the ZFP genetic modulator modulates only the wild type Htt allele. In other embodiments, the ZFP genetic modulator modulates only the mutant form of Htt.

In other embodiments, repressing modulators comprising ZFPs as described herein are provided which preferentially bind to known SNPs associated with the expanded HD Htt alleles. In this way, the genetic repressors are specific for mutant Htt alleles which contain the SNP, allowing for specific repression of the mutant Htt allele. In another aspect, genetic modulators specifically activate the wild-type Htt allele by interacting with SNPs associated with wild-type alleles are provided. In this way, only the wild-type Htt allele is activated.

In certain embodiments, the ZFP genetic modulators comprise at least one regulatory domain (or functional domain). The functional domain can be, for example, a transcriptional activation domain, a transcriptional repression domain and/or a nuclease (cleavage) domain. By selecting either an activation domain or repression domain for fusion with the ZFP DNA-binding domain, these artificial transcription factors can be used either to activate or to repress gene expression. In some embodiments, a fusion molecule comprising a ZFP DNA-binding domain targeted to a mutant Htt as described herein fused to a transcriptional repression domain that can be used to down-regulate mutant Htt expression is provided. In some embodiments, an artificial transcription factor comprising a ZFP DNA-binding domain targeted to a wild-type Htt allele fused to a transcription activation domain that can up-regulate the wild type Htt allele is provided. In certain embodiments, the activity of the regulatory domain is regulated by an exogenous small molecule or ligand such that interaction with the cell's transcription machinery will not take place in the absence of the exogenous ligand. Such external ligands control the degree of interaction of the artificial transcription factor with the transcription machinery. The regulatory (functional) domain(s) may be operatively linked to or otherwise associated with any portion(s) of one or more of the ZFP DNA-binding domains, including between one or more zinc finger domains, exterior to one or more ZFPs and any combination thereof. Any of the fusion proteins described herein may be formulated into a pharmaceutical composition.

In some embodiments, the genetic modulators described herein comprise artificial nucleases comprising an engineered ZFP protein as described herein and a cleavage (nuclease domain). These artificial zinc finger nucleases (ZFNs) can be utilized for targeting mutant Htt alleles in stem cells such as induced pluripotent stem cells (iPSC), human embryonic stem cells (hESC), mesenchymal stem cells (MSC) or neuronal stem cells wherein the activity of the nuclease fusion will result in an Htt allele containing a wild type number of CAG repeats. In certain embodiments, pharmaceutical compositions comprising the modified stem cells are provided for ex vivo administration to a subject.

In yet another aspect, a polynucleotide encoding any of the ZFP DNA binding genetic modulators (or components thereof) described herein is provided. Such polynucleotides can be administered to a subject in which it is desirable to treat Huntington's Disease.

In still further aspects, the invention provides methods and compositions for the generation of specific model systems for the study of Huntington's Disease. In certain embodiments, provided herein are models in which mutant Htt alleles are generated using embryonic stem cells to generate cell and animal lines in which trinucleotide expansion tracts of specific (50 (SEQ ID NO:72), 80 (SEQ ID NO:73), 109 (SEQ ID NO:74) and 180 CAG repeats (SEQ ID NO:75), for example) are inserted into a wild-type Htt allele using Htt-targeted artificial nucleases as described herein to drive targeted integration. In certain embodiments, the model systems comprise in vitro cell lines, while in other embodiments, the model systems comprise transgenic animals. In any of the animal models described herein, the animal may be, for example, a rodent (e.g., rat, mouse), a primate (e.g., non-human primate) or a rabbit.

In yet another aspect, a gene delivery vector comprising any of polynucleotides encoding ZFP modulators as described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). Thus, also provided herein are adenovirus (Ad) vectors, LV or adenovirus associate viral vectors (AAV) comprising a sequence encoding at least one genetic modulator as described herein, optionally further encoding one or more donor sequences for targeted integration into a target gene following nuclease-mediated cleavage. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

In some embodiments, model systems are provided for Huntington's disease wherein the target alleles (e.g., mutant Htt) are tagged with expression markers. In certain embodiments, the mutant alleles (e.g., mutant Htt) are tagged. In some embodiments, the wild type allele (e.g., wild-type Htt) is tagged, and in additional embodiments, both wild type and mutant alleles are tagged with separate expression markers. In certain embodiments, the model systems comprise in vitro cell lines, while in other embodiments, the model systems comprise transgenic animals.

Additionally, pharmaceutical compositions comprising one or more of the genetic modulators described herein are also provided. For example, certain compositions include a nucleic acid comprising a sequence that encodes a ZFP-TF as described herein in combination with a pharmaceutically acceptable carrier or diluent such that upon administration to subject, the ZFP-TF is expressed and modulates Htt expression in the subject. In certain embodiments, the genetic modulators encoded are specific for a HD Htt allele. In these pharmaceutical compositions, protein ZFP-TFs may also be used in conjunction with or as an alternative to the nucleic acids encoding genetic modulators as described herein.

In yet another aspect also provided is an isolated cell comprising any of the ZFP genetic modulators and/or compositions as described herein.

In another aspect, provided herein are methods for treating and/or preventing Huntington's Disease using the methods and compositions described herein. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations.

These and other aspects will be readily apparent to the skilled artisan in light of disclosure as a whole.

BRIEF DESCRIPTION OF THE DRAWINGS

FIG. 1A is diagram of the structure and desired behavior of allele-specific repressors of HTT. A designed ZFP-KRAB protein engineered to bind within the poly-CAG tract with appropriate affinity and target spacing should exhibit highly selective repression of the expanded disease allele. ZFP-TFs are screened for differential repression of wild type (<22) and disease (>39) alleles in patient cell lines bearing downstream SNPs, which enable independent quantitation of allele levels using SNP-specific qRT-PCR reagents targeting rs363099, rs362331 and rs362307. FIG. 1B shows 1- and 2-finger units and 1- and 2-base-spanning linkers used for assembling candidate ZFPs. Alternate shadings indicate alternative designs with distinct sets of DNA-contacting residues and binding properties. See Table 1 for sequence details. FIG. 1C shows ZFP-TF sense- (left) and antisense-strand (right) targeted designs screened for selective repression of mHTT. 1- and 2-finger modules targeting either strand of the poly-CAG tract were linked together to generate 3, 4, 5 or 6 finger ZFPs using alternative linkers to enables skipping of 0, 1 or 2 bases between adjacent fingers. Targeted sequences are indicated by the DNA sequence at left, middle and right. FIG. 1D shows transcript levels for normal (top plot) and disease (bottom plot) alleles of HTT were assessed 24 hours after delivery of 100 ng ZFP-TFs mRNA via nucleofection to patient fibroblasts (GM02151 or GM04723) bearing distinct poly-CAG tract lengths. Allele-selective repressors (ZFPs A, B and D) and one nonselective repressor (ZFP-C) were chosen for further study. n=3 biological replicates; mean±SD. FIG. 1D discloses SEQ ID Nos:81, 82, 79 and 80, respectively, in order of appearance. FIG. 1E shows allele-specific repression of three ZFPs chosen for further study and analyzed as in FIG. 1D. Studies were performed in patient GM04723 fibroblasts. Total HTT levels are also shown. n=3 biological replicates; mean±SD. FIG. 1E discloses SEQ ID Nos:81 and 82, respectively, in order of appearance. FIG. 1F shows selective downregulation of mHTT (upper band of top blot) protein by ZFP-A and ZFP-B as gauged by Western blot 72 hours after transfection of GM04723 fibroblasts with 100 ng or 30 ng of ZFP or control mRNA. Wild type HTT (lower band of top blot) is undiminished. Calnexin loading control (lower blot). FIG. 1G (FIG. 1G discloses SEQ ID Nos:81 and 82, respectively, in order of appearance), 1I (FIG. 1I discloses SEQ ID Nos:79 and 80, respectively, in order of appearance) and 1J (FIG. 1J discloses SEQ ID Nos:83 and 84, respectively, in order of appearance) show dose response of allele-specific repression in patient GM04723 (Figure G), GM02151 (Figure I), or GM30259 (Figure J) fibroblasts. qRT-PCR for total, WT and mutant HTT was performed on RNA isolated from patient fibroblasts transfected with ZFP mRNA across a 100,000-fold dose range (1,000-0.01 ng at ~half-log dose steps). n=3 biological replicates; mean±SD. FIG. 1H are plots showing the frequency of CAG repeat lengths in HD population. HD patient allele frequencies were calculated based on the third Enroll-HD periodic dataset. All entries with CAG high >35 (n=6602) were used for the analysis of mean and median mHTT allele length. Median alleles are indicated for CAG17 (SEQ ID NO:76) and CAG43 (SEQ ID NO:77) boxes. Circles below CAG numbers denote allele lengths tested in this study. FIG. 1K depicts the activity for ZFP 45249 in the GM02151 and GM30259 fibroblasts where the data is shown in doublets, and the bar on the right side of each doublet represents Htt expression on the expanded allele while the bar on the left side of each doublet represents Htt expression on the wild type Htt allele. FIG. 1K discloses SEQ ID Nos:79, 80, 83 and 84, respectively, in order of appearance.

FIG. 2A shows an overview timeline of studies performed using NSCs derived from GENEA020 hESCs (CAG17/48, SEQ ID NOS 76/78). FIG. 2B discloses SEQ ID Nos:76 and 78, respectively, in order of appearance. FIG. 2C discloses SEQ ID Nos:76 and 78, respectively, in order of appearance. FIG. 2D discloses SEQ ID Nos:76 and 78, respectively, in order of appearance. FIG. 2E discloses SEQ ID Nos:76 and 78, respectively, in order of appearance. In FIG. 2M, two ZFP-TFs were compared: ZFP-B, and ZFP-45249. Dots depict genes regulated >2 fold as compared to no ZFP-TF treatment. FIG. 2N depicts repression of a mHtt allele and a wild type allele in GeneA020 neurons using ZFP-45249. Also shown is repression of CPEB1 and MBD5 for these same ZFPs (see Example 5). FIG. 2N discloses SEQ ID Nos:76 and 78, respectively, in order of appearance.

FIG. 3A is a timeline overview of behavioral and molecular endpoints assessed in wildtype and AAV-treated R6/2 mice. FIG. 3B shows the percentage of mice displaying clasping behavior assessed weekly following treatment with AAV2/6 encoding either ZFP-B (left bars) or GFP (right bars). n=14 per group; treatment effect P=0.024, log-rank test. FIGS. 3C and 3D show the results from open field testing for rearing frequency (3C) or total distance traveled (3D) was performed at 4 (baseline), 6, 8, 10 and 12 weeks of age on wild-type (left), ZFP-B-treated R6/2 (middle), or GFP-treated (right) R6/2 mice. Repeated measures ANOVA, (3C, 3D) genotype main effect P<0.0001, (FIG. 3C) treatment effect P<0.009, (3D) treatment effect P<0.038. FIG. 3E depicts WT and mutant Htt (R6/2) mRNA measured 7 weeks after delivery by qRT-PCR. n=14-20 hemispheres; mean±SD. FIG. 3F is a qRT-PCR assessment of mRNA levels of the striatal neuron markers DARPP32, PDE10A, DRD1A and DRD2 as in (3E); n=6 (wildtype), 14 (GFP), and 20 (ZFP-B) hemispheres per group; mean±SD shown. FIG. 3G is a correlation between either mHtt, DARPP32, PDE10A, DRD1A or DRD2 levels and ZFP-B mRNA levels. All striatal subsections are included. The 95% confidence band is shown.

FIGS. 4A and 4B depict mouse or mutant HTT mRNA (FIG. 4A) or soluble protein (FIG. 4B) levels in zQ175 neurons 10 days after infection with AAV2/1+2 encoding ZFP-B or ΔDBD.T2A.GFP. mRNA was assessed by qRT-PCR. Protein was assessed on Singulex (mouse HTT) or MSD (mHTT) platforms. FIGS. 4S and 4T show the rescue of the dendritic index in 2-6 mo (s) or 4-6 mo (t) cohorts for zQ175 HETs treated with ZFP-D.T2A.tdTomato (n=10-17) compared with ΔDBD.T2A.tdTomato zQ175 (n=6-11) and ZFP-D.T2A.tdTomato WT mice (n=10-15). Mann-Whitney U, one-tailed.

FIGS. 5A through 5F show autoradiography analysis of mice (n=10/group) injected unilaterally with either AAV2/1+2 encoding ZFP-D (right) or GFP (left). Mice were injected at 2 months and analyzed at 6 months (FIG. 5C) or at 4 months and analyzed at 10 months (FIGS. 5D-5F) using markers for D1 (FIGS. 5A and 5D), D2 (FIGS. 4B and 4E) and PDE10 (FIGS. 5C and 5F). The specific binding for D1, D2 and PDE10 was significantly increased in mice treated with AAV2/1+2 ZFP-D (paired t-test) in both studies. FIG. 5G shows the % difference in BPND of [18F]MNI-659 in the injected vs. un-injected striatum of zQ175 mice treated with AAV2/1+2 ZFP encoding ZFP-D or GFP at 6.5/7M and 10M of age (n=33-41 mice/group/timepoint). The percent difference between the right and left striatum between the two treatment groups was compared by unpaired t-test. (FIG. 5H) Average [18F]MNI-659% SUV-images of 10M old zQ175 het mice treated with AAV2/1+2 ZFP-D averaged from 15 to 63 minutes. The template MRI (upper row) PET (middle row) are shown co-registered in the bottom row. Both the left (untreated) and right (treated) striatum are shown in the sagittal plane (n=36). Asterisk marks the increase in PDE10 binding obtained in the ZFP-D treated striatal hemisphere.

FIG. 6A shows results using plasmid templates that were prepared that correspond to the rs63099T (099T) and rs363099C (099C) SNPs of HTT. The 099T SNP is in phase with WT HTT in GM02151 CAG18/45 (SEQ ID NOS 79/80) and GM04723 CAG15/67HD (SEQ ID NOS 81/82) fibroblasts, while 099C is in phase with mutant HTT in the same cells. The plasmids were then used to prepare reciprocal serial dilutions as shown. To accomplish this, the 099C template was serially diluted two-fold from 5 fg to 0.156 fg in the presence of a fixed amount (1.25 fg) of the 099T template (099C:099T from 0.125:1 to 4:1); and the 099T template was serially diluted two-fold from 5 fg to 0.156 fg in the presence of a fixed amount (1.25 fg) of the 099C template (099T:099C from 0.125:1 to 4:1). Serial dilutions were assembled in the presence of a fixed amount of total cDNA prepared from a third patient fibroblast line from which HTT and mHTT expression had been depleted (see Methods in Examples). In this line, HTT and mHTT were also in phase with (respectively) 099T and 099C. Plasmid levels were chosen so that the qRT-PCR signal from the 1:1 plasmid ratio was approximately the same as that from the HTT and mHTT cDNA from the undepleted cells. The 099C-specific (right bars) and 099T-specific (left bars) qRT-PCR assays were performed for each of the dilution samples. Relative quantities are plotted as a fraction of the value obtained for the sample with 1:1 ratio of 099T and 099C template. FIG. 6B shows results from the plasmid templates for rs362331T (331T, in phase with WT HTT in ND30259 CAG21/38 (SEQ ID NOS 83/84) HD fibroblasts) and rs362331C (331C, in phase with mHTT in ND30259 CAG21/38 (SEQ ID NOS 83/84) HD fibroblasts) were serially diluted into cDNA made from GM21756 fibroblasts (CAG15/70 (SEQ ID NOS 81/85)) that had been transfected with a bi-allelic ZFP repressor that represses both WT and mutant HTT by >90%. The 331C template was serially diluted two-fold from 2 fg to 0.0625 fg in the presence of a fixed amount (0.5 fg) of the 331T template; the 331T template was serially diluted two-fold from 2 fg to 0.0625 fg in the presence of a fixed amount (0.5 fg) of the 331C template. The 331C-specific (red bars) and 331T-specific (blue bars) qRT-PCR assays were performed for each of the dilution samples. Relative quantities are plotted as a fraction of the value obtained for the sample with 1:1 ratio of 331T and 331C template.

FIG. 7A shows HD fibroblasts (GM04723, CAG15/67 (SEQ ID NOS 81/82)) that were transfected with ZFP mRNA at doses of 1000, 300, 100, 30 and 10 ng per $2\times10^5$ cells. Five hours after transfection, cells were harvested for ZFP Western blot using an anti-FLAG antibody (Sigma F1804). FIG. 7B shows ZFP and GAPDH protein levels that were quantified using an Odyssey CLx imager, ZFP/GAPDH ratios for each sample was scaled to that of the 1,000 ng ZFP-C sample, which was set to 1.

FIGS. 8A and 8B show a comparison allele-selectivity exhibited by candidate ZFP-TF designs in the screening system used for this study (patient fibroblasts; CAG18/45 (SEQ ID NOS 79/80)) (FIG. 8B) vs mouse cells used in a prior work (cells from the STHdhQ111/HdhQ7 mouse model; CAG 4/111 (SEQ ID NOS 86/87)) (FIG. 8A). Only three tested designs (ZFP-A, ZFP-B, ZFP-D) exhibit highly allele-specific repression in the patient fibroblast system (>75% repression of the mutant allele with <10% repression of the wild type allele). In contrast 25 designs manifest such behavior in the less stringent mouse cells. For the mouse cell study, allele-specific qRT-PCR was used to measure WT (CAG4 (SEQ ID NO: 86)) and KI (CAG111 (SEQ ID NO: 87)) Htt alleles at 24 hours after transfection of STHdhQ111/HdhQ7 mouse striatal cells with 100 ng of ZFP or GFP mRNA. Htt signal is normalized to the mean of EIF4a2, ATP5b, and GAPDH, then scaled to GFP (set as 1); n=3 biological replicates; mean±SD.

FIG. 10A shows NSC-specific PAX6 (lighter shading) and Nestin (darker shading) expression as confirmed by IHC in NSCs differentiated from CAG17/48 (SEQ ID NOS 76/78) ESCs (GENEA020). FIG. 10B shows expression levels for a panel of pluripotency markers (OCT4, NANOG, and REX1) or NSC markers (PAX6, SOX1 and NES) were measured by qRT-PCR in ESCs or differentiated NSCs. Gene expression was normalized to GAPDH, and scaled to the normalized expression levels (set as 1) in ESCs (top panels) or NSC (bottom panels); n=2 biological replicates; mean±SD. FIG. 10C shows neuron-specific PIII-tubulin expression (darker shading) was confirmed by IHC in differentiated CAG17/48 (SEQ ID NOS 76/78) neurons (DAPI, lighter shading). FIG. 10D shows expression levels for a panel of neuronal markers (MAP2, GAD1 and FOXG1) or NSC markers (PAX6, SOX1 and NES) that were measured by qRT-PCR from CAG17/48 (SEQ ID NOS 76/78) NSCs or differentiated neurons. Gene expression was normalized to GAPDH, and scaled to the normalized expression levels (set as 1) in neurons (top) or NSC (bottom); n=2 biological replicates; mean±SD.

FIGS. 11A through 11D show ZFP specificity assessment in HD fibroblasts. FIG. 11A shows fold change in gene expression with the indicated ZFP-TFs. Each dot represents the fold change in transcript level (x-axis) and p-value (y-axis) for a single gene in cells treated with the indicated ZFP compared to control-treated cells. Genes regulated >2-fold with a p-value <0.01 are shown. FIG. 11B shows fold repression of the indicated gene. FIG. 11B discloses SEQ ID Nos:79 and 80, respectively, in order of appearance. FIG. 11C shows percent normalized expression of the indicated genes. FIG. 11D depicts a Venn diagram of regulated genes in FIG. 11C. See, Examples text for further description.

FIGS. 12A and 12B are graphs showing confirmation of allele-selective HTT repression in samples used for microarray studies. Allele-specific qRT-PCR analysis was performed to confirm regulation of mHTT in RNA samples (6 biological replicates per treatment) that were subject to microarray analysis for GENEA020 neurons (shown in FIG. 12A (SEQ ID Nos:76 and 78, respectively, in order of appearance); corresponding to FIGS. 2F and 2G) and GMO2151 fibroblasts (shown in FIG. 12B (SEQ ID NOS 79 and 80, respectively, in order of appearance); corresponding to FIG. 11A). Allele specific qPCR was analyzed as in FIG. 2B (GENEA020 Neurons) and FIG. 1I (GMO2151 fibroblasts).

FIGS. 13A through 13C show R6/2 mouse study body weight and additional behavioral data for wild-type ("R62 WT") subjects and subjects treated with GFP transgenes ("R62_Tg GFP") or ZFP-TF 33074 ("R62_Tg 33074"). FIG. 13A are graphs depicting body weight at the indicated week. Separate graphs for gender combined, male and female subjects are shown. FIG. 13B are graphs depicting fall times under the indicated conditions. Separate graphs for gender combined, male and female subjects are shown. FIG.

13C are graphs depicting normalized ratio of forelimb grip strength:body weight at the indicated week. See, also, Examples text for further description.

Figure 14A:
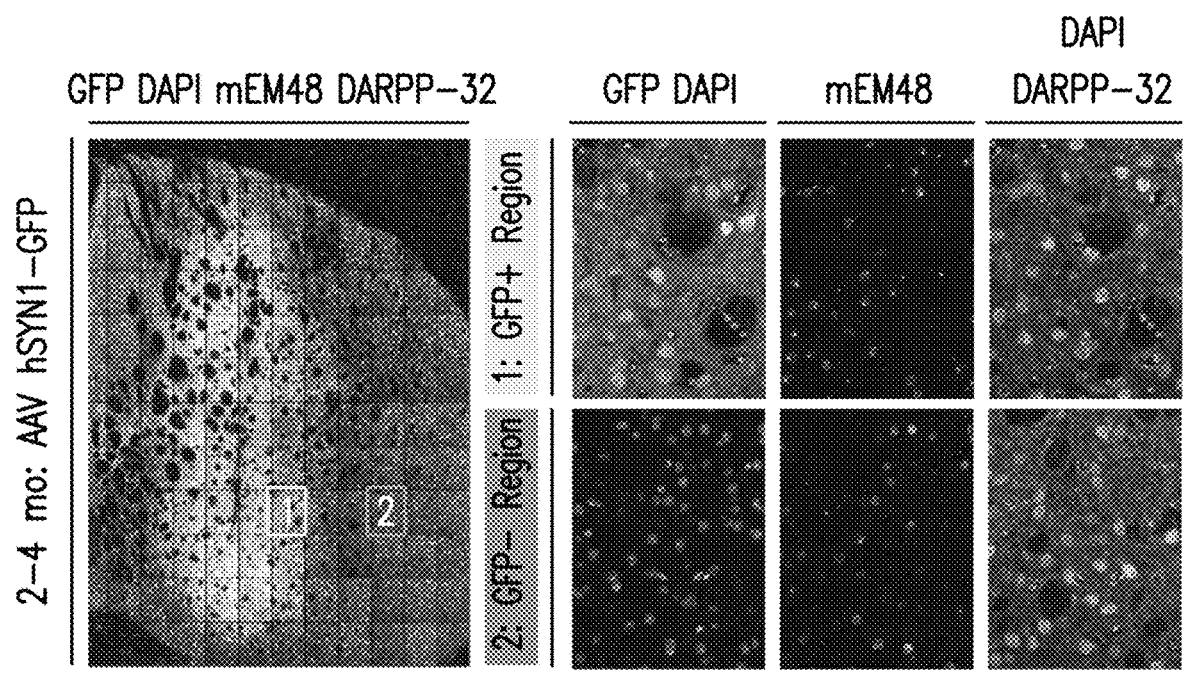
Figure 14B:
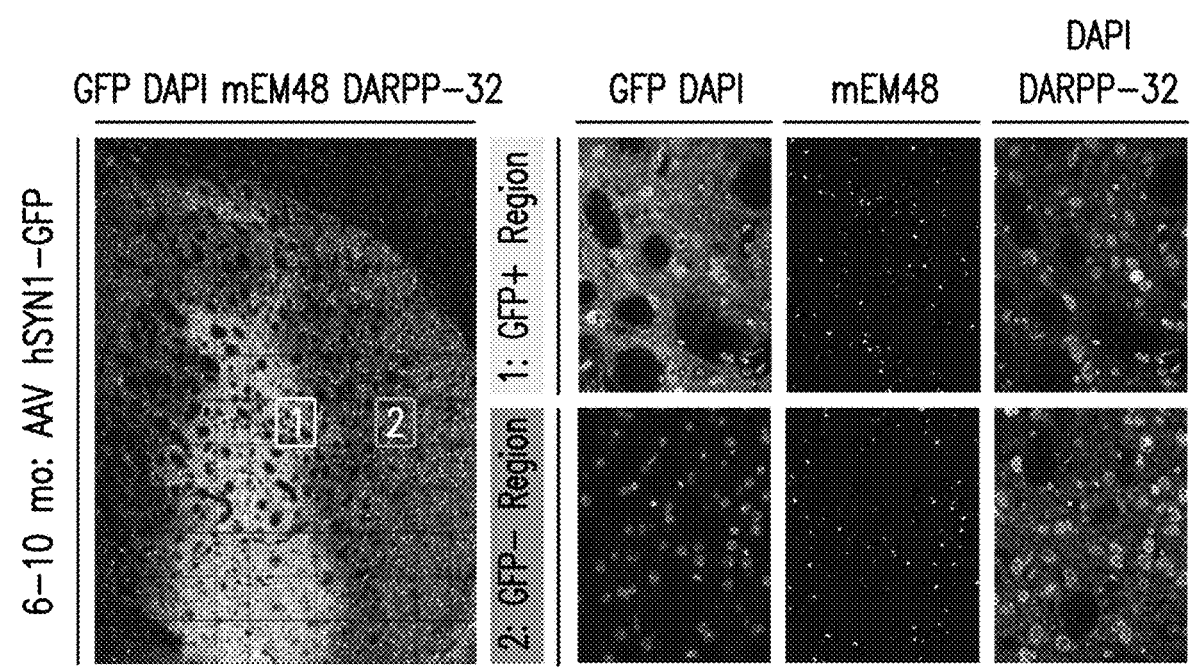
Figure 14C:
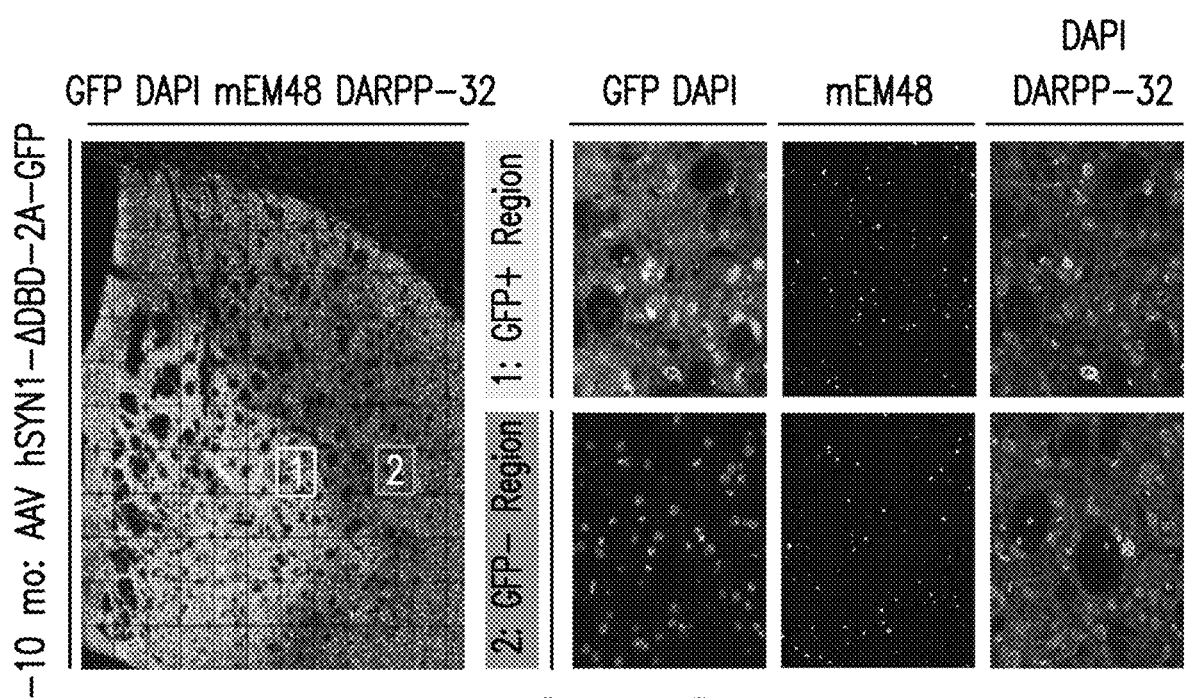

FIGS. 14A through 14C show IHC analysis of zQ175 mice injected with AAV1/2-hSYN1-GFP and AAV1/2-hSYN1-GFP. Representative images of mEM48 immunostaining in striata of heterozygous zQ175 mice injected with control constructs. FIG. 14A shows results from subjects injected with AAV2/1+1-hSYN1-GFP at 2 months of age and analyzed at 4 months of age; FIG. 14B shows results from subjects injected with AAV2/1+1-hSYN1-GFP at 6 months of age and analyzed at 10 months of age; and FIG. 14C shows results from subjects injected with AAV2/1+1-hSYN1-ΔDBD.T2A.GFP at 6 months of age and analyzed at 10 months of age. Color not shown as follows: Htt inclusions (mEM48): yellow, GFP: green, DARPP-32: red, DAPI: blue.

Figure 15A:
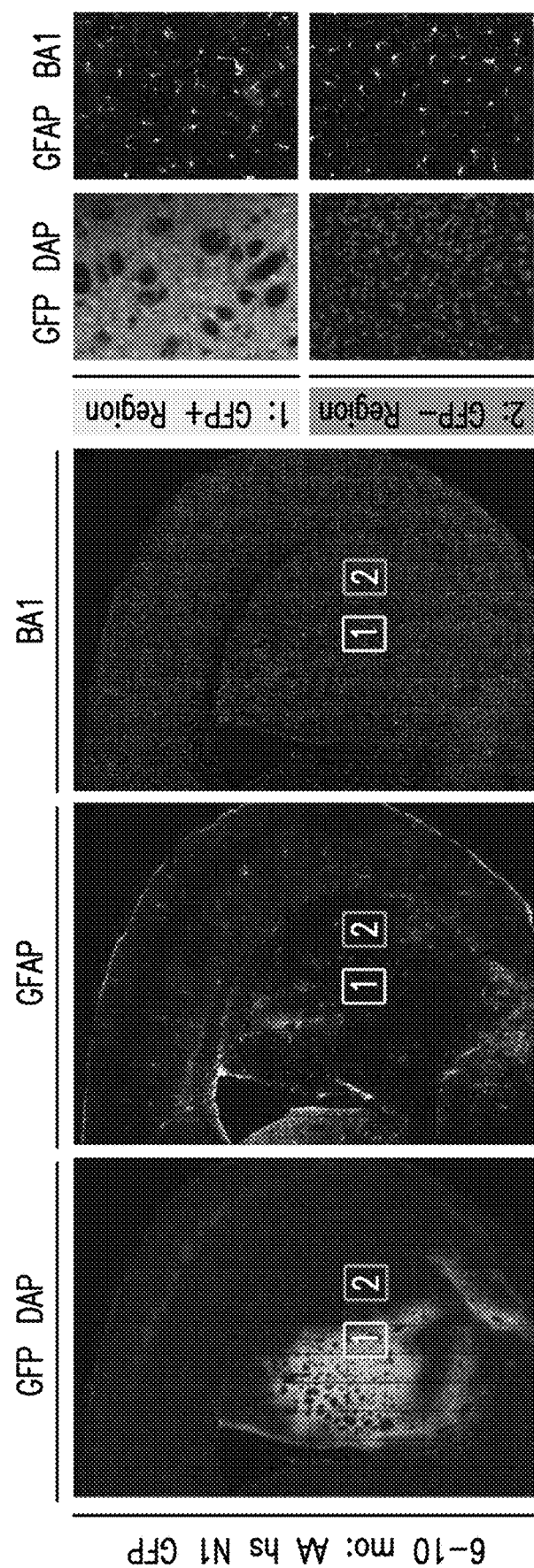
Figure 15B:
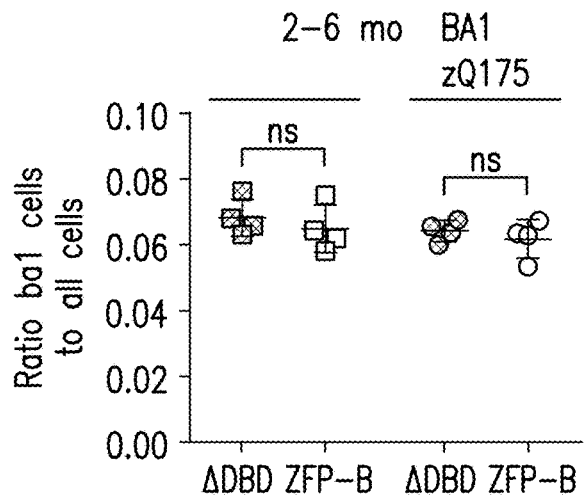
Figure 15C:
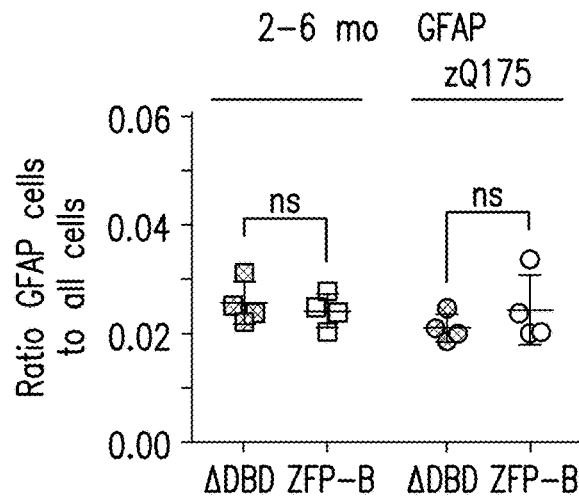
Figure 15D:
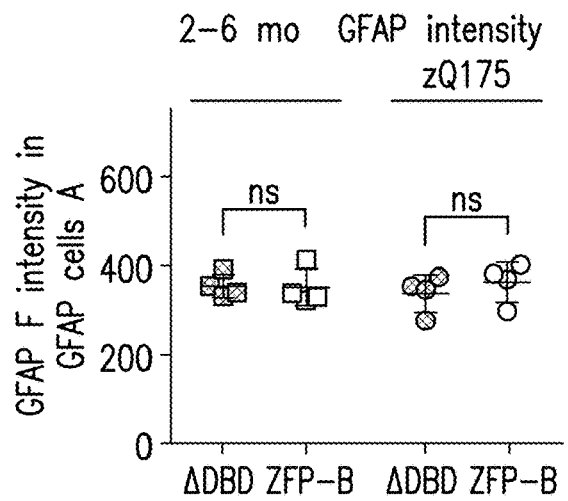
Figure 15E:
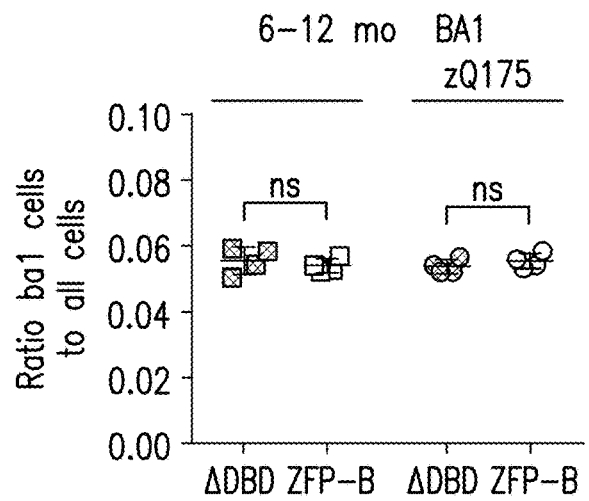
Figure 15F:
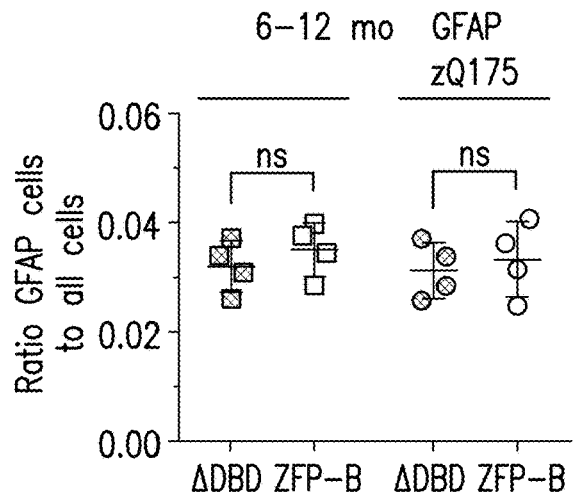
Figure 15G:
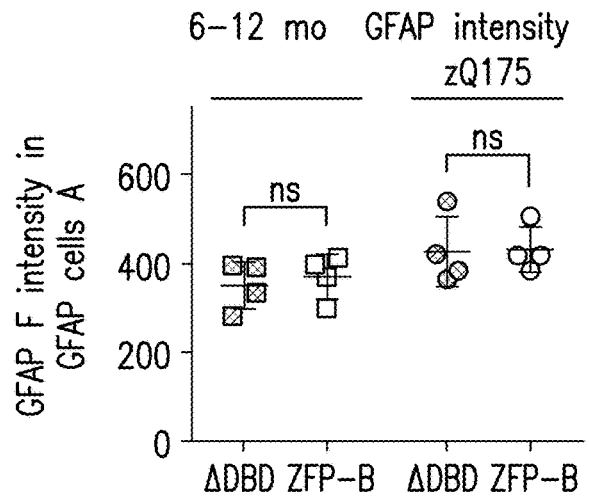

FIGS. 15A through 15G show neuroinflammation assessment in treated wild-type and zQ175 mice. FIG. 15A shows results of immunostaining for the indicated molecules (GFP, DAP, GFAP, BA1). FIG. 15B is a graph showing the ratio of ba1 cells to all cells at 2-6 months in the subjects treated as indicated. FIG. 15C is a graph showing the ratio of GFAP cells to all cells at 2-6 months in the subjects treated as indicated. FIG. 15D is a graph showing GFAP F intensity in GFAP cells at 2-6 months in subjects treated as indicated. FIG. 15E is a graph showing the ratio of ba1 cells to all cells at 6-12 months in the subjects treated as indicated. FIG. 15F is a graph showing the ratio of GFAP cells to all cells at 6-12 months in the subjects treated as indicated. FIG. 15G is a graph showing GFAP F intensity in GFAP cells at 6-12 months in subjects treated as indicated See, also, Examples text for further description.

Figure 16A:
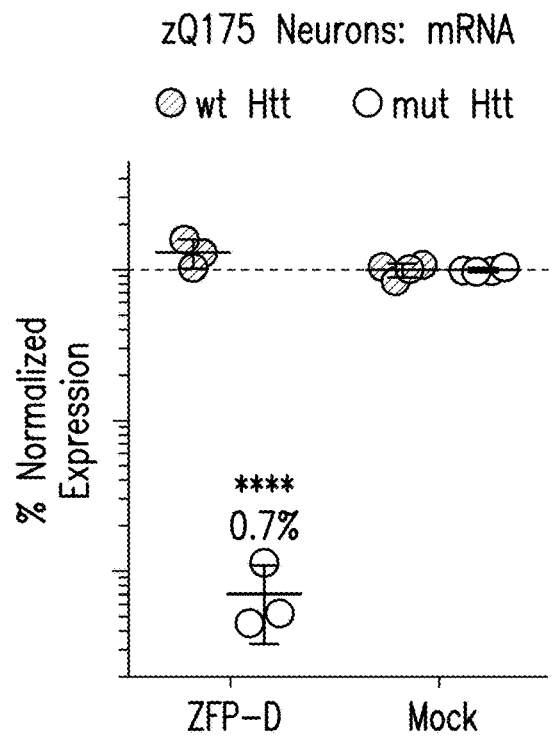
Figure 16B:
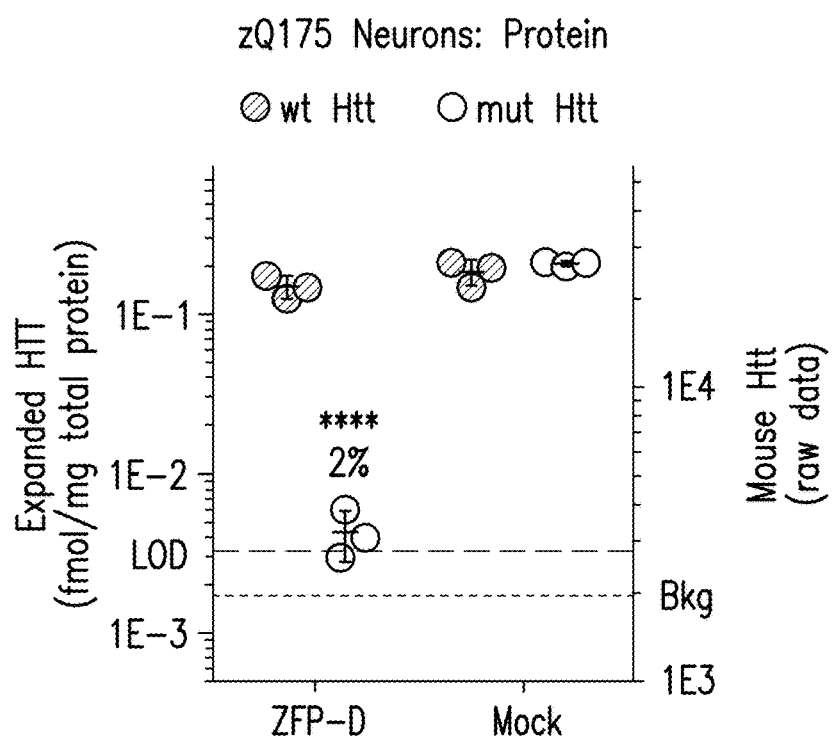
Figure 16C:
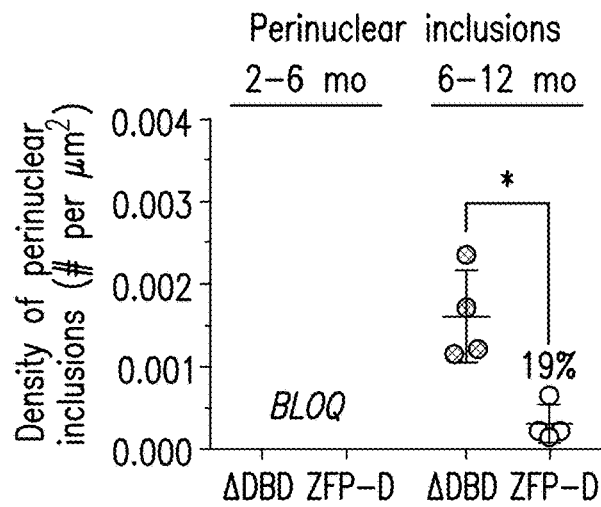
Figure 16D:
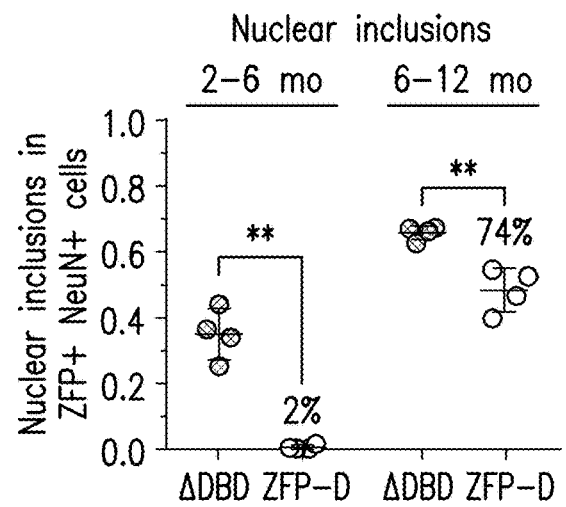
Figure 16E:
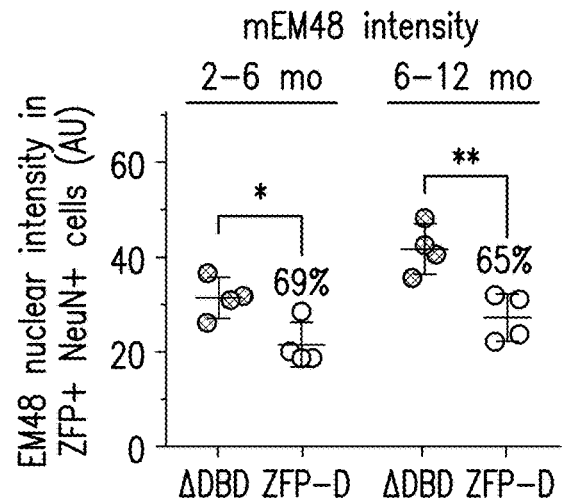

FIGS. 16A through 16E show molecular and histopathological bridging data for ZFP-D in zQ175 mice. FIG. 16A shows normalized mRNA expression of wild-type and mutant Htt in neurons of subjects treated with ZFP-D or Mock. FIG. 16B HTT protein expression of wild-type and mutant Htt under the indicated conditions. FIG. 16C shows the density of perinuclear inclusions in the subjects treated as indicated at 2-6 months (left) or 6-12 months (right) after treatment. FIG. 16C shows nuclear inclusions in ZFP+ and NueN+ neurons of the subjects treated as indicated at 2-6 months (left) or 6-12 months (right) after treatment. FIG. 16D shows EM48 nuclear intensity in ZFP+ and NueN+ neurons of the subjects treated as indicated at 2-6 months (left) or 6-12 months (right) after treatment See, also, Examples text for further description.

Figure 17A:
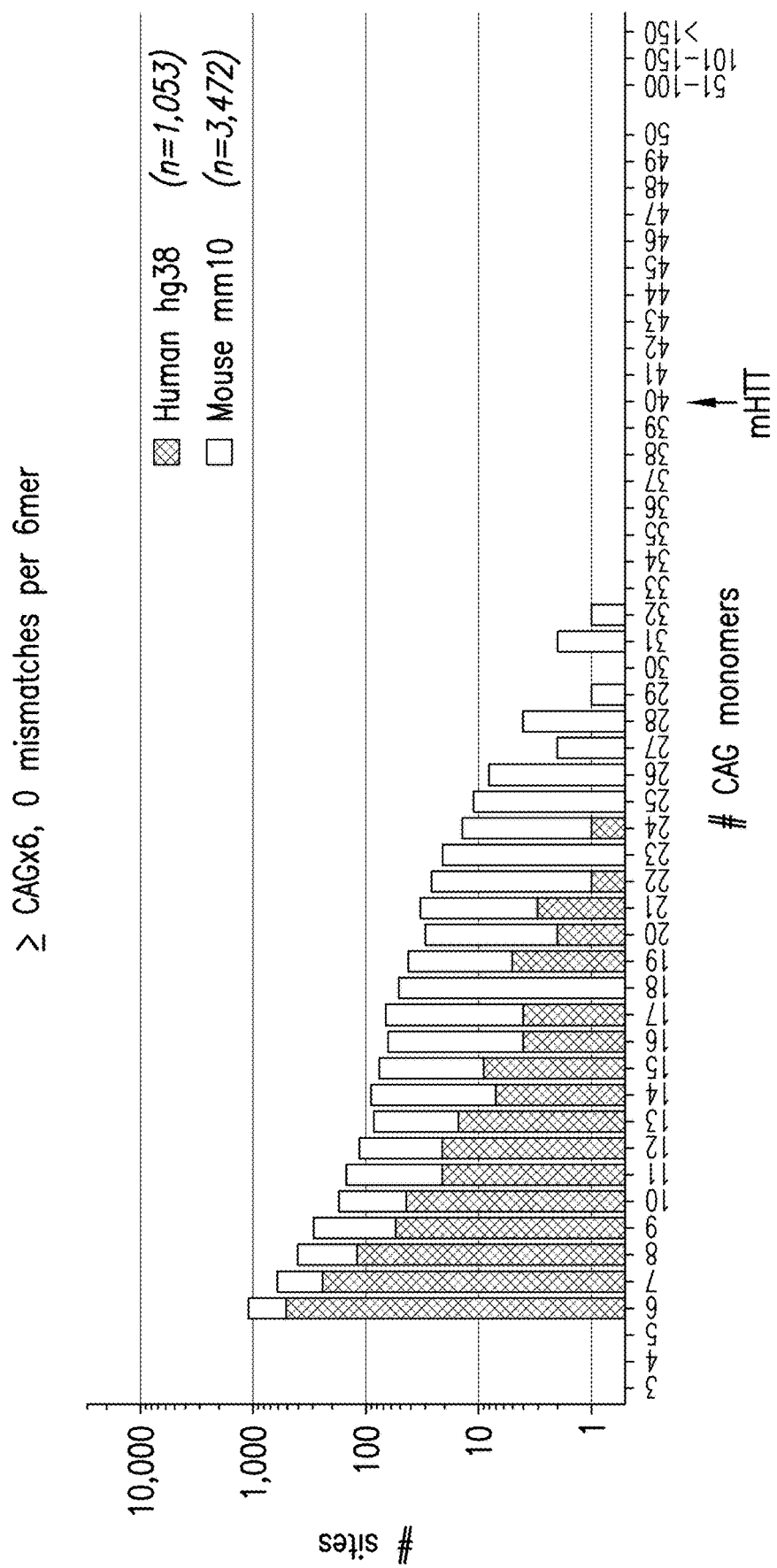
Figure 17B:
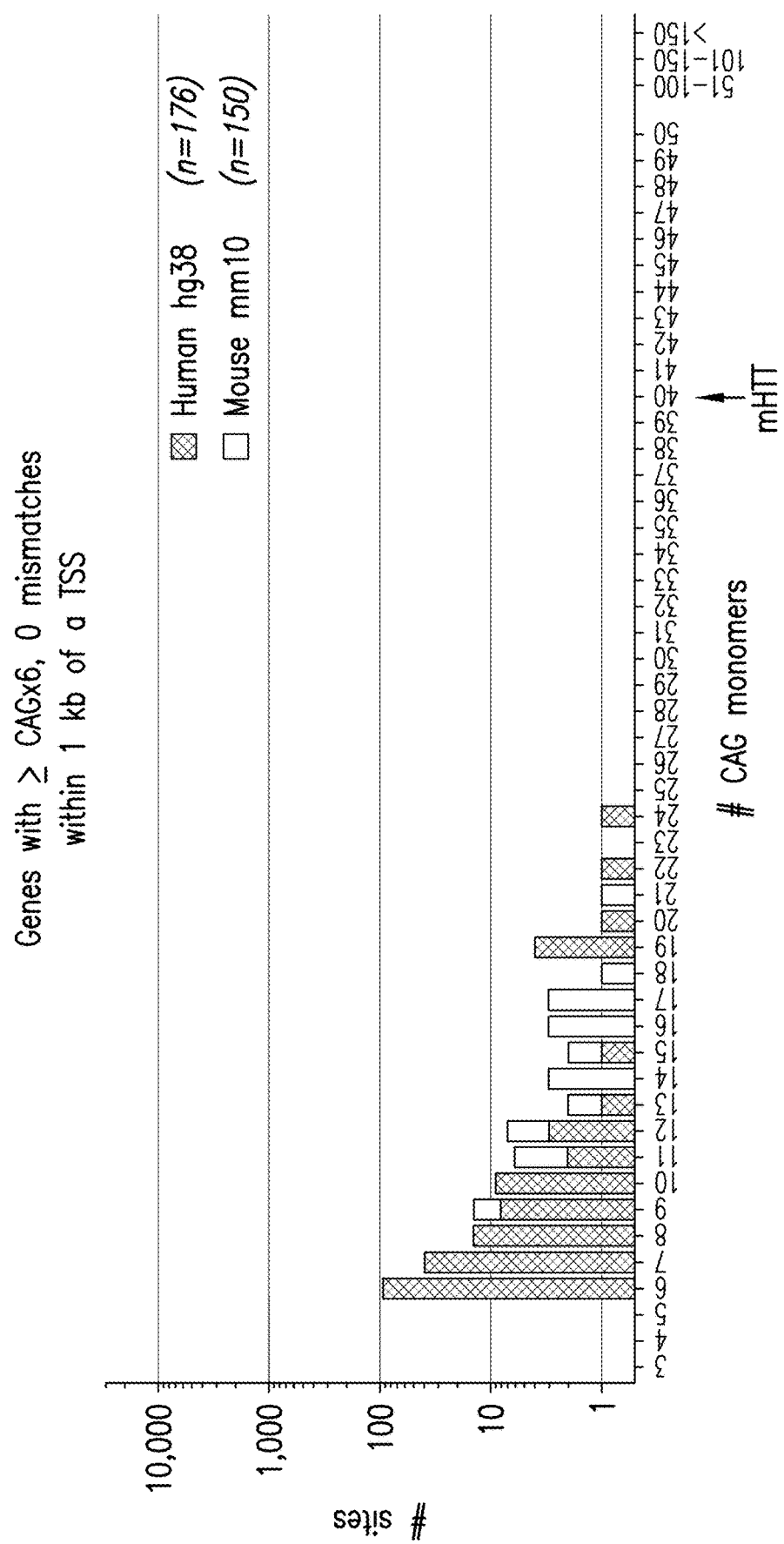
Figure 17C:
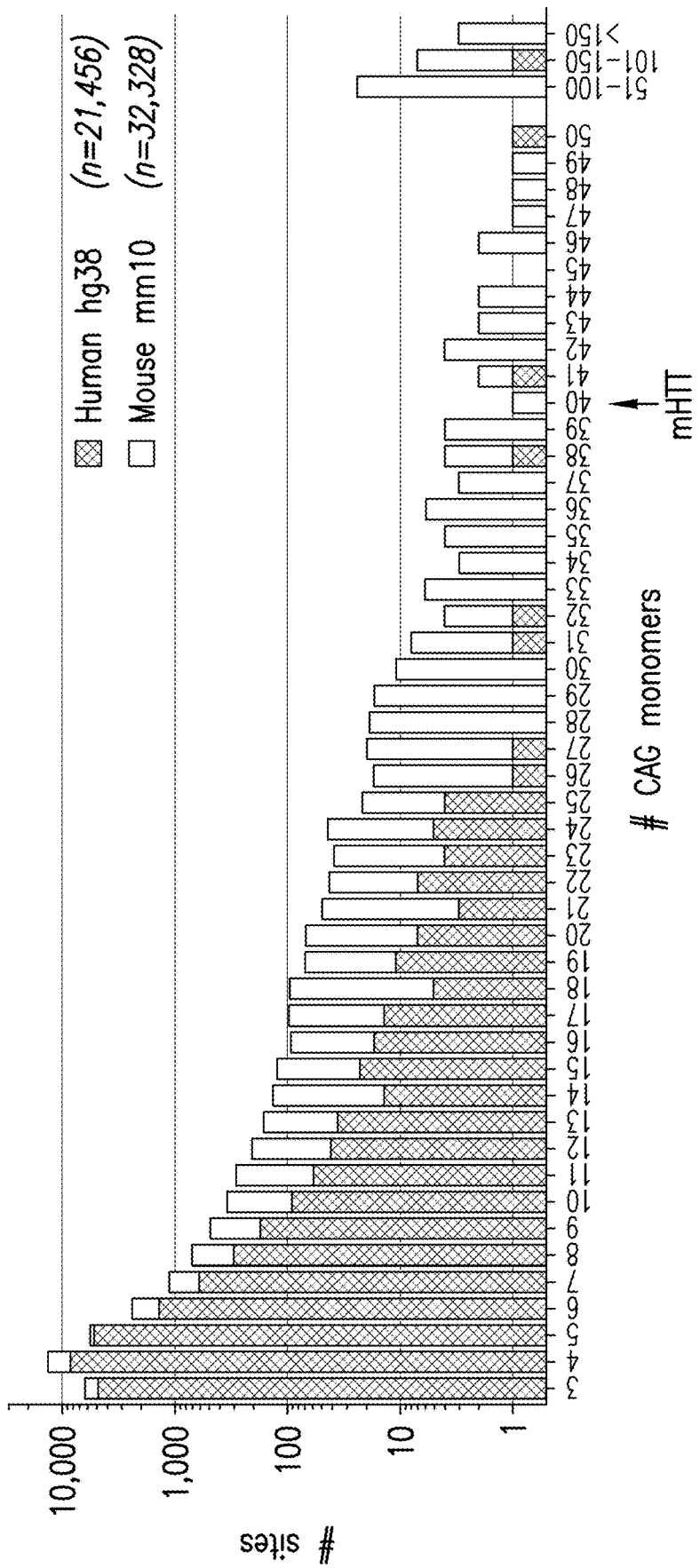
Figure 17D:
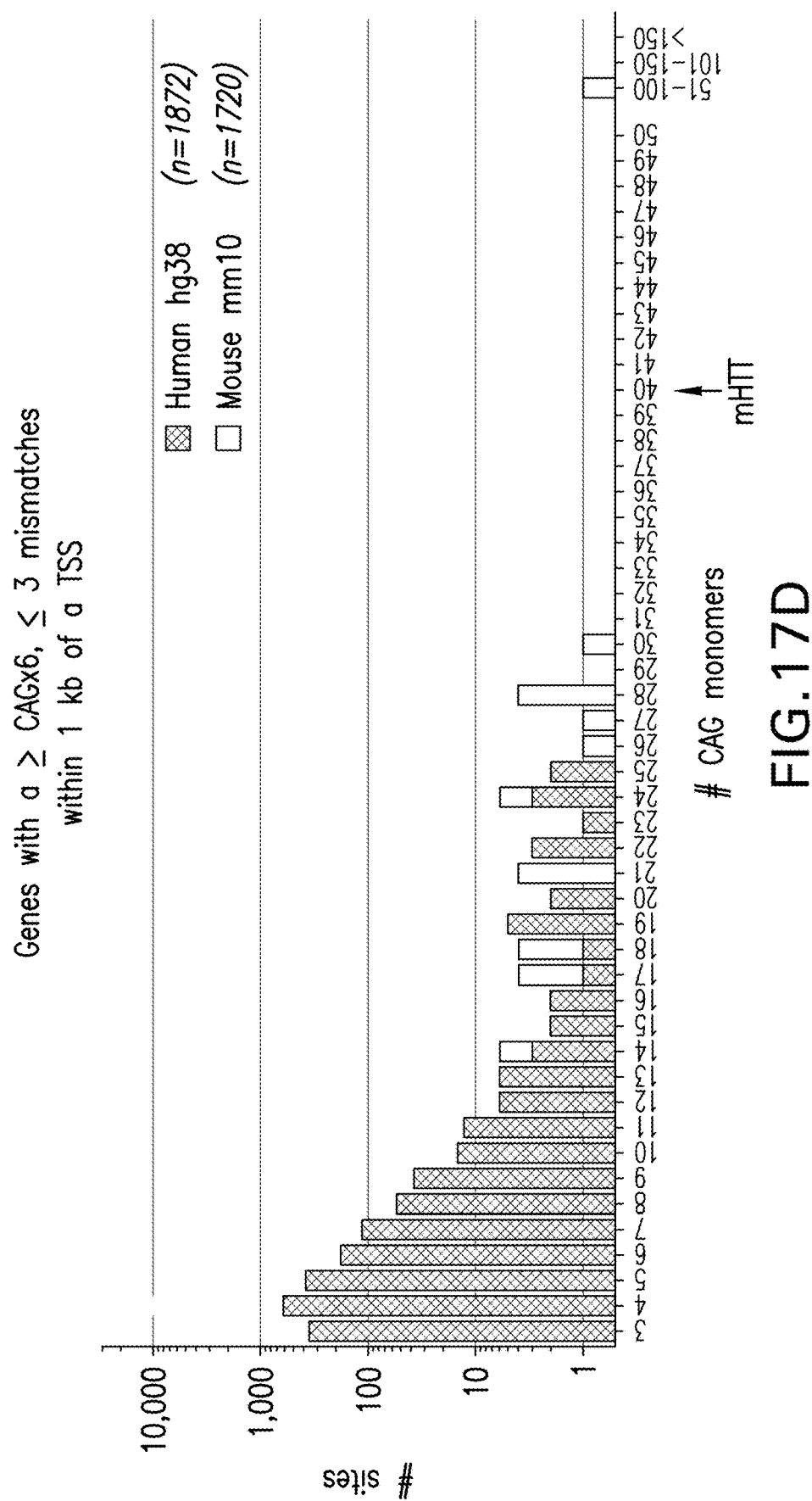
Figure 17E:
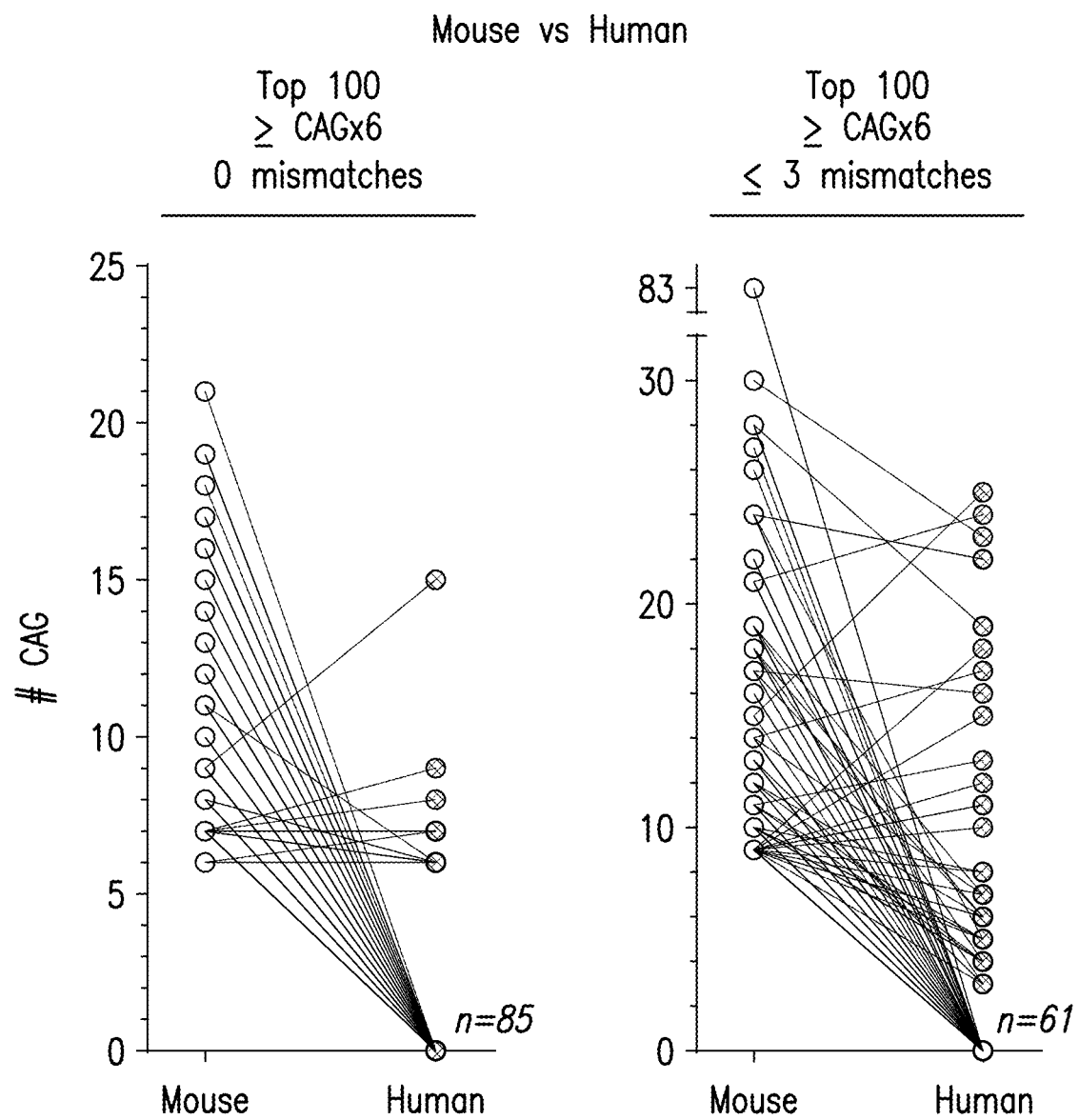
Figure 17F:
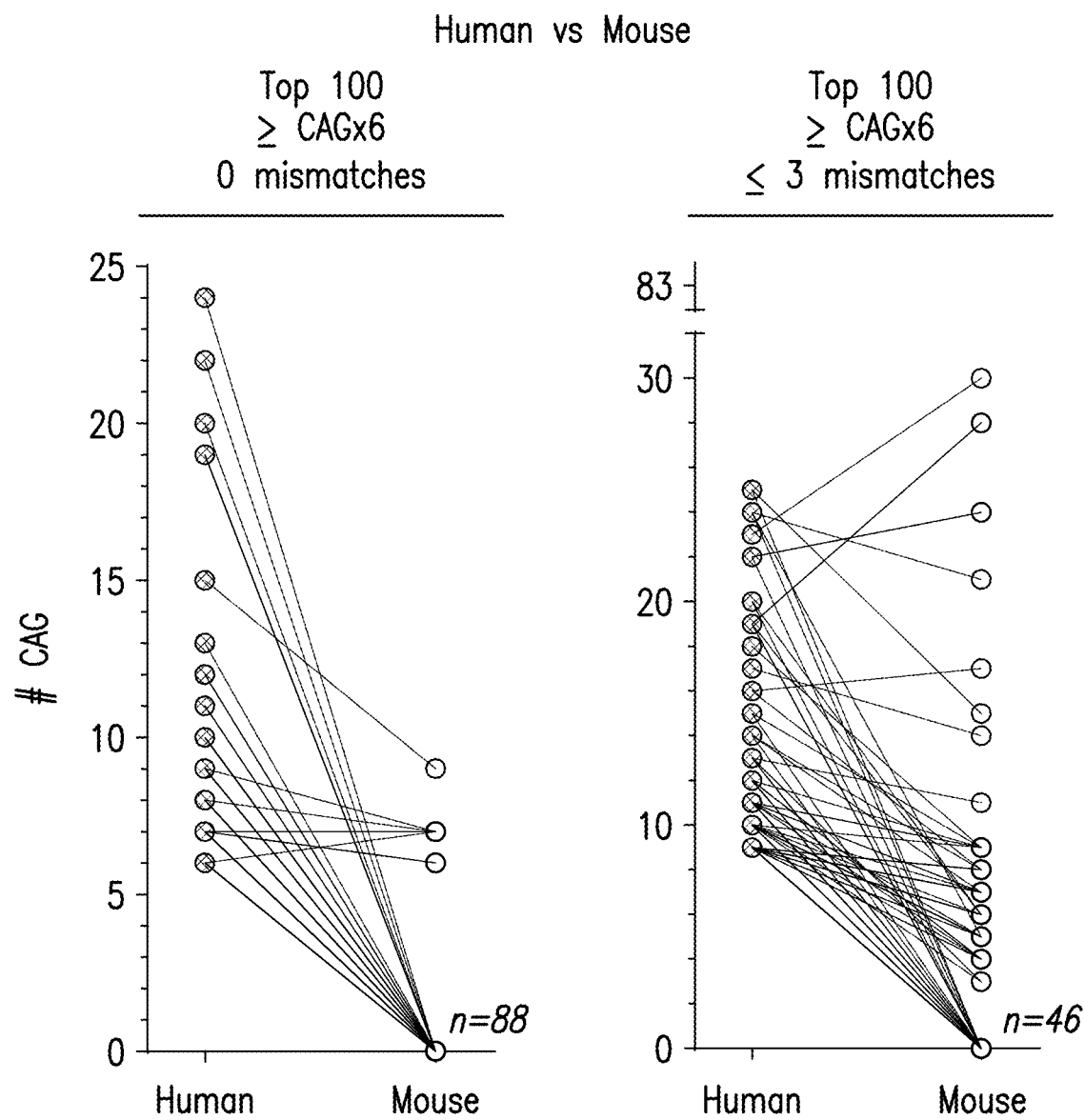

FIGS. 17A through 17F show analysis of CAG repeat content in the human and mouse genomes of genes with greater than or equal to 6 CAG repeats ("≥CAGx6"). FIG. 17A shows results of screening for 0 mismatches per 6 mer. FIG. 17B shows results of screening for 0 mismatches within 1 kb of a transcription site site (TSS). FIG. 17C shows results of screening for ≤3 mismatches per 6mer. FIG. 17D shows results for screening for <3 mismatches within 1 kb of a TSS. FIG. 17E shows a comparison of mouse and human of the top 100 genes with 0 mismatches (left) and top 100 genes with ≤3 mismatches (right). FIG. 17F shows a comparison of human and niyse of the top 100 genes with 0 mismatches (left) and top 100 genes with ≤3 mismatches (right). See, also, Examples text for further description.

DETAILED DESCRIPTION

Disclosed herein are compositions and methods for lowering levels of toxic mHTT protein levels in a subject using ZFP genetic modulators of mutant Htt alleles. The genetic repressors described herein selectively repress >99% of HD-causing alleles over an 80-fold dose range, while preserving expression of >86% of wild type alleles found in the HD population. At the same time, expression of other CAG-containing genes is minimally affected, and virally delivered repressors were active and well tolerated in HD neurons beyond 100 days in culture and at least 4 months in the mouse brain. In addition, the genetic repressors described herein result in molecular, histopathological, electrophysiological, and phenotypic correction of HD in multiple accepted animal models of the disease.

The methods and compositions described herein provide allele-selective transcriptional repression at the native HTT locus. Results from extensive testing in patient-derived cells demonstrate that expression from mHTT alleles with ≥38 CAG repeats can be repressed by 79-93%, while expression from normal alleles with ≤21 CAG repeats (the longest normal repeat length tested) is repressed by only 0-31%. Thus, allele-selective ZFP-TFs exhibit a remarkable ability to discriminate between 100% of fully penetrant mutant alleles and at least 86% of normal HTT alleles in the HD population. Compared to SNP-based allele-selective mHTT lowering approaches, each limited to a subpopulation of HD patients (Pfister et al. (2009) *Cur Biol* 19(9):774-778; Southwell et al. (2014) *Mol Ther* 22(12):2093-106)), CAG-targeted ZFP repressors described in this study have the potential to selectively down-regulate expression from the pathogenic allele in a large majority of HD patients.

While partial reduction (~45%) of normal HTT expression is tolerated in the nonhuman primate striatum (Grondin et al. (2012) *Brain* 135(4):1197-1209; McBride et al. (2011) *Mol Ther* 19:2152-2162; Stiles et al. (2012) *Exp Neurol* 233: 463-471), the long-term ramifications of further reductions are unclear. HTT has roles in a myriad of biological functions (Zuccato, ibid), including intracellular trafficking, energetics, transcriptional regulation and autophagy. In mice, Htt knockout is embryonic lethal (Duyao et al. (1995) *Science* 269:407-410; Zeitlin et al. (1995) *Nat Genet* 11:155-163; Nasir et al. (1995) *Cell* 81:811-823) and perinatal loss leads to motor dysfunction and other neuropathology (Dragatsis et al. (2000) *Nat Genet* 26:300-306; Arteaga-Bracho et al. (2016) *Neurobiol Dis* 96:144-155) suggesting an important role in nervous system development. Although conditional knockout in the adult mouse brain appears to be tolerated (Wang et al. (2016) *Proc Natl Acad Sci USA* 113:3359-3364), compound heterozygous hypomorphic HTT variants have been linked to Rett Syndrome-like disorders (Lopes, F., et al. (2016) *J Med Genet* 53:190-199; Rodan et al. (2016) *Eur J Hum Genet* 24:1833), suggesting a critical role in humans. Therefore, reducing normal HTT concomitant with mHTT, especially below 50% of baseline levels, poses an unknown risk. Consequently, the development of an allele-selective mHTT lowering approach suitable for clinical use has been a long-sought goal.

Various RNA-targeted modalities have been investigated to selectively downregulate mHTT transcripts by degradation or translational inhibition. For example, ASO- and RNAi-based strategies targeting single nucleotide polymorphisms (SNPs) linked to the mHTT allele (Pfister et al. (2009) *Cur Biol* 19(9):774-778; Lombardi et al. (2009) *Exp Neurol* 217:312-319; Carroll et al. (2011) *Mol Ther.* 19(12): 2178-85) have been shown to selectively lower mHTT in HD mouse models. A substantial hurdle to the clinical development of these approaches is that each SNP-specific therapy can only treat the patient subpopulation carrying that particular SNP (Kay et al. (2015) *Mol Ther* 23:1759-1771).

Alternatively, targeting the CAG repeat directly would in principal constitute a single therapy for all HD patients. However, ASO- and RNAi-based reagents against the CAG repeat have so far yielded only modest levels of allelic discrimination (Evers et al. (2011) *PLoS One* 6(9):e24308; Gagnon et al. (2010) *Biochemistry* 49:10166-10178; Hu et al. (2009) *Nat Biotech* 27:478-484; Yu et al. (2012) *Cell* 150:895-908; Fiszer et al. (2011) *Nuc Acids Res* 39:5578-5585), possibly due to a common reliance on mass action effects to achieve selectivity.

As described herein, repression of transcription via direct binding to the expanded CAG tract, which lies close to the promoter effectively lowers mHtt levels. Without being bound by one theory, this approach provides a greater degree of allelic discrimination by taking advantage of functional synergies (Lutz et al. (2000) *Biochem Soc Trans* 28:386-389) and cooperativities (Reiter et al. (2017) *Curr Opin Genet Dev* 43:73-81) in transcriptional regulation and can utilize multiple local regulatory elements in setting levels of transcript synthesis. Our approach offers the added benefit of reducing levels of mutant RNA, which is itself a potential pathogenic factor (Marti (2016) *Brain Pathol* 26:779-786) Transcriptional repression can also provide a more effective means to achieve complete ablation of mHTT, as this approach requires recognition of just a single copy of the therapeutic target—the endogenous mHTT gene—in contrast to other approaches that involve binding tens of thousands of mutant RNA or protein species per cell. In a prior study, designed transcription factors targeted to poly-CAG were used to attempt allele-selective regulation, albeit via the simpler and less powerful mechanism of mass action (Garriga-Canut et al. (2012) *Proc Nat Acad Sci USA* 109 (45):e3136-45). Differential repression was demonstrated only in mouse cells bearing a nonpathogenic repeat array that was too small (CAG4 (SEQ ID NO:86)) to comprise even a single target for the examined reagents. Moreover, the allele skew was highly exaggerated (4 (SEQ ID NO:86) vs 111 CAGs (SEQ ID NO:87); length ratio of 28) and over ten-fold greater than found in the typical patient (17 (SEQ ID NO:76) vs 43 CAGs (SEQ ID NO:77); length ratio of 2.5).

Furthermore, using an allele-selective repressor as described herein (ZFP-B) that is also highly specific genome-wide, we demonstrate robust in vivo repression of mHtt expression at time points between 7 weeks and 4 months in three different HD mouse models, with the resultant correction of molecular, histological, electrophysiological and phenotypic pathology. We also establish sustained ZFP expression and efficacy for >100 days in HD neurons, as well as the rescue of MSN marker gene expression in R6/2 and zQ175 mice, indicating that chronic expression of a highly potent, mHTT-selective ZFP in the target brain region and human cell type is well-tolerated.

Here, we present a transcription-targeted approach that differs from prior efforts in terms of scale, complexity of designs tested, and the use of screens that query directly for desired behavior: allele-selective repression of the endogenous human gene across a wide dose range. We identify a novel class of functionally synergistic ZFPs for which repression is highly dependent on poly-CAG tract length. These ZFP repressors strongly discriminate between >86% of the combinations of HD patient normal and disease alleles (Landwehrmeyer et al. (2017) *Movement Disorders Clinical Practice* 4: 212-224), and exhibit a high degree of specificity for mHTT vs. other CAG-repeat genes. Using three HD mouse models, we demonstrate improvements in a range of molecular, histopathological, electrophysiological, and functional endpoints. Finally, we demonstrate that allele-selective ZFPs are well-tolerated out to at least 9 months following administration to the mouse striatum and are efficacious in multiple models of HD pathology.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs (including first and second ZFNs also known as left and right ZFNs) that dimerize to cleave the target gene.

Zinc finger binding domains can be "engineered" to bind to a predetermined nucleotide sequence, for example via engineering (altering one or more amino acids) of the recognition helix region of a naturally occurring zinc finger. Therefore, engineered DNA binding proteins (zinc fingers) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 8,585,526; see also International Patent Publication Nos. WO 98/53058; WO 98/53059; WO 98/53060; WO 02/016536; and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; and International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g., Swarts et al. (2014) *Nature* 507(7491):258-261; G. Sheng et al. (2013) *Proc. Natl. Acad. Sci. U.S.A.* 111:652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. Target sites may be any length, for example, 9 to 20 or more nucleotides and length and the bound nucleotides may be contiguous or non-contiguous.

An "exogenous" molecule is a molecule that is not normally present in a cell but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene modulator refers to any change in gene expression as compared to a cell that does not include a ZFP genetic modulator as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within nontranscribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion molecule in which a ZFP DNA-binding domain is fused to or otherwise associated with a transcription repression domain, the DNA-binding domain and the repression domain are in operative linkage if, in the fusion molecule, the ZFP DNA-binding domain portion is able to bind its target site and/or its binding site, while the activation domain is able to upregulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

Zinc Finger DNA-Binding Domains

Described herein are DNA binding domains comprising a zinc finger protein that binds to an Htt gene. See, for example, U.S. Pat. No. 8,841,260.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; WO 01/88197 and GB 2,338,237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned International Patent Publication No. WO 02/077227.

Selection of target sites; ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA binding domain is an engineered zinc finger protein that binds (in a sequence-specific manner) to a target site in a Htt gene and modulates expression of Htt. The ZFPs can bind selectively to either a mutant Htt allele or a wild-type Htt sequence. Htt target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remade et al. (1999) *EMBO Journal* 18(18):5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs or may be positioned between the ZFPs (attached to both ZFPs).

Fusion Proteins

Fusion proteins comprising DNA-binding proteins (e.g., ZFPs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Application Publication Nos. 2005/0064474; 2006/0188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al. (1997) *J. Virol.* 71:5952-5962) nuclear hormone receptors (see, e.g., Torchia et al. (1998) *Curr. Opin. Cell. Biol.* 10:373-383); the p65 subunit of nuclear factor kappa B (Bitko & Bank (1998) *J. Virol.* 72:5610-5618 and Doyle & Hunt (1997) *Neuroreport* 8:2937-2942); Liu et al. (1998) *Cancer Gene Ther.* 5:3-28), or artificial chimeric functional domains such as VP64 (Beerli et al. (1998) *Proc. Natl. Acad. Sci. USA* 95:14623-33), and degron (Molinari et al. (1999) *EMBO J.* 18:6439-6447). Additional exemplary activation domains include, Oct 1, Oct-2A, Sp1, AP-2, and CTF1 (Seipel et al. (1992) *EMBO J.* 11:4961-4968 as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Publication Nos. 2002/0115215 and 2003/0082552 and in co-owned International Patent Publication No. WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

In certain embodiments, the target site bound by the DNA binding domain is present in an accessible region of cellular chromatin. Accessible regions can be determined as described, for example, in co-owned International Patent Publication No. WO 01/83732. If the target site is not present in an accessible region of cellular chromatin, one or more accessible regions can be generated as described in co-owned International Patent Publication No. WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and U.S. Patent Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example U.S. Patent Publication No. 2009/0136465). Thus, the ZFP may be operably linked to the regulatable functional domain wherein the resultant activity of the ZFP-TF is controlled by the external ligand.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824; and U.S. Patent Publication No. 2014/0335063, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992)

Science 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al. (1995) *Current Topics in Microbiology and Immunology* Doerfler and Bohm (eds.); and Yu et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, lipid nanoparticles (LNP), naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc. (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424, WO 91/16024. In some aspects, the nucleases are delivered as mRNAs and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS* 81:6466-6470; and Samulski et al. (1989) *J. Virol.* 63:03822-3828. Any AAV serotype can be used, including AAV1, AAV3, AAV4, AAV5, AAV6 and AAV8, AAV 8.2, AAV9, and AAV rh10 and pseudotyped AAV such as AAV9.45, AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94(22):12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3; Kearns et al. (1996) *Gene Ther.* 9:748-55). Other AAV serotypes, including AAV1, AAV3, AAV4, AAV5, AAV6, AAV8, AAV9, AAV9.45 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al. (1998) *Hum. Gene Ther.* 7:1083-1089). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; and Topf et al. (1998) *Gene Ther.* 5:507-513.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

EXAMPLES

Example 1: Materials and Methods mRNA Production for Transient Transfection

Templates for in vitro transcription was generated from pVAX-ZFP or pVAX-GFP plasmids using PCR (forward primer GCAGAGCTCTCTGGCTAACTAGAG (SEQ ID NO:1); reverse primer (T(180)): CTGGCAACTAGAA GGCACAG (SEQ ID NO:2)). mRNA was synthesized using mMESSAGE mMACHINE® T7 ULTRA Transcription Kit (ThermoFisher Scientific) as per manufacturer's instruction and purified using RNeasy96 columns (Qiagen).

Production of Lentiviral Vectors

The coding sequence for ZFP-2A-GFP was cloned into the lentivirus transfer vector pRRL downstream of the CMV promoter. HEK293T cells cultured in 15-cm tissue culture dishes were transfected with the following plasmids: pRRL-CMV-ZFP-2A-GFP (37.5 μg), the VSVG envelope plasmid (18.75 μg), and the packaging plasmids (pMDL and pREV, 18.75 μg for each (Dull, T., et al. (1998) *J Virol* 72(11): 8463-8471), using Lipofectamine 2000 (ThermoFisher Scientific). The viral supernatants (30 ml) were harvested 48 and 72 hr post-transfection and filtered through a 0.45-μm filter before being concentrated 300-fold by ultracentrifugation at 4° C. (Optima L-80K preparative ultracentrifuge, Beckman Coulter) at 50,000×g for 90 min. The pellets were then suspended in an appropriate volume of Hank's Buffered Salt Solution (Lonza). To determine infectious titer, $2\times10^4$ HEK293T cells were transduced in triplicate with 100 μl of serially diluted vector preps overnight, then incubated for an additional 48 hr at 37° C. with 5% CO2. The infectious titer was determined using dilutions that gave a linear dose response for GFP expression.

Production of AAV Vectors

AAV6-CMV-GFP and AAV6-CMV-ZFP (A, B and C) were generated by baculovirus-based AAV production according to standard methods in the art. All AAV6 vectors were purified by double CsCl ultracentrifugation, buffer-exchanged to PBS with 0.001% Pluronic F-68. AAV titers were determined using qPCR.

Chimeric AAV serotype 1/2 (Hauck, B., et al. (2003) *Mol Ther* 7:419-425) vectors were generated by Evotec AG (Hamburg, Germany) to express ZFP-2A-GFP and GFP control under the control of human Synapsin 1 (hSYN1) promoter. AAV1/2 vectors were produced by HEK293 transfection and purified by iodixanol gradient as described (Heikkinen et al. (2012) *PLoS ONE* 7:e50717, doi:10.1371/journal.pone.0050717).

Cell Culture and mRNA Transfection

Immortalized mouse striatal cell line STHdhQ111/HdhQ7 (Q111/Q7, Trettel et al. (2000) *Human Molecular Genetics* 9:2799-2809, doi:10.1093/hmg/9.19.2799) was a gift from the CHDI Foundation (CHDI). The Q111/Q7 cells were maintained in DMEM with 10% FBS, Penicillin/streptomycin, and G418 (0.4 mg/ml) at 33° C. mRNA transfection was performed using 96-well Shuttle Nucleofector (Lonza), 100 ng ZFP mRNA per $1\times10^5$ cells was transfected using P3 solution and program EN-132. Twenty-four hours after transfection, cells were harvested for gene expression analysis by qRT-PCR.

HD fibroblasts lines GM04723 (CAG15/67 (SEQ ID NO: 81/82)), GM02151 (CAG18/45 (SEQ ID NO:79/80)) and ND30259 (CAG21/38 (SEQ ID NO:83/84)) were obtained from Coriell Cell Repository and maintained in complete MEM with 20% FBS. CAG repeat lengths were confirmed by sequencing. mRNA transfection was performed using 96-well Shuttle Nucleofector (Lonza). 0.01-1000 ng ZFP mRNA per $1.5\times10^5$ cells was transfected using P2 solution and program CA-137; for doses less than 100 ng ZFP mRNA, GFP mRNA was added to bring the total amount of mRNA transfected to 100 ng. Twenty-four hours after transfection, cells were harvested for gene expression analysis by qRT-PCR.

HD ESC line GENEA018 (CAG17/48 (SEQ ID NO:76/78), Bradley et al. (2011) *Stem Cells Dev* 20:495-502, doi:10.1089/scd.2010.0120) was a gift from CHDI. CAG repeat lengths were confirmed by sequencing. HD-ESCs were passaged with accutase and cultured on matrigel coated plates in E8 media (Thermo Fisher Scientific). Neural stem cells were derived using StemPro Neural Induction Medium (Thermo Fisher Scientific). Briefly, ESCs were seeded into geltrex coated 6-well dish with $2\times10^5$ cells/well and when 10-20% confluent the medium was changed to StemPro Neural Induction Medium (Thermo Fisher Scientific). Medium was changed every 2 days and NSCs were harvested and expanded on day 7. StemPro NSC SFM medium (Life Technologies) was used to culture HD-NSCs and non-HD NSCs (HIP™ Neural Stem Cells, Globalstem. NSCs were passaged with accutase on geltrex coated plates. mRNA transfection was performed using 96-well Shuttle Nucleofector (Lonza). NSCs were prepared by in accordance with the NSC subculture protocol (StemPro NSC, Life Technologies), $2\times10^5$ cells transfected using 20 μL SF solution and program CM-130. Immediately afterwards 80 μL of media was added to the well before transferring to a 96 well plate containing 50 μL of warm media.

Neuronal differentiation from NSC was induced by changing to neural differentiation media (NDIFF) consisting of Neurobasal media with B-27 Serum-Free Supplement and GlutaMAX™ (ThermoFisher Scientific). Medium was changed every 3-4 days. After 7 days in NDIFF, cells adopt neuronal morphology.

To confirm NSC and neuron differentiation, HD NSC or neurons were cultured on chamber slides (Lab-Tek, Thermo Fisher) for immunohistochemistry analysis of neuronal marker genes. Briefly, cells were fixed and permeablized using the BD Cytofix/Cytoperm™ Kit (BD Biosciences). Slides were blocked with 4% NGS and stained with primary antibodies anti-PAX6 (AB2237, Millipore), anti-Nestin-488 (MAB5326A4, Millipore) or anti-β-III tubulin (MAB119, R&D Systems) overnight at 4 C. Appropriate Alexa 488 or 555 conjugated secondary antibodies (Molecular Probes) were diluted 1:500 for secondary staining.

Western Blot Analysis for HD Protein Knockdown

GMO4723 (CAG15/67 (SEQ ID NO:81/82)) human fibroblasts were transfected with ZFP (300 ng) at 150,000 cells/transfection in quadruplicate using Lonza program CA-137 in P2 solution. Cells were pooled post transfection in complete media, then separated into 4 wells of a 24-well plate and incubated at 37°, 5% CO2 for 72 hours. Cells were trypsinized, washed, pelleted and lysed in hot 95° Laemmli sample buffer and incubated at 95° for 5 minutes. Samples were loaded onto a Bio-Rad 4-15% TGX gel at 5 μL/lane and ran at 150V for 3.5 hours at RT in tris/glycine/SDS running buffer. Wet transfer onto PVDF membrane was performed at 4° for 2.5 hours at 90V in transfer buffer containing MeOH (10%). Membranes were blocked at 4° in Odyssey blocking buffer, then incubated with primary antibodies for 3 hours at RT: mouse anti-Htt (1:500; Millipore MAB2166) and rabbit anti-Calnexin (1:5000; Sigma C4731) in 0.2% Tween-20 Odyssey blocking buffer. Blots were washed 3×10 min in PBS-T (PBS+0.1% Tween-20). Blots were then incubated with secondary antibodies for 1 hour at RT with protection from light: goat anti-Mouse IgG1 (1:5000; Li-Cor IRDye 800CW 926-32350) and goat anti-Rabbit (1:10,000; LiCor IRDye 680RD #926-68071) in Odyssey blocking buffer containing 0.2% Tween-20, 0.01% SDS. With light protection, blots were washed 3×10 min in PBS-T, dried between Whatman paper, and scanned on a Li-Cor Odyssey near-infrared fluorescence imaging system.

Generation of Stable NSC Lines that Express ZFPs

Lentiviral vectors with a CMV promoter driving expression of a ZFP linked with a 2A peptide to GFP were used to create HD-NSCs expressing ZFP. Concentrated vectors were inoculated with 1×106 cells in a 6 well plate. After several passages, the resulting cells were subjected to cell sorting to enrich GFP-positive cells. Sorted cells were further expanded and differentiated into neurons as described above.

Gene Expression Analysis Using qRT-PCR

Total RNA was extracted from cultured cells and mouse striata using HighPure RNA isolation kit (Roche) and Purelink RNA mini Kit (Ambion), respectively. cDNA was generated using High capacity cDNA reverse transcription kits (Thermo Fisher Scientific), quantitative PCR was performed using SsoAdvanced Universal probes supermix (Bio-Rad) and CFX real-time PCR instrument (Bio-Rad). qRT-PCR primer/probe sets for gene expression analysis were ordered from IDT: mouse total Htt (Mm.PT.58.6953479), DRD1A (Mm.PT.56a.43576955.g), DRD2 (Mm.PT.56a.7811767), PDE10A (Mm.PT.56a.16919824), DARPP-32 (Mm.PT.53a.9253526.gs), ATP5B (Mm.PT.53a.17279462), EIF4A2 (Mm.PT.53a.9498195.g), RPL38 (Mm.PT.58.42993403.g) AIF1 (Mm.PT.58.7014816); human total HTT (Hs.PT.49a.14676852.g), STC1 (Hs.PT.51.14992722), NAP1L3 (Hs.PT.56a.24655549.g), ATXN2 (Hs.PT.58.40126607), ORC4 (Hs.PT.56a.24527823.g), THAP11 (Hs.PT.49a.15404553.g), GLS (Hs.PT.53a.20624732), FBXO11 (Hs.PT.58.2665601), DNM1 (Hs.PT.58.25262501), TBP (Hs.PT.56a.20792004), FOXP2 (Hs.PT.58.15357735), ENO2 (Hs.PT.53a.25227282), B2M (Hs.PT.20234084), TOP1 (Hs.PT.53a.19541381), NES (Hs.PT.53a.20758620), SOX1 (Hs.PT.53a.28041414.g), PAX6 (Hs.PT.53a.814314), OCT4 (Hs.PT.58.14494169.g), REX1 (Hs.PT.53a.23001209), NANOG (Hs.PT.53a.21480849), GAD1 (Hs.PT.56a.21283000), MAP2 (Hs.PT.53a.40791337.g), and FOXG1 (Hs.PT.56a.26906112.g).

ZFP and GFP mRNA expressed from the AAV6 vector were detected by a common primer/probe set for the 5' UTR:

```
Forward primer:
                                        (SEQ ID NO: 3)
GGAACGGTGCATTGGAACG Reverse primer:
                                        (SEQ ID NO: 4)
GTTCGAATCCCAATTCTTTGCC Probe:
                                        (SEQ ID NO: 5)
AGCACGTTGCCCAGGAGGTCAC
```

Mutant Htt mRNA in R6/2 mice was detected using the following primer/probe set:

```
Forward primer:
                                        (SEQ ID NO: 6)
CGCAGGCTGCAGGGTTAC Reverse primer:
                                        (SEQ ID NO: 7)
GCTGCACCGACCGTGAGT Probe:
                                        (SEQ ID NO: 8)
CAGCTCCCTGTCCCGGCGG
```

Allele-specific detection of human HTT expression in HD fibroblasts GM04723 (CAG15/67 (SEQ ID NOS:81/82)) and GM02151 (CAG18/45 (SEQ ID NOS:79/80)) was performed with custom designed primers based on SNP rs363099 C/T (Exon29):

```
363099C-F (099-C Forward primer):
                                        (SEQ ID NO: 9)
AGTTTGGAGGGTTTCTC 363099T-F (099-T Forward primer):
                                        (SEQ ID NO: 10)
AGTTTGGAGGGTTTCTT 363099T-BL (099-T Blocker):
                                        (SEQ ID NO: 11)
AGGGTTTCTCCGCTCAGC/phos/
```

363099-R (Reverse primer, used with both 099-C and 099T forward primer): TCGACTAAAGCAGGATTTC AGG (SEQ ID NO:12).

The 099-T blocker oligo was designed to anneals to the "C/G" allele and was phosphorylated at the 3'-end base to suppress amplification of the mutant allele (Morlan et al. (2009) *PLOS ONE* 4:e4584), it was added at a 2:1 molar ratio relative to the 099T forward primer. For each sample, 10 µL qPCR reactions were set up for 099T and 099C as follows: 5 µL SsoFast Evagreen Supermix (Bio-Rad), 0.5 µL of 20×099C or 099T Mastermix (final concentration is 0.5 µM for each of the primers and 1 µM of blocker oligo in 099T assays), 2.5 µL H2O and 2 µL of cDNA sample. Thermal cycling conditions were as follows: 1) 98° C. for 2 min, 2) 98° C. for 5 sec, 3) 58.3° C. for 9 sec for the 099C assay or 55.6° C. for 9 sec for the 099T assay, 4) Plate Read, 5) Repeat steps 2 to 4, 45 times, 6) End.

Allele-specific detection of human HTT expression in HD fibroblasts ND30259 (CAG21/38 (SEQ ID NOS:83/84)) was performed with custom designed primers based on SNP rs362331 C/T (Exon 50): 362331-F (331 Forward primer): TCTCCTCCACAGAGTTTGTGA (SEQ ID NO:13), 362331-R (331 Reverse primer): CCTTCTTTCTGGAC TAAGAAGCTG (SEQ ID NO:14), 362331C Probe: TCC CTC ATC+C+AC TGT GT (SEQ ID NO:15), and 362331T Probe: CTC+A+T+C+T+A+C TGT GT (SEQ ID NO:16).

For each assay, allele-specific Taqman probes to detect 331 C or 331T, which contained Locked Nucleic Acid (LNA) bases (indicated by "+N"), were added. The LNA probes were utilized to improve allele discrimination, as compared to unmodified DNA probes (Latorra et al. (2003) *Hum Mutat* 22:79-85, doi:10.1002/humu.10228 and You et al. (2006) *Nucleic Acids Research* 34:e60, doi:10.1093/nar/gkl175). For each sample, 10 µL qPCR reactions were set up for 331T and 331C as follows: 5 µL SsoFast Probes Supermix (Bio-Rad), 1 µL of 10×331-C Mastermix (final concentration in assay 0.5 µM each of F and R primers and 0.25 µM of 331C Probe) or 331T Mastermix (final concentration in assay 0.5 µM each of F and R primers and 0.25 µM of 331-T Probe), 2 µL H2O and 2 µL of cDNA sample. Thermal cycling conditions were as follows: 1) 95° for 45 sec, 2) 95° for 5 sec, 3) 62° for 1 min for the 331C assay or 62.7° for 1 min for the 331T assay, 4) Plate Read, 5) Repeat steps 2 to 4, 45 times, 6) End.

Microarray

In vitro-transcribed mRNA encoding the ZFP-TFs (100 ng) was transfected into 150,000 HD fibroblasts (GM02151) in biological sextuplicate (Amaxa shuttle, setting CA-137, solution P2, Lonza). After 24 hours, cells were washed 1× with PBS, then processed for total RNA extraction (High Pure, Roche). Each replicate (50 ng total RNA) was processed according to the manufacturer's protocol for sample preparation, hybridization, fluidics, and scanning (Human Primeview GeneChip arrays, Affymetrix). Robust Multi-array Average (RMA) was used to normalize the raw signal from each probe set. Fold-change analysis was performed using Transcriptome Analysis Console 3.0 (Affymetrix) with the "Gene Level Differential Expression Analysis" option. Samples transfected with ZFP-A, ZFP-B, and ZFP-C were compared to samples treated with a non-CAG targeted ZFP-TF that has two known targets in fibroblasts (PAPPA and LMCD1, both repressed by <2 FC). Change calls are reported for transcripts (probe sets) with a >2 fold difference in mean signal relative to control, and a P-value <0.05 (one-way ANOVA analysis, unpaired T-test for each probe-set). For any gene with more than one probeset, the probeset with the highest Fold Change was chosen for downstream analysis.

Bioinformatics Analysis

Human chromosomes 1-22, X, and Y (version GRCh38) were scanned for hexameric CAG motifs (ZFP-A and ZFP-C) or CAGCAGnnGCAGCAnCAGCAG motifs (SEQ ID NO:17) (ZFP-B) with the 'moods_dna.py' Python script from the MOODS package (ver 1.9.2), with thresholds set to detect either zero or up to three mismatches in the motif. Regions found with this approach were converted to BED format using a custom python script. BED regions were sorted and motif regions which were adjacent or overlapping were fused into single regions using BEDtools (v2.26.0) 'merge' command independent of strandedness.

ENSEMBL human transcripts and their transcription start site coordinates (Ensembl release 87) were obtained from ENSEMBL Biomart and filtered for only those with a GENCODE (v25) BASIC annotation and biotype of 'protein_coding'. Distance of a CAG motif from a given transcription start site (or vice versa) was determined via the bedtools command 'bedtools closest –D'. Affymetrix Primeview probeset ID to ENSEMBL transcript mapping was performed using Biomart hg38 data. Affymetrix Primeview probesets which mapped to multiple genes according to ENSEMBL biomart annotations (GRCh38.7, release 87), or did not overlap an ENSEMBL transcript were removed from further analysis. In cases where multiple transcripts mapped to a Primeview probeset, the transcript with the least distance between a CAG motif and the TSS was chosen.

Expression RPKM values for human tissue expression were obtained from the GTEX project data (Mele et al. (2015) *Science* 348:660-665, doi:10.1126/science.aaa0355) available via the UCSC genome browser for the following categories: brain_caudate, brain_cortex, brain_putamen, and transformed_fibroblasts.

Measuring ATP Levels in Cultured Neurons

In vitro differentiated CAG17/48 (SEQ ID NOS:76/78) neurons and normal neurons (~1.5×105 cells) were infected in triplicate with Lenti-CMV-ZFP-2A-GFP or Lenti-CMV-GFP at MOI of 500. Twenty-one days after infection, intracellular ATP levels were measured using the CellTiter-Glo® Luminescent Assay (Promega), cell numbers in each sample were determined using the ApoLive-Glo® assay (Promega). ATP levels per cell from different cells/treatment were then normalized to that of mock-infected HD neurons.

Measuring Apoptosis Induced by Growth Factor Withdrawal in Cultured Neurons

In vitro differentiated CAG17/48 (SEQ ID NOS:76/78) neurons and normal neurons (~1.5×10$^5$ cells) were infected in triplicate with Lenti-CMV-ZFP-2A-GFP or Lenti-CMV-GFP at MOI of 500. Five days after infection, media was changed to fresh neurobasal media without growth factors. After 48 hours of growth factor withdrawal, levels of cell death were measured using a terminal deoxynucleotidyl transferase dUTP nick end labeling (TUNEL) assay kit (ApoBrdU Red DNA fragmentation kit, BioVision). Flow cytometry was used to measure percent of apoptotic cells (positive for anti-BrdU staining) among lenti-transduced (GFP-positive) cells.

Mouse Studies

The HdhQ50/Hdh+ (Q50) and R6/2 mouse studies were performed at PsychoGenics Inc. (Tarrytown, N.Y.) in accordance with the United States Public Health Service Policy on Humane Care and Use of Laboratory Animals, and procedures were approved by the Institutional Animal and Use Committee at PsychoGenics. The zQ175 mouse study was performed at Evotec AG (Hamburg, Germany) in accordance with the regulations of the German animal welfare act and the EU legislation (EU directive 2010/63/EU). Animals were enrolled in different treatment groups based on age, gender, CAG number and body weight.

Q50 Mouse Study

The HdhQ50/Hdh+ (Q50) C57BL/6J mice were provided by CHDI. At 11 weeks of age, AAV6-CMV-ZFP or AAV6-CMV-GFP (1×1013 vg/ml) was bilaterally delivered to the striatum of Q50 mice using stereotaxic injection (n=4 per group, 2 males and 2 females, group size determined by pilot studies). To increase vector coverage of the striatum, two injection sites were used in each striatum: 5 µL was delivered into the anterior site (coordinate: A/P+1.4 mm, M/L+/−1.7 mm, D/V−3.5 mm) and 4 µL was delivered into the posterior site (coordinate: A/P+0.2 mm, M/L+/−2.3 mm, D/V−3.2 mm.) at a rate of 0.5 µL/min using a stepped cannula design. Body weight was monitored twice per week through the course of the study. At 7 weeks of post injection, mice were decapitated and the brain was rapidly removed from the skull and rinsed in ice cold saline to remove any surface blood. The striatum was dissected on a chilled surface and subdivided into 3 equal-sized pieces representing the rostral, middle and caudal portions of the striatum; striatal tissues were treated in RNALater (Qiagen) at 4° C. overnight then stored at −80° C. until RNA extraction. Because AAV injection does not lead to complete and uniform coverage of the striatum (data not shown), each striatum was dissected into 3 sections to reduce the likelihood that baseline Htt levels in poorly transduced regions would interfere with detection of Htt regulation in well-transduced regions. For each striatal section, Htt as well as ZFP expression was quantified by qRT-PCR.

zQ175 Mouse Study

The zQ175 C57B/L6J knock-in mice was obtained from the Jackson Laboratory (Bar Harbor, Me., USA). At 2 or 6 months of age, heterozygous zQ175 mice (n=5 per group, mixed gender) received intrastriatal injections of AAV1/2-hSYN1-ZFP-2A-GFP (1×10$^{13}$ vg/mL) in the right hemisphere and AAV1/2-hSYN1-GFP (1×10$^{13}$ vg/ml) in the left hemisphere. A total of 2 μL of AAV vectors per striatum was delivered using a Hamilton gas tight syringe (Model 1801 RN) and a customized gauge 26 needle at a constant flow rate of 200 0.5 μL/min., and the injection coordinate was A/P+0.8 mm, M/L+/−1.8 mm, D/V −3.8 mm.

zQ175 mice were euthanized 2 or 4 months post injection by transcardial perfusion with 30 mL of ice-cold PBS followed by 50 mL of 4% paraformaldehyde using a peristaltic pump. Brain samples were removed from the skull and processed for sectioning; immunohistochemistry, image acquisition and automated image analysis were performed as previously described (Carty et al. (2015) PLoS One 10:e0123527, doi:10.1371/journal.pone.0123527).

R6/2 Mouse Study

R6/2 transgenic mice were bred in PsychoGenics' colony by crossing ovarian transplanted females on a CBAxC57BL/6 background (Jackson Laboratories) with C57BL/6 wild-type males. CAG repeat length was confirmed in transgenic mice to be 123±0.6. All experimenters were blinded to group treatments. At 5 weeks of age, AAV6-CMV-ZFP or AAV6-CMV-GFP (1×10$^{13}$ vg/mL) was bilaterally delivered to the striatum of R6/2 mice using stereotaxic injection (n=14 per group, 7 males and 7 females, group size was chosen based on historical studies testing other agents in the same model); the same injection volume and coordinates were used as in the Q50 mouse study. Mice were monitored for survival twice per day. Body weights (BW) were measured once per week until 12 weeks of age, when mice were euthanized. No statistically significant differences in BW was observed between the two groups.

Clasping behavior was recorded during each body weight session. In brief, each mouse was removed from its home cage, the cage lid was turned upside down, and the mouse was placed onto this surface. The animal was then gently pulled backward and upward by the observer in a smooth motion until the animal was suspended above the surface by about 12 inches. The animal was observed for 30 seconds. A full clasp, defined by simultaneous hindlimb and forelimb clasp pulled tightly into the core, was recorded and used for analysis.

Mice were also subjected to open field (OF) testing at 4 (baseline), 6, 8, 10 and 12 weeks of age. Animals were placed in plexiglass square chambers (27.3×27.3×20.3 cm; Med Associates Incs., St Albans, Vt.) surrounded by infrared photobeam sources for 30 minutes. Total horizontal activity (distance traveled) and vertical activity (rearing) were measured from consecutive beam breaks.

Three mice in the AAV-CMV-ZFP group and five mice in the AAV-CMV-GFP group died during the course of the study. After mice were euthanized at 12 weeks of age, striatum was dissected out (n=7 and 10 mice for the GFP and ZFP group, respectively) for gene expression analysis as described for the Q50 mouse study.

Analysis of HTT Aggregates in ZFP-Treated zQ175 Mice (Animal Studies)

Male and female zQ175 C57B/L6J knock-in mice were obtained from the Jackson Laboratory (Bar Harbor, Me., USA). The zQ175 line was derived from a spontaneous expansion of the CAG copy number in the CAG 140 knock-in mice, and generated at Psychogenics (Tarrytown, N.Y., USA). Transgenic mice were backcrossed to C57BL/6J to generate heterozygous zQ175 mice and wild-type littermates. Animals were housed in Eurostandard Type II long cages and given access to food and water ad libitum. Environmental conditions were kept as follow: 21±1° C. ambient temperature, 55±10% humidity and 12:12 light: dark cycle, with lights on from 7 am to 7 pm. Animals were checked for health status daily. All animal handling was carried out in accordance with the regulations of the German animal welfare act and the EU legislation (EU directive 2010/63/EU). The study protocol was approved by the local Ethics committee of the Authority for Health and Consumer Protection of the city and state of Hamburg ("Behörde für Gesundheit and Verbraucherschutz" BGV, Hamburg) under the file number #V11307/591 00.33.

AAV Vector Construction and Production

For expression of ZFPs, plasmids were modified from the adeno-associated virus (AAV) vector pAAV-6P-SWB (Minderer et al. (2012) J Physiol 590(1):99-107). ZFP-C (FLAG-tagged) was cloned after the human synapsin 1 promoter (phSyn1) to generate pAAV-SWB-ZFP-C. In addition, an inactive ZFP control construct was generated by deleting the ZFP DNA binding domain from ZFP-B (ZFP-ΔDBD). Pseudotyped rAAV2/1+2 particles were produced and purified as previously described (Zolotukhin, S., et al. (1999) Gene Ther. 6(6):973-85. PMID: 10455399); Carty, N., et al. (2015) PLOS ONE 10:e0123527).

In brief, HEK293 cells were co-transfected with AAV vector carrying the transcription units of interest and plasmids containing rep and cap genes (pDP1rs and pDP2rs, Plasmid Factory) in equimolar ratios by polyethylenimine-mediated plasmid transfection. Cells were lyzed 48 hours after transfection by three freeze-thaw cycles, and cellular debris were removed by centrifugation. The supernatant containing viral particles was treated with benzonase, and subjected to iodixanol density centrifugation (S6, S7) at 60,000 rpm. Iodixanol was removed and viral particles were concentrated in PBS 300 MK (300 mM NaCl, 1 mM MgCl2, 2.5 mM KCl) by filter centrifugation. The remaining rAAV solution was filtered through a Millex GV 0.22 μm pore size. Sterile rAAV particles were stored at 4° C. and diluted 1:1 with sterile PBS buffer to obtain PBS MK (150 mM NaCl, 0.5 mM MgCl2, 1.25 mM KCl) for in vivo application. AAV titers were determined using qPCR. Prior to in vivo application, ZFP-expressing rAAV particles were tested in vitro for downregulation of WT or mutant Htt in primary striatal neurons from zQ175 het mice. In brief, striatal cultures were prepared in 24-well plates at a cell density of 2E5 cells/well. rAAV particles (3E8 genome containing copies, GSs) were added at 3 DIV and cells harvested at 14 DIV. Wt and mutant Htt knockdown was assessed via qPCR using the primers: forward CAG GTC CGG CAG AGG AAC C (SEQ ID NO:18) and reverse TTC ACA CGG TCT TTC TTG GTG G (SEQ ID NO:19) for WT, and forward GCC CGG CTG TGG CTG A (SEQ ID NO:20) and reverse TTC ACA CGG TCT TTC TTG GTG G (SEQ ID NO:21) for mutant Htt, respectively.

AAV-ZFP In Vivo Application

Two groups of 16 zQ175 het mice (8 males and 8 females) received bilateral intra-striatal injections of rAAV constructs either encoding the HTT allele-specific ZFP30640 or the ZFP-ΔDBD control at 2 months of age. Mice were individually anaesthetized with 3% isoflurane at a flow rate of 1 L/min and placed in a stereotaxic instrument (Kopf, Model No. 940). Anesthesia was maintained throughout the surgical procedure via gas nose cone delivery of 2% isoflurane at a flow rate of 0.5 L/min. A longitudinal mid-sagittal incision of 1 cm in length was made in the scalp after sterilization with 70% ethanol and iodine solution, and lidocaine application. Following skin incision, a small hole corresponding to the striatal injection site was made in the skull using an electrical drill (Foredom; Model No. H.30). The coordinates measured according to the mouse bregma were 0.8 mm anterior, 1.8 mm lateral on right and 3.8 mm deep from bregma with flat skull nosebar setting. A total volume of 44, (4E10 GCs) ZFP viral vectors were administered using a Hamilton gas tight syringe (model 1801 RN, customized gauge 26 needle) connected to an automated microinjection pump at constant flow rate of 200 nL/min. After injection, the surgery wound was sealed and the animals were kept in a heating pad until fully recovered.

Histology and Immunohistochemistry

Mice were euthanized at the age of 6 and 10 months by transcardial perfusion. For perfusions mice were deeply anesthetized by intraperitoneal injection of ketamine/xylazine mixture (120 mg/15 mg per kg in 15 µl/g body weight) using small diameter 27 G needles. Before starting the perfusion animals were assessed for the loss of toe pinch reflex and corneal reflex to ensure the correct level of anesthesia was achieved. Mice were transcardially perfused with 30 mL of ice-cold PBS followed by 50 mL of 4% paraformaldehyde using a peristaltic pump. Brain samples were removed from the skull and post-fixed overnight in the same fixative at 4° C., and cryoprotected by incubating in 30% sucrose solutions until saturated. Whole brains were embedded in TissueTek and stored at −80° C. Coronal sections of 25 µm were cut using a cryostat, collected as free floating in 24-well plates, and directly used for staining or stored in a cryoprotection solution (25 mM Na-phosphate buffer pH 7.4, 30% ethylene glycol, 20% glycerol) at −20° C. until time of use. The following primary antibodies were used for immunostaining: monoclonal mouse anti-mutant huntingtin (1:100; EM48, Millipore, MAB5374, lot #2135055), monoclonal rabbit anti-DARPP-32 (1:250; clone 19A3, Cell Signaling, #2306, lot #2), polyclonal rabbit anti-NeuN (1:1000; Millipore, ABN78, lot #2140086), monoclonal mouse anti-GFAP (1:1500, Millipore, MAB3402, lot #1990686), polyclonal rabbit anti-Iba1 (1:1000, Wako, #019-19741, lot #SAE6921). All stainings were performed with floating sections. Sections were permeabilized in 0.3% Triton X-100/PBS, blocked in 10% normal goat serum/PBS and incubated with the primary antibody diluted in 1% normal goat serum, 0.1% Triton X-100 in PBS at 4° C. overnight. Sections were washed three times in PBS for 15 min and incubated in secondary antibody for 2 hours at room temperature. Sections were washed in PBS as described above and mounted using aqueous mounting medium containing DAPI (Fluoroshield, Sigma, F6057) in 24-well glass-bottom plates (Sensoplate, Greiner, #662892) suitable for imaging with the Opera High Content Screening system (PerkinElmer Inc.).

Image Acquisition and Automated Image Analysis

Image acquisition and analysis were performed as previously described (Carty, N., et al. ibid). In brief, automated image acquisition was conducted using the Opera® High Content Screening system and Opera software 2.0.1 (PerkinElmer Inc.) using a 40× water immersion objective (Olympus, NA 1.15, pixel size: 0.32 µm) for imaging of mHTT inclusions, or 20× water immersion objective (Olympus, NA 0.7, pixel size: 0.64 µm) for analysis of glia cells in tissue. Image analysis scripts for characterization and quantification of mHTT inclusions were developed using Acapella® Studio 3.1 (PerkinElmer Inc.) and the integrated Acapella® batch analysis as part of the Columbus® system. To identify astro- and microglia cells, the algorithm searched for neurite-like cell extensions in the GFAP and Iba1 channels. Extensions that connected to the previously determined nucleus border in a 4 pixel wide rim around the nucleus were considered valid. A cell was considered GFAP or Iba1-positive, only if extensions could be detected. Subsequently, a "local" background signal intensity was determined within an extra-nuclear rim region of 3px width and 2px distance from the previously determined nucleus border. Finally, only cells with a nuclear GFAP or Iba1 intensity higher than the mean "local" background intensity were considered astroglia or microglia, respectively. Image data from six sections were averaged per animal, and five animals per treatment group were used for statistical evaluation.

Tissue Homogenization for Meso Scale Discovery (MSD) Analysis

Whole striata dissected from the brain hemispheres were lysed in 80 µL of tissue lysis buffer (20 mM Tris (pH 7.5), 150 mM NaCl, 1 mM EDTA, 1 mM EGTA, 1% Triton X-100, 10 mM NaF, 1 mM PMSF, Phosphatase Inhibitor Cocktail II (Sigma), Phosphatase Inhibitor Cocktail III (Sigma), Protease Inhibitors (Roche Diagnostics)) using a FastPrep24 homogenizer (MP Biomedicals). Crude lysates were centrifuged three consecutive times for 10 min at 16,000 rcf and 4° C., and the supernatant collected after each centrifugation step. The total protein concentration was determined using the bicinchoninic acid assay (BCA; Thermo Scientific) and adjusted to 1 mg/mL using lysis buffer. Homogenates were aliquoted, snap-frozen, and stored at −80° C. until analysis.

Meso Scale Discovery Analysis

MSD plates (384-well) were coated overnight at 4° C. with 10 µL of coating antibody in carbonate-bicarbonate coating buffer (15 mM Na2CO3/35 mM NaHCO3, pH 9.6) per well. Plates were then washed 3 times with 35 µL of wash buffer (0.2% Tween-20 in PBS) per well and blocked with 35 µL of blocking buffer (2% probumin/0.2% Tween-20 in PBS) per well for 1 h at RT with rotational shaking. Striatal extracts were diluted to 0.5 mg/mL in a mixture of 50% tissue lysis buffer and 50% blocking buffer. After an additional washing step, 10 µL per sample were transferred to each well of the antibody-coated MSD plate and incubated with shaking for 1 h at RT. After disposal of samples and four wash cycles with 35 µL of wash buffer each, 10 µL of the detection antibody were added to each well and incubated with shaking for 1 h at RT. After three times washing with wash buffer, 35 µL of read buffer T with surfactant (Meso Scale Discovery) were added to each well and the plate was imaged on a Sector Imager 6000 (Meso Scale Discovery) according to manufacturers' instructions. The following antibody combinations were used: 4 µg/mL 2B7/0.1 µg/mL 4C9-ST; 4 µg/mL MW8/1 mg/mL 4C9-ST; 4 µg/mL MW8/5 µg/mL MW8-ST (ST: SULFO-tag). Samples were quantified against human HTT-Q73, aa 1-573 (for assay 2B7/4C9-ST) or aggregated exon1-Q46 (for MW8/4C9-ST and MW8/MW8-ST assays) standard curves.

Data Analysis and Statistics

Statistical analyses were conducted using GraphPad Prism® 6.0 software. For all analyses, p-values less than 0.05 were considered statistically significant. Quantitative analyses (n=5 animals with 6 sections per animal per treatment group) were performed using t-test with Welch's correction; $p<0.05^*$; $p<0.01^{}$; $p<0.001^{*}$ Animals Used for Receptor Autoradiography (ARG) and microPET Studies Heterozygous zQ175 mice (mixed gender) were injected unilaterally with AAV1/2-hSYN1-ZFP-D or AAV2/1-hSYN1-ΔDBD-ZFP at Evotec Hamburg, Germany at either 2 months or 4 months of age.

The brains of two cohorts of zQ175 het mice were examined with ARG using the three striatal markers [3H]raclopride (D2 ligand), [3H]MNI-659 (PDE10 ligand), and [3H]NNC112 (D1 ligand). One cohort (n=10 mice/group) of animals injected at 2 months of age was sacrificed at 6 months, shipped to Karolinska Institutet and the brains were examined with in vitro ARG using the radioligands.

A second cohort was injected at 4 months of age (n=33-41 mice/group). Animals were shipped to Karolinska Institutet (Stockholm, Sweden) and microPET imaging was performed with the dopamine D2/D3 receptor radioligand [11C]Raclopride and with [18F]MNI-659, a radioligand for the PDE10A enzyme, at 6.5-7 and 10 months of age. A subset of this group (n=10 animals/group) was sacrificed at the end of the 10 months' imaging study and used for ARG using [3H]raclopride (D2 ligand), [3H]MNI-659 (PDE10 ligand), and [3H]NNC112 (D1 ligand).

At Karolinska Insititutet, animals were housed at the animal department of Karolinska University Hospital in a temperature (±21° C.) and humidity (±40%) controlled environment on a 12 h light/dark cycle (lights on 7:00 AM) with access to food and water ad libitum. Animals were allowed at least one week to habituate to the animal department before the start of the imaging sessions. All experiments were conducted during the light phase of the cycle. All experiments were performed in accordance with the guidelines of the Swedish National Board of Laboratory Animals under protocols approved by the Animal Ethics Review Board of Northern Stockholm, Sweden (N558/11).

Brain Removal and Sectioning

Brains were quickly removed from the skull, placed to freeze in isopentane (2-methylbutane 99% solution) at approximately −40° C. for 15-20 seconds. Frozen brains were wrapped in tin foil and stored in −80° C. until use. The central part or the striatum (approx 1 mm) was sectioned (coronal) at 14 µm thickness on a cryostat cryomicrotome (Leica CM 1860). Three sections per slide (75 sections=1 mm tissue=25 slides). Sections were thaw-mounted on microscope slides (SuperFrost®Plus, Menzel-Glaser, Germany), air-dried and directly refrozen in the cryostat. Slides were kept at −20° C. until used. Sectioning was done sequentially, meaning that there are sections from three levels on the same slide.

Fluorescent Immunohistochemistry (IHC) for HTT Aggregates

Sections were placed in phosphate buffered saline (PBS) and then incubated for 72 h with mouse anti-HTT primary antibody (MAB5374 from Chemicon, Anti-Huntingtin Protein Antibody, clone mEM48, mouse origin) diluted 1/300 in 0.3% TX-100, 0.1% NaN3 in PBS. Sections were washed in Tris-HCl buffered saline (pH 7.4) containing 0.5% tween, blocked (Perkin Elmer) and incubated in blocking buffer containing 488-conjugated anti-mouse secondary antibody (1/200, Jackson) followed by several washes in Tris-HCl buffered saline containing 0.5% tween. All sections were counterstained with the nuclear marker Hoechst (1/5.000) and tissue autofluorescence was blocked using 1% Sudan Black (in 70% ethanol) and mounted with polyvinyl alcohol/glycerol containing 2.5% DABCO (Sigma). All IHC slides were analyzed using the MetaViewer Image Software, MetaSystems.

Radioligands

[3H]NNC112 (77 Ci/mmol) was synthesized at Karolinska Institutet, Department of Clinical Neuroscience. [3H]Raclopride (81 Ci/mmol) was purchased from Novandi Chemistry AB, (Sodertalje, Sweden). [3H]MNI659 (57 Ci/mmol) was provided by the CHDI foundation. The radiochemical purity of all radioligands was measured prior to the ARG experiments (>95%).

In Vitro Autoradiography (ARG)

Slides were thawed at room temperature and pre-incubated for approximately 20 min in binding buffer (Tris HCl 50 mM, pH 7.4 incl. 120 mM NaCl, 5 mM KCl, 2 mM CaCl2, 1 mM MgCl2). The slides were then incubated at 1 nM radioligand in binding buffer for 60 min at room temperature.

In a duplicate set of containers butaclamol ([3H]NNC112 and [3H]raclopride) or MP-10 ([3H]MNI659) at 10 µM was added to establish non-displaceable binding. After incubation the slides were washed 3 times for 10 min in Tris HCl 50 mM, pH 7.4 followed by a brief wash in distilled water. The slides were dried over night in room temperature or for approximately 30 min on a heated (37° C.) plate. Slides were placed along with autoradiographic microscale standards (American Radiolabeled Chemicals Inc.) and exposed on tritium sensitive phosphor imaging plates (Fujifilm Plate BAS-TR2025, Fujifilm, Tokyo, Japan) for 90 hours.

The tissue sections used for [3H]MNI659 was subjected to fixation in 4 paraformaldehyde (PFA) prior to exposure to the phosphor imaging plates. This results in a decrease in signal strength which is essential for analyzing the signal due to that the radioligand is very potent. This technique with post fixation of the tissue was previously used to enable multiple use of phosphor imaging plates of low energy isotopes like tritium (3H). In this context we use post fixation to decrease signal strength of [3H]MNI659 in the tissue to utilize binding at higher concentrations (e.g 1 nM) which is essential to reach equilibrium between bound and free fraction. Without the post fixation step we are limited to perform binding at concentrations below 0.15 nM and that is not enough to reach equilibrium and hence not enough to visualize discrepancy between wild type and Q175 [3H]MNI659 in vitro binding.

The drawback of the post fixation with [3H]MNI659 is that the deceased signal influences the image analysis in lower quantitative values of the specific binding (fmol/mg tissue). Nevertheless, the ratio between analyzed brain regions remains the same meaning that the difference in specific binding between groups is equivalent.

Image Analysis

The phosphor imaging plates were scanned and the resulting images are processed in a Fujifilm BAS-5000 phosphor imager (Fujifilm, Tokyo, Japan). Region of interest (ROI) analysis were applied by manual delineation of the injection site based on the EM48 immunoreactivity visualized by fluorescence IHC. Mean pixel values of the ROIs from 6 sections were then transformed into radioactivity values and to binding density (fmol/mg tissue, tissue wet weight) using the micro scale standard. Quantitative analysis was performed using Multi Gauge 3.2 phosphorimager software (Fujifilm, Tokyo, Japan). Specific binding was calculated by subtracting the level of non-specific binding from the total binding for each section.

Radiosynthesis

Radiosynthesis of [11C] raclopride: [11C]Raclopride was synthesized at Karolinska Institutet as described earlier (Langer et al. (1999) *Nucl Med Biol* 26(5):509-18) by methylation of the desmethyl precursor analogue using [11C]methyltriflate. The incorporate rate was >50% and the radiochemical purity was >99%.

Radiosynthesis of [18F] MNI659: Radiosynthesis were carried out as described in PMID 27856625.

In Vivo Imaging with [11C]Raclopride and [18F]MNI-659

PET measurements were performed using the Mediso nanoScan® PET-Mill and the nanoScan® PET-CT preclinical small animal imaging systems. The two systems have identical PET performance (Nagy et al. (2013) *J. Nucl Med* 54(10):1825-32) and were calibrated to provide consistent result. The first PET measurement was performed when the animals were 6.5 to 7 months of age. On the experimental day, the animal was anesthetized with inhalation of isoflurane (4-5% isoflurane in 100% oxygen). After induction of anesthesia, the isoflurane concentration was lowered to 1.5-2% (50/50 air/oxygen) and the animals were positioned in the scanner in a designated mouse bed. A cannula was inserted in the tail vein through which the radioligand was administered. A 63-minute dynamic PET scan was initiated immediately upon intravenous injection of the radioligand. Upon completion the imaging sessions, the animal returned to its cage. The animals were housed at the animal department at Karolinska Institutet until 10 months of age, where the imaging was repeated using the same radioligands.

Image- and Statistical Analysis

The acquired list mode data, was reconstructed into 25 timeframes (63 min scan=4×10 s, 4×20 s, 4×60 s, 7×180 s, 6×360 s). The image reconstruction was made with a fully 3-dimensional maximum-likelihood expectation maximization algorithm (MLEM) with 20 iterations, without scatter and attenuation correction. The reconstructed dynamic PET images were co-registered to an inbuilt mice MRI template available in PMOD, which also incorporates volumes of interest (VOI's) sets (PMOD Technologies Ltd., Zurich, Switzerland). With the help of these VOI sets, decay corrected time activity curves (TAC) were generated. The binding potential (BPND) was calculated in PMOD with the simplified reference tissue model (SRTM) using cerebellum as a reference region. The % difference between left and right striatum was calculated according to the following equation:

% difference=((Right Striatum−Left Striatum))/(Left Striatum)×100

The difference between the two sides of the striatum was analyzed with a within subject paired t-test using GraphPad Prism version 5.00 for Windows (GraphPad Software, San Diego Calif. USA). In addition, the % difference between left and right striatum between the control treated group and the repressor treated group was analyzed using between subject unpaired t-test.

Electrophysiological Recordings

For electrophysiological recordings slices were transferred to a submersion-style recording chamber mounted on an Olympus BX51 upright microscope (60×/0.9 NA objective) equipped with infrared differential interference contrast. Whole-cell patch clamp electrophysiological recordings were performed with Multiclamp 700B amplifier. Signals were filtered at 1 KHz and converted to digital format with Digidata 1400. Stimulation and display of electrophysiological recordings were obtained with custom-written software WinFluor (John Dempster, Strathclyde University, Glasgow, UK) that synchronizes two-photon imaging and electrophysiology. Targeted electrophysiological recordings were obtained from iSPN or dSPN. Patch pipettes (4-6 MΩ) were prepared with a Sutter Instruments horizontal puller using borosilicate glass with filament and filled with (in mM): 135 KMeSO4, 5 KCl, 5 HEPES, 0.05 EGTA, 2 ATP-Mg2, 0.5 GTP-Na, 10 phosphocreatine-di(tris); pH was adjusted to 7.25 with KOH and osmolarity to 270-280 mosM. To record Ca2+ transients in dendritic spines and shafts, cells were filled with 100 µM Fluo-4 pentapotassium salt and 25 µM Alexa Fluor 568 hydrazide Na salt (Invitrogen). All recordings were made 30 min after whole cell configuration was established. Electrophysiological characterization of neurons was made in current clamp configuration. The amplifier bridge circuit was adjusted to compensate for electrode resistance. Access resistances were continuously monitored and experiments were discarded if changes >20% were observed. Only stable recorded neurons were considered for analysis. 30% of our recordings were discarded because of changes in access resistance. Membrane potential was maintained at −80 mV. Digitized data were imported for analysis with commercial software (IGOR Pro 6.0, WaveMetrics, Oregon).

Two Photon $Ca^{2+}$ Imaging

Ca2+ transients were evoked by back propagating action potentials (bAPs) (five bAP triplets, each; 50 Hz intra train; 5 Hz between trains; in the ZFP experiments, bAP were generated with a single 50 Hz triplet). Ca2+ transients were recorded at proximal (50~60 µm) and distal dendritic spines (>100 µm) from co-planar sections of the same dendrite using Ultima Laser Scanning Microscope system (Bruker Technologies, former Prairie) attached to a tunable laser (Chameleon, Coherent Laser Group, Santa Clara, Calif.) with 820 nm excitation wavelength (80-MHz pulse frequency; 250 fs pulse duration). Red signals from Alexa Fluor 568 (580-630 nm) were used to visualize dendrites, whereas green signals from Fluo-4 (490-560 nm) were used to record Ca2+ transients. The red channel was used to normalize the signals obtained from proximal and distal sections. Thus, Ca2+ transients were expressed as the ratio between green and red fluorescence (G/R). Only proximal and distal dendrites lying in the same focal plane whose red fluorescence were <10% different were considered for further analysis avoiding dye diffusion artifacts. Line scan signals were acquired with 512 pixel resolution per line and 10 µs/pixel dwell time. For the ZFP experiments using the triplet bAP, IGOR Pro (WaveMetrics, Lake Oswego, Oreg.) was used for data smoothing and statistics. The mean fluorescence as a function of time (F(t)) was the spatial average of 5 adjacent pixels, while the basal fluorescence, Fo, was average of the first 30 time points within a line scan. The normalized difference in Ca2+ signal (ΔF/Fo) due to current injection was defined as the maximum fluorescence change normalized by the basal fluorescence.

Two Photon Laser Uncaging

Simultaneous two-photon Ca2+imaging and two-photon laser uncaging were performed using two different femtosecond-pulsed attached to the microscope (Ultima, Bruker Corporation). MNI-glutamate (5 mM) was superfused in the recorded area and excited at 720 nm by the photostimulation laser (Chameleon, Coherent Laser Group, Santa Clara, Calif.). The two laser beams on sample are individually controlled by two independent sets of galvanometric scanning mirrors. Pulses of 1 ms (~10 mW) were delivered to single spines located in the same focal plane (5-10 spines). Single spine stimulation was calibrated to evoke a somatic excitatory postsynaptic potential of 1-2 mV for each stimulated spine. Custom written software (WinFluor) was used to synchronize Ca2+ transients, electrophysiological recordings and two-photon laser stimulation.

ZFP Constructs

The plasmid containing ZFP-D cDNA and non-binding ZFP cDNA were subcloned and packaged into AAV9 by Virovek (Hayward, Calif.). The expression of N-term NLS and C-term FLAG tagged human mutant Htt-repressor ZFP and tdTomato is bridged by viral 2A cleavage peptide. A striatal derived cell line ST HDH Q7/111 (Coriell, CHDI-90000072) from a knock in transgenic mouse containing heterozygous Huntingtin (HTT) loci with a humanized Exon 1 with 111 polyglutamine repeats and the other with a wild-type mouse HTT with 7 polyglutamine repeats was used to test the ZFP mediated repression of mHTT expression. Cells were plated in 12 well plates and then infected with AAV carrying ZFP-30645 after overnight incubation and harvested after 72 h of infection for RNA isolation.

ZFP Mediation Repression in Ata-Q175 HETs

Stereotaxic injections of AAV carrying ZFP and tdTomato genes were made in striatum (ML=−1.7, AP=−0.98, DV=−3.6) of isoflurane-anesthetized 4-month-old A2a-EGFP and A2a-EGFP/Q175 het mice. Mice were allowed to recover for at least 2 months post-injection.

Quantitative Real-Time PCR Analysis of Htt mRNA Expression

RNA was isolated from ST HDH Q7/111 cells and striatal tissue of mice injected with ZFP AAV using RNAeasy kit (Qiagen). The RNA was reverse transcribed with Superscript III RT enzyme (Life Technologies). Quantitative real-time PCR was performed using an ABI StepOnePlus rtPCR system with SYBR-Green PCR Master Mix (Applied Biosystems, Forster City, Calif.). The relative abundance of different transcripts was assessed by SYBR quantitative PCR using a the 2−[delta][delta] Ct method (ABS, User bulletein2). The following primers (IDT) were used for PCR amplification wild-type-mouse Htt_fw: CAG GTC CGG CAG AGG AAC C (SEQ ID NO:22), Mut-mouse-Htt_Q175_fw: GCC CGG CTG TGG CTG A (SEQ ID NO:23), Mut & wild-type Htt_rv*: TTC ACA CGG TCT TTC TTG GTG G (SEQ ID NO:24), ZFP_fw: CTG GCT GGT GGA GAG AGA AAT T (SEQ ID NO:25) and ZFP_rv: TCG TCG TCC TTG TAG TCA ACT GA (SEQ ID NO:26), (*wild-type and mutant HTT share the same reverse primer sequence). Briefly experimental Ct values were normalized to GAPDH values using the formula: $\Delta Ct = Ct (Htt) - Ct (GAPDH)$. Expression levels were calculated relative to controls using the formula: $\Delta\Delta Ct = Ct (treated) - \Delta Ct (control)$. The final expression levels were obtained using the formula $2-\Delta\Delta Ct$.

Example 2: Identification of ZFP-TFs that Selectively Repress HTT Alleles Bearing an Expanded Poly-CAG Tract In undertaking these studies, the binding properties of poly-CAG-targeted ZFP-TFs which exhibit highly synergistic function and would manifest a steep dependence on poly-CAG tract length in its ability to repress Htt (FIG. 1A) could not be predicted. Moreover, to address the fact that environmental factors that enable an allele-specific response would be difficult emulate in a model system, we pursued a strategy that emphasized screening a diverse panel of ZFP-TFs directly for allele-specific repression in situ in the context of the endogenous HTT promoter in patient cells.

Figure 1A:
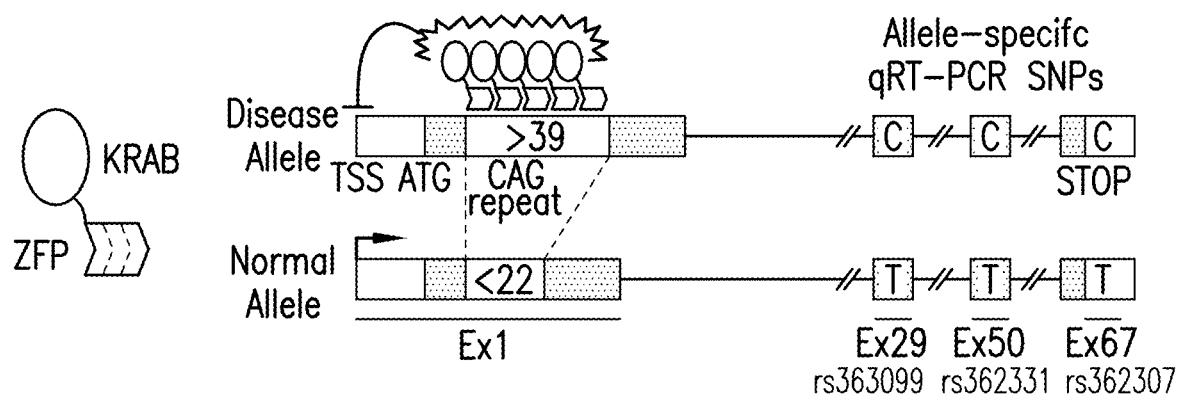
FIGS. 1A through 1K depict design and testing of allele-selective ZFPs targeting mHtt.
Figure 1B:
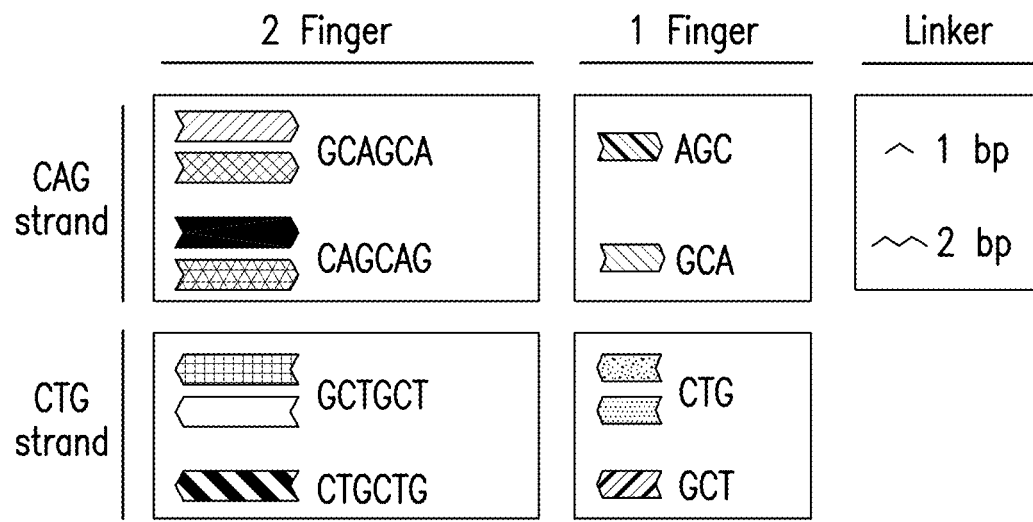
Figure 1C:
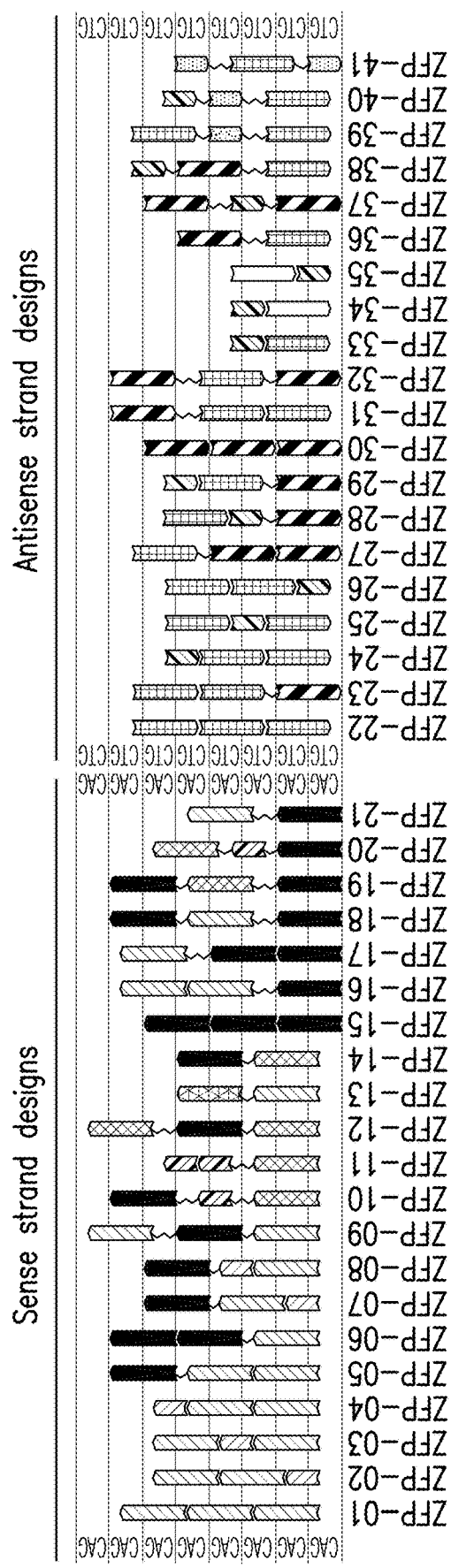

Accordingly, a diverse panel of ZFP-TFs was screened directly for allele-specific repression in situ, in the context of the endogenous Htt promoter in patient cells. As shown in FIGS. 1B and 1C as well as in Tables 1 and 2 below, a set of 41 distinct ZFPs was assembled (essentially as described in U.S. Pat. No. 8,841,260) bearing a diversity of architectures, target lengths and binding periodicities within the poly-CAG tract. Each ZFP was linked to the KRAB transcriptional repression domain from the KOX1 protein as previously described. As is standard practice, the ZFPs are assembled from either one or two-fingered modules, and the proteins used different finger linkers between the ZFP modules (termed "Mod link" in Table 1 below). The linkers used are as follows: "0a" is TGEKPFQ (SEQ ID NO:27); "0c" is TGSQKPFQ (SEQ ID NO:28); "1c" is THPRAPIPKPFQ (SEQ ID NO:88); "2f" is TPNPHRRTDPSHKPFQ (SEQ ID NO:29). The 0a and 0c linkers do not skip any nucleotide bases between modules, while 1c and 2f skip 1 bp and 2 bp respectively.

TABLE 1

Zinc Finger Designs

| ZFP ID | ZFP aka | Module 1 F1 | Module 1 F2 | Mod link | Module 2 F3 | Module 2 F4 | Mod link | Module 3 F5 | Module 3 F6 |
|---|---|---|---|---|---|---|---|---|---|
| ZFP-1 | 30639 | QSSDLSR (SEQ ID NO: 30) | QWSTRKR (SEQ ID NO: 31) | 0c | QSSDLSR (SEQ ID NO: 30) | QWSTRKR (SEQ ID NO: 31) | 0c | QSSDLSR (SEQ ID NO: 30) | QWSTRKR (SEQ ID NO: 31) |
| ZFP-2 | 30640- "ZFP-A" | QSSDLSR (SEQ ID NO: 30) | QWSTRKR (SEQ ID NO: 31) | 0c | QSSDLSR (SEQ ID NO: 30) | QWSTRKR (SEQ ID NO: 31) | 0a | QSDGLTR (SEQ ID NO: 32) | N/A |
| ZFP-3 | 30641 | QSSDLSR (SEQ ID NO: 30) | QWSTRKR (SEQ ID NO: 31) | 0c | QSDGLTR (SEQ ID NO: 32) | N/A | 0a | QSSDLSR (SEQ ID NO: 30) | QWSTRKR (SEQ ID NO: 31) |
| ZFP-4 | 30642 | QSGDLTR (SEQ ID NO: 32) | N/A | 0a | QSSDLSR (SEQ ID NO: 30) | QWSTRKR (SEQ ID NO: 31) | 0c | QSSDLSR (SEQ ID NO: 30) | QWSTRKR (SEQ ID NO: 31) |
| ZFP-5 | 30643 | RSDNLSE (SEQ ID NO: 33) | KRCNLRC (SEQ ID NO: 34) | 0c | QSSDLSR (SEQ ID NO: 30) | QWSTRKR (SEQ ID NO: 31) | 0c | QSSDLSR (SEQ ID NO: 30) | QWSTRKR (SEQ ID NO: 31) |
| ZFP-6 | 30644 | RSDNLSE (SEQ ID NO: 33) | KRCNLRC (SEQ ID NO: 34) | 0c | RSDNLSE (SEQ ID NO: 33) | KRCNLRC (SEQ ID NO: 34) | 1c | QSSDLSR (SEQ ID NO: 30) | QWSTRKR (SEQ ID NO: 31) |

TABLE 1-continued

Zinc Finger Designs

| ZFP ID | ZFP aka | Module 1 F1 | Module 1 F2 | Mod link | Module 2 F3 | Module 2 F4 | Mod link | Module 3 F5 | Module 3 F6 |
|---|---|---|---|---|---|---|---|---|---|
| ZFP-7 | 30645-"ZFP-D" | RSDNLSE (SEQ ID NO: 33) | KRCNLRC (SEQ ID NO: 34) | 1c | QSSDLSR (SEQ ID NO: 30) | QWSTRKR (SEQ ID NO: 31) | 0a | QSGDLTR (SEQ ID NO: 32) | N/A |
| ZFP-8 | 30646 | RSDNLSE (SEQ ID NO: 33) | KRCNLRC (SEQ ID NO: 34) | 1c | QSGDLTR (SEQ ID NO: 32) | n/a | 0a | QSSDLSR (SEQ ID NO: 30) | QWSTRKR (SEQ ID NO: 31) |
| ZFP-9 | 30647 | QSSDLSR (SEQ ID NO: 30) | QWSTRKR (SEQ ID NO: 31) | 2f | RSDNLSE (SEQ ID NO: 33) | KRCNLRC (SEQ ID NO: 34) | 1c | QSSDLSR (SEQ ID NO: 30) | QWSTRKR (SEQ ID NO: 31) |
| ZFP-10 | 33078 | RSDNLSE (SEQ ID NO: 33) | KRCNLRC (SEQ ID NO: 34) | 2f | MACCRYA (SEQ ID NO: 35) | n/a | 2f | QSGDLTR (SEQ ID NO: 32) | QSGDLTR (SEQ ID NO: 32) |
| ZFP-11 | 33079 | MACCRYA (SEQ ID NO: 35) | n/a | 0a | MACCRYA (SEQ ID NO: 35) | n/a | 2f | QSGDLTR (SEQ ID NO: 32) | QSGDLTR (SEQ ID NO: 32) |
| ZFP-12 | 33080 | QSGDLTR (SEQ ID NO: 32) | QSGDLTR (SEQ ID NO: 32) | 2f | RSDNLSE (SEQ ID NO: 33) | KRCNLRC (SEQ ID NO: 34) | 1c | QSGDLTR (SEQ ID NO: 32) | QSGDLTR (SEQ ID NO: 32) |
| ZFP-13 | 33060 | RSDNLSE (SEQ ID NO: 33) | RLWNRKQ (SEQ ID NO: 33) | 1c | QSSDLSR (SEQ ID NO: 30) | QWSTRKR (SEQ ID NO: 31) | | N/A | N/A |
| ZFP-14 | 33061 | RSDNLSE (SEQ ID NO: 33) | KRCNLRC (SEQ ID NO: 34) | 1c | QSGDLTR (SEQ ID NO: 32) | QSGDLTR (SEQ ID NO: 32) | | N/A | N/A |
| ZFP-15 | 30648-"ZFP-C" | RSDNLSE (SEQ ID NO: 33) | KRCNLRC (SEQ ID NO: 34) | 0c | RSDNLSE (SEQ ID NO: 33) | KRCNLRC (SEQ ID NO: 34) | 0c | RSDNLSE (SEQ ID NO: 33) | KRCNLRC (SEQ ID NO: 34) |
| ZFP-16 | 30649 | QSSDLSR (SEQ ID NO: 30) | QWSTRKR (SEQ ID NO: 31) | 0c | QSSDLSR (SEQ ID NO: 30) | QWSTRKR (SEQ ID NO: 31) | 2f | RSDNLSE (SEQ ID NO: 33) | KRCNLRC (SEQ ID NO: 34) |
| ZFP-17 | 30650 | QSSDLSR (SEQ ID NO: 30) | QWSTRKR (SEQ ID NO: 31) | 2f | RSDNLSE (SEQ ID NO: 33) | KRCNLRC (SEQ ID NO: 34) | 0c | RSDNLSE (SEQ ID NO: 33) | KRCNLRC (SEQ ID NO: 34) |
| ZFP-18 | 30651 | RSDNLSE (SEQ ID NO: 33) | KRCNLRC (SEQ ID NO: 34) | 1c | QSSDLSR (SEQ ID NO: 30) | QWSTRKR (SEQ ID NO: 31) | 2f | RSDNLSE (SEQ ID NO: 33) | KRCNLRC (SEQ ID NO: 34) |
| ZFP-19 | 33074-"ZFP-B" | RSDNLSE (SEQ ID NO: 33) | KRCNLRC (SEQ ID NO: 34) | 1c | QSGDLTR (SEQ ID NO: 32) | QSGDLTR (SEQ ID NO: 32) | 2f | RSDNLSE (SEQ ID NO: 33) | KRCNLRC (SEQ ID NO: 34) |
| ZFP-20 | 33076 | QSGDLTR (SEQ ID NO: 32) | QSGDLTR (SEQ ID NO: 32) | 1c | MACCRYA (SEQ ID NO: 35) | n/a | 1c | RSDNLSE (SEQ ID NO: 33) | KRCNLRC (SEQ ID NO: 34) |
| ZFP-21 | 33077 | QSSDLSR (SEQ ID NO: 30) | QWSTRKR (SEQ ID NO: 31) | 2f | RSDNLSE (SEQ ID NO: 33) | KRCNLRC (SEQ ID NO: 34) | | N/A | N/A |
| ZFP-22 | 30656 | QSSDLSR (SEQ ID NO: 30) | HRSTRNR (SEQ ID NO: 37) | 0c | QSSDLSR (SEQ ID NO: 30) | HRSTRNR (SEQ ID NO: 37) | 0c | QSSDLSR (SEQ ID NO: 30) | HRSTRNR (SEQ ID NO: 37) |
| ZFP-23 | 30657 | RSDTLSE (SEQ ID NO: 38) | RRWTLVG (SEQ ID NO: 39) | 1c | QSSDLSR (SEQ ID NO: 30) | HRSTRNR (SEQ ID NO: 37) | 0c | QSSDLSR (SEQ ID NO: 30) | HRSTRNR (SEQ ID NO: 37) |
| ZFP-24 | 30658 | QSSDLSR (SEQ ID NO: 30) | HRSTRNR (SEQ ID NO: 37) | 0c | QSSDLSR (SEQ ID NO: 30) | HRSTRNR (SEQ ID NO: 37) | 0a | QSSDLSR (SEQ ID NO: 30) | N/A |

TABLE 1-continued

Zinc Finger Designs

| ZFP ID | ZFP aka | Module 1 F1 | F2 | Mod link | Module 2 F3 | F4 | Mod link | Module 3 F5 | F6 |
|---|---|---|---|---|---|---|---|---|---|
| ZFP-25 | 30659 | QSSDLSR (SEQ ID NO: 30) | HRSTRNR (SEQ ID NO: 37) | 0c | QSSDLSR (SEQ ID NO: 30) | n/a | 0a | QSSDLSR (SEQ ID NO: 30) | HRSTRNR (SEQ ID NO: 37) |
| ZFP-26 | 30660 | QSSDLSR (SEQ ID NO: 30) | n/a | 0a | QSSDLSR (SEQ ID NO: 30) | HRSTRNR (SEQ ID NO: 37) | 0c | QSSDLSR (SEQ ID NO: 30) | HRSTRNR (SEQ ID NO: 37) |
| ZFP-27 | 30661 | RSDTLSE (SEQ ID NO: 38) | RRWTLVG (SEQ ID NO: 39) | 0c | RSDTLSE (SEQ ID NO: 38) | RRWTLVG (SEQ ID NO: 39) | 1c | QSSDLSR (SEQ ID NO: 30) | HRSTRNR (SEQ ID NO: 37) |
| ZFP-28 | 30662 | RSDTLSE (SEQ ID NO: 38) | RRWTLVG (SEQ ID NO: 39) | 1c | QSSDLSR (SEQ ID NO: 30) | HRSTRNR (SEQ ID NO: 37) | 0a | QSSDLSR (SEQ ID NO: 30) | N/A |
| ZFP-29 | 30663 | RSDTLSE (SEQ ID NO: 38) | RRWTLVG (SEQ ID NO: 39) | 1c | QSSDLSR (SEQ ID NO: 30) | n/a | 0a | QSSDLSR (SEQ ID NO: 30) | HRSTRNR (SEQ ID NO: 37) |
| ZFP-30 | 30665 | RSDTLSE (SEQ ID NO: 38) | RRWTLVG (SEQ ID NO: 39) | 0c | RSDTLSE (SEQ ID NO: 38) | RRWTLVG (SEQ ID NO: 39) | 0c | RSDTLSE (SEQ ID NO: 38) | RRWTLVG (SEQ ID NO: 39) |
| ZFP-31 | 30666 | QSSDLSR (SEQ ID NO: 30) | HRSTRNR (SEQ ID NO: 37) | 0c | QSSDLSR (SEQ ID NO: 30) | HRSTRNR (SEQ ID NO: 37) | 2f | RSDTLSE (SEQ ID NO: 38) | RRWTLVG (SEQ ID NO: 39) |
| ZFP-32 | 30667 | RSDTLSE (SEQ ID NO: 38) | RRWTLVG (SEQ ID NO: 39) | 1c | QSSDLSR (SEQ ID NO: 30) | HRSTRNR (SEQ ID NO: 37) | 2f | RSDTLSE (SEQ ID NO: 38) | RRWTLVG (SEQ ID NO: 39) |
| ZFP-33 | 33062 | QSSDLSR (SEQ ID NO: 30) | HRSTRNR (SEQ ID NO: 37) | 0a | QSSDLSR (SEQ ID NO: 30) | N/A | N/A | N/A | N/A |
| ZFP-34 | 33063 | QSSDLSR (SEQ ID NO: 30) | QSSDLRR (SEQ ID NO: 40) | 0a | QSSDLSR (SEQ ID NO: 30) | N/A | N/A | N/A | N/A |
| ZFP-35 | 33064 | QSSDLSR (SEQ ID NO: 30) | n/a | 0a | QSSDLSR (SEQ ID NO: 30) | QSSDLRR (SEQ ID NO: 40) | N/A | N/A | N/A |
| ZFP-36 | 33084 | QSSDLSR (SEQ ID NO: 30) | HRSTRNR (SEQ ID NO: 37) | 2f | RSDTLSE (SEQ ID NO: 38) | RRWTLVG (SEQ ID NO: 39) | N/A | N/A | N/A |
| ZFP-37 | 33086 | RSDTLSE (SEQ ID NO: 38) | RRWTLVG (SEQ ID NO: 39) | 1c | QSSDLSR (SEQ ID NO: 30) | n/a | 2f | RSDTLSE (SEQ ID NO: 38) | RRWTLVG (SEQ ID NO: 39) |
| ZFP-38 | 33087 | QSSDLSR (SEQ ID NO: 30) | HRSTRNR (SEQ ID NO: 37) | 2f | RSDTLSE (SEQ ID NO: 38) | RRWTLVG (SEQ ID NO: 39) | 1c | QSSDLSR (SEQ ID NO: 30) | N/A |
| ZFP-39 | 33088 | QSSDLSR (SEQ ID NO: 30) | HRSTRNR (SEQ ID NO: 37) | 2f | RSAVLSE (SEQ ID NO: 41) | n/a | 1c | QSSDLSR (SEQ ID NO: 30) | HRSTRNR (SEQ ID NO: 37) |
| ZFP-40 | 33089 | QSSDLSR (SEQ ID NO: 30) | HRSTRNR (SEQ ID NO: 37) | 2f | RSDVLSE (SEQ ID NO: 42) | n/a | 1c | QSSDLSR (SEQ ID NO: 30) | n/a |
| ZFP-41 | 33090 | RSDVLSE (SEQ ID NO: 42) | n/a | 1c | QSSDLSR (SEQ ID NO: 30) | HRSTRNR (SEQ ID NO: 37) | 2f | RSDVLSE (SEQ ID NO: 42) | n/a |
|  | 45249 | DTGLLNR (SEQ ID NO: 69) | QSGDLTR (SEQ ID NO: 32) | 0c | DTGLLNR (SEQ ID NO: 69) | QSGDLTR (SEQ ID NO: 32) | 2f | KRCNLRC (SEQ ID NO: 34) | SSYNLKT (SEQ ID NO: 70) |

TABLE 2

Zinc Finger Target Sites

| ID | AKA | Strand | Size | Binding Site (upper case shows contacted nucleotides) | SEQ ID NO. |
|---|---|---|---|---|---|
| ZFP-1 | | Top | 6F | GCAGCAGCAGCAGCAGCA | 43 |
| ZFP-2 | ZFP-A | Top | 5F | GCAGCAGCAGCAGCA | 44 |
| ZFP-3 | | Top | 5F | GCAGCAGCAGCAGCA | 44 |
| ZFP-4 | | Top | 5F | GCAGCAGCAGCAGCA | 44 |
| ZFP-5 | | Top | 6F | GCAGCAGCAGCAgCAGCAG | 45 |
| ZFP-6 | | Top | 6F | GCAGCAgCAGCAGCAGCAG | 45 |
| ZFP-7 | ZFP-D | Top | 5F | GCAGCAGCAgCAGCAG | 46 |
| ZFP-8 | | Top | 5F | GCAGCAGCAgCAGCAG | 46 |
| ZFP-9 | | Top | 6F | GCAGCAgCAGCAGcaGCAGCA | 47 |
| ZFP-10 | | Top | 5F | GCAGCAgcAGCAgCAGCAG | 45 |
| ZFP-11 | | Top | 4F | GCAGCAgcAGCAGC | 90 |
| ZFP-12 | | Top | 6F | GCAGCAgCAGCAGcaGCAGCA | 47 |
| ZFP-13 | | Top | 4F | GCAGCAgCAGCAG | 48 |
| ZFP-14 | | Top | 4F | GCAGCAgCAGCAG | 48 |
| ZFP-15 | ZFP-C | Top | 6F | CAGCAGCAGCAGCAGCAG | 49 |
| ZFP-16 | | Top | 6F | CAGCAGcaGCAGCAGCAGCA | 50 |
| ZFP-17 | | Top | 6F | CAGCAGCAGCAGcaGCAGCA | 50 |
| ZFP-18 | | Top | 6F | CAGCAGcaGCAGCAgCAGCAG | 51 |
| ZFP-19 | ZFP-B | Top | 6F | CAGCAGcaGCAGCAgCAGCAG | 51 |
| ZFP-20 | | Top | 5F | CAGCAGcAGCaGCAGCA | 52 |
| ZFP-21 | | Top | 4F | CAGCAGcaGCAGCA | 53 |
| ZFP-22 | | Bottom | 6F | GCTGCTGCTGCTGCTGCT | 54 |
| ZFP-23 | | Bottom | 6F | GCTGCTGCTGCTgCTGCTG | 55 |
| ZFP-24 | | Bottom | 5F | GCTGCTGCTGCTGCT | 56 |
| ZFP-25 | | Bottom | 5F | GCTGCTGCTGCTGCT | 56 |
| ZFP-26 | | Bottom | 5F | GCTGCTGCTGCTGCT | 56 |
| ZFP-27 | | Bottom | 6F | GCTGCTgCTGCTGCTGCTG | 55 |
| ZFP-28 | | Bottom | 5F | GCTGCTGCTgCTGCTG | 57 |
| ZFP-29 | | Bottom | 5F | GCTGCTGCTgCTGCTG | 57 |
| ZFP-30 | | Bottom | 6F | CTGCTGCTGCTGCTGCTG | 58 |
| ZFP-31 | | Bottom | 6F | CTGCTGctGCTGCTGCTGCT | 59 |
| ZFP-32 | | Bottom | 6F | CTGCTGctGCTGCTgCTGCTG | 60 |
| ZFP-33 | | Bottom | 3F | GCTGCTGCT | 61 |
| ZFP-34 | | Bottom | 3F | GCTGCTGCT | 61 |
| ZFP-35 | | Bottom | 3F | GCTGCTGCT | 61 |
| ZFP-36 | | Bottom | 4F | CTGCTGctGCTGCT | 62 |
| ZFP-37 | | Bottom | 5F | CTGCTGctGCTgCTGCTG | 58 |
| ZFP-38 | | Bottom | 5F | GCTgCTGCTGctGCTGCT | 54 |

TABLE 2-continued

Zinc Finger Target Sites

| ID | AKA | Strand | Size | Binding Site (upper case shows contacted nucleotides) | SEQ ID NO. |
|---|---|---|---|---|---|
| ZFP-39 | | Bottom | 5F | GCTGCTgCTGctGCTGCT | 54 |
| ZFP-40 | | Bottom | 4F | GCTgCTGctGCTGCT | 56 |
| ZFP-41 | | Bottom | 4F | CTGctGCTGCTgCTG | 63 |
| 45249 | | Top | 6F | CAGCAGcaGCAGCAGCAGCA | 68 |

Figure 1D:
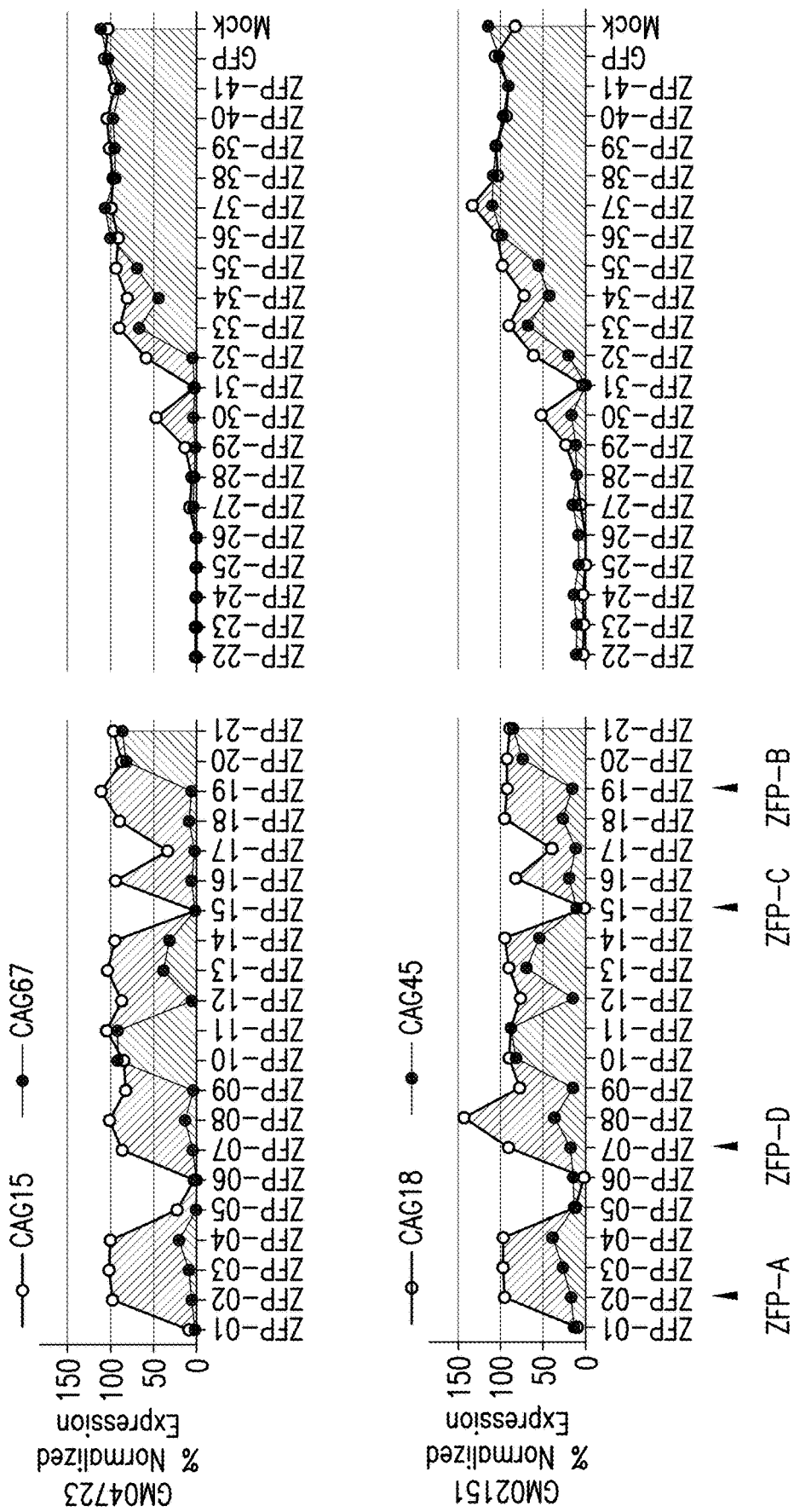
Figure 6A:
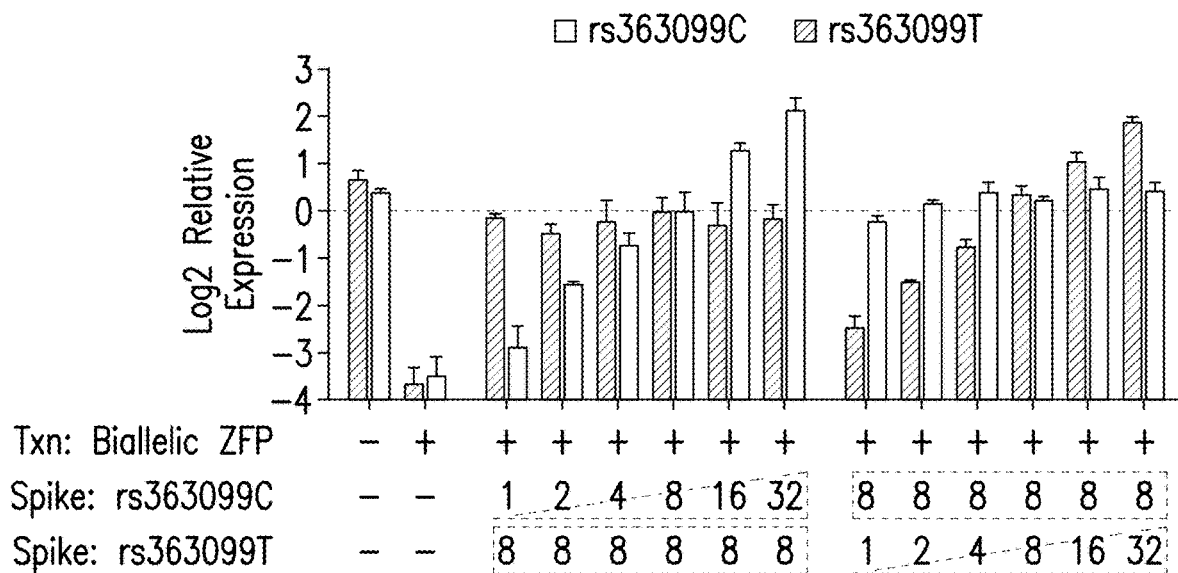
FIGS. 6A and 6B show validation of allele-specific qRT-PCR assays.
Figure 6B:
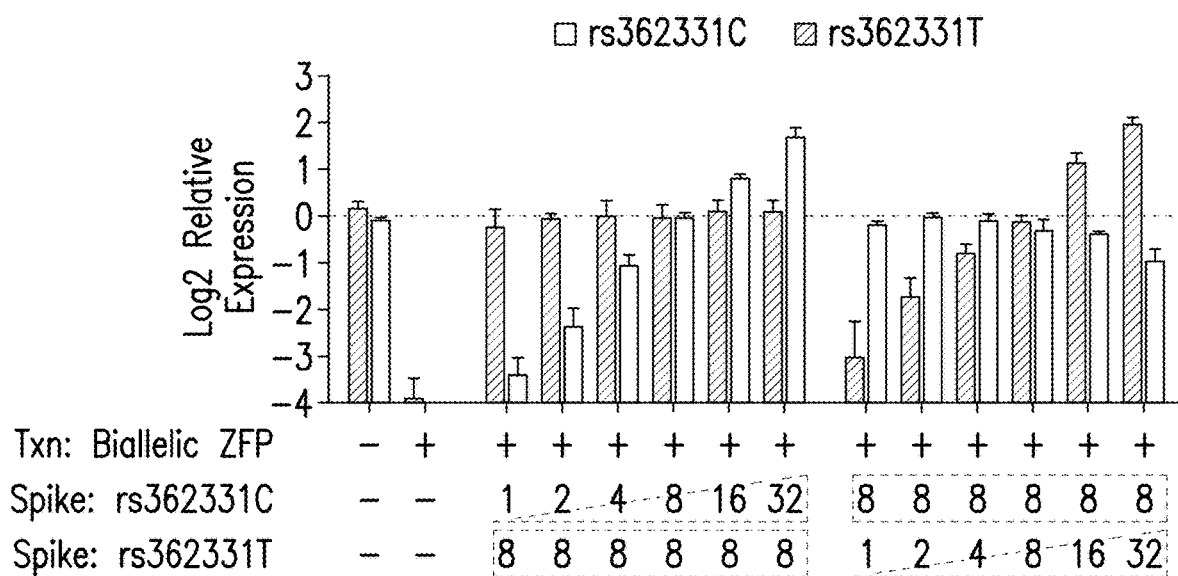
Figure 7A:
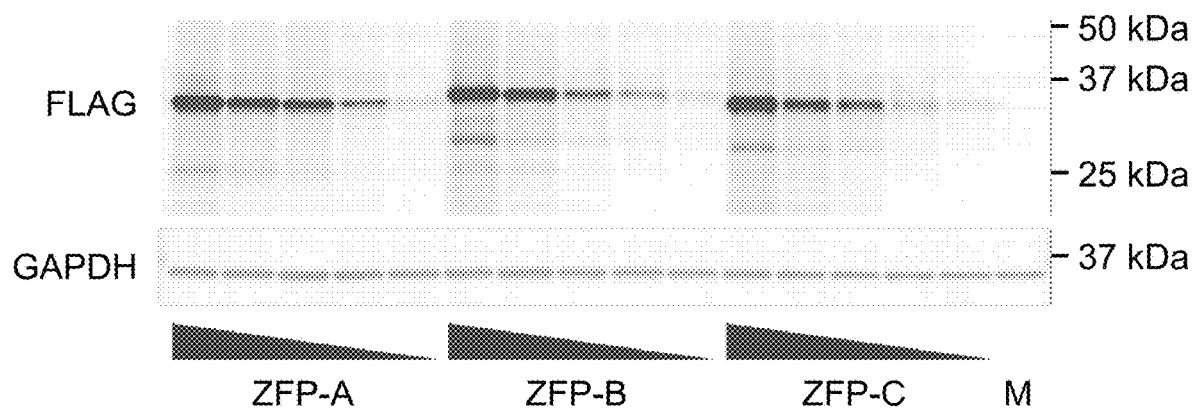
FIGS. 7A and 7B show dose-dependent ZFP protein expression over 100-fold of transfected ZFP mRNA.
Figure 7B:
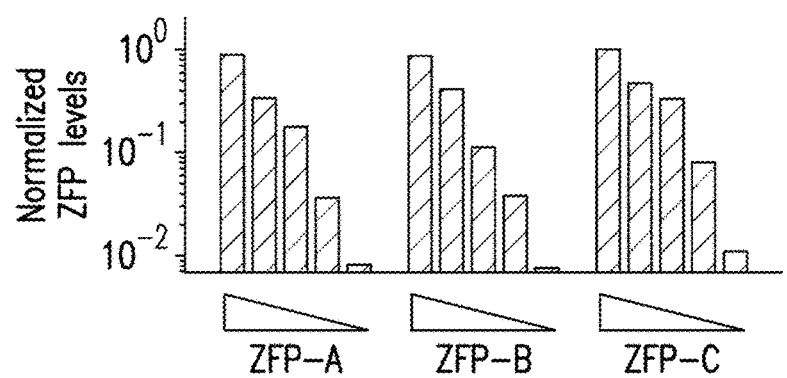

*nucleotides in upper case are contacted by the DNA-binding domain; lowercase shows un-contacted nucleotides These proteins were then screened for allele selective repression when delivered via RNA nucleofection into fibroblast cells from two different HD patients, each bearing a distinct combination of mutant and wild type poly-CAG tract lengths (FIG. 1D). Independent monitoring of wild type and mutant transcript levels was accomplished via SNP-based allele-specific qRT-PCR (FIG. 1A and FIG. 6).

This screen yielded a diverse range of Htt repression behaviors, including clear evidence of allele specificity for some of the designs (see, e.g., FIG. 1D).

Example 3: Allele-Selective Repression of mHTT Over a Broad ZFP Dose Range

We next extended assessed dose ranges compatible with allele-specific repression, as well via quantitation of Htt protein product using two ZFP-TFs that selectively repressed the mutant allele in the initial screen (ZFP-A and ZFP-B, FIG. 1C). Full sequences for ZFP-A through ZFP-D are provided in Table 3 below.

TABLE 3

Amino acid sequences for ZFP-A, ZFP-B, ZFP-C and ZFP-D

| ZFP ID | AKA | AA sequence (helix, intramodule linker, intermodule linker) |
|---|---|---|
| ZFP-A | ZFP-02 | MAPKKKRKVGIHGVPAAMAERPFQCRICMRNFSQSSDLSRHIRTHTG EKPFACDICGRKFAQWSTRKRHTKIHTGSQKPFQCRICMRNFSQSSDL SRHIRTHTGEKPFACDICGRKFAQWSTRKRHTKIHTGEKPFQCRICMRK FAQSGDLTRHTKIHLRQKDAARGSGMDAKSLTAWSRTLVTFKDVFVD FTREEWKLLDTAQQIVYRNVMLENYKNLVSLGYQLTKPDVILRLEKGEE PWLVEREIHQETHPDSETAFEIKSSV (SEQ ID NO: 64) |
| ZFP-B | ZFP-19 | MAPKKKRKVGIHGVPAAMAERPFQCRICMRNFSRSDNLSEHIRTHTG EKPFACDICGRKFAKRCNLRCHTKIHTHPRAPIPKPFQCRICMRNFSQS GDLTRHIRTHTGEKPFACDICGRKFAQSGDLTRHTKIHTPNPHRRTDPS HKPFQCRICMRNFSRSDNLSEHIRTHTGEKPFACDICGRKFAKRCNLRC HTKIHLRQKDAARGSGMDAKSLTAWSRTLVTFKDVFVDFTREEWKLLD TAQQIVYRNVMLENYKNLVSLGYQLTKPDVILRLEKGEEPWLVEREIHQ ETHPDSETAFEIKSSV (SEQ ID NO: 65) |
| ZFP-C | ZFP-15 | MAPKKKRKVGIHGVPAAMAERPFQCRICMRNFSRSDNLSEHIRTHTG EKPFACDICGRKFAKRCNLRCHTKIHTGSQKPFQCRICMRNFSRSDNLS EHIRTHTGEKPFACDICGRKFAKRCNLRCHTKIHTGSQKPFQCRICMRN FSRSDNLSEHIRTHTGEKPFACDICGRKFAKRCNLRCHTKIHLRQKDAA RGSGMDAKSLTAWSRTLVTFKDVFVDFTREEWKLLDTAQQIVYRNVM LENYKNLVSLGYQLTKPDVILRLEKGEEPWLVEREIHQETHPDSETA-FEIK SSV (SEQ ID NO: 66) |
| ZFP-D | ZFP-07 | MAPKKKRKVGIHGVPAAMAERPFQCRICMRNFSRSDNLSEHIRTHTG EKPFACDICGRKFAKRCNLRCHTKIHTHPRAPIPKPFQCRICMRNFSQSS DLSRHIRTHTGEKPFACDICGRKFAQWSTRKRHTKIHTGEKPFQCRICM RKFAQSGDLTRHTKIHLRQKDAARGSGMDAKSLTAWSRTLVTFKDVF VDFTREEWKLLDTAQQIVYRNVMLENYKNLVSLGYQLTKPDVILRLEKG EEPWLVEREIHQETHPDSETAFEIKSSV (SEQ ID NO: 67) |

Figure 1E:
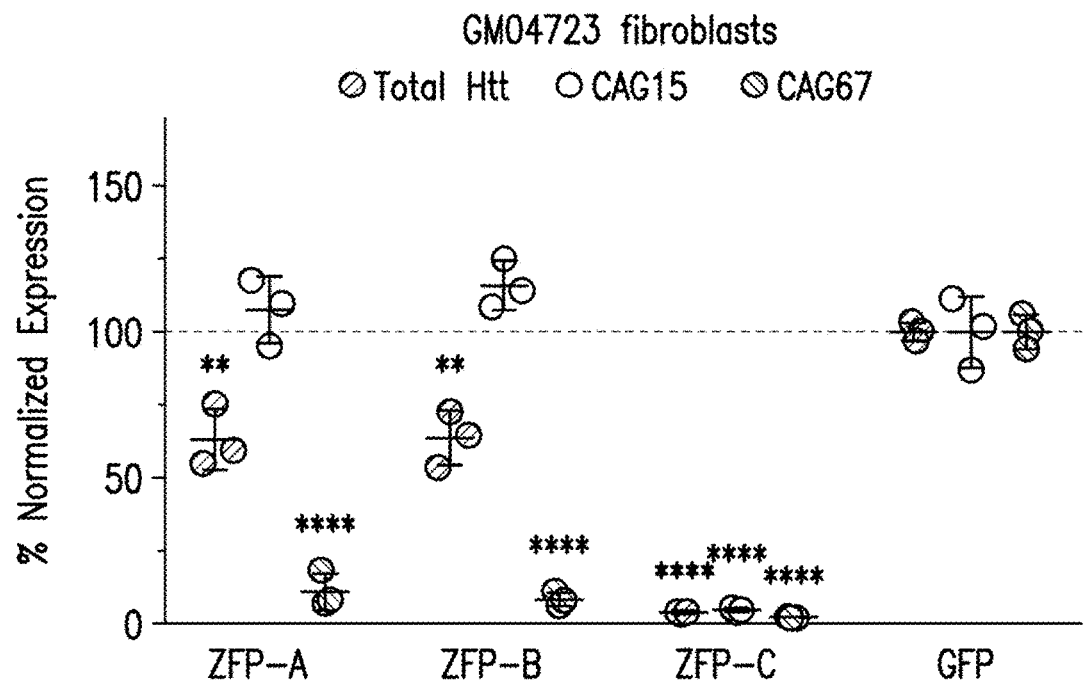
Figure 1F:
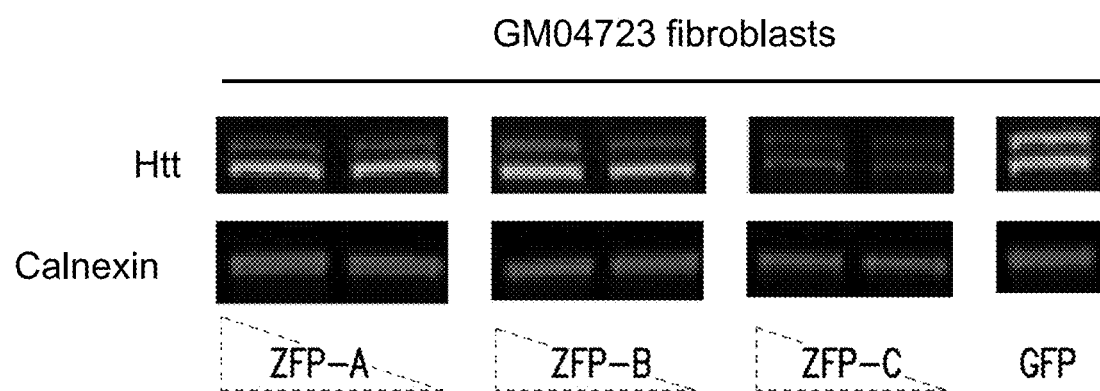

As shown in FIG. 1E, in studies in CAG15/67 (SEQ ID NOS:81/82) fibroblasts, both ZFP-A and ZFP-B ZFP-TFs exhibited exclusive repression of the expanded allele. Moreover, as shown in FIG. 1F, both repressors were shown to selectively reduce only the mHtt protein as gauged via Western blot (FIG. 1F, compare upper (mHtt) vs lower (wtHtt) bands.

Next, we evaluated these ZFP-TFs in a titration study as described above.

Figure 1G:
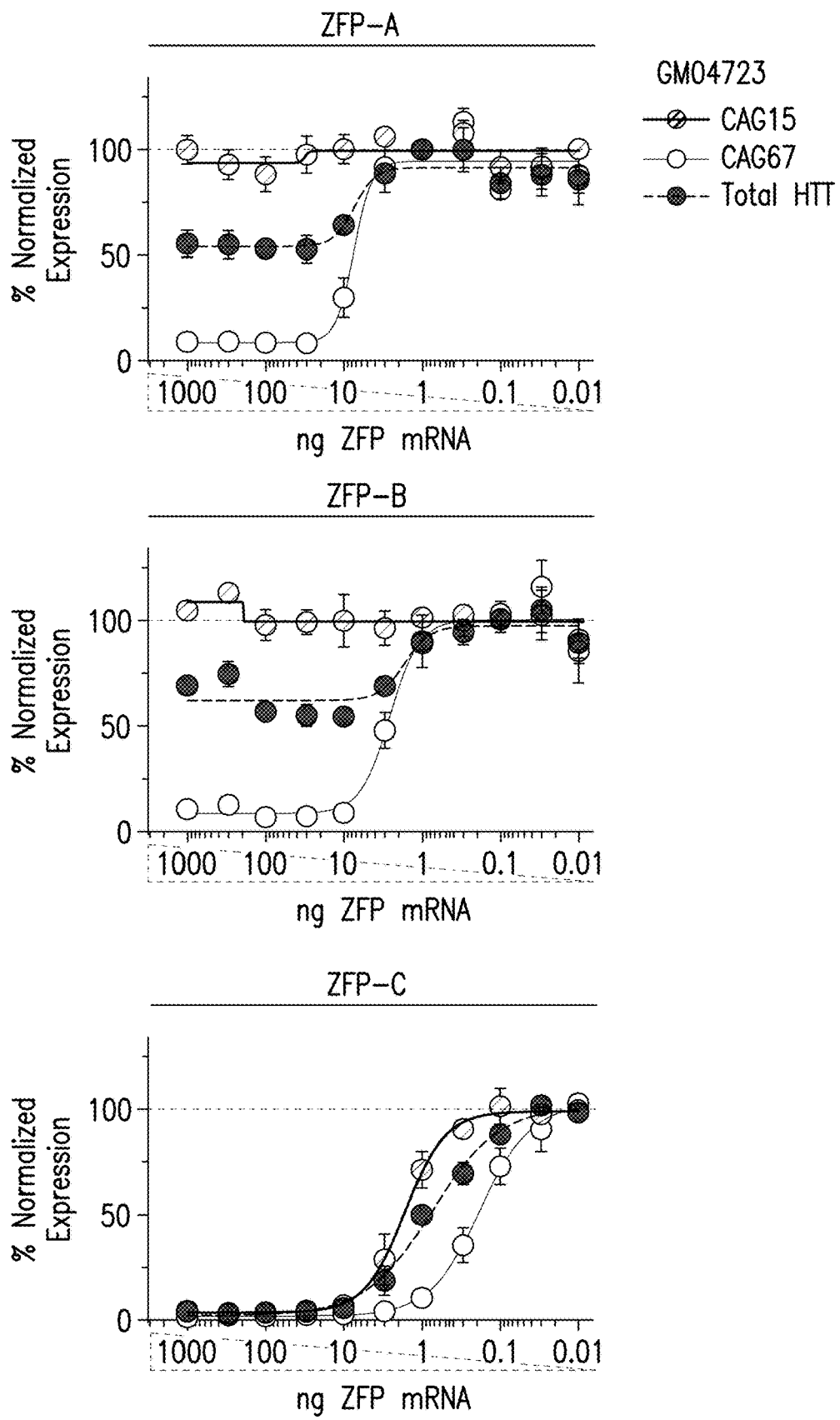

As shown in FIG. 1G, allele specific repression over a wide dose range was observed. ZFP-B in particular exhibited >92% repression of the disease allele over a 100-fold range of delivered RNA dose (10 ng-1000 ng of delivered RNA) with an $EC_{50}$ of 2.58 ng ($R^2$ 0.96) and no repression of the wild type HTT. Notably, ZFP expression mirrored delivered RNA levels across this dosing range. Together, these studies established that a designed ZFP-TF could exclusively downregulate mHTT transcript over a 100-fold range of ZFP expression, leading to selective reduction in the mHTT protein product.

Example 4: Allele-Selective Repression Across Diverse HD Genotypes

Figure 1H:
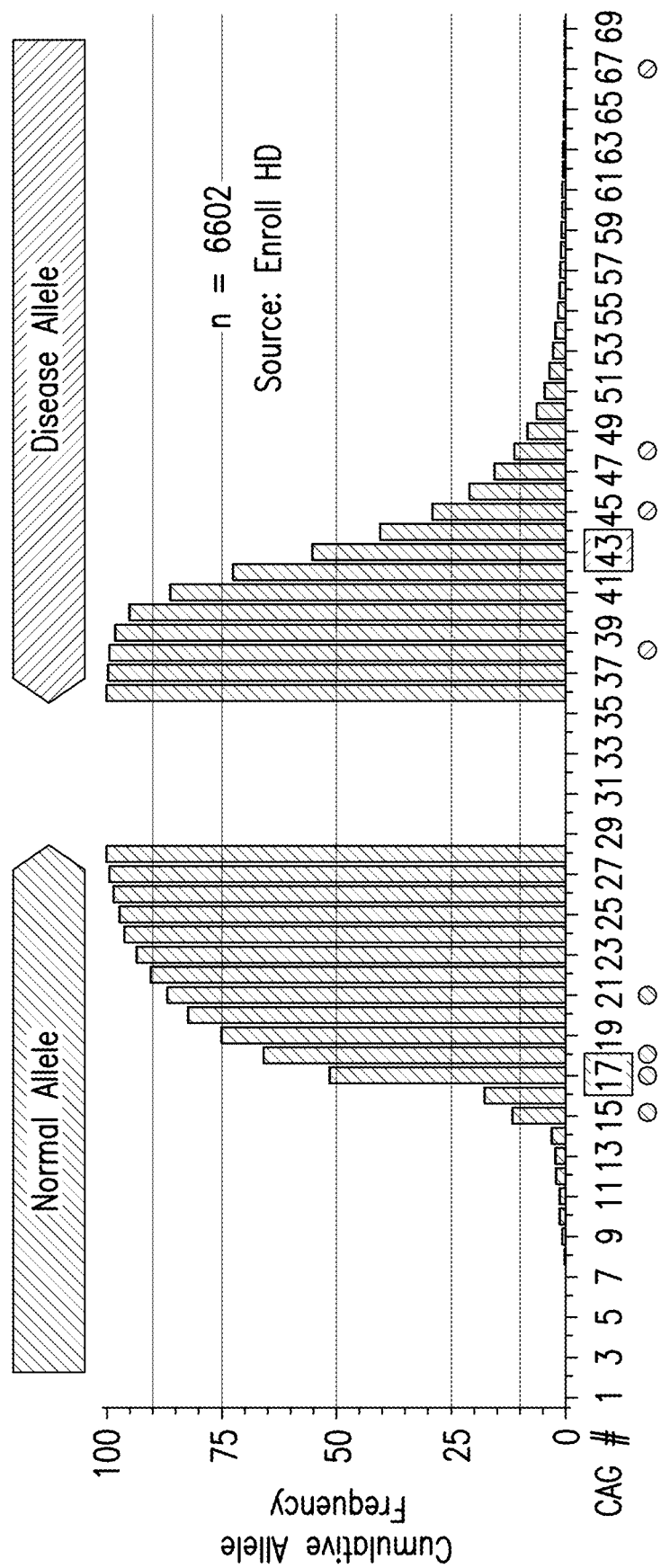
Figure 1I:
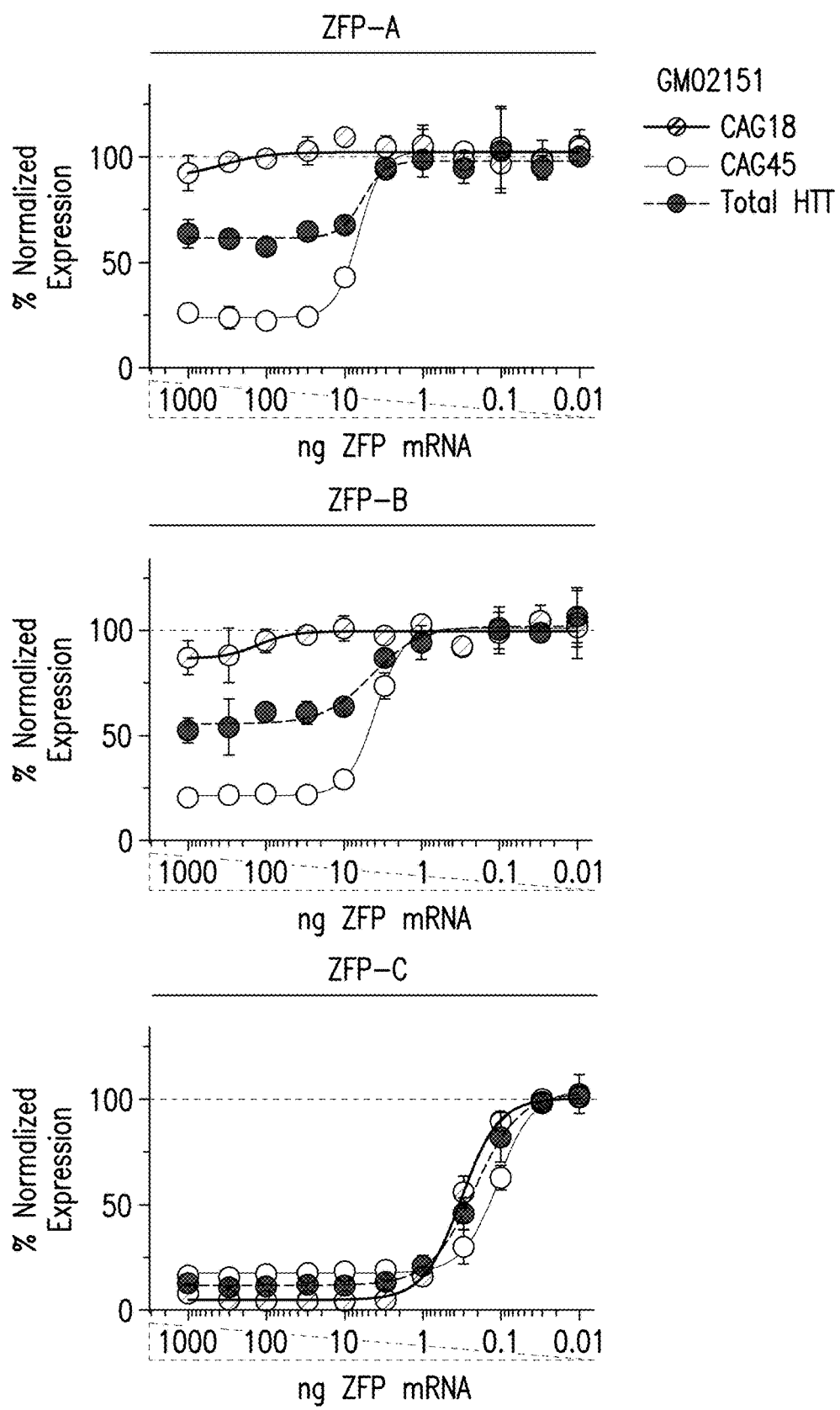

We next performed titration studies in fibroblasts bearing poly-CAG tracts that representative of the HD population (FIG. 1H). To accomplish this, repressors ZFP-A and ZFP-B were first assessed in GM02151 fibroblasts, which exhibit poly-CAG tracts of 18 (SEQ ID NO:79) and 45 repeats (SEQ ID NO:80).

As shown in FIG. 1G, ZFP-A and ZFP-B selectively repressed mHTT over a ~100 fold dose range with <15% repression of the CAG18 (SEQ ID NO:79) allele seen at any dose.

In addition, the effect of the repressors was also examined in patient fibroblasts that have an atypically narrow separation between wild type and mutant poly-CAG tract lengths, 21 (SEQ ID NO:83) and 38 repeats (SEQ ID NO:84).

Figure 1J:
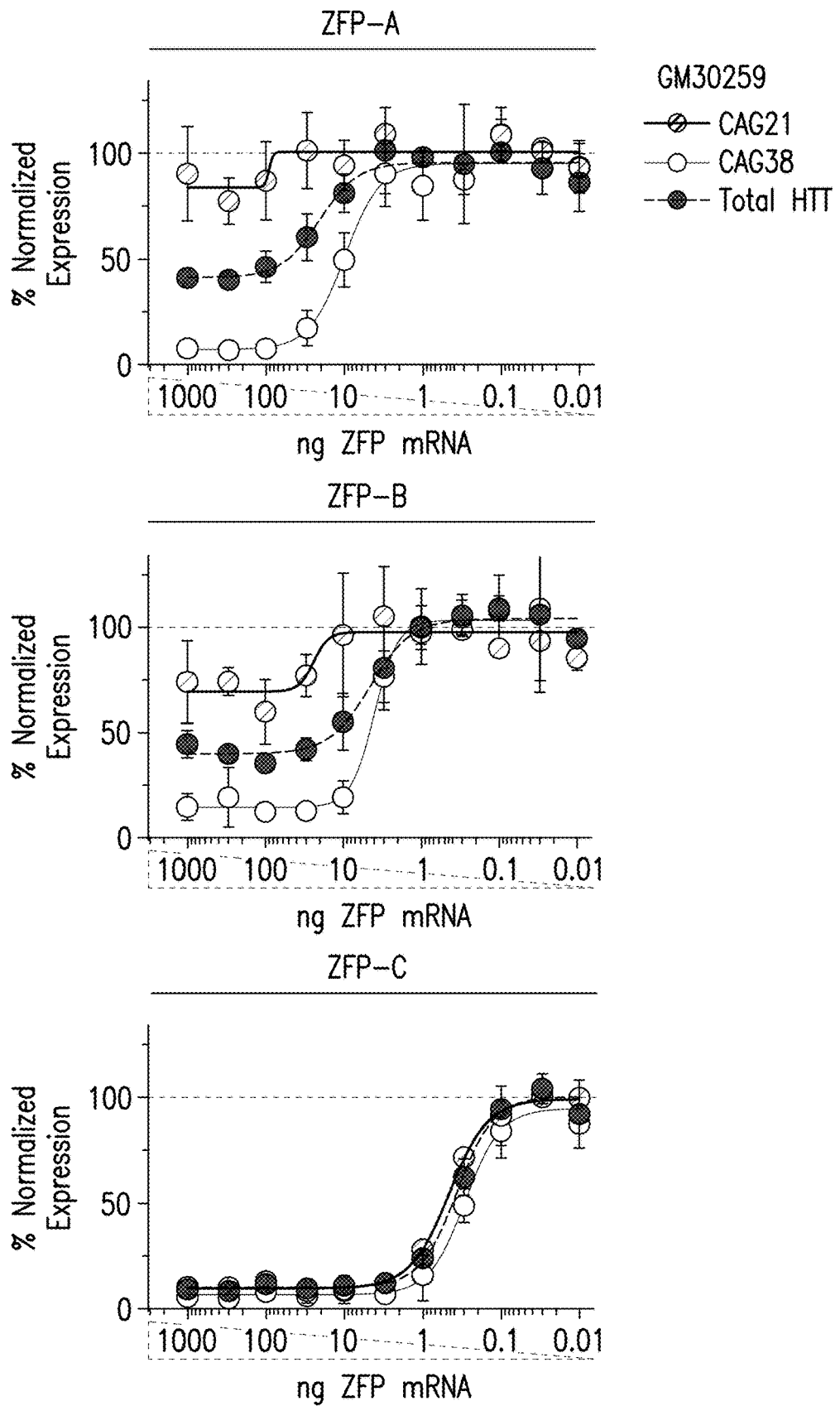
Figure 1K:
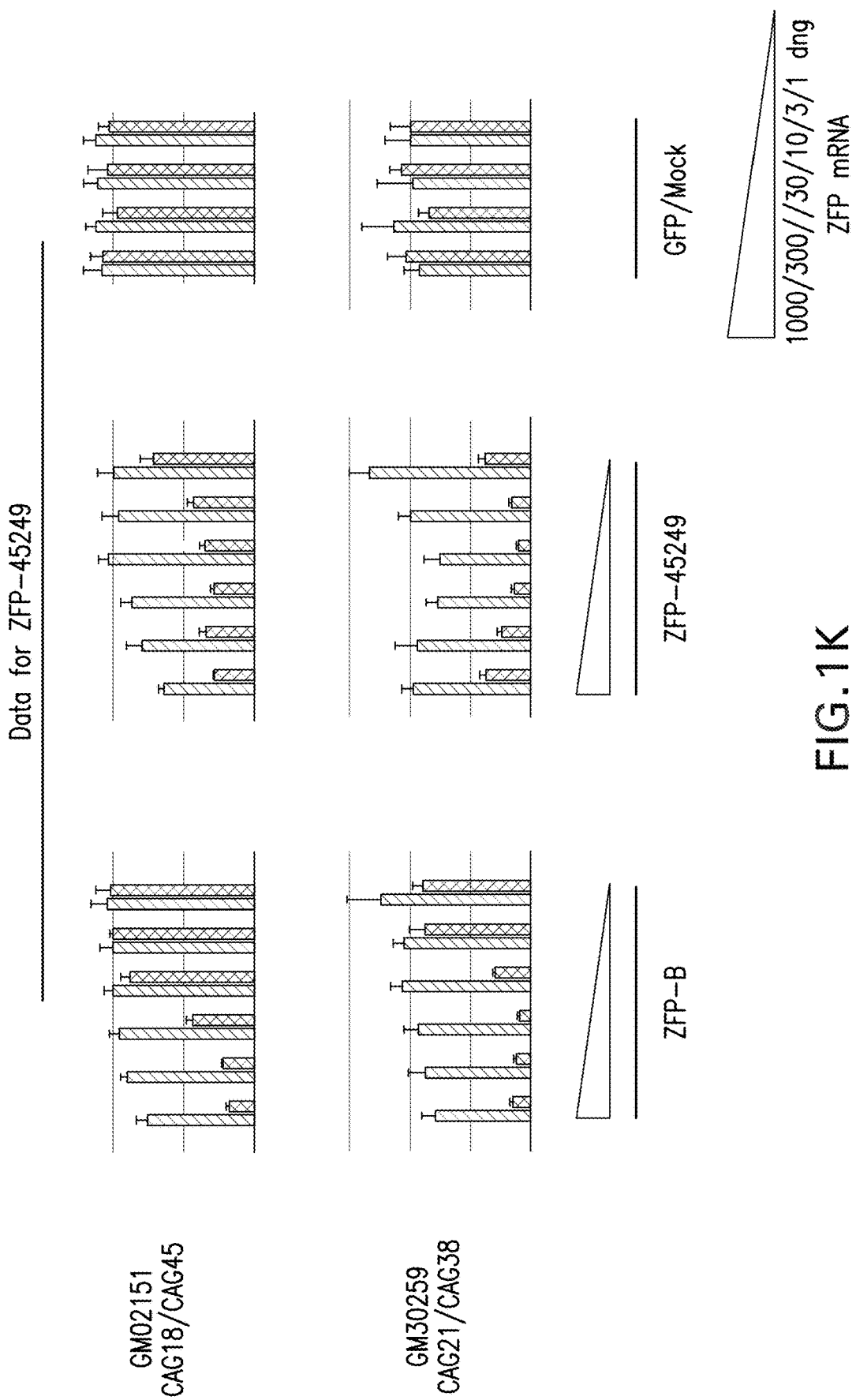

As shown in FIG. 1H, ZFP-A and ZFP-B drove selective and potent repression of the CAG38 allele (SEQ ID NO:84) (up to 93% reduction) over a 100-fold dose (ZFP-A EC50=9.8 ng, R2=0.94; ZFP-B EC50=3.9 ng R2=0.94), albeit with some repression of the CAG21 allele (SEQ ID NO:83) (generally <25%) seen at higher doses (FIG. 1J).

These results confirmed that designed genetic repressors as described herein can drive endogenous allele-selective repression over a 100-fold range of ZFP levels, which is substantially larger than previously demonstrated for other modalities targeted to the poly-CAG (e.g. ASO or RNAi, see Gagnon et al., ibid; Hu et al., ibid; and Yu et al., ibid). Moreover, by bracketing the allele lengths that are susceptible to repression (CAG≥38) or resistant to repression (CAG≤21) these studies highlight the ability of ZFP-A and ZFP-B to downregulate 100% of fully penetrant mutant alleles (CAG>39), while discriminating against at least 87% of normal alleles found in HD patients (FIG. 1H).

Figure 8A:
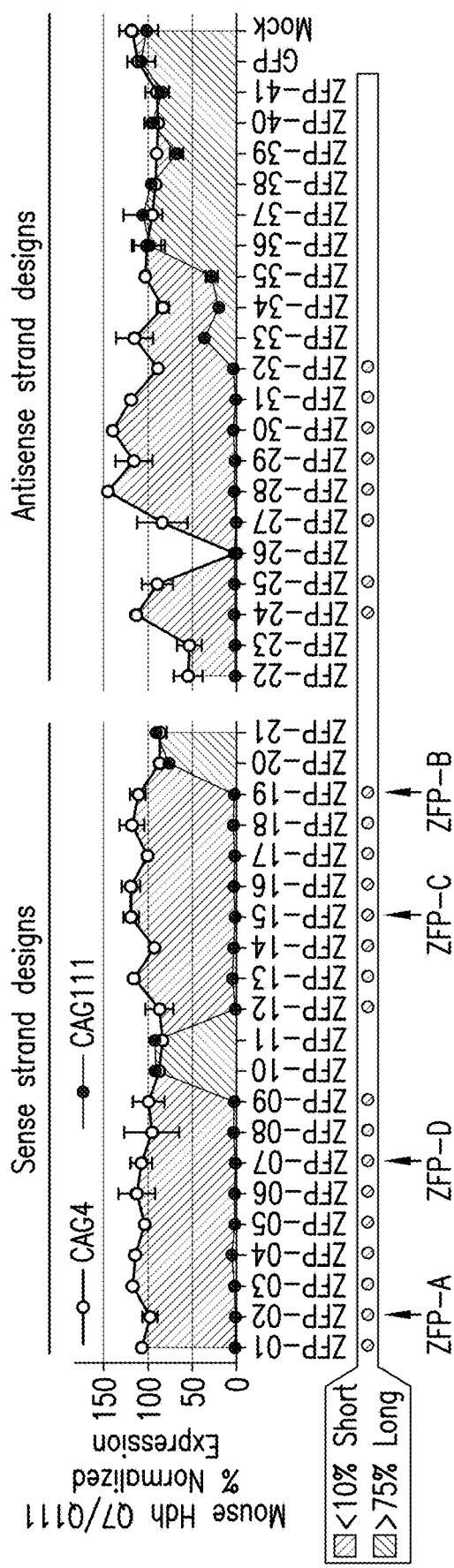
FIGS. 8A and 8B show testing of candidate ZFP designs in Hdh Q7/Q111 striatal cells.
Figure 8B:
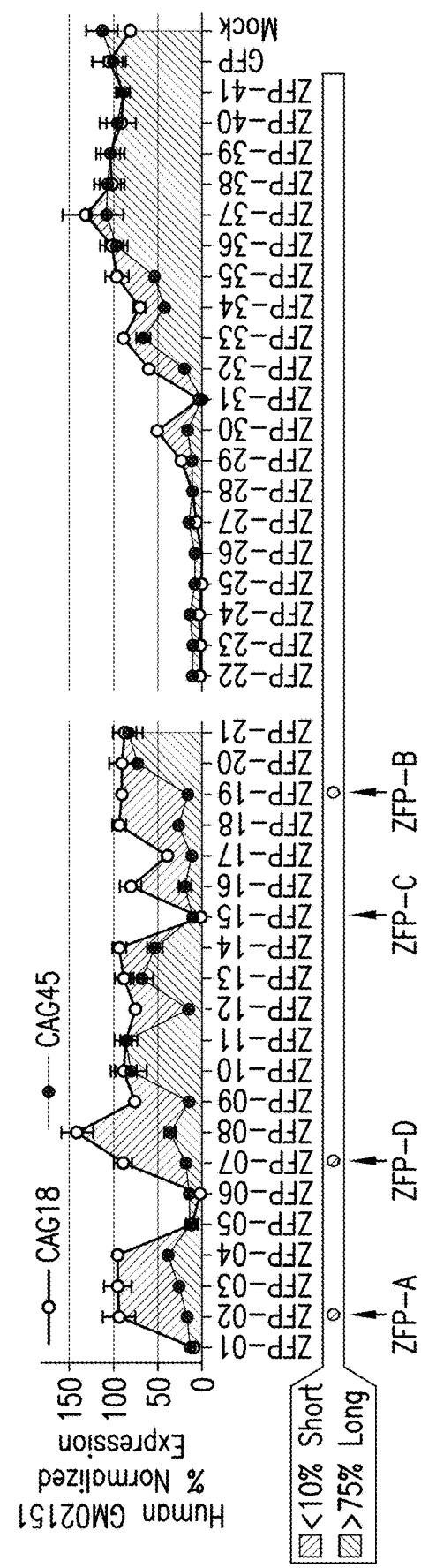
Figure 9:
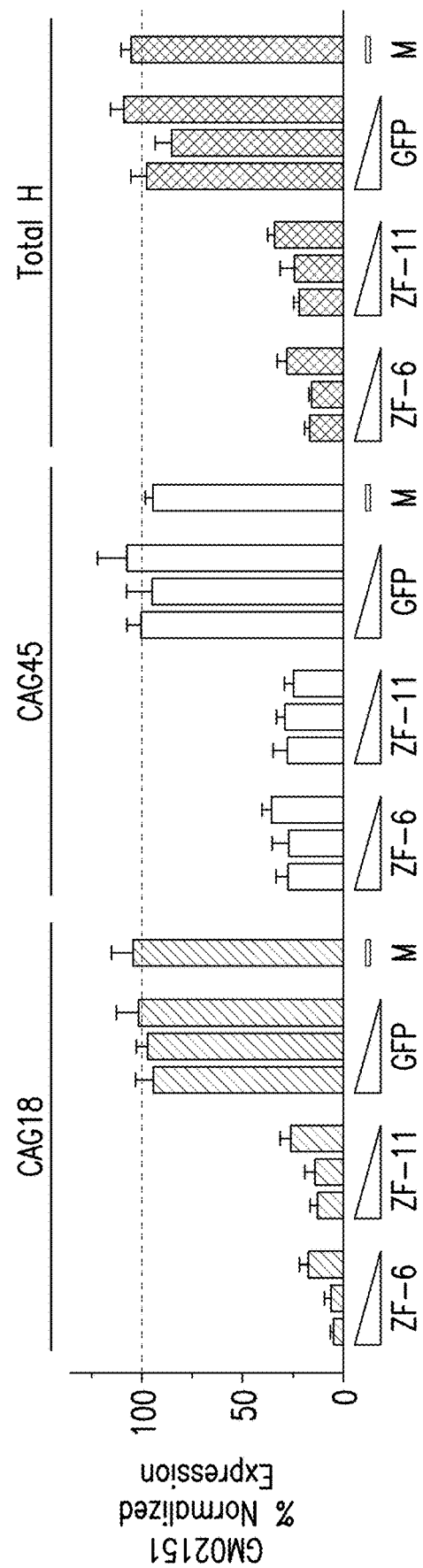
FIG. 9 shows testing of CAG-targeted ZFPs from Garriga-Canut et al. (2012) *Proc Natl Acad Sci USA* 109(45): e3136-45 in HD fibroblasts and shows a comparison of allele-selective repression in patient fibroblasts (CAG 18/45 (SEQ ID NOS 79/80)) from a prior study (ZF6 and ZF11, see Garriga-Canut et al. (2012) *Proc Natl Acad Sci USA* 109(45):e3136-45)). Allele-specific qRT-PCR for total, WT (CAG18 (SEQ ID NO: 86)) and mutant (CAG45 (SEQ ID NO: 87)) HTT mRNA at 24 hours after transfection of GM02151 fibroblasts with either 1000, 300, or 100 ng of ZFP mRNA. HTT expression was normalized as in (FIG. 1D). The published ZF6-Kox and ZF11-Kox sequences were cloned into the same expression cassette used in the current study and in vitro transcribed mRNA for all ZFPs tested in FIG. 1D were prepared in parallel; n=3 technical replicates; mean±SD.
Figure 10A:
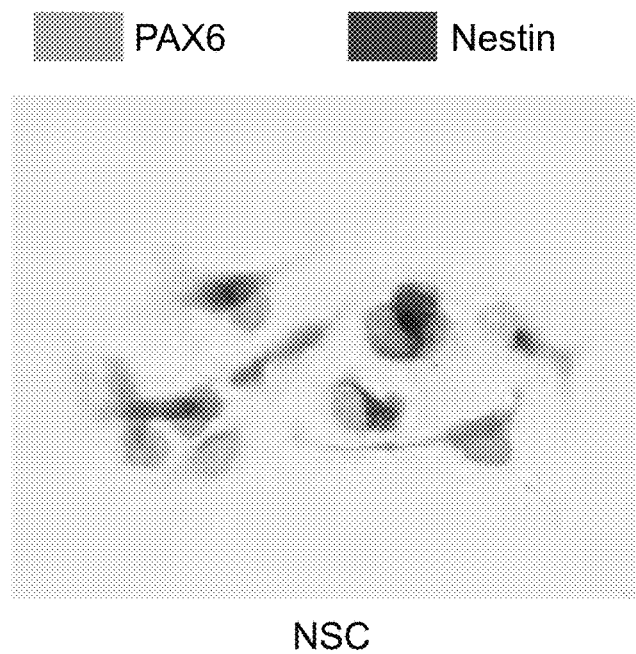
FIGS. 10A through 10D show expression of NSC and neuronal markers in differentiated CAG17/48 (SEQ ID NOS 76/78) hESCs.
Figure 10B:
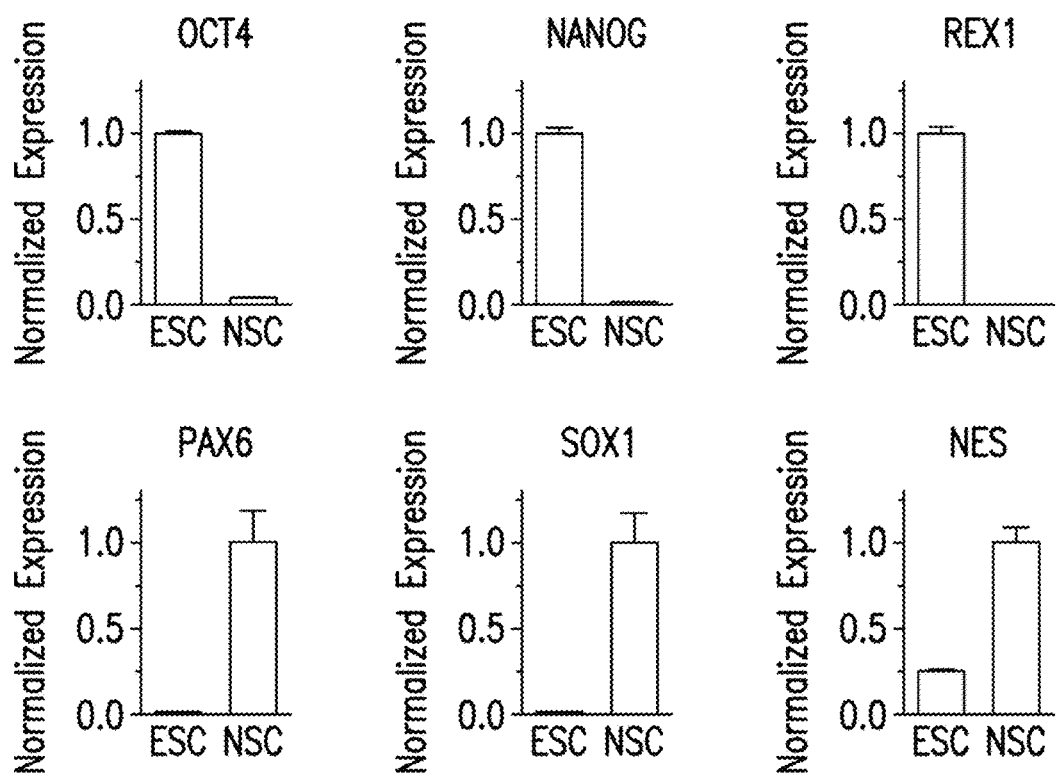
Figure 10C:
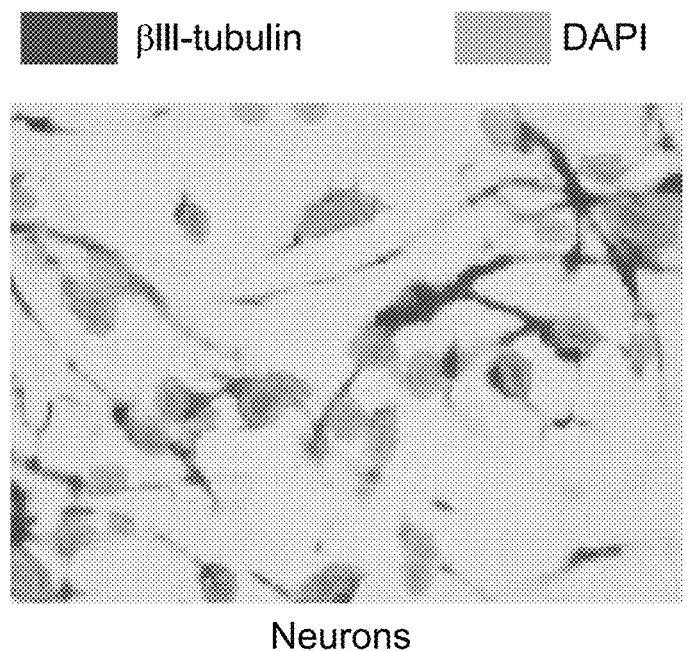
Figure 10D:
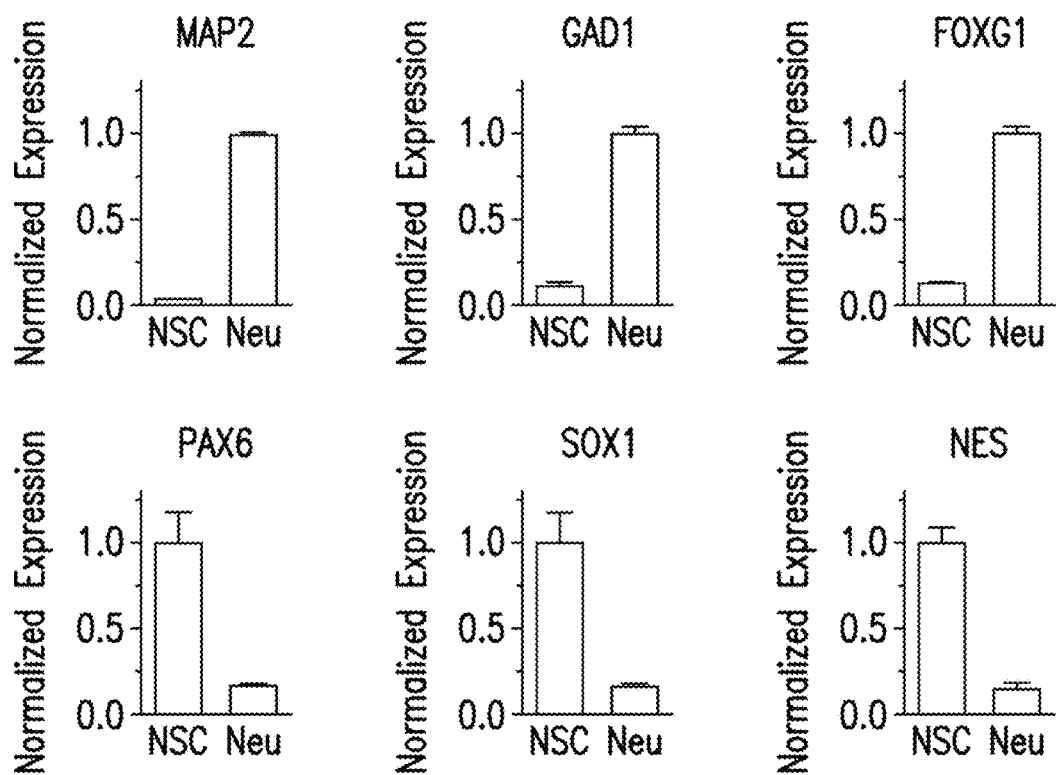

The high degree of allele-selectivity exhibited by ZFP-A and ZFP-B contrasted with the behavior of HTT repressors reported in a prior study (Garriga-Canut et al., ibid), which appeared much less sensitive to the length of the poly-CAG tract. We suspected that this distinction was due to our having screened for allele selectivity in a more stringent and disease-relevant setting (patient fibroblasts), which enabled us to distinguish rare repressors manifesting bona fide functional synergy from more common designs that discriminate alleles less effectively via simple mass action. Consistent with this, evaluation of our candidate designs in the mouse cell system of Garriga-Canut (HdhQ7/Q111, comprising contiguous CAG repeats alleles of 4 (SEQ ID NO:86) and 111 (SEQ ID NO:87), respectively) yielded a much higher frequency of apparently allele-selective hits, with 25 ZFP-TFs exhibiting >75% reduction of mHTT and <10% reduction of wild type HTT (FIG. 8). In contrast, only three ZFP-TFs yielded quantitatively comparable behavior in our more stringent patient fibroblast screening model (CAG 18/45 (SEQ ID NOS:79/80)). Consistent with this observation, a control ZFP (ZFP-C) that was allele-selective only in CAG 4/111 (SEQ ID NOS 86/87) cells was not allele-selective in the same follow up studies used to characterize ZFP-A and ZFP-B (see FIG. 1E to 1J). Finally, a direct evaluation of the two lead ZFPs from Garriga-Canut et al., ibid showed that neither exhibited allele-selectivity when tested in patient fibroblasts (GMO2151) bearing disease-relevant poly-CAG tracts (CAG 18/45 (SEQ ID NOS: 79/80)) (FIG. 9).

Example 5: Long-Term Allele-Selective Repression of mHTT and Improvement of HD-Related Phenotypes in Human Neurons and Mouse Striatum Since HD pathology is characterized by neuronal dysfunction, we performed a series of studies to assess ZFP performance in neural stem cells (NSCs) and neurons differentiated from a well-characterized line of CAG17/48 (SEQ ID NOS:76/78) embryonic stem cells (ESCs; Genea020) (FIG. 2A; FIG. 10). Initial studies queried for allele-specific repression as described above.

Figure 2A:
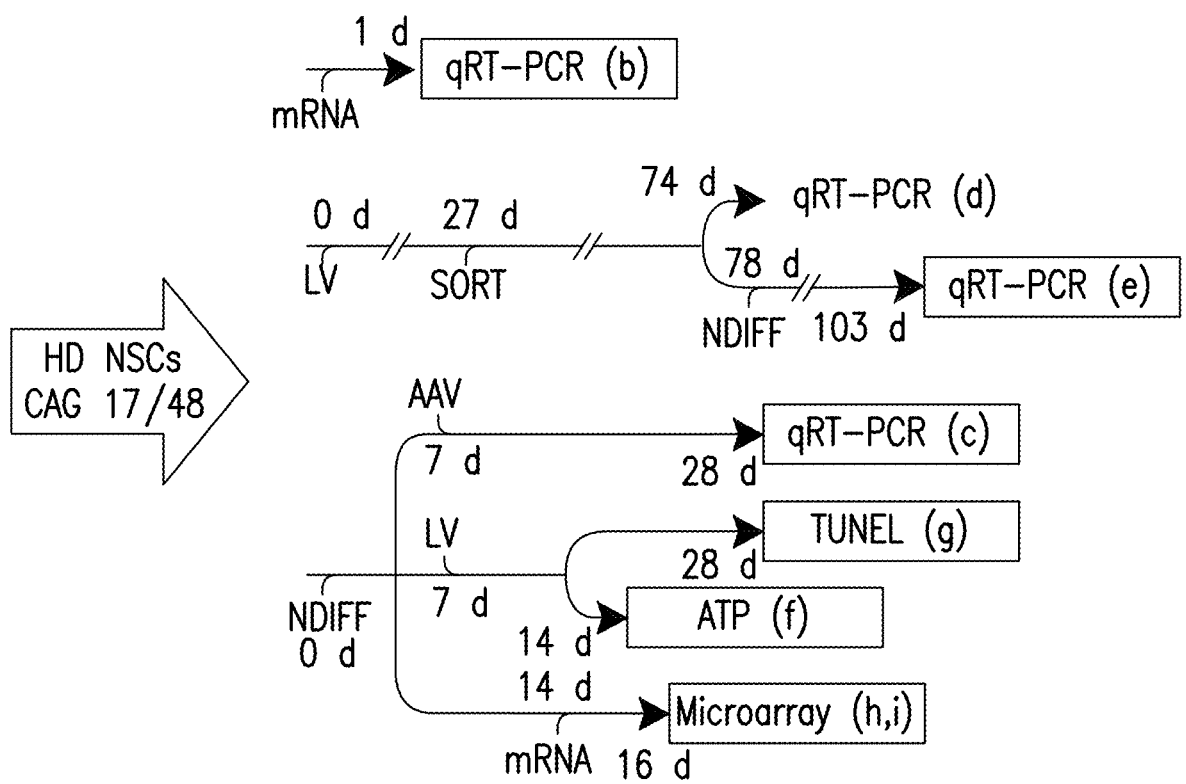
FIGS. 2A through 2N depict allele-selective repression, specificity and phenotypic correction in HD neurons.
Figure 2B:
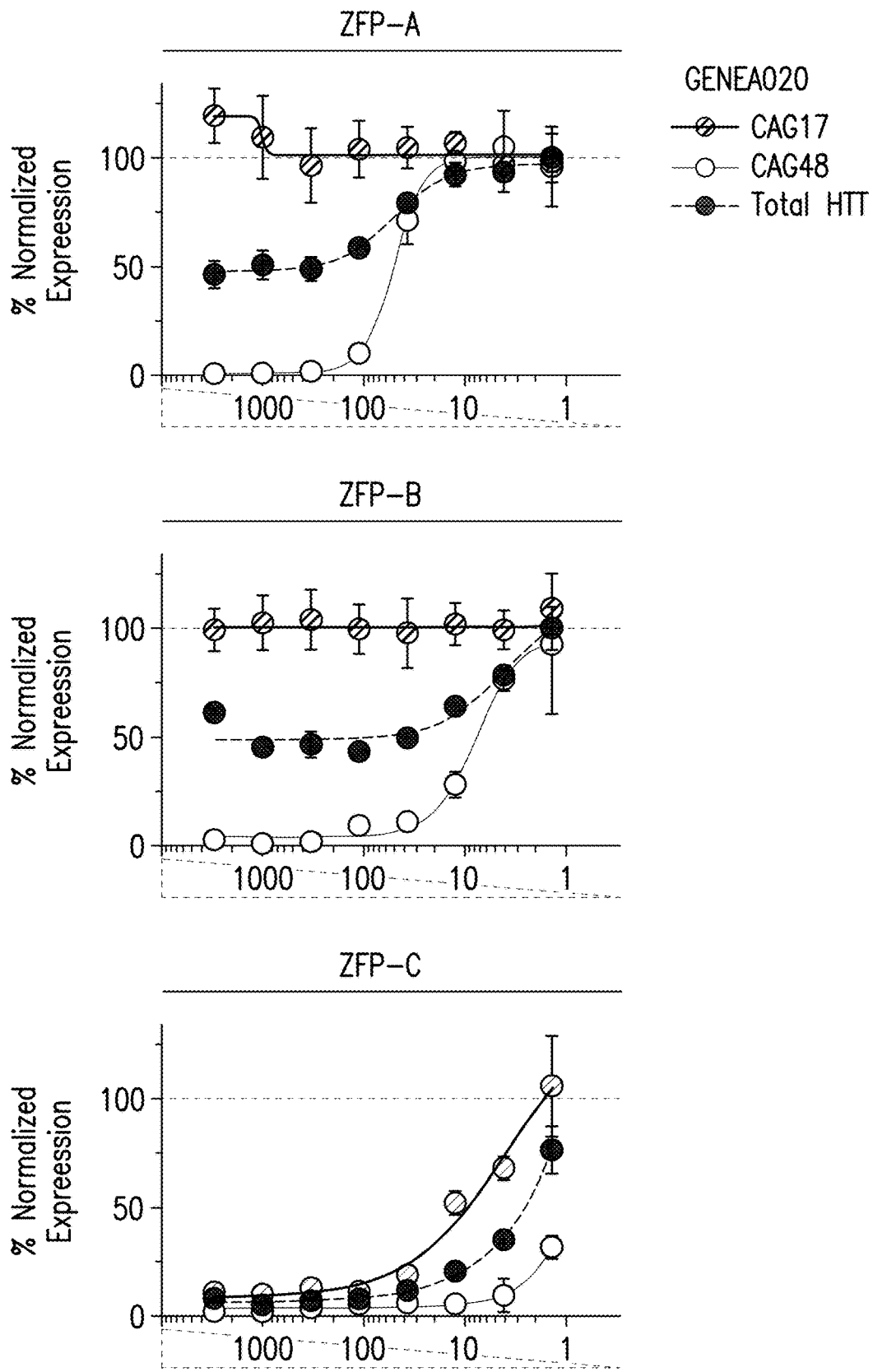
FIG. 2B shows a dose response of allele-specific repression in HD NSCs. Total HTT or SNP-specific (r5362307) qRT-PCR for WT (CAG17) and mutant (CAG48) HTT was performed on RNA isolated from NSCs transfected with ZFP mRNA across a 3,000-fold dose range (3,000-1 ng at ~half-log dose steps); n=3 biological replicates; mean±SD.
Figure 2C:
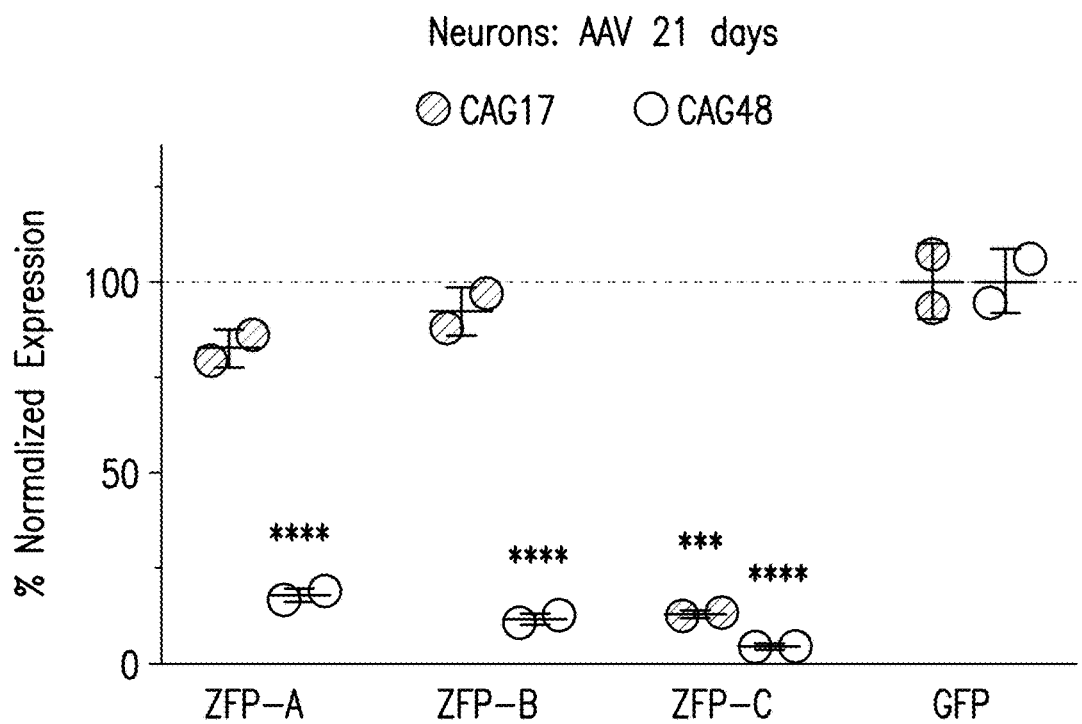
FIG. 2C depicts differentiated HD neurons that were infected with AAV6-ZFP or AAV6-GFP ($1\times10^5$ vg/cell) for 21 days. The figure shows qRT-PCR for WT and mHTT as in FIG. 2B; n=2 biological replicates; mean±SD.

As shown in FIG. 2B, delivery of ZFPs via transient mRNA transfection revealed allele-selective repression across a wide dosing range, similar to results as described in Example 1. ZFP-B in particular exhibited >90% repression of the disease allele over a 100-fold range of delivered RNA dose (30 ng-3000 ng) with no repression of the wild type HTT. In differentiated neurons, delivery of ZFPs via AAV transduction also yielded highly allele-specific repression (FIG. 2C; see Table 4 below for a summary of all AAV vectors used in this study), albeit with modest reductions in CAG17 (SEQ ID NO:76) (approximately 17% and 8% for ZFP-A and ZFP-B, respectively), which may reflect higher ZFP expression levels in this system. Similar to its behavior in HD fibroblasts, ZFP-C strongly repressed both the normal and disease alleles in NSCs and neurons.

TABLE 4

AAV serotypes and transgenes used in this study

| FIG. | Serotype | Transgene (promoters, repressors, tags etc) |
|---|---|---|
| 2c | AAV2/6 | CMV.ZFP-A.KRAB, CMV.ZFP-B.KRAB, CMV.ZFP-C.KRAB, CMV.eGFP |
| 2k, l | AAV2/6 | CMV.ZFP-B.KRAB, CMV.eGFP |
| 3b-g | AAV2/6 | CMV.ZFP-B.KRAB, CMV.eGFP |
| 4a, b | AAV2/1 + 2 | SYN1.ZFP-B.KRAB, SYN1.ΔDBD.KRAB |
| 4d, h, n | AAV2/1 + 2 | SYN1.ZFP-B.KRAB.T2A.eGFP |
| 4e-g | AAV2/1 + 2 | SYN1.ZFP-B.KRAB.T2A.eGFP, SYN1.eGFP |
| 4i-k, m, o, p | AAV2/1 + 2 | SYN1.ZFP-B.KRAB.T2A.eGFP, SYN1.ΔDBD.KRAB.T2A.eGFP, SYN1.eGFP |
| 4q | AAV2/9 | SYN1.ZFP-D.KRAB.T2A.tdTomato |
| 4r-t | AAV2/9 | SYN1.ZFP-D.KRAB.T2A.tdTomato, SYN1.ΔDBD.KRAB.T2A.tdTomato |
| 5b-e | AAV2/1 + 2 | SYN1.ZFP-D.KRAB.FLAG, SYN1.eGFP |
| 5f | AAV2/1 + 2 | SYN1.ZFP-D.KRAB.FLAG |
| 13 | AAV2/6 | CMV.ZFP-B.KRAB, CMV.eGFP |
| 14A, B | AAV2/1 + 2 | SYN1.eGFP |
| 14C | AAV2/1 + 2 | SYN1.ΔDBD.KRAB.T2A.eGFP |
| 15A | AAV2/1 + 2 | SYN1.eGFP |

TABLE 4-continued

AAV serotypes and transgenes used in this study

| FIG. | Serotype | Transgene (promoters, repressors, tags etc) |
|---|---|---|
| 15B-G | AAV2/1 + 2 | SYN1.ZFP-B.KRAB.FLAG, SYN1.ΔDBD.KRAB.FLAG |
| 16A, B | AAV2/1 + 2 | SYN1.ZFP-D.KRAB.FLAG |
| 16C-E | AAV2/1 + 2 | SYN1.ZFP-D.KRAB.FLAG, SYN1.ΔDBD.KRAB.FLAG |
| 17G-I | AAV2/1 + 2 | SYN1.ZFP-A.KRAB.T2A.eGFP, SYN1.ZFP-B.KRAB.T2A.eGFP, SYN1.ΔDBD.KRAB.T2A.eGFP |

We next examined the ZFPs for evidence of cellular tolerability and durable efficacy. To accomplish this, lentiviral delivery was used to drive chronic ZFP expression throughout a 103-day study in NSCs and neurons. Infected NSCs were expanded and FACS-enriched for ZFP expression after 27 days, expanded for 51 days, and finally differentiated into neurons and cultured a further 25 days; allelic expression was assessed on days 74 and 103 (FIG. 2A).

Figure 2D:
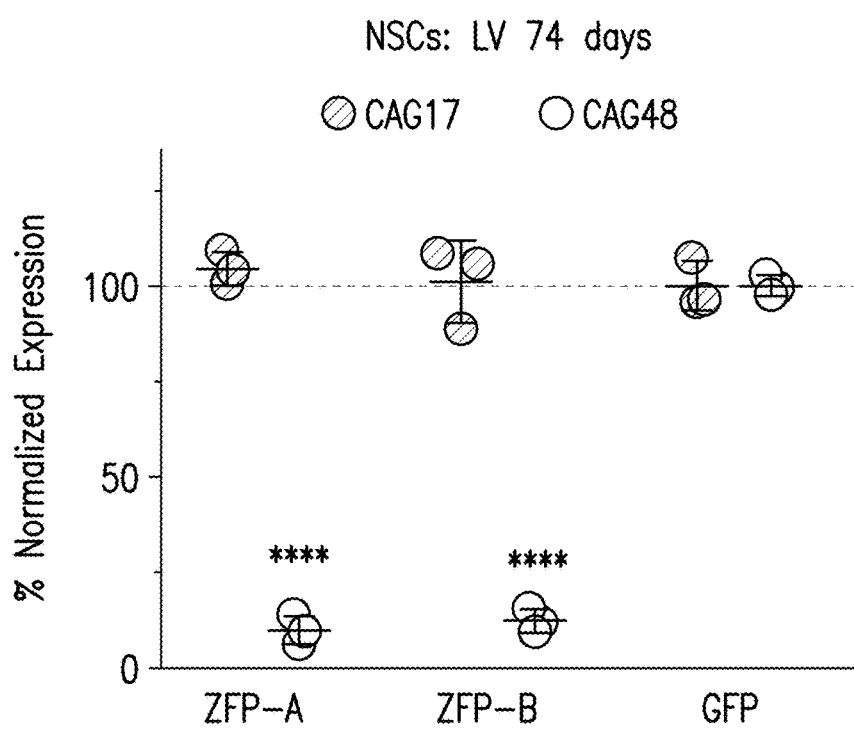
FIG. 2D shows HD NSCs infected with lentivirus encoding either ZFP-2A-GFP or GFP that were cell-sorted for GFP expression at 27 days after infection to enrich transduced cells. Shown is qRT-PCR data at 74 days as in FIG. 2B; n=3 biological replicates; mean±SD.
Figure 2E:
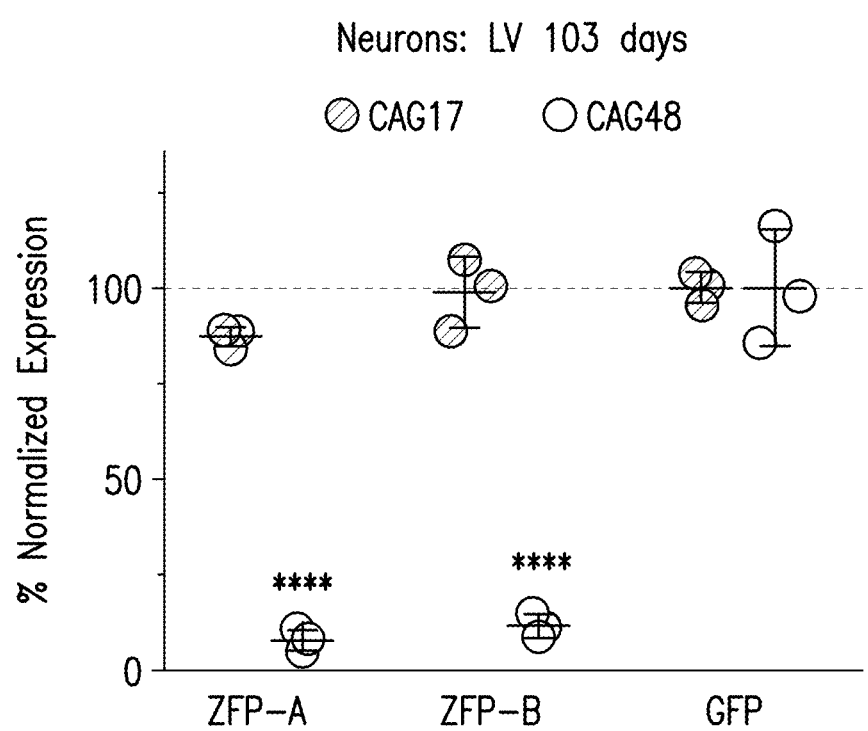
FIG. 2E shows GFP-sorted NSCs from FIG. 2D that were differentiated into neurons. Shown is qRT-PCR data at 25 days after initiation of neuron differentiation (103 days after lentiviral infection) as in FIG. 2B; n=3 biological replicates; mean±SD.
Figure 2F:
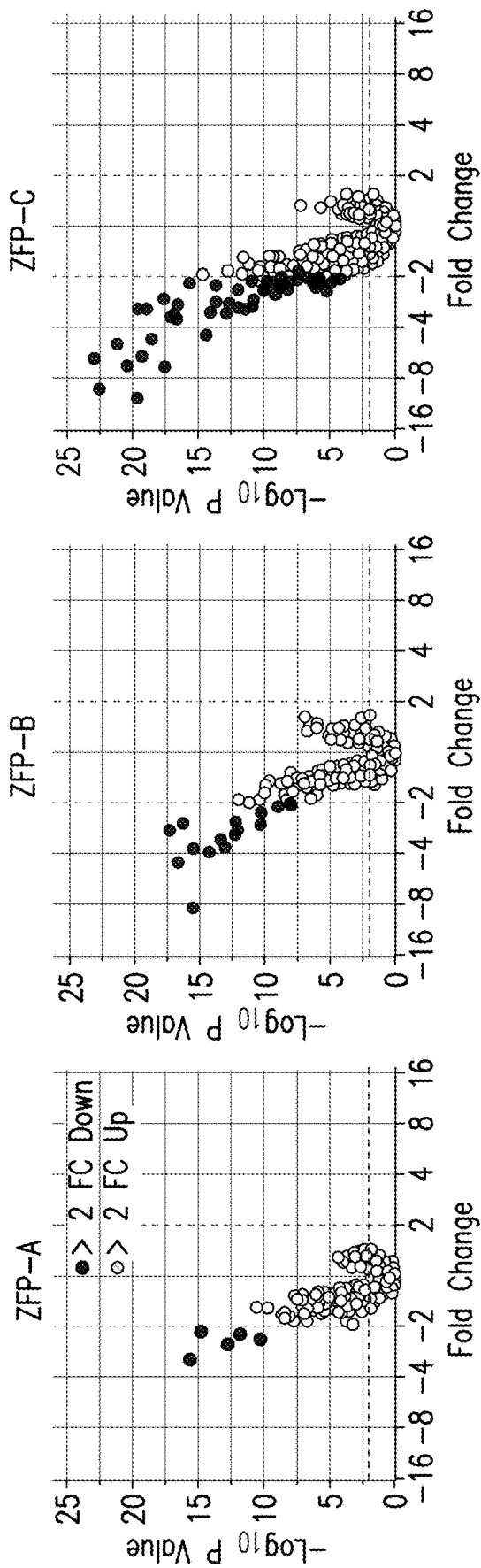
FIG. 2F depicts a genome-wide specificity assessment HD Neurons (CAG17/48 (SEQ ID NOS 76/78)) using microarrays (Affymetrix GeneChip Primeview, n=4-6 biological replicates per treatment) 24 hours after transfection with 1500 ng of ZFP mRNA. Each dot represents the fold change in transcript level (x-axis) and p-value (y-axis) for a single gene in cells treated with the indicated ZFP compared to control-treated cells. Genes regulated >2-fold with a p-value <0.01 are shown.
Figure 2G:
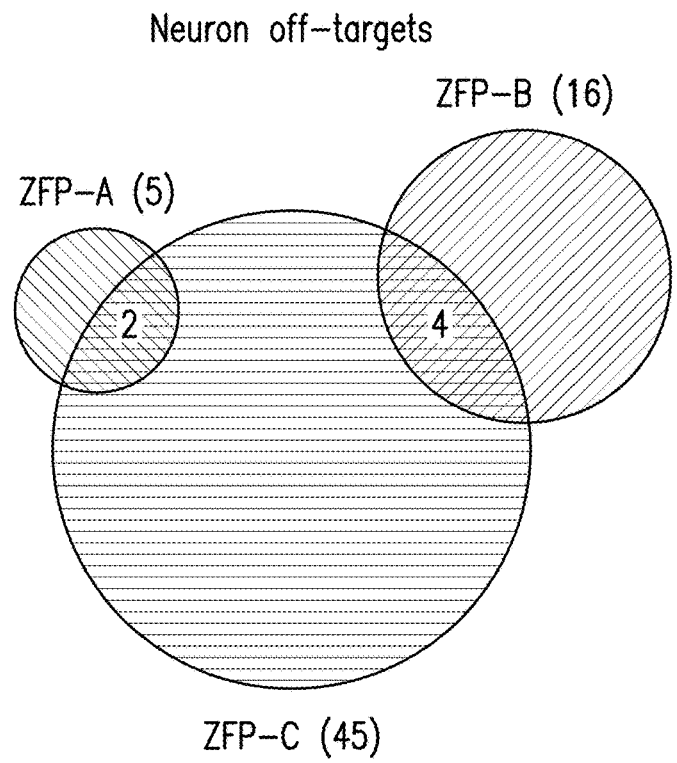
FIG. 2G depicts a Venn diagram of regulated genes in FIG. 2F.
Figure 11A:
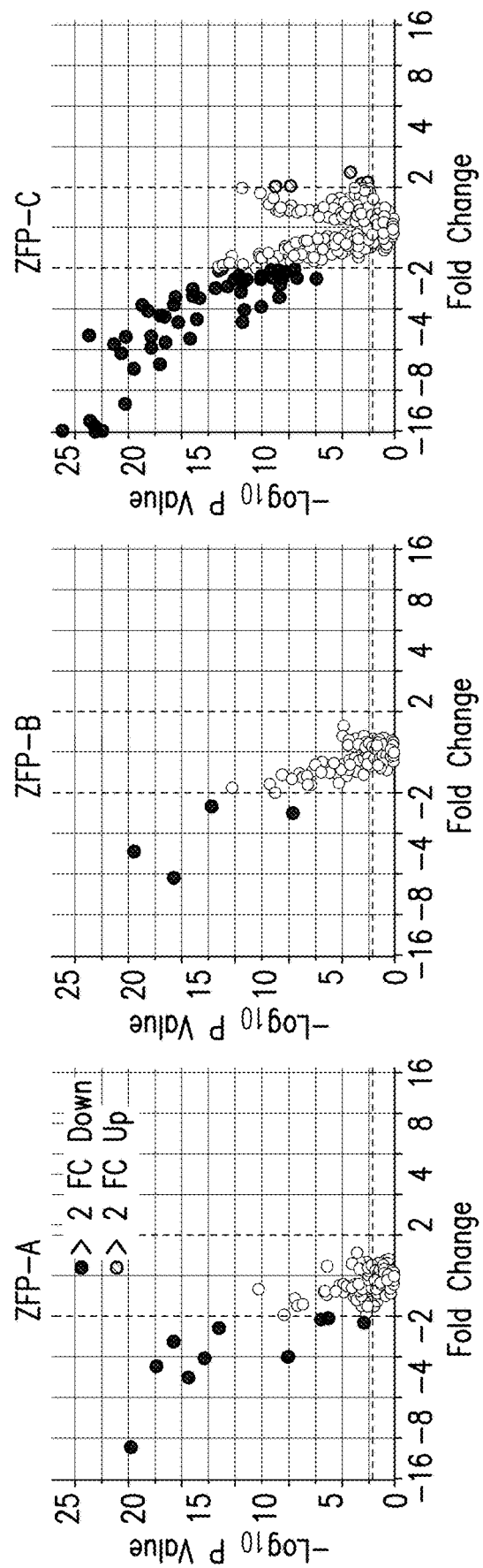
Figure 11C:
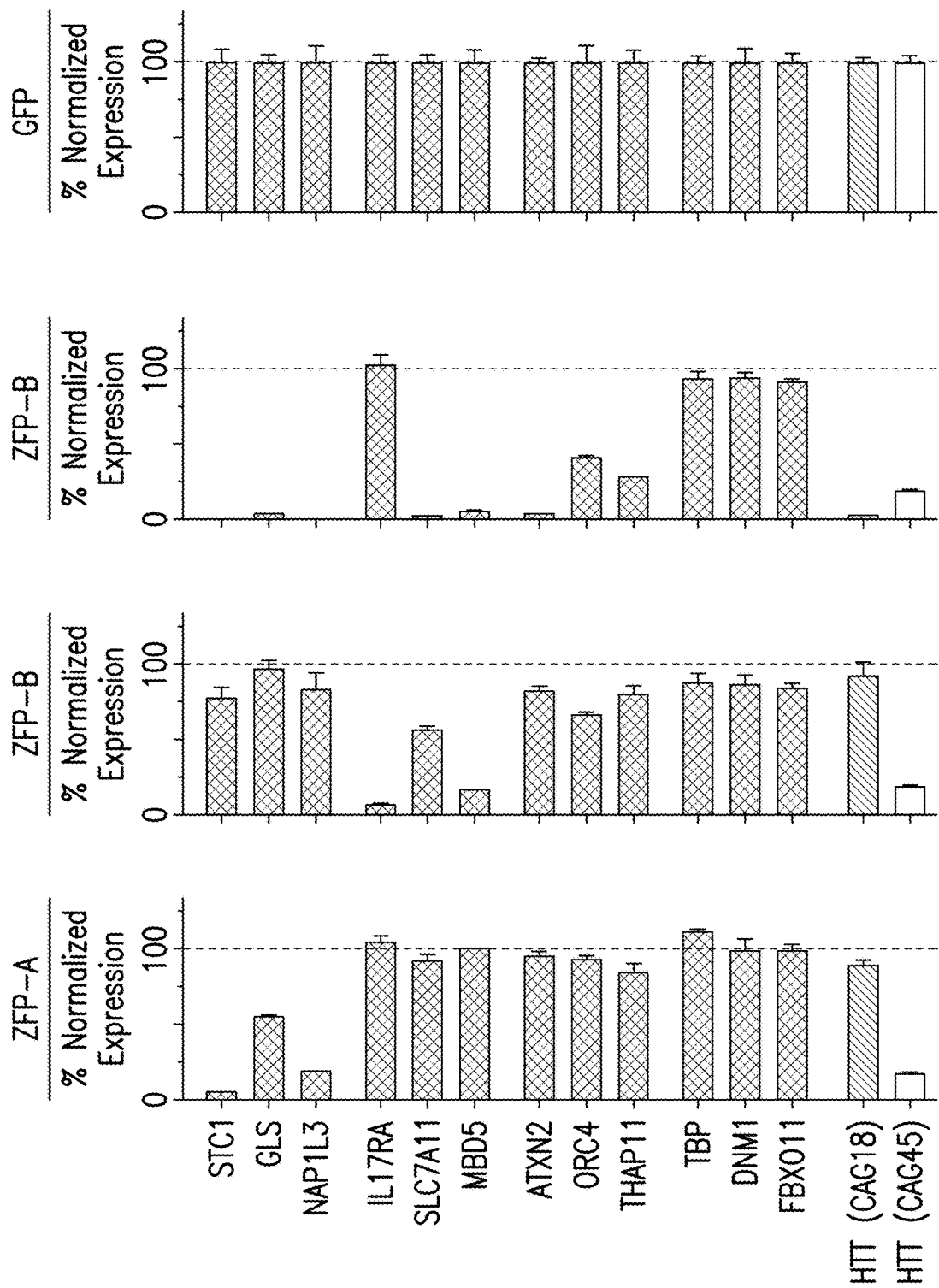
Figure 11D:
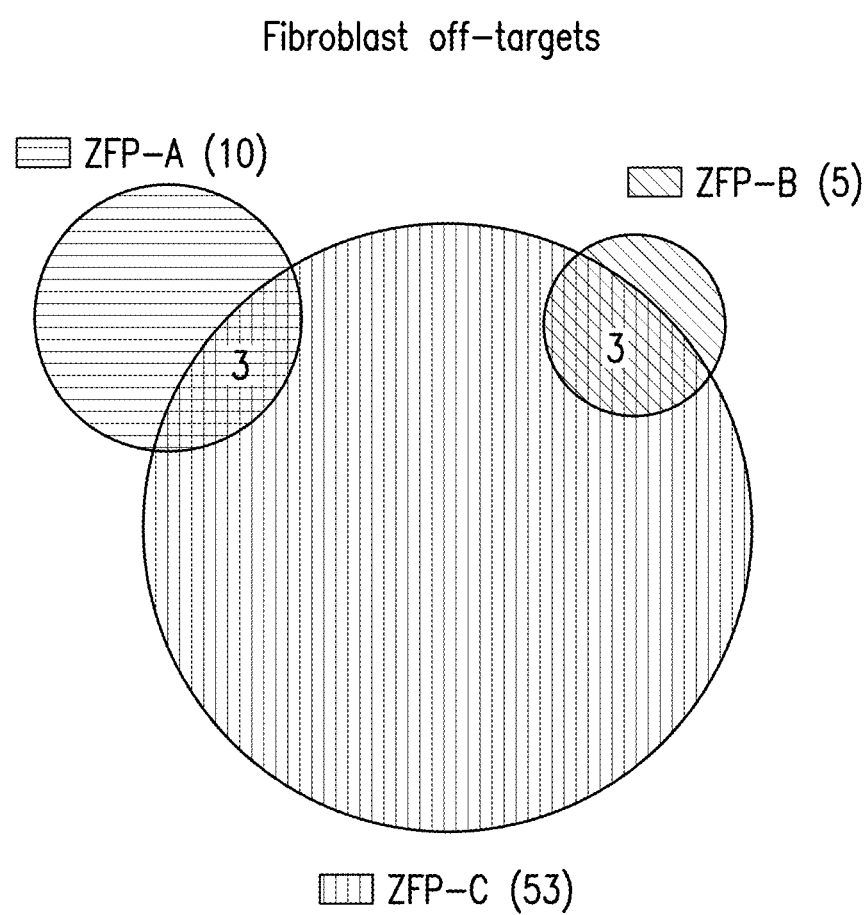

As shown in FIGS. 2D and 2E, regulation was highly selective (>88% reduction of CAG48 (SEQ ID NO:78) with <12% repression of CAG17 (SEQ ID NO:76)) and undiminished on the second sample day, indicating that ZFP expression was well tolerated during all study phases. Consistent with this result, transcriptome-wide specificity analyses by microarray (n=18,149 genes queried) revealed limited levels of off-target gene repression in CAG17/48 (SEQ ID NOS:76/78) neurons ((n=5, ZFP-A; n=16, ZFP-B), FIG. 2F; Table 5 below) as well as CAG18/45 (SEQ ID NOS:79/80) fibroblasts ((n=10, ZFP-A; n=5, ZFP-B), FIG. 11A; Table 6 below) under conditions of robust on-target allele specific regulation (FIG. 11). A substantially greater number of genes were repressed by the non-allele selective ZFP-C in neurons (n=53) and fibroblasts (n=45), most of which contain a CAG array within 1 kb of the TSS (FIG. 2G, FIG. 11D). Microarray performance was broadly confirmed via qRT-PCR of a control transcript set (FIGS. 11B and 11C). Importantly, membership analyses of microarray data revealed no overlap between genes regulated by ZFP-A and ZFP-B (FIG. 2G, FIG. 11D), and examination of the corresponding promoters showed no strict correspondence between whether a gene was regulated and the presence, length or location of a CAG repeat (see Tables 5 and 6). Together these results ruled out the possibility that a CAG-targeted approach to allele-specific mHTT repression might unavoidably repress certain other genes bearing repeat arrays that were even longer and/or more readily bound, and instead suggest that further optimization of our designs will yield ZFP-TFs that uniquely repress mHtt.

TABLE 5

Microarray analysis results in neurons for ZFP A, B and C

| 2FC ZFP | Gene Symbol | Chr | Strand | ZFP vrs Control, fold change | | | ZFP vrs Control, P-Value | | | TSS dist. (bp) | total CAG | contiguous CAG | site length (bp) |
|---|---|---|---|---|---|---|---|---|---|---|---|---|---|
| | | | | ZFP-A | ZFP-B | ZFP-C | ZFP-A | ZFP-B | ZFP-C | | | | |
| ZFP-A | NAP1L3 | chrX | − | −3.13 | −1.07 | −6.81 | 2.41E−16 | 1.57E−01 | 3.54E−21 | 393 | 19 | 6 | 87 |
| ZFP-A | ABHD15 | chr17 | − | −2.53 | −1.00 | −1.02 | 1.79E−13 | 8.20E−01 | 8.43E−01 | −12788 | 3 | 2 | 18 |
| ZFP-A | GLS | chr2 | + | −2.36 | −1.60 | −3.42 | 5.49E−11 | 1.45E−06 | 1.12E−14 | 36 | 15 | 15 | 57 |
| ZFP-A | CRYAB | chr11 | − | −2.22 | 1.07 | −1.01 | 1.55E−12 | 2.96E−01 | 8.62E−01 | 186925 | 5 | 4 | 24 |
| ZFP-A | ESYT1 | chr12 | + | −2.13 | −1.07 | 1.05 | 1.64E−15 | 6.12E−02 | 5.67E−01 | 37306 | 4 | 4 | 21 |
| ZFP-A | NRP2 | chr2 | + | 2.04 | −1.19 | −1.37 | 1.23E−07 | 2.07E−01 | 2.64E−03 | 138 | 7 | 4 | 36 |
| ZFP-A | EZR | chr6 | − | 2.19 | −1.01 | −2.03 | 8.67E−06 | 9.66E−01 | 2.96E−05 | −4829 | 3 | 1 | 21 |
| ZFP-B | IL17RA | chr22 | + | −1.06 | −8.44 | 1.05 | 4.72E−01 | 3.32E−16 | 9.39E−01 | 174 | 6 | 2 | 27 |
| ZFP-B | MBD5 | chr2 | + | −1.35 | −4.50 | −3.26 | 4.13E−05 | 2.48E−17 | 8.34E−15 | 0 | 19 | 5 | 75 |
| ZFP-B | COL13A1 | chr10 | + | 1.03 | −3.87 | 1.22 | 6.55E−01 | 5.81E−15 | 1.27E−02 | −14156 | 4 | 2 | 18 |
| ZFP-B | FLG | chr1 | − | −1.04 | −3.73 | −1.26 | 5.46E−01 | 3.67E−16 | 7.66E−04 | −74282 | 4 | 1 | 18 |
| ZFP-B | KCNN3 | chr1 | − | −1.84 | −3.64 | −2.12 | 2.00E−07 | 9.82E−16 | 1.16E−08 | 396 | 11 | 7 | 45 |
| ZFP-B | CPEB1 | chr15 | − | −1.00 | −3.28 | 1.06 | 8.36E−01 | 4.83E−14 | 2.63E−01 | −9805 | 4 | 2 | 18 |
| ZFP-B | ADSSL1 | chr14 | + | −1.09 | −3.04 | 1.04 | 2.59E−01 | 4.94E−13 | 5.71E−01 | −44745 | 4 | 2 | 18 |
| ZFP-B | DACH1 | chr13 | − | −1.16 | −2.89 | −5.01 | 7.13E−04 | 5.79E−18 | 5.90E−22 | 408 | 22 | 7 | 87 |
| ZFP-B | RNF215 | chr22 | − | −1.09 | −2.87 | −1.35 | 1.29E−01 | 8.58E−13 | 4.73E−04 | 139 | 9 | 5 | 39 |
| ZFP-B | GALNT5 | chr2 | + | 1.05 | −2.64 | −1.24 | 3.79E−01 | 5.12E−11 | 2.89E−03 | 385 | 9 | 8 | 36 |
| ZFP-B | CIZ1 | chr9 | − | 1.02 | −2.62 | −1.22 | 7.71E−01 | 5.92E−17 | 1.26E−04 | 7 | 24 | 6 | 96 |
| ZFP-B | CCDC90B | chr11 | − | 1.08 | −2.58 | 1.13 | 5.99E−02 | 5.93E−13 | 4.65E−02 | −2E+05 | 5 | 3 | 18 |
| ZFP-B | MBP | chr18 | − | 1.02 | −2.23 | 1.04 | 7.49E−01 | 5.53E−11 | 6.87E−01 | −6231 | 4 | 3 | 18 |
| ZFP-B | MAB21L1; MIR548F5 | chr13 | − | −1.53 | −2.08 | −10.69 | 2.02E−05 | 1.01E−09 | 2.12E−20 | 851 | 19 | 19 | 66 |
| ZFP-B | GJB2 | chr13 | − | −1.07 | −2.03 | 1.07 | 3.45E−01 | 1.15E−08 | 5.60E−01 | −4700 | 3 | 1 | 18 |
| ZFP-B | ADAM21 | chr14 | + | 1.21 | 2.46 | 1.43 | 8.56E−02 | 3.59E−09 | 1.77E−03 | 49998 | 5 | 3 | 18 |
| ZFP-C | MAB21L1; MIR548F5 | chr13 | − | −1.53 | −2.08 | −10.69 | 2.02E−05 | 1.01E−09 | 2.12E−20 | 851 | 19 | 19 | 66 |
| ZFP-C | ASCL1 | chr12 | + | −1.51 | −1.91 | −9.29 | 8.37E−08 | 1.11E−10 | 2.81E−23 | 202 | 3 | 2 | 21 |
| ZFP-C | SERPINB8 | chr18 | + | −1.29 | −1.06 | −6.86 | 7.07E−03 | 2.92E−01 | 2.58E−18 | 0 | 6 | 6 | 33 |
| ZFP-C | NAP1L3 | chrX | − | −3.13 | −1.07 | −6.81 | 2.41E−16 | 1.57E−01 | 3.54E−21 | 393 | 19 | 6 | 87 |
| ZFP-C | SLC7A11 | chr4 | − | −1.39 | −1.59 | −6.16 | 8.06E−08 | 4.01E−10 | 1.10E−23 | 15 | 7 | 7 | 30 |
| ZFP-C | SRPX | chrX | − | −1.43 | −1.19 | −5.95 | 3.36E−05 | 2.41E−03 | 4.67E−20 | 132 | 12 | 7 | 48 |
| ZFP-C | DACH1 | chr13 | − | −1.16 | −2.89 | −5.01 | 7.13E−04 | 5.79E−18 | 5.90E−22 | 408 | 22 | 7 | 87 |
| ZFP-C | IRS1 | chr2 | − | −1.21 | 1.03 | −4.67 | 1.89E−03 | 2.48E−01 | 2.24E−19 | 363 | 11 | 8 | 48 |
| ZFP-C | RAET1G; RAET1L; ULBP2 | chr6 | + | −1.07 | −1.08 | −4.44 | 5.01E−01 | 3.07E−01 | 3.85E−15 | 111 | 3 | 2 | 18 |
| ZFP-C | GLS | chr2 | + | −2.14 | −1.51 | −3.56 | 1.39E−12 | 1.51E−07 | 2.23E−17 | 36 | 15 | 15 | 57 |
| ZFP-C | PAPD5 | chr16 | + | −1.17 | −1.09 | −3.48 | 3.87E−03 | 1.62E−01 | 8.13E−18 | −4 | 6 | 6 | 30 |
| ZFP-C | ULBP2 | chr6 | + | −1.04 | 1.04 | −3.32 | 3.77E−01 | 7.84E−01 | 1.33E−13 | 111 | 3 | 2 | 18 |
| ZFP-C | THAP11 | chr16 | + | −1.65 | −1.51 | −3.32 | 4.01E−09 | 9.16E−08 | 1.40E−17 | 778 | 25 | 10 | 93 |

TABLE 5-continued

Microarray analysis results in neurons for ZFP A, B and C

| 2FC ZFP | Gene Symbol | Chr | Strand | ZFP vrs Control, fold change | | | ZFP vrs Control, P-Value | | | TSS dist. (bp) | total CAG | contiguous CAG | site length (bp) |
|---|---|---|---|---|---|---|---|---|---|---|---|---|---|
| | | | | ZFP-A | ZFP-B | ZFP-C | ZFP-A | ZFP-B | ZFP-C | | | | |
| ZFP-C | MBD5 | chr2 | + | −1.35 | −4.50 | −3.26 | 4.13E−05 | 2.48E−17 | 8.34E−15 | 0 | 19 | 5 | 75 |
| ZFP-C | CRIPT | chr2 | + | −1.04 | −1.02 | −3.11 | 3.61E−01 | 8.71E−01 | 4.58E−12 | 6 | 6 | 30 | 80 |
| ZFP-C | IRF2BPL | chr14 | − | −1.09 | −1.00 | −3.10 | 1.24E−02 | 8.84E−01 | 2.48E−20 | 1214 | 19 | 10 | 75 |
| ZFP-C | ATRN | chr20 | + | −1.03 | −1.01 | −3.09 | 5.28E−01 | 6.73E−01 | 1.10E−19 | 173 | 5 | 5 | 30 |
| ZFP-C | FAM155A | chr13 | − | −1.61 | −1.41 | −3.05 | 4.68E−06 | 3.68E−04 | 1.11E−12 | 347 | 22 | 9 | 93 |
| ZFP-C | THSD7A | chr7 | − | −1.17 | −1.46 | −2.98 | 5.21E−02 | 2.53E−04 | 1.17E−11 | 319 | 12 | 4 | 57 |
| ZFP-C | PPP2R2B | chr5 | − | −1.21 | −1.16 | −2.92 | 1.10E−03 | 2.16E−03 | 2.79E−17 | 2 | 12 | 10 | 42 |
| ZFP-C | RAET1L; ULBP2 | chr6 | + | −1.13 | 1.04 | −2.87 | 7.26E−02 | 6.42E−01 | 2.27E−13 | 111 | 3 | 2 | 18 |
| ZFP-C | HTT; MSANTD1 | chr4 | + | −1.48 | −1.77 | −2.81 | 2.45E−06 | 3.19E−09 | 2.16E−14 | 192 | 20 | 19 | 69 |
| ZFP-C | AHNAK2 | chr14 | − | 1.07 | −1.00 | −2.72 | 3.22E−01 | 8.10E−01 | 1.61E−11 | 16252 | 4 | 4 | 21 |
| ZFP-C | HDAC2 | chr6 | − | 1.13 | −1.12 | −2.69 | 6.02E−03 | 8.70E−01 | 2.09E−18 | 180 | 8 | 8 | 42 |
| ZFP-C | RIMS1 | chr6 | + | −1.28 | 1.22 | −2.55 | 2.18E−02 | 2.29E−02 | 6.62E−10 | −131 | 6 | 6 | 30 |
| ZFP-C | ARID1B | chr6 | + | −1.10 | −1.10 | −2.44 | 3.59E−01 | 2.62E−01 | 9.49E−11 | 332 | 16 | 7 | 63 |
| ZFP-C | ZFR | chr5 | − | 1.69 | 1.12 | −2.43 | 5.05E−05 | 4.37E−01 | 5.56E−06 | 83 | 4 | 4 | 18 |
| ZFP-C | CNKSR2 | chrX | + | −1.09 | −1.10 | −2.37 | 2.22E−01 | 1.43E−01 | 9.38E−13 | 147 | 12 | 12 | 51 |
| ZFP-C | JAK1 | chr1 | − | 1.10 | 1.09 | −2.36 | 4.62E−02 | 1.12E−01 | 5.35E−09 | −54818 | 4 | 1 | 18 |
| ZFP-C | C1RL | chr12 | − | −1.06 | −1.25 | −2.32 | 8.86E−01 | 1.63E−01 | 9.08E−07 | 248 | 7 | 7 | 27 |
| ZFP-C | PCDH7 | chr4 | + | −1.15 | −1.48 | −2.31 | 1.22E−01 | 1.57E−05 | 1.04E−10 | 539 | 5 | 4 | 30 |
| ZFP-C | SETD2 | chr3 | − | 1.73 | −1.08 | −2.30 | 9.76E−05 | 9.20E−01 | 1.67E−06 | 47 | 4 | 1 | 21 |
| ZFP-C | SLC4A7 | chr3 | − | −1.11 | −1.16 | −2.27 | 3.31E−01 | 4.36E−01 | 3.09E−06 | −3E+05 | 3 | 3 | 21 |
| ZFP-C | NCALD | chr8 | − | −1.13 | −1.19 | −2.24 | 1.47E−02 | 2.15E−03 | 2.13E−14 | 26 | 3 | 2 | 18 |
| ZFP-C | FREM2 | chr13 | + | −1.04 | −1.01 | −2.20 | 8.89E−01 | 6.87E−01 | 2.06E−09 | 296 | 7 | 6 | 33 |
| ZFP-C | POU3F2 | chr6 | + | −1.06 | −1.27 | −2.19 | 2.25E−02 | 1.04E−06 | 2.27E−16 | 92 | 7 | 4 | 45 |
| ZFP-C | RIF1 | chr2 | + | 1.09 | 1.07 | −2.15 | 6.41E−01 | 4.34E−01 | 4.86E−07 | 611 | 4 | 4 | 24 |
| ZFP-C | CADM3 | chr1 | + | −1.14 | 1.06 | −2.13 | 1.25E−01 | 5.28E−01 | 6.14E−10 | 177 | 4 | 2 | 21 |
| ZFP-C | TMEM55A | chr8 | − | −1.68 | −1.90 | −2.13 | 1.18E−07 | 4.92E−09 | 1.80E−10 | −63 | 13 | 4 | 57 |
| ZFP-C | KIF21A | chr12 | − | 1.31 | 1.05 | −2.13 | 4.01E−03 | 5.06E−01 | 3.00E−08 | 320220 | 4 | 2 | 18 |
| ZFP-C | KCNN3 | chr1 | − | −1.84 | −3.64 | −2.12 | 2.00E−07 | 9.82E−14 | 1.16E−08 | 396 | 11 | 7 | 45 |
| ZFP-C | ST6GALNAC5 | chr1 | + | −1.15 | −1.03 | −2.12 | 9.46E−02 | 8.93E−01 | 1.05E−11 | 1145 | 11 | 7 | 45 |
| ZFP-C | KMT2C | chr7 | − | −1.13 | 1.17 | −2.10 | 4.70E−01 | 2.01E−01 | 2.28E−05 | −43540 | 5 | 2 | 18 |
| ZFP-C | PRRC2C | chr1 | + | 1.31 | −1.04 | −2.05 | 2.68E−02 | 9.64E−01 | 6.95E−05 | 24008 | 7 | 3 | 30 |
| ZFP-C | EZR | chr6 | − | 2.19 | −1.01 | −2.03 | 8.67E−06 | 9.66E−01 | 2.96E−05 | −4829 | 3 | 1 | 21 |
| ZFP-C | SMC5 | chr9 | + | 1.15 | −1.02 | −2.02 | 1.64E−02 | 5.70E−01 | 1.81E−07 | | | | |
| ZFP-C | DYNC1H1 | chr14 | − | 1.30 | 1.36 | −2.02 | 1.73E−01 | 8.18E−02 | 2.73E−05 | 271 | 4 | 3 | 18 |
| ZFP-C | MLLT4 | chr6 | + | −1.10 | −1.04 | −2.01 | 3.97E−01 | 7.16E−01 | 1.41E−06 | −80807 | 4 | 2 | 18 |
| ZFP-C | NUDT4; NUDT4P1; NUDT4P2 | chr12 | + | −1.12 | 1.12 | −2.00 | 2.40E−01 | 1.01E−01 | 2.03E−09 | −235 | 6 | 6 | 33 |

TABLE 6

Microarray analysis results in fibroblasts for ZFP A, B and C

| 2FC ZFP | Gene Symbol | Chr | Strand | ZFP vrs Control, fold change | | | ZFP vrs Control, P-value | | | TSS dist. (bp) | total CAG | contiguous CAG | site length (bp) |
|---|---|---|---|---|---|---|---|---|---|---|---|---|---|
| | | | | ZFP-A | ZFP-B | ZFP-C | ZFP-A | ZFP-B | ZFP-C | | | | |
| ZFP-A | STC1 | chr8 | − | 19.21 | −1.29 | 34.09 | 1.51E−25 | 4.14E−04 | 2.70E−27 | 30 | 18 | 6 | 78 |
| ZFP-A | NAP1L3 | chrX | − | −5.80 | −1.04 | 21.39 | 1.14E−19 | 6.72E−01 | 2.10E−25 | 393 | 19 | 6 | 87 |
| ZFP-A | ESYT1 | chr12 | + | −4.71 | −1.03 | −1.06 | 1.25E−23 | 1.20E−21 | 3.79E−02 | 37306 | 4 | 4 | 21 |
| ZFP-A | ABHD15 | chr17 | − | −4.34 | −1.04 | −1.12 | 3.20E−18 | 5.28E−01 | 3.36E−01 | −12788 | 3 | 2 | 18 |
| ZFP-A | ISG20 | chr15 | + | −3.92 | 1.07 | 1.89 | 7.72E−10 | 9.65E−01 | 5.61E−04 | 13993 | 5 | 3 | 18 |
| ZFP-A | TP53I13 | chr17 | + | −3.06 | −1.02 | 1.01 | 4.08E−20 | 8.80E−01 | 5.82E−01 | 11281 | 3 | 2 | 18 |
| ZFP-A | HNRNPDL | chr4 | − | −2.44 | −1.06 | −1.00 | 3.89E−16 | 4.00E−01 | 5.87E−11 | 12639 | 6 | 5 | 30 |
| ZFP-A | GLS | chr2 | + | −2.19 | −1.19 | −9.11 | 1.00E−07 | 6.03E−02 | 7.95E−17 | 36 | 15 | 15 | 57 |
| ZFP-A | RSAD2 | chr2 | + | −2.10 | 1.05 | 2.35 | 4.83E−03 | 9.89E−01 | 2.17E−03 | 64817 | 5 | 4 | 21 |
| ZFP-A | FRMD5 | chr15 | − | −2.04 | −1.12 | −1.08 | 8.11E−07 | 3.27E−01 | 7.24E−01 | 174 | 3 | 3 | 18 |
| ZFP-B | CPEB1 | chr15 | − | 1.02 | −8.72 | −1.06 | 8.18E−01 | 1.91E−21 | 2.29E−01 | −9805 | 4 | 2 | 18 |
| ZFP-B | IL17RA | chr22 | + | −1.05 | −5.52 | −1.09 | 7.92E−02 | 5.91E−24 | 3.01E−02 | 174 | 6 | 2 | 27 |
| ZFP-B | MBD5 | chr2 | + | −1.08 | −2.91 | −3.36 | 2.39E−01 | 5.29E−11 | 3.49E−12 | 90 | 6 | 5 | 24 |
| ZFP-B | CCDC90B | chr11 | − | 1.02 | −2.61 | 1.08 | 3.33E−01 | 1.54E−17 | 9.24E−03 | −231403 | 5 | 3 | 18 |
| ZFP-B | SLC7A11 | chr4 | − | −1.03 | −2.06 | −1.00 | 6.26E−01 | 2.23E−12 | 3.15E−28 | 15 | 7 | 7 | 30 |
| ZFP-B | SERPINB8 | chr18 | + | 1.02 | −2.00 | −50.34 | 8.18E−01 | 6.00E−01 | 3.37E−30 | 0 | 6 | 6 | 33 |
| ZFP-C | STC1 | chr8 | − | −17.95 | −1.30 | −40.33 | 9.36E−26 | 1.48E−04 | 3.27E−28 | 30 | 18 | 6 | 78 |
| ZFP-C | SLC7A11 | chr4 | − | −1.03 | −2.06 | −33.38 | 6.26E−01 | 2.23E−12 | 3.15E−28 | 15 | 7 | 7 | 30 |
| ZFP-C | CRIPT | chr2 | + | 1.06 | 1.01 | −30.20 | 4.99E−01 | 8.53E−01 | 1.53E−27 | | | | |
| ZFP-C | GLS | chr2 | + | −1.84 | 1.04 | −26.72 | 2.34E−11 | 8.93E−01 | 1.17E−27 | 36 | 15 | 15 | 57 |

TABLE 6-continued

Microarray analysis results in fibroblasts for ZFP A, B and C

| 2FC ZFP | Gene Symbol | Chr | Strand | ZFP vrs Control, fold change | | | ZFP vrs Control, P-value | | | TSS dist. (bp) | total CAG | contiguous CAG | site length (bp) |
|---|---|---|---|---|---|---|---|---|---|---|---|---|---|
| | | | | ZFP-A | ZFP-B | ZFP-C | ZFP-A | ZFP-B | ZFP-C | | | | |
| ZFP-C | NAP1L3 | chrX | − | −5.80 | −1.04 | −21.39 | 1.14E−19 | 6.72E−01 | 2.10E−25 | 393 | 19 | 6 | 87 |
| ZFP-C | RUNX2 | chr6 | + | 1.04 | −1.07 | −11.26 | 6.73E−01 | 3.70E−01 | 1.23E−25 | 101 | 19 | 6 | 75 |
| ZFP-C | TTC13 | chr1 | − | −1.15 | −1.11 | −10.53 | 6.04E−02 | 1.52E−01 | 5.38E−22 | 20 | 7 | 6 | 30 |
| ZFP-C | HDAC2 | chr6 | − | 1.02 | −1.05 | −8.50 | 6.49E−01 | 4.06E−01 | 6.17E−25 | 180 | 8 | 8 | 42 |
| ZFP-C | TMEM55A | chr8 | − | −1.64 | −1.36 | −7.63 | 8.20E−09 | 2.90E−05 | 4.42E−22 | −63 | 13 | 4 | 57 |
| ZFP-C | MAB21L1; MIR548F5 | chr13 | − | −1.48 | −1.49 | −7.29 | 1.09E−10 | 9.28E−12 | 1.35E−26 | 851 | 19 | 19 | 66 |
| ZFP-C | PAPSS2 | chr10 | + | 1.06 | 1.02 | −6.90 | 7.25E−01 | 8.60E−01 | 3.47E−21 | 154 | 9 | 8 | 42 |
| ZFP-C | C1RL | chr12 | + | −1.01 | 1.07 | −6.67 | 6.93E−01 | 1.97E−01 | 8.03E−19 | 248 | 7 | 7 | 27 |
| ZFP-C | ATXN2 | chr12 | − | −1.06 | −1.10 | −6.55 | 1.82E−01 | 3.75E−02 | 1.51E−22 | −122 | 22 | 13 | 81 |
| ZFP-C | PAPD5 | chr16 | + | −1.03 | 1.02 | −6.50 | 6.91E−01 | 7.40E−01 | 1.06E−24 | −4 | 6 | 6 | 30 |
| ZFP-C | IRF2BPL | chr14 | − | 1.03 | 1.03 | −6.26 | 7.32E−01 | 3.86E−01 | 6.68E−28 | 1214 | 19 | 10 | 75 |
| ZFP-C | IRS1 | chr2 | − | 1.00 | −1.05 | −5.06 | 9.53E−01 | 2.65E−01 | 1.08E−20 | 363 | 11 | 8 | 48 |
| ZFP-C | GALNT5 | chr2 | + | −1.05 | −1.43 | −5.01 | 2.91E−01 | 4.56E−05 | 5.74E−15 | | | | |
| ZFP-C | BRI3BP; THRIL | chr12 | + | 1.16 | 1.16 | −4.70 | 3.85E−02 | 1.46E−02 | 1.49E−18 | 129 | 11 | 9 | 45 |
| ZFP-C | NUDT4; NUDT4P1; NUDT4P2 | chr12 | + | −1.04 | −1.02 | −4.60 | 5.35E−01 | 7.73E−01 | 3.83E−22 | −235 | 6 | 6 | 33 |
| ZFP-C | ATRN | chr20 | + | −1.05 | −1.02 | −4.59 | 5.36E−01 | 7.35E−01 | 1.28E−21 | 173 | 5 | 5 | 30 |
| ZFP-C | MLLT3 | chr9 | − | −1.04 | −1.01 | −4.22 | 4.92E−01 | 9.95E−01 | 2.97E−14 | 36 | 7 | 6 | 33 |
| ZFP-C | THAP11 | chr16 | + | −1.30 | −1.15 | −4.15 | 5.75E−07 | 4.63E−03 | 7.51E−23 | 778 | 25 | 10 | 93 |
| ZFP-C | LRP8 | chr1 | − | −1.14 | −1.28 | −3.91 | 1.32E−01 | 6.36E−03 | 2.69E−14 | 31 | 14 | 11 | 51 |
| ZFP-C | BPGM | chr7 | + | 1.02 | −1.03 | −3.72 | 7.75E−02 | 5.60E−01 | 2.56E−20 | 61 | 8 | 8 | 33 |
| ZFP-C | CUL4B | chrX | − | −1.08 | −1.07 | −3.68 | 3.01E−02 | 1.45E−02 | 7.18E−24 | 94 | 6 | 4 | 24 |
| ZFP-C | GABBR2 | chr9 | − | −1.07 | 1.02 | −3.40 | 6.47E−02 | 7.31E−01 | 2.70E−18 | 527 | 9 | 3 | 39 |
| ZFP-C | MBD5 | chr2 | + | −1.08 | −2.91 | −3.36 | 2.39E−01 | 5.29E−11 | 3.49E−12 | 90 | 6 | 5 | 24 |
| ZFP-C | SRPX | chrX | − | −1.02 | −1.06 | −3.28 | 4.32E−01 | 1.17E−01 | 1.42E−20 | 132 | 12 | 7 | 48 |
| ZFP-C | ARID1B | chr6 | + | 1.02 | 1.02 | −3.26 | 4.23E−01 | 6.33E−01 | 2.17E−19 | 332 | 16 | 7 | 63 |
| ZFP-C | SLC27A3 | chr1 | + | 1.07 | −1.40 | −2.96 | 6.74E−01 | 1.24E−05 | 2.46E−14 | 214 | 10 | 4 | 51 |
| ZFP-C | ARV1 | chr1 | + | 1.04 | 1.02 | −2.85 | 7.33E−01 | 8.00E−01 | 3.81E−17 | −231 | 7 | 6 | 30 |
| ZFP-C | NAAA | chr4 | − | −1.01 | 1.03 | −2.84 | 9.35E−01 | 7.83E−01 | 3.31E−19 | 64 | 6 | 6 | 24 |
| ZFP-C | SEMA6D | chr15 | + | 1.00 | −1.03 | −2.73 | 4.50E−01 | 9.70E−01 | 2.16E−17 | 47 | 6 | 6 | 27 |
| ZFP-C | MAP2 | chr2 | + | −1.34 | −1.16 | −2.56 | 5.95E−04 | 1.83E−01 | 1.24E−11 | 22 | 7 | 7 | 30 |
| ZFP-C | FAM155A | chr13 | − | −1.16 | −1.30 | −2.55 | 1.69E−02 | 1.30E−06 | 2.55E−15 | 347 | 22 | 9 | 93 |
| ZFP-C | SEC16B | chr1 | − | −1.03 | −1.06 | −2.45 | 5.64E−01 | 7.70E−01 | 2.05E−16 | −14015 | 4 | 3 | 21 |
| ZFP-C | ORC4 | chr2 | − | −1.08 | −1.56 | −2.42 | 4.43E−01 | 9.42E−06 | 2.12E−11 | 80 | 19 | 5 | 75 |
| ZFP-C | IL1RL1 | chr2 | + | −1.18 | −1.04 | −2.42 | 9.26E−01 | 5.54E−01 | 2.36E−15 | 2642 | 5 | 5 | 21 |
| ZFP-C | TMOD2 | chr15 | + | −1.11 | −1.03 | −2.41 | 1.11E−01 | 2.94E−01 | 7.86E−15 | 18839 | 4 | 2 | 21 |
| ZFP-C | EGR1 | chr5 | + | −1.32 | 1.01 | −2.40 | 9.85E−03 | 3.61E−01 | 3.40E−10 | 441 | 8 | 6 | 36 |
| ZFP-C | HTT; MSANTD1 | chr4 | + | −1.43 | −1.42 | −2.39 | 6.38E−08 | 4.67E−07 | 2.02E−15 | 192 | 20 | 19 | 69 |
| ZFP-C | SPP1 | chr4 | + | −1.06 | 1.01 | −2.37 | 2.90E−01 | 7.76E−01 | 2.44E−09 | 0 | 4 | 4 | 18 |
| ZFP-C | WNT2B | chr1 | + | −1.12 | −1.07 | −2.34 | 1.83E−01 | 4.59E−01 | 1.18E−11 | 613 | 6 | 4 | 30 |
| ZFP-C | PDE7B | chr6 | + | −1.95 | −1.44 | −2.30 | 3.43E−11 | 3.58E−07 | 3.51E−13 | −36 | 17 | 6 | 75 |
| ZFP-C | HRCT1 | chr9 | + | −1.09 | −1.11 | −2.26 | 3.36E−01 | 2.11E−01 | 2.69E−14 | 155 | 7 | 7 | 27 |
| ZFP-C | BRI3BP | chr12 | + | −1.00 | 1.00 | −2.19 | 9.28E−01 | 9.76E−01 | 2.48E−10 | 129 | 11 | 9 | 45 |
| ZFP-C | PCDH7 | chr4 | + | −1.24 | −1.49 | −2.14 | 5.76E−03 | 1.60E−06 | 7.03E−12 | 539 | 5 | 4 | 30 |
| ZFP-C | ULBP2 | chr6 | + | −1.01 | 1.03 | −2.13 | 9.38E−01 | 9.46E−01 | 8.46E−17 | 111 | 3 | 2 | 18 |
| ZFP-C | TRMT10B | chr9 | + | −1.06 | 1.01 | −2.10 | 8.48E−01 | 3.01E−01 | 1.19E−11 | 56593 | 3 | 3 | 18 |
| ZFP-C | SMNDC1 | chr10 | − | 1.03 | −1.02 | −2.08 | 9.75E−01 | 5.33E−01 | 1.80E−09 | 111 | 6 | 4 | 30 |
| ZFP-C | RAET1L; ULBP2 | chr6 | + | 1.02 | 1.01 | −2.06 | 8.23E−01 | 8.32E−01 | 4.49E−17 | 111 | 3 | 2 | 18 |
| ZFP-C | SORCS2 | chr4 | + | −1.01 | −1.04 | −2.05 | 4.09E−01 | 1.59E−01 | 2.58E−11 | 207 | 7 | 7 | 33 |
| ZFP-C | FAM171B | chr2 | + | 1.04 | −1.03 | −2.01 | 7.88E−01 | 5.52E−01 | 1.50E−13 | 219 | 6 | 6 | 30 |
| ZFP-C | CXCL11 | chr4 | − | −1.24 | −1.22 | 2.01 | 7.51E−02 | 4.09E−01 | 1.96E−03 | | | | |
| ZFP-C | TLR3 | chr4 | + | −1.51 | 1.09 | 2.05 | 1.07E−02 | 9.86E−01 | 1.50E−03 | 76907 | 5 | 3 | 18 |
| ZFP-C | CXCL10 | chr4 | − | −1.64 | −1.04 | 2.09 | 4.19E−02 | 7.26E−01 | 1.24E−03 | −12499 | 7 | 3 | 36 |
| ZFP-C | BATF2 | chr11 | − | −1.28 | −1.02 | 2.10 | 6.53E−01 | 8.65E−01 | 1.32E−05 | 14728 | 5 | 4 | 21 |
| ZFP-C | BST2 | chr19 | − | −1.44 | 1.21 | 2.12 | 4.26E−01 | 4.64E−01 | 3.17E−05 | 1913 | 4 | 2 | 18 |
| ZFP-C | GIMAP2 | chr7 | + | −1.43 | 1.08 | 2.13 | 6.14E−02 | 5.65E−01 | 5.72E−04 | 56994 | 4 | 3 | 18 |
| ZFP-C | ADAM21 | chr14 | + | 1.19 | 1.15 | 2.14 | 5.20E−02 | 8.18E−02 | 1.52E−11 | 49998 | 5 | 3 | 18 |
| ZFP-C | ALDH1A3 | chr15 | + | 1.41 | 1.25 | 2.14 | 2.04E−02 | 1.06E−01 | 4.12E−06 | −8958 | 3 | 1 | 18 |
| ZFP-C | ANGPTL1 | chr1 | − | −1.23 | 1.27 | 2.19 | 1.26E−01 | 2.09E−01 | 2.84E−02 | 223973 | 3 | 2 | 18 |
| ZFP-C | TNFSF10 | chr3 | − | −1.32 | 1.25 | 2.27 | 1.73E−01 | 1.74E−01 | 8.02E−05 | 78550 | 3 | 2 | 18 |
| ZFP-C | IFIT2 | chr10 | + | −1.49 | 1.45 | 2.50 | 6.39E−02 | 1.89E−01 | 2.47E−05 | −76760 | 4 | 3 | 21 |
| ZFP-C | RSAD2 | chr2 | + | −1.73 | 1.18 | 2.50 | 2.97E−02 | 7.18E−01 | 2.98E−03 | 64817 | 5 | 4 | 21 |
| ZFP-C | TRMT10A | chr4 | − | 1.43 | 1.24 | 2.61 | 2.82E−04 | 5.23E−02 | 1.95E−12 | 70682 | 5 | 3 | 18 |
| ZFP-C | HERC5 | chr4 | + | −1.56 | 1.31 | 2.79 | 2.94E−02 | 2.85E−01 | 8.07E−05 | −160020 | 5 | 2 | 21 |

We then evaluated ZFP-B-treated CAG17/48 (SEQ ID NOS:76/78) neurons for amelioration of HD-related phenotypes (FIG. 2A).

Figure 2H:
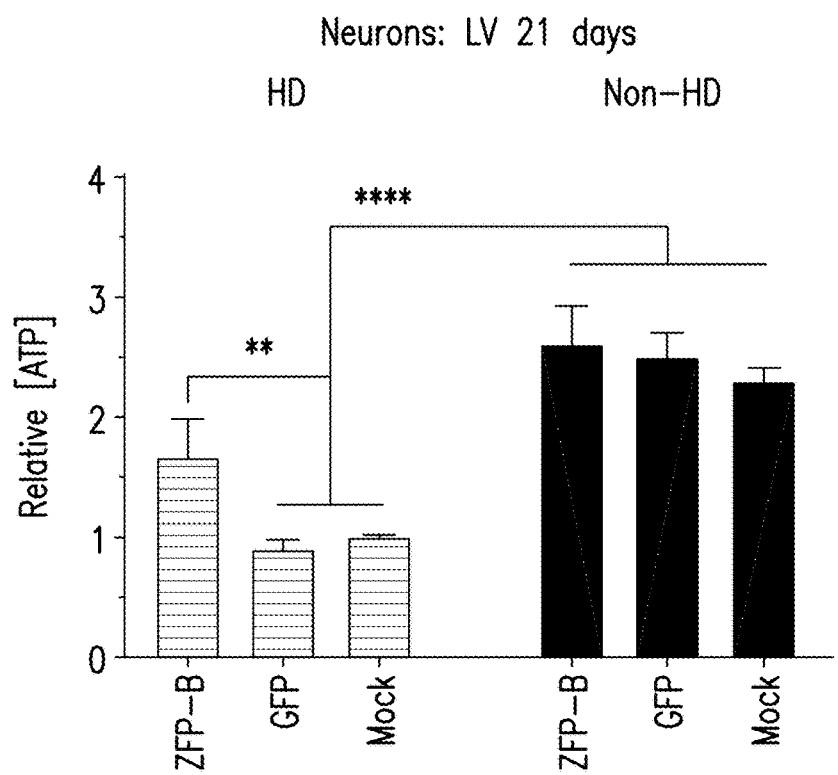
FIG. 2H shows an increase in intracellular levels of ATP in neurons treated with ZFP-B. Intracellular ATP levels in HD and normal neurons were measured 21 days after lentiviral infection of either ZFP-2A-GFP or CMV-GFP.
Figure 2I:
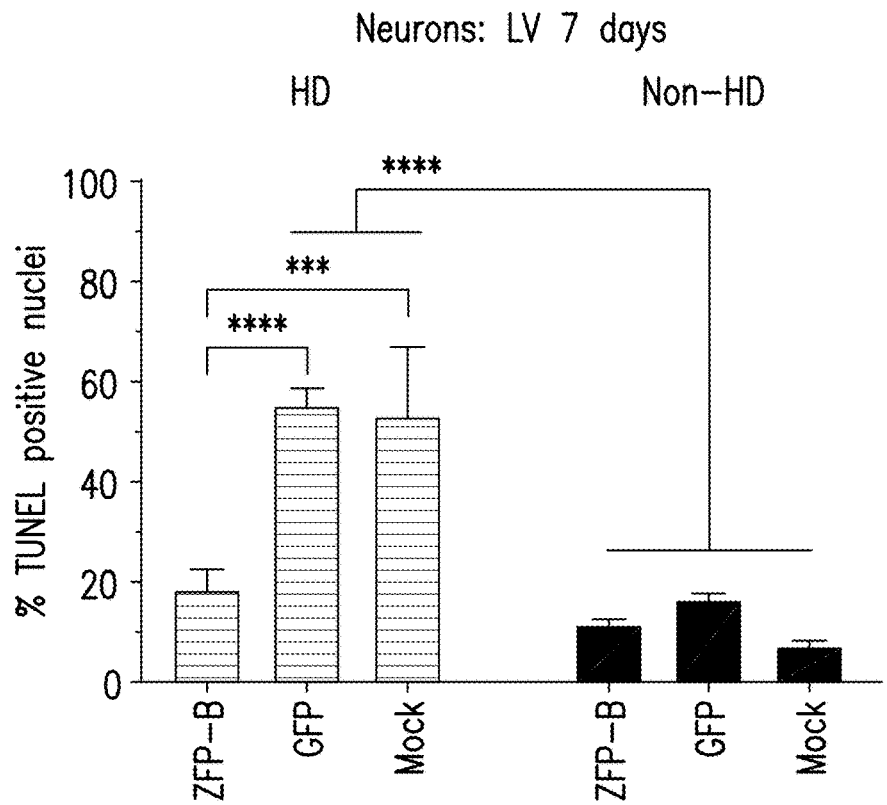
FIG. 2I demonstrates reduced apoptosis in neurons treated with ZFP-B. Apoptosis was assessed by TUNEL staining of neurons infected with either lentivirus encoding ZFP-2A-GFP or CMV-GFP for five days followed by 48 hours of growth factor withdrawal.

As shown in FIG. 2H, CAG17/48 (SEQ ID NOS:76/78) neurons had a significant decrease in intracellular ATP levels and an increased susceptibility to apoptosis compared to non-HD neurons (FIGS. 2H and 2I) compared to non-HD neurons. After 21 days of ZFP-B expression, ATP levels increased ~70% compared to control-treated neurons, suggesting that ZFP-mediated suppression of mHTT can improve HD-related metabolic defects. Cultured HD neurons also exhibit an increased susceptibility to apoptosis. Seven days following growth factor withdrawal, the percentage of CAG17/48 (SEQ ID NOS:76/78) neurons undergoing apoptosis was 3.3-fold higher than that of non-HD neurons, and ZFP expression restored apoptosis to baseline levels. As shown in FIG. 2I, expression of ZFP-B reduced apoptosis levels to that of normal neurons.

Thus, selective repression of the mHTT allele by a ZFP-TF led to a reversal of cellular phenotypes relevant to the key pathological features of HD.

Figure 2J:
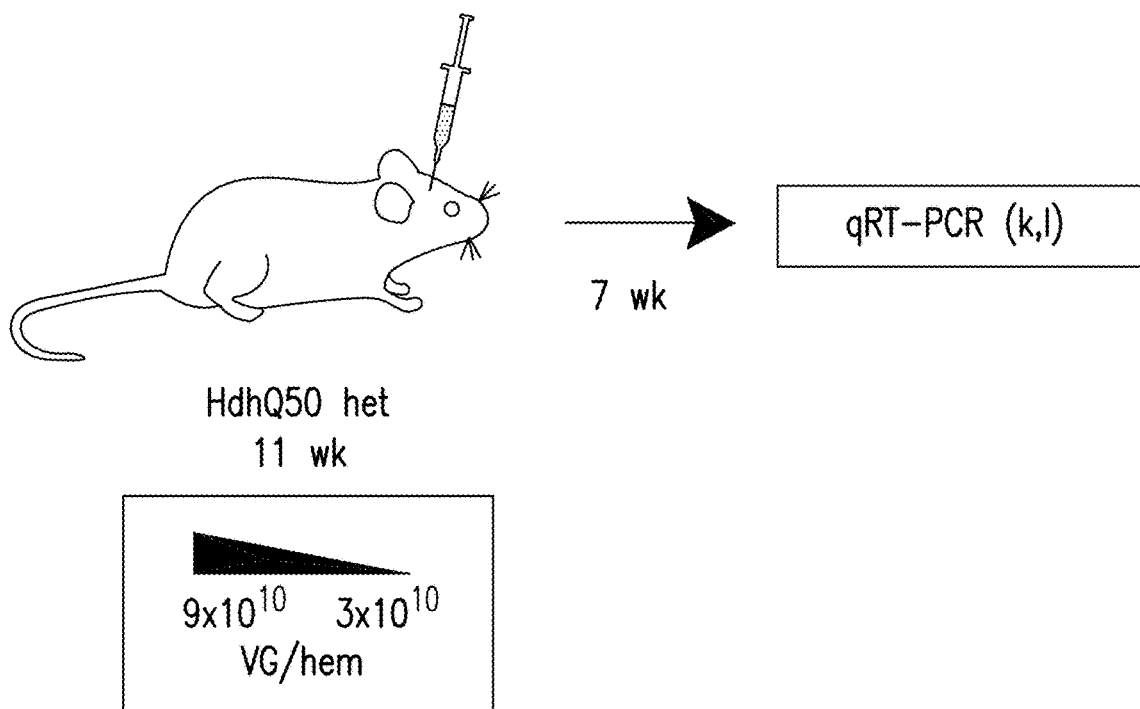
FIG. 2J is an overview of HdhQ50 mouse experiment.

Given that artificially long CAG tracts are required to induce HD-like disease in rodents, prior to conducting phenotypic studies we evaluated ZFP-B performance in heterozygous Q50 (HdhQ50/Hdh+) mice, which harbor a knock-in allele of human exon 1 encoding 48 CAGs (SEQ ID NO:78) at the endogenous mouse Htt gene. Although phenotypically normal, the Q50 model enables the assessment of mHtt repression in the context of a CAG array typical of HD patients and identical in length to that used in our human neuron studies. AAVs encoding either ZFP-B or GFP were administered by bilateral intrastriatal injection to 11-week-old Q50 heterozygotes at two doses ($3\times10^{10}$ or $9\times10^{10}$ VG/hemisphere; FIG. 2J). Seven weeks after delivery, transgene expression and Htt regulation were assessed by qRT-PCR.

Figure 2K:
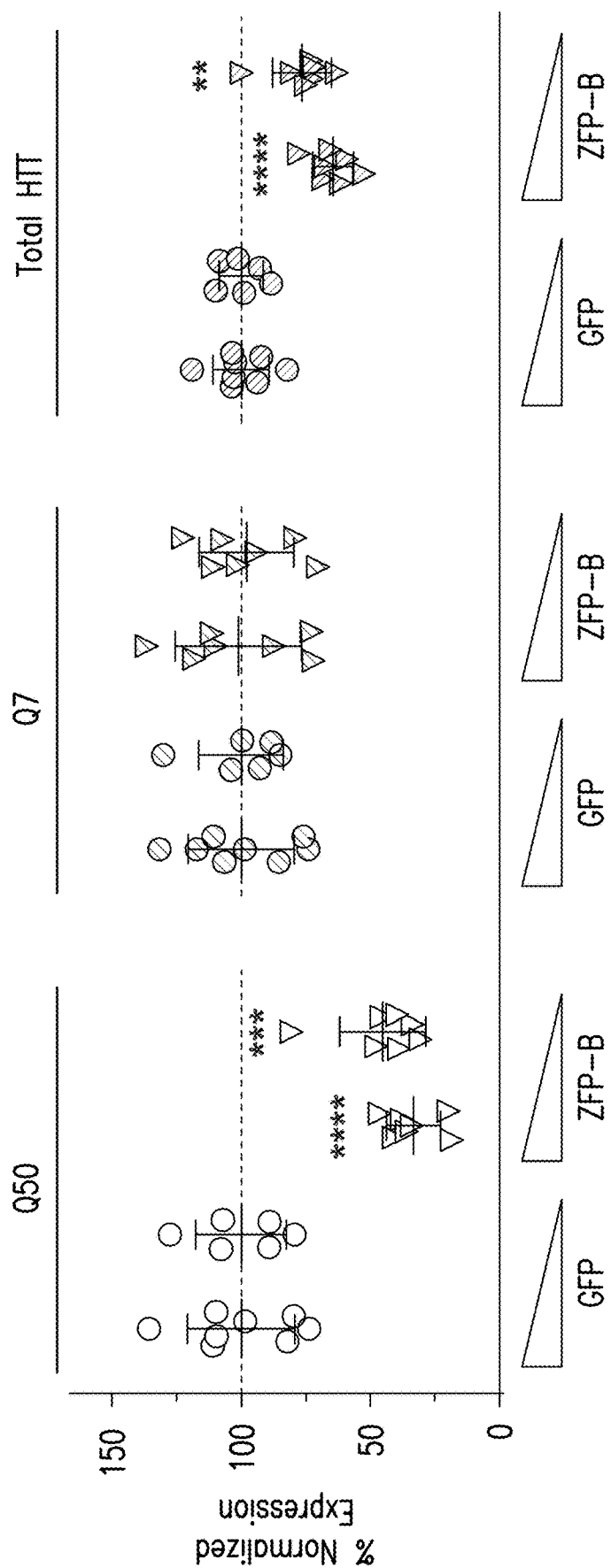
FIG. 2K shows striatal WT (Q7) and KI (Q50) Htt mRNA levels in heterozygous Q50 mice were measured by allele-specific qRT-PCR seven weeks after injection of AAV2/6 encoding either ZFP-B or GFP; n=6-8 hemispheres per group, mean±SD.
Figure 2L:
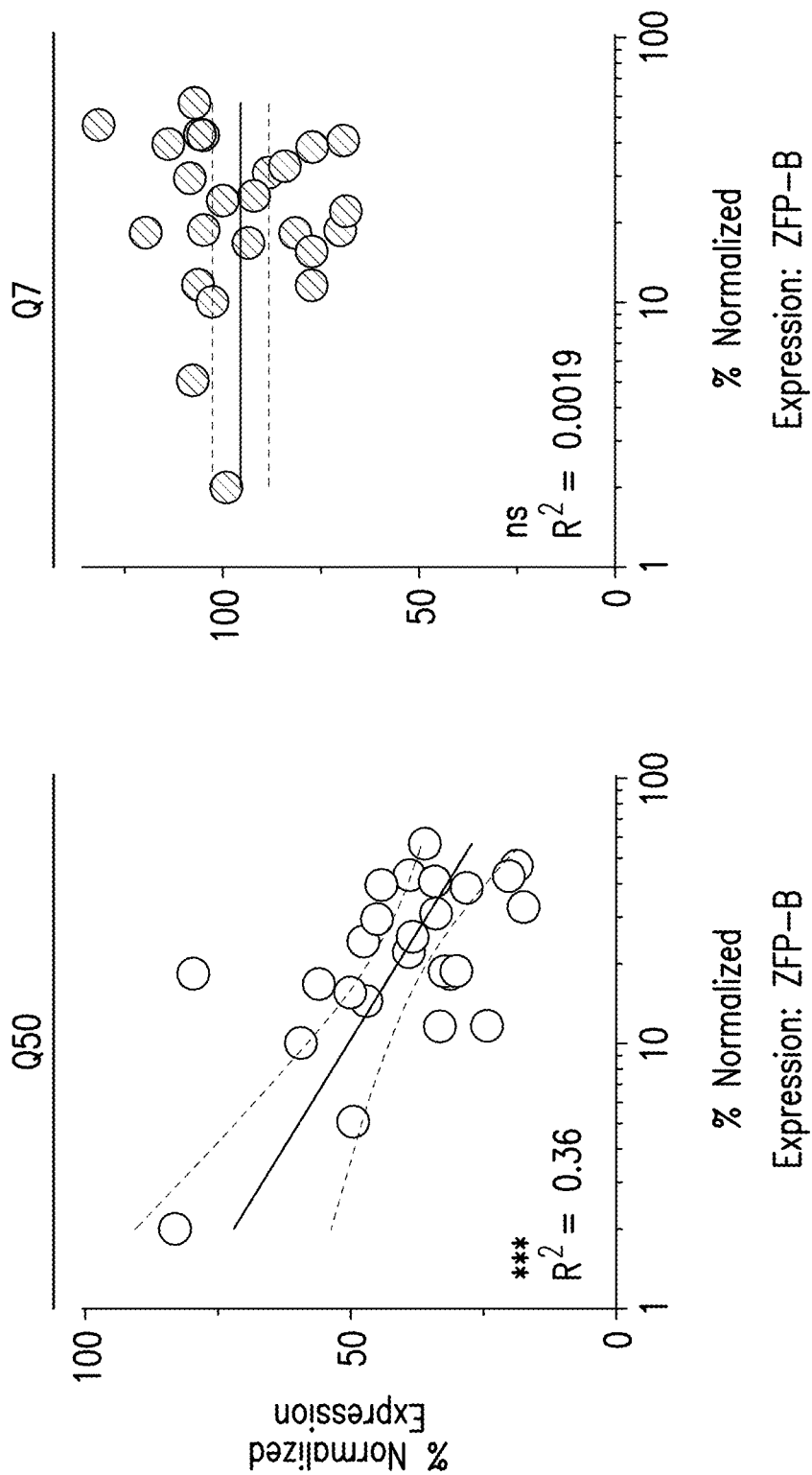
FIG. 2L is a regression analysis of either Q50 or Q7 and ZFP-B mRNA levels assessed by qRT-PCR. All striatal subsections are included. 95% confidence band is shown.
Figure 2M:
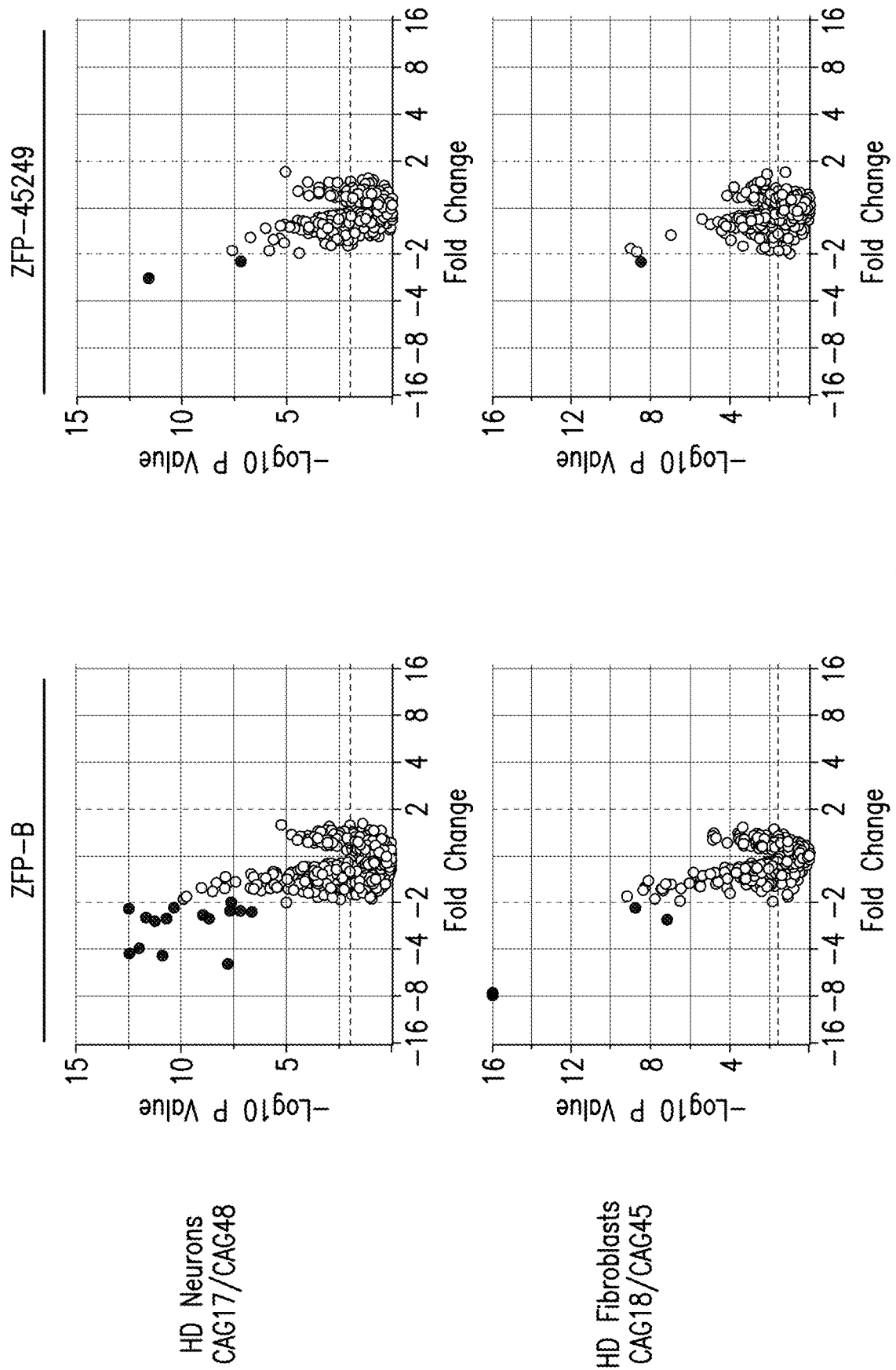
FIG. 2M depicts a genome-wide specificity assessment in HD Neurons (CAG17/48 (SEQ ID NOS 76/78)) and HD Fibroblasts (CAG18/45 (SEQ ID NOS 79/80)) using microarrays (Affymetrix GeneChip Primeview, n=4-6 biological replicates per treatment) 24 hours after transfection with 1500 ng of ZFP mRNA as described above for 2F.
Figure 2N:
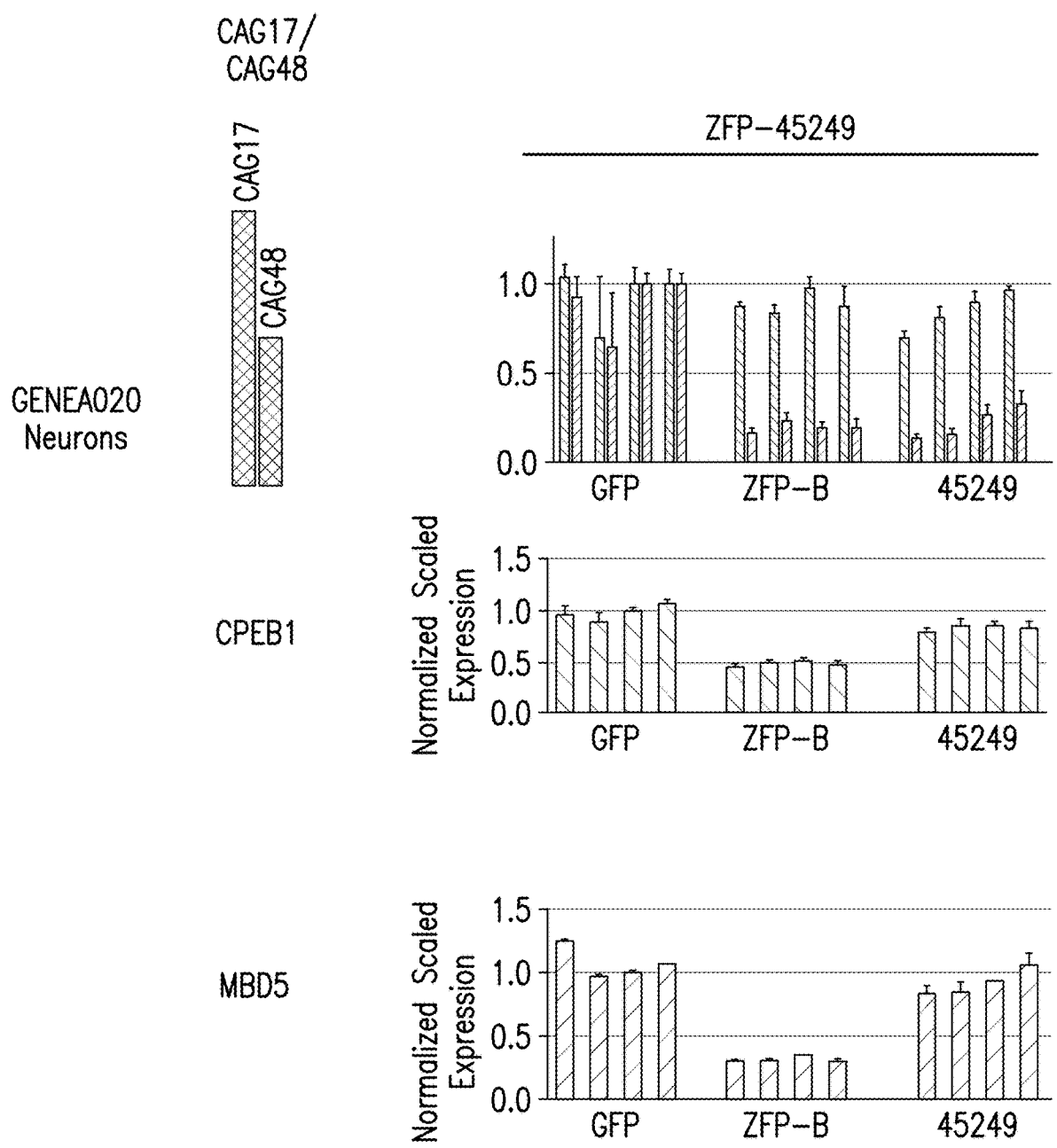

As shown in FIG. 2K, the Q50 allele was repressed by 55% (P<0.001) or 67% (P<0.0001) at the low and high dose, respectively. The endogenous mouse Q7 allele (CAG4 (SEQ ID NO:86)) was not repressed by ZFP-B at either dose, and total Htt levels were in agreement with the observed levels of allele-selective Q50 repression. Further, as shown in FIG. 2L, regression analysis of all striatal sections revealed an inverse correlation between expression levels of ZFP-B and Q50 (P<0.001, $R^2$=0.36) but not Q7. Variability in ZFP expression and Q50 repression levels among striatal sections was consistent with incomplete AAV striatal coverage that we observed throughout our stereotaxic delivery studies (typically 30-70% of the striatum covered). In addition, the ZFP-TF 45794 was also tested in GENEA020 Neurons (see FIG. 2N).

Altogether these results demonstrate that a ZFP can achieve durable and selective repression of disease-relevant CAG alleles in both human HD neurons and the mouse striatum.

A key consideration for any therapeutic strategy is the evaluation of specificity and off-target effects. Of particular interest for this approach was the prevalence of the other 1,053 endogenous CAG arrays (length 6 to account for the approximate DNA footprint of a 6 finger ZFP) in the human genome that, collectively, are adjacent to the promoters of 176 genes (See methods). Partially discontiguous arrays (up to 3 mismatches per hexamer) are even more abundant, with 21,456 total sites (all CAG arrays) proximal to 1,872 human genes. While no other human gene has a TSS-adjacent CAG tract as large as the minimum fully-penetrant mHTT allele (CAG40 (SEQ ID NO:91); see FIG. 1H), the potential regulation of certain CAG-adjacent off-target genes could pose a risk for clinical use of this strategy.

To investigate this, we employed global transcriptional profiling in patient neurons and fibroblasts. In contrast to previous CAG-targeted strategies, we selected an unbiased approach to interrogate specificity due to the uncertain influence of promoter context, epigenetic modifications, and potential of our ZFP-TFs to synergize with other factors, any of which could unpredictably affect off-target behavior. In our first design attempt—which is the focus of the current report—we identified ZFPs that exhibited a high degree of genome-wide specificity without performing any optimization for this property. Particularly informative was the apparent architectural influence on specificity for the allele-selective ZFPs. Whereas ZFP-A and ZFP-B had similar on-target behavior for all queried mHTT alleles, they had mutually exclusive off-target profiles in two cellular contexts (FIG. 2G, FIG. 11). For example, MBD5, a CAG-adjacent gene with a discontiguous CAG tract (CAG19 (SEQ ID NO:92), 0 bp from the TSS), was repressed by ZFP-B, but not ZFP-A (FIGS. 11B and 11C). ZFP-A and ZFP-B target different frames of the CAG tract, are composed of different ZF modules, and employ different linker architectures, suggesting that their off-target properties may be design-dependent and therefore amenable to optimization. We also note that recent advances in engineering ZF modules (e.g., with improved preference for the targetable frames in the CAG/CTG array), as well as the ablation of non-specific interactions between the ZF and DNA backbones, provide potential complementary paths for optimizing ZFP specificity and the development of a ZFP suitable for clinical use.

While our initial design effort produced allele-selective ZFPs with a high degree of genome-wide specificity in human fibroblasts and neurons, we anticipated that our proteins could also manifest some off-target activity in mice, albeit at different loci given the substantial lack of CAG-repeat conservation between orthologs. Surprisingly, 85 of the top 100 mouse genes with the largest TSS-adjacent CAG arrays have no corresponding repeat in the human genome. We nevertheless conducted a biased off-target analysis for mouse genes with the largest TSS-adjacent CAG arrays (+/−1 kb of a TSS) in the mouse genome following intrastriatal ZFP treatment in both wildtype and zQ175 het mice. Of the mouse genes that were significantly regulated by ZFP-B and/or ZFP-D in vivo, all had substantially larger CAG repeats in the mouse ortholog compared to human. For example, DNAJC12—a gene with 19 CAG repeats (SEQ ID NO:92) present in the mouse promoter, but absent in the human ortholog—was regulated in the mouse striatum but not in human fibroblasts or neurons, underscoring the need to assess specificity in human cells. Among orthologs, only NAP1L3 was regulated in human neurons and fibroblasts, and only by ZFP-A (3.1- to 5.8-fold repression) but not ZFP-B (no change detected), further confirming our observations that CAG off-target regulation is highly influenced by the ZFP design.

Critically, we conducted extensive long-term tolerability and safety studies to understand whether the ZFPs resulted in any detectable toxicity at the molecular, cellular or behavior levels (FIGS. 4, 16 and 17). We note that under conditions of chronic expression in both human neurons and in the mouse striatum using multiple promoters and AAV serotypes, we observed no evidence of neurodegeneration, neuroinflammation or toxicity out to at least 15 months of age and 9 months of ZFP exposure, suggesting that under these delivery and expression conditions the ZFPs were well tolerated. Given the on-target potency and allele-selectivity window of ZFP-A and ZFP-B—and that we performed our off-target analyses at ZFP doses 1-2.5 orders of magnitude above on-target EC50 doses—the use of weaker cell-type specific promoters may be useful when investigating aspects of HTT biology with these reagents outside of our experimental systems (e.g., alternate serotypes or routes of administration).

Example 6: ZFP-Driven Neuroprotection and Amelioration of Behavioral Deficits in the R6/2 Model Having established robust mHTT repression in several in vitro settings and the brain, we proceeded to evaluate whether an allele-selective ZFP could improve hallmark neuropathological and behavioral phenotypes in HD mice. We first investigated ZFP performance in the R6/2 mouse model, which overexpresses an exon 1 fragment of human HTT bearing an expanded CAG array (~120 CAGB). R6/2 mice exhibit early and progressive changes in neuronal physiology, body weight (BW) loss, motor and cognitive alterations—including clasping and a hypolocomotor state—and substantial reductions in medium spiny neuron (MSN) markers, including DARPP32, phosphodiesterase 10a (PDE10a), dopamine receptors D1 (DRD1) and D2 (DRD2) (see Example 1).

Figure 3A:
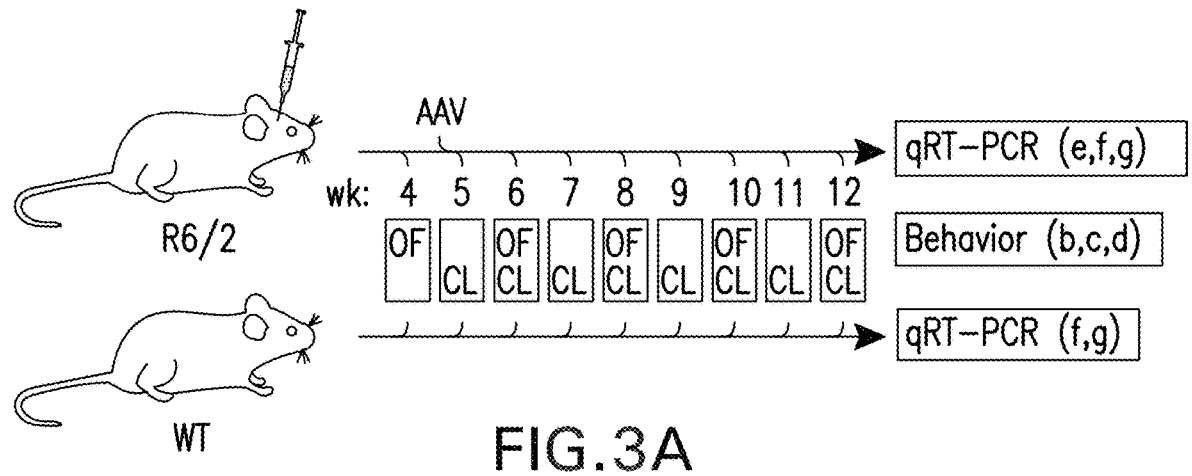
FIGS. 3A through 3G depict improvements in behavioral deficits and neuroprotection in R6/2 mice.

In these studies, 5-week-old R6/2 mice were bilaterally intrastriatal injections of AAV encoding either ZFP-B or GFP and compared to non-transgenic, age-matched controls for all endpoints (FIG. 3A).

Figure 3B:
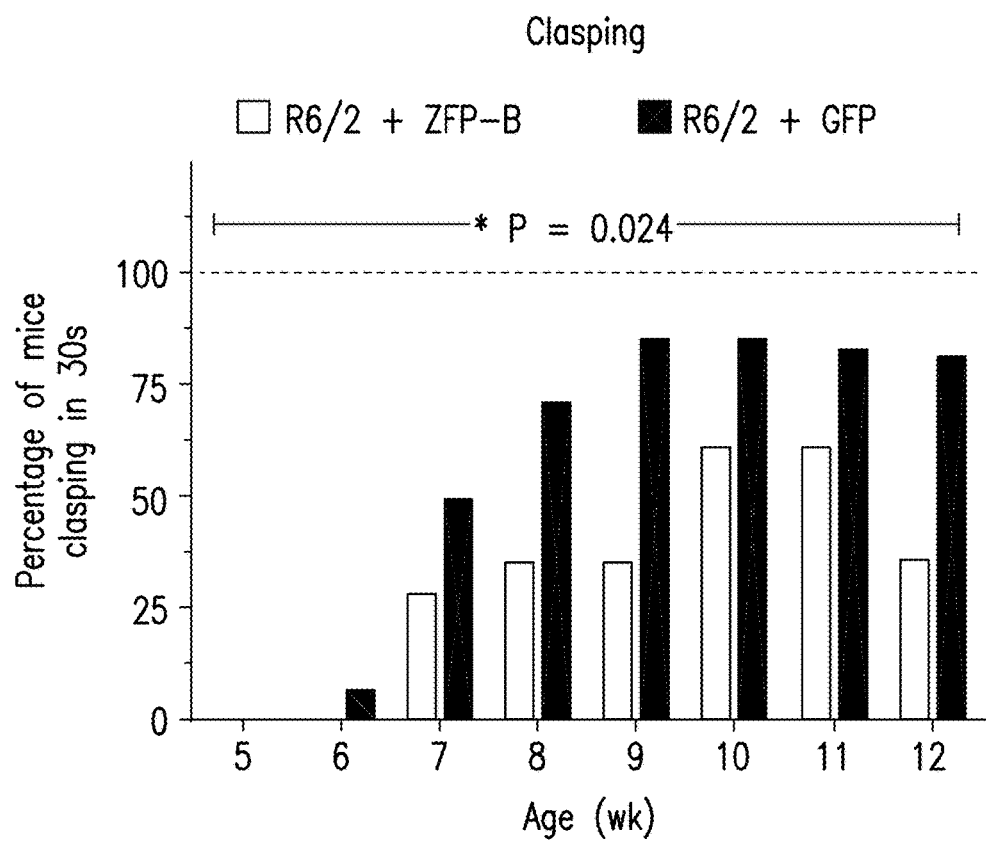

As shown in FIG. 3B, ZFP-B conferred a significant reduction in clasping over the 7-week duration of the study (P=0.024, log-rank test), and fewer ZFP-treated mice clasped compared to the GFP-treated group each week. Over the 7-week study, the ZFP-treated group was 2.4 times less likely to clasp than the GFP group (FIG. 3B).

Figure 3C:
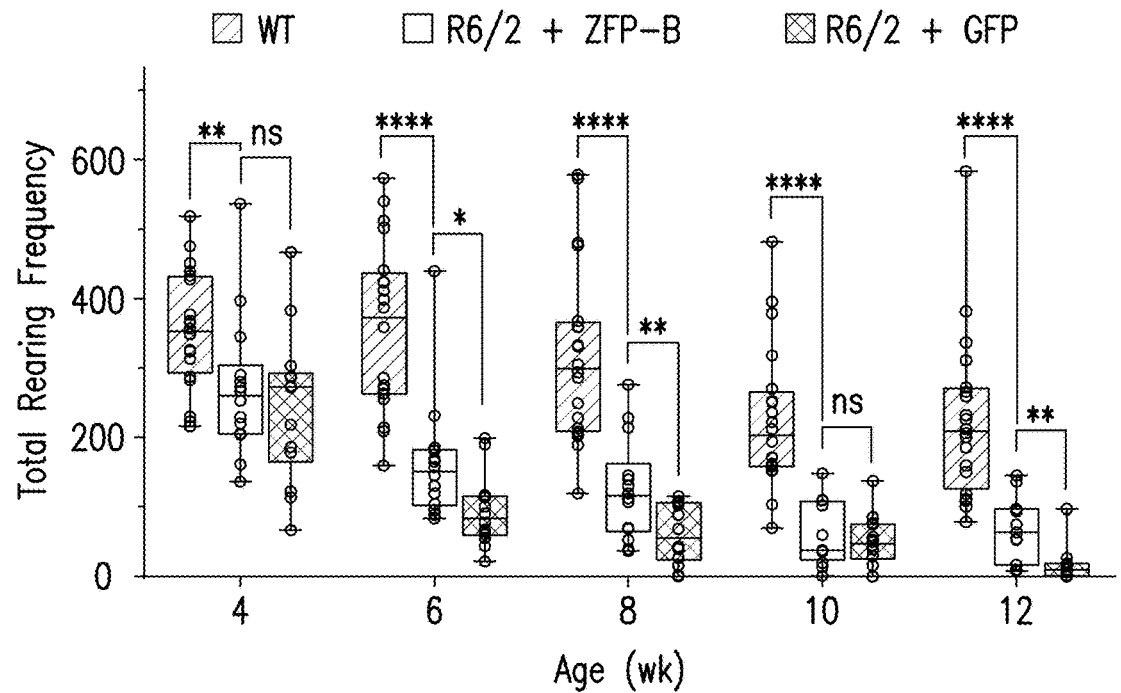
Figure 3D:
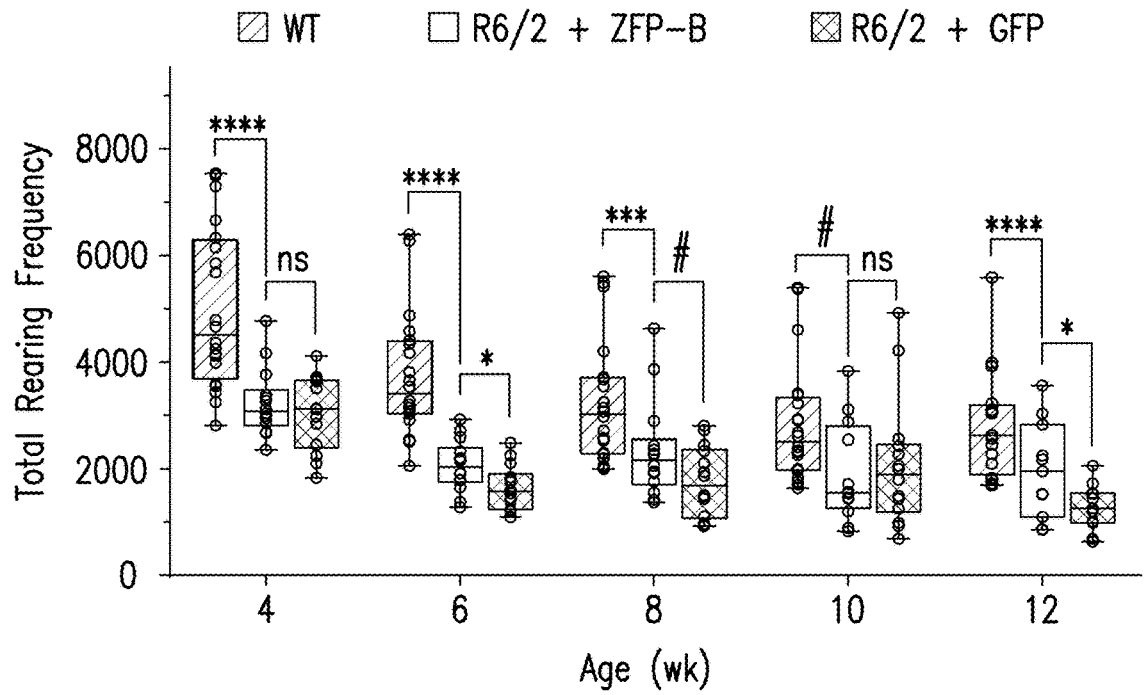
Figure 13A:
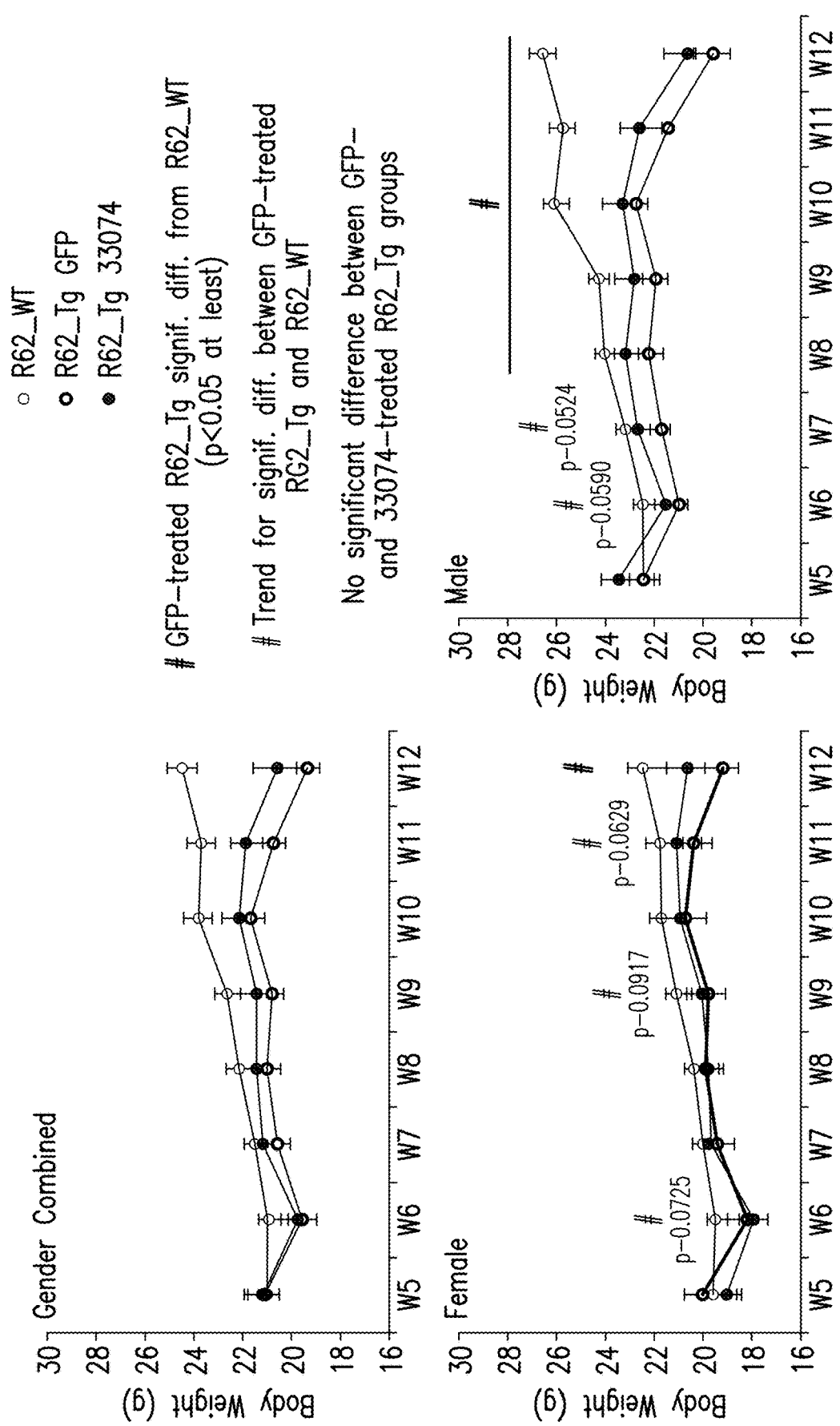
Figure 13B:
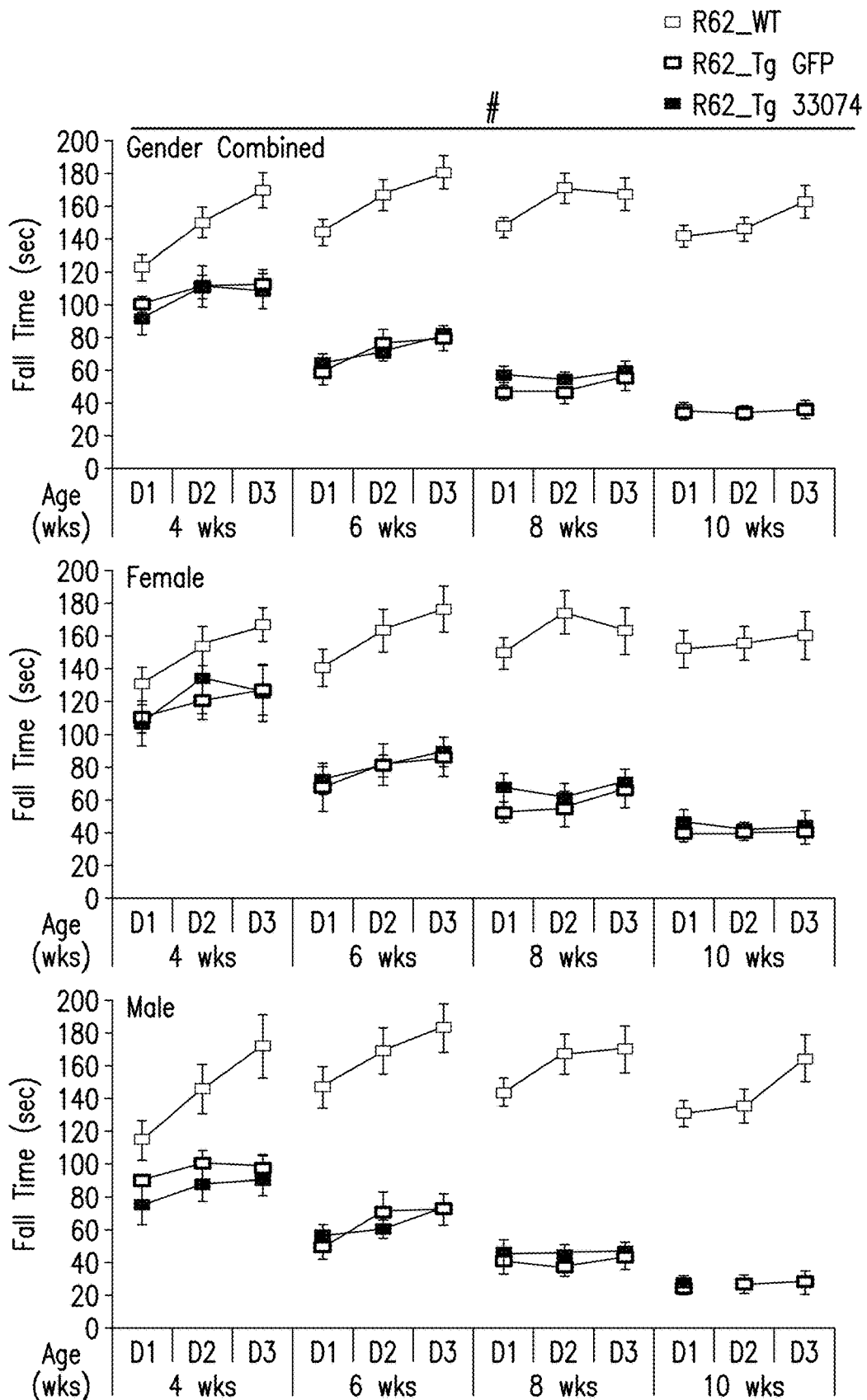

Hypolocomotion was also examined biweekly using the open field test. As shown in FIG. 3C, in biweekly open field assessments for spontaneous locomotion, ZFP-treatment conferred a significant longitudinal improvement compared to GFP-treated controls for both rearing frequency (P=0.009) and total distance traveled (FIG. 3D; P=0.038). Moreover ZFP-treated mice performed significantly better at several timepoints after ZFP administration, and the greatest benefit relative to control-treated mice was observed at the final time point (12 weeks). Notably, there was no significant BW difference for ZFP-treated mice compared to controls, nor did we detect a ZFP-treatment effect for measurements of grip strength or rotarod performance (FIG. 13).

The improvements we observed in certain behavioral endpoints raised the prospect that ZFP-expressing neurons in the AAV-transduced striatal region were protected. To explore this possibility, mice were sacrificed following the 12-week behavioral assessment, and striatal tissue was subjected to qRT-PCR analysis for ZFP, HTT, and MSN marker expression (see methods above).

Figure 3E:
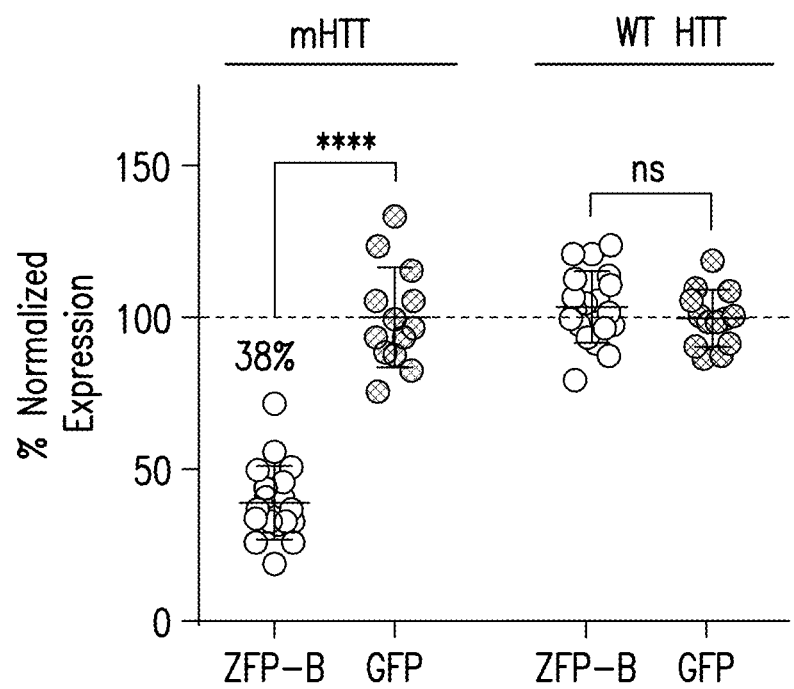
Figure 3F:
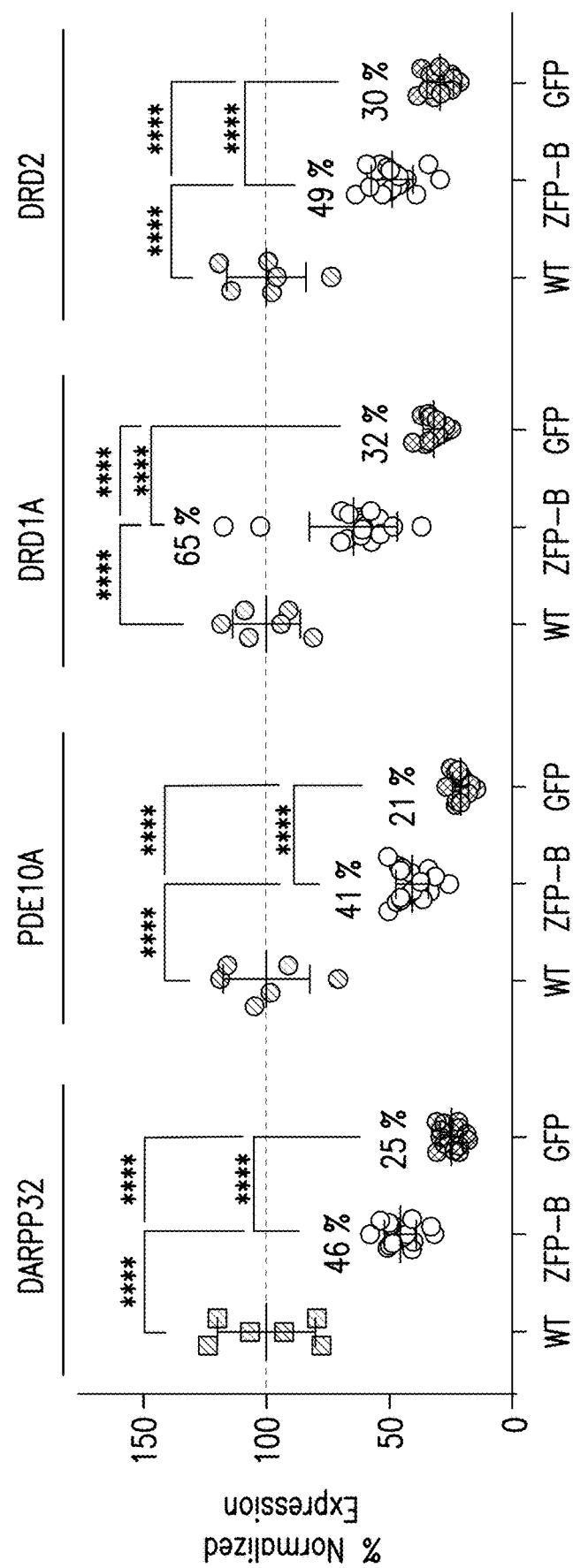
Figure 3G:
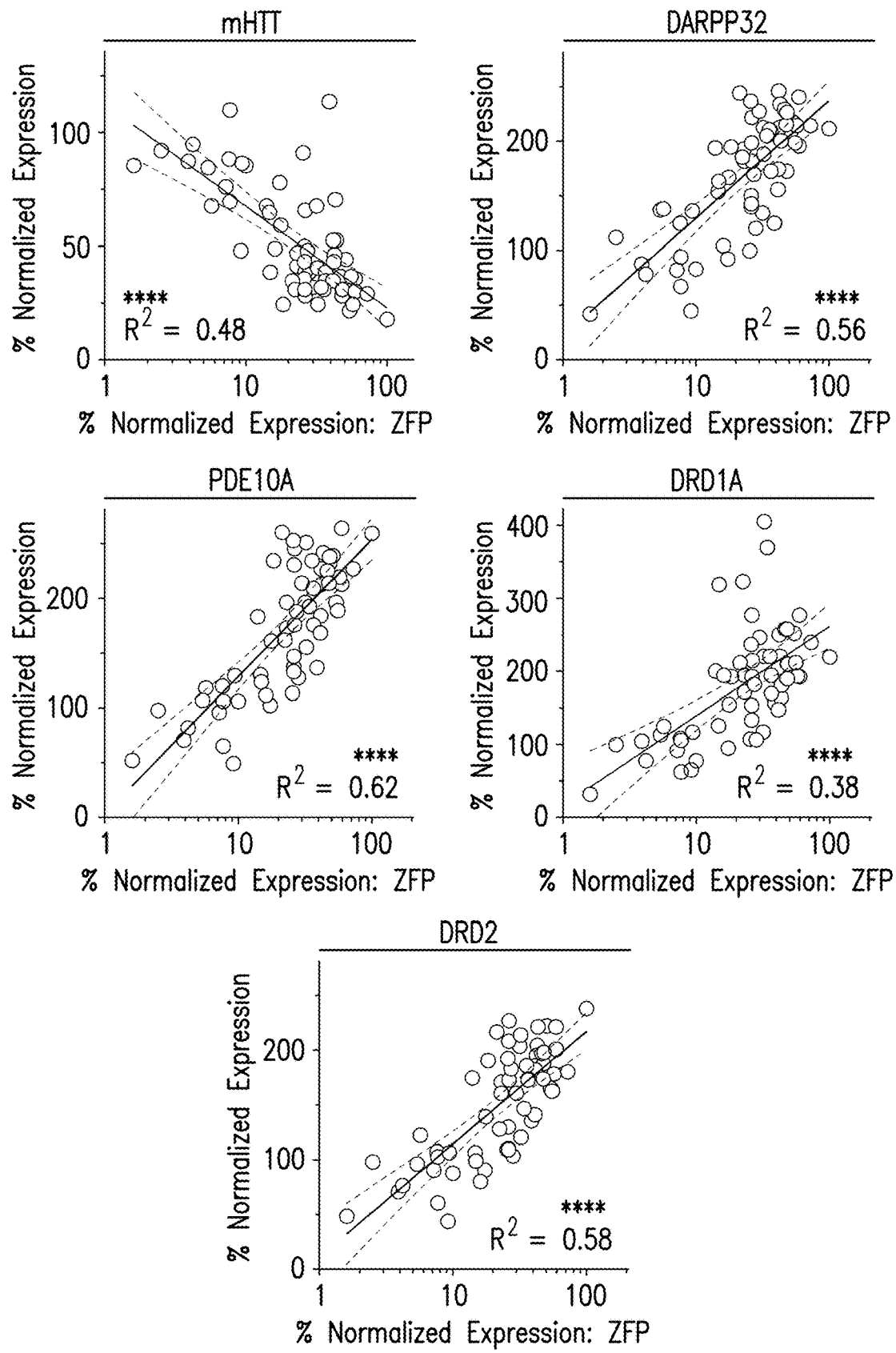

As shown in FIG. 3E, similar to our results seen for bulk tissue analysis in Q50 mice (FIGS. 2K and 2L), ZFP-treatment resulted in 62% reduction of mHtt (P<0.0001), whereas the expression of native mouse Htt was unchanged. We examined GFP fluorescence in a subset of animals from the control group and found that AAV coverage ranged from ~50-70% of the striatum, suggesting near-maximal repression of mHTT in the delivered area (data not shown). Transcript levels of DARPP32, PDE10A, DRD1A and DRD2 in ZFP-treated mice ranged from 1.6-2.0× higher than those of GFP-treated mice (all P<0.0001; FIG. 3F), albeit at levels 1.5-2.3× lower than age-matched non-transgenic controls (all P<0.0001), consistent with incomplete vector coverage of the analyzed striatal regions and preexisting neurodegeneration at the age of intervention. Importantly, regression analysis of every striatal sample revealed a significant negative relationship between ZFP and mHTT transcript levels ($R^2$=0.48, P<0.0001; FIG. 3G), and a correspondingly positive relationship between ZFP expression and the levels of all MSN markers ($R^2$=0.38-0.62, all P<0.0001). Together, our findings in R6/2 mice provided evidence of ZFP-driven improvements in both behavioral and molecular neuropathological endpoints, and prompted further investigation into the potential neuroprotective benefit of an allele-selective ZFP at the cellular level in the context of a less aggressive disease model.

Figure 4A:
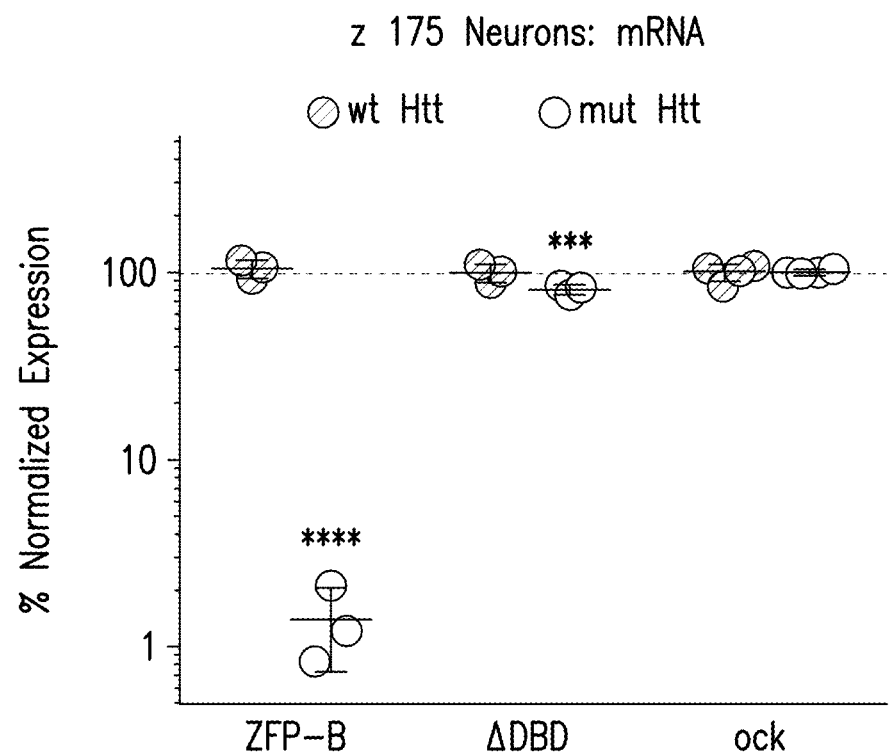
FIGS. 4A through 4T show ZFP-driven repression of mHTT in knock-in HD mouse models.
Figure 4B:
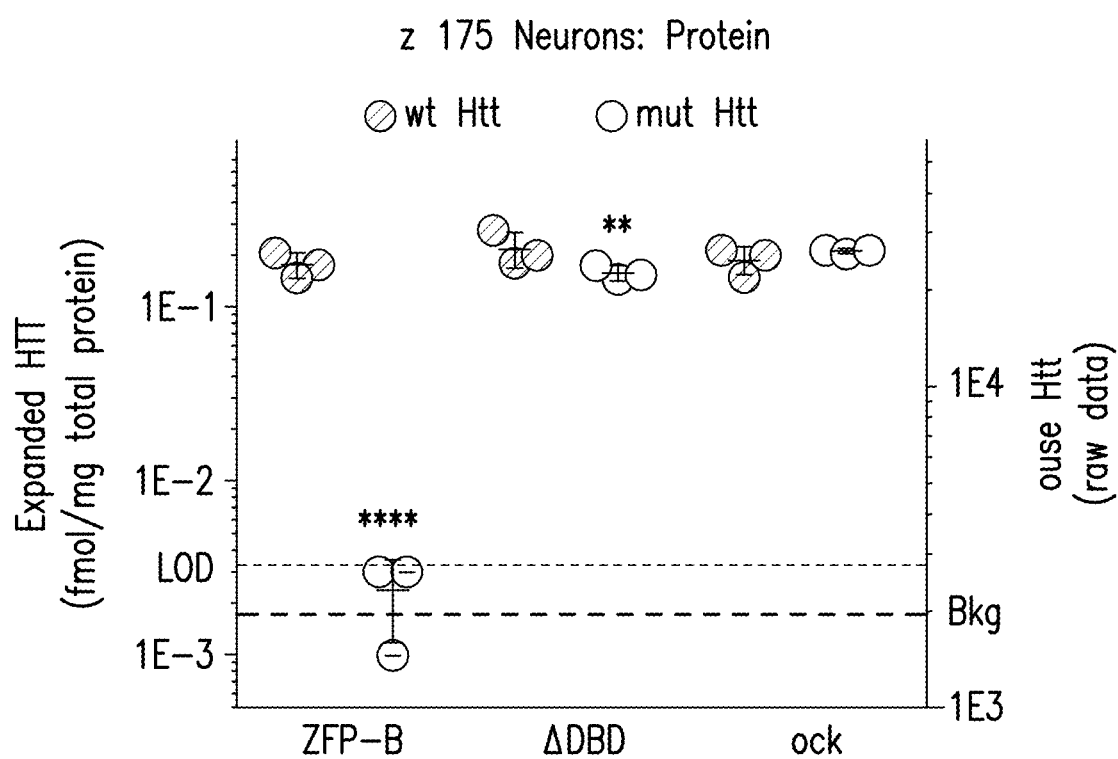

Example 7: Repression of mHtt and Correction of Histopathology and Electrophysiology Deficits in zQ175 Heterozygous Mice Due to the limitations imposed by intraparenchymal AAV delivery in mice and rapid R6/2 disease progression, we focused on whether a ZFP-TF could impact key neuropathological deficits in the slower progressing zQ175 model. These mice harbor a knock-in mHtt human exon 1 allele with ~188 CAG repeats, and display HD-related molecular, histological, electrophysiological, and behavioral phenotypes. See Example 1. Heterozygous zQ175 mice develop hallmark mHTT-containing inclusions at 3-4 months of age that continue to accumulate through 12 months of age, molecular and electrophysiological disease signatures between 4-6 months of age, and a delayed onset of relatively mild locomotor deficits at 10-12 months of age (Menalled et al. (2012) *PLoS ONE* 7:e49838; Heikkinen et al. (2012) *PLoS ONE* 7:e50717; Carty et al. (2015) *PLoS One* 10:e0123527; Beaumont et al. (2016) *Neuron* 92:1220-1237), thus permitting an assessment of ZFP efficacy at different stages of disease progression. We first confirmed that AAV delivery of ZFP-B resulted in selective repression of mutant HTT mRNA (99%, P<0.00 01) and protein (99%; P<0.0001) in cultured primary heterozygous zQ175 striatal neurons (FIGS. 4A and 4B). As expected, no reduction of wild-type mouse HTT was observed, and a control virus lacking the ZFP DNA-binding domain (ΔDBD) failed to substantially lower mutant HTT.

Figure 4C:
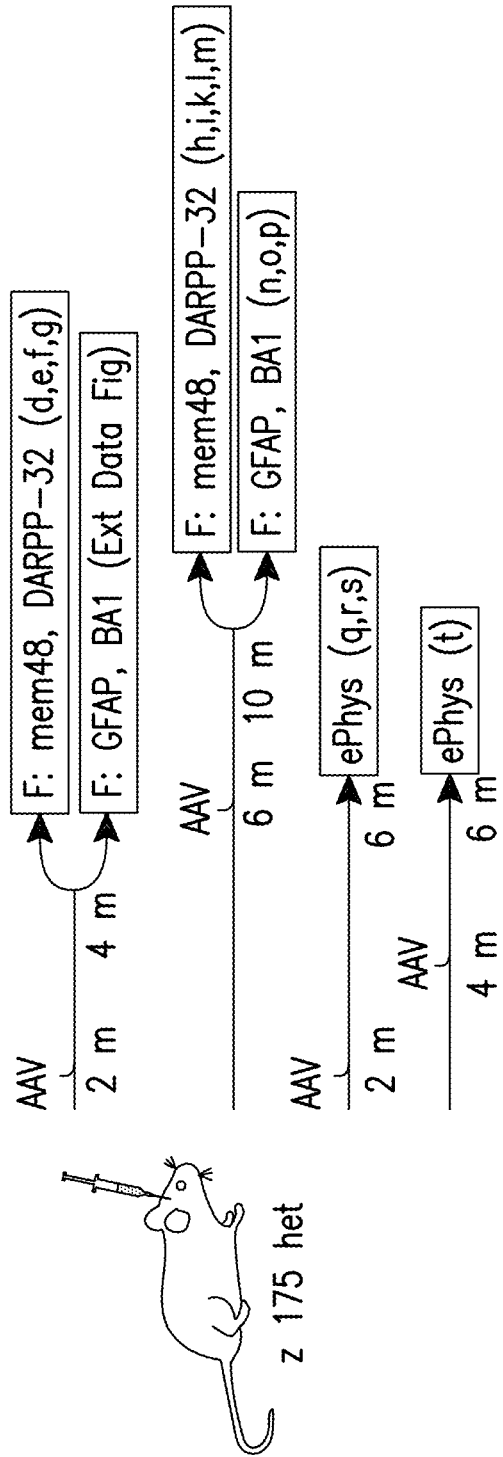
FIG. 4C is a timeline overview showing endpoints in zQ175 heterozygous mouse studies.
Figure 4D:
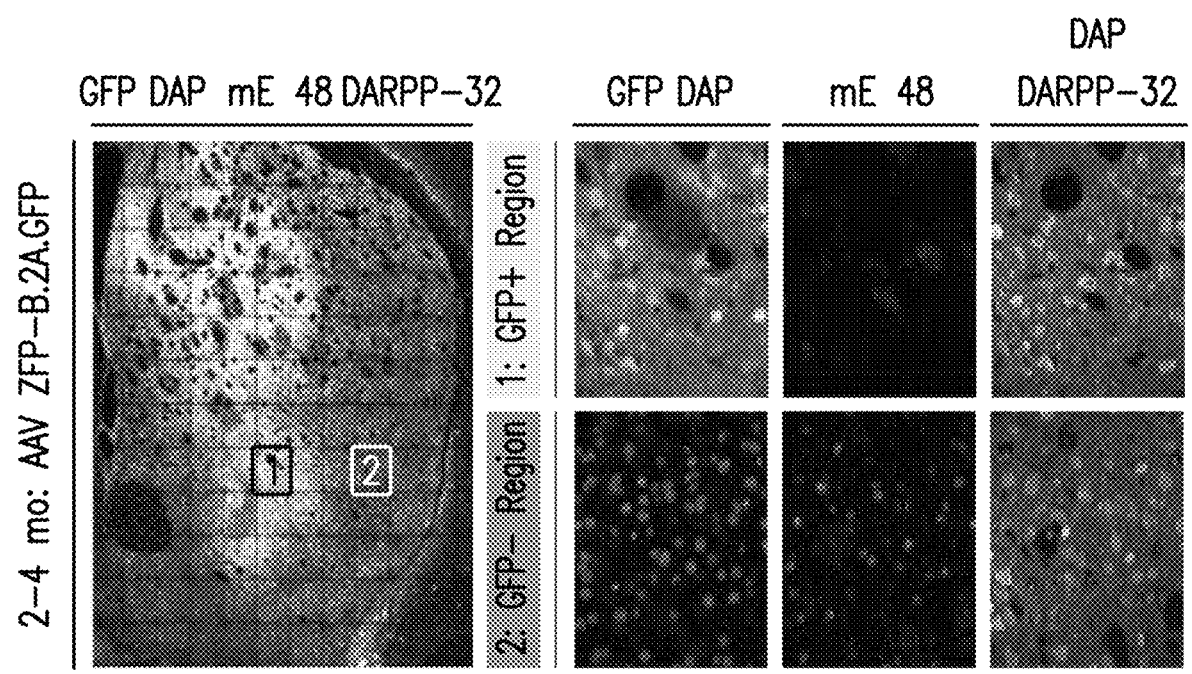
FIG. 4D shows representative images of mEM48 immunostaining in heterozygous zQ175 striata injected with AAV2/1+2 encoding ZFP-B.T2A.GFP at 2 months of age and analyzed at 4 months of age by staining for mEM48, GFP, DARPP-32 and DAPI (color not shown but as follows: HTT inclusions (mEM48): yellow, GFP: green, DARPP-32: red, DAPI: blue). Expanded GFP+ and GFP– regions are shown at right.
Figure 4E:
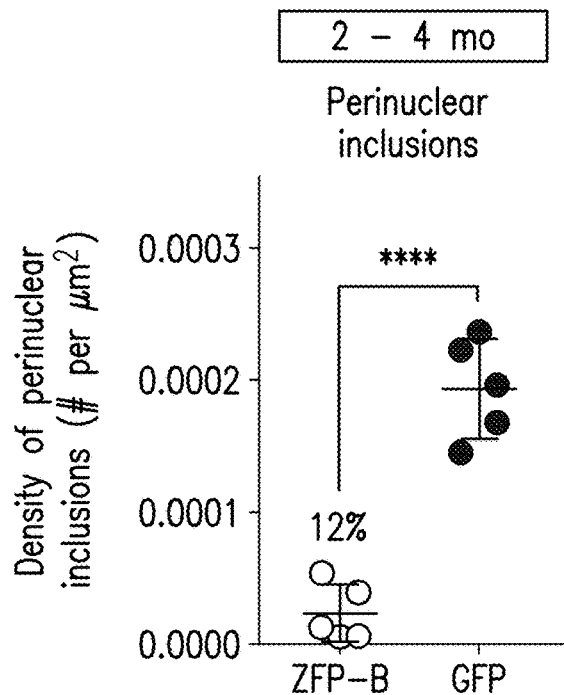
FIGS. 4E and 4F show quantitation of perinuclear (FIG. 4E) and nuclear (FIG. 4F) mHTT inclusions in striatal MSNs from the 2-4 month treatment cohort; n=5; mean±SD. Statistical analysis used in 4E through 4O: two-tailed t-test with Welch's correction.
Figure 4F:
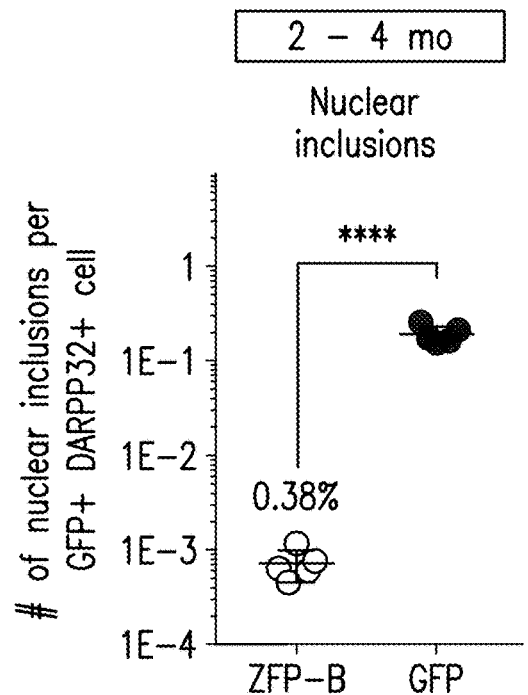
Figure 4G:
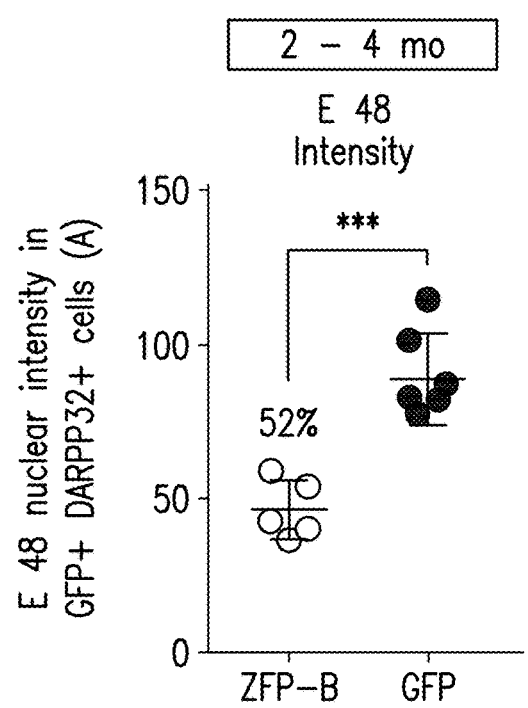
FIG. 4G shows quantitation of mEM48 intensity in GFP+ cells as in (4E and 4F); n=5; mean±SD.
Figure 4H:
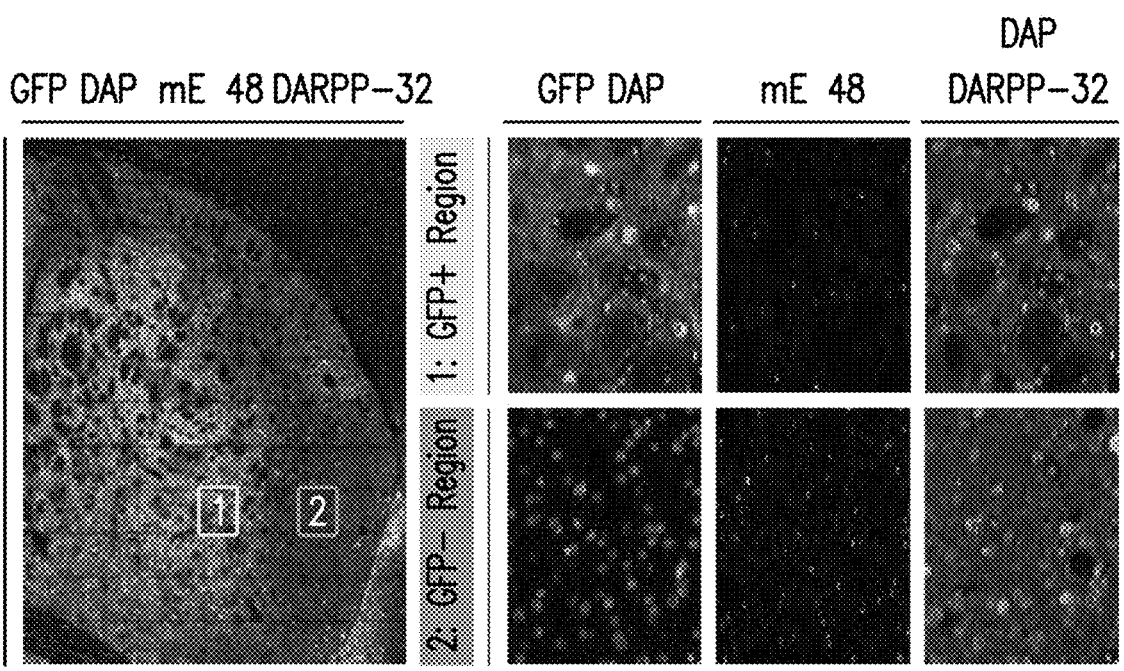
FIG. 4H shows data as in 4D, except for using heterozygous mice that were injected with AAV2/1+2 encoding ZFP-B.T2A.GFP at 6 months of age and analyzed at 10 months of age.
Figure 4I:
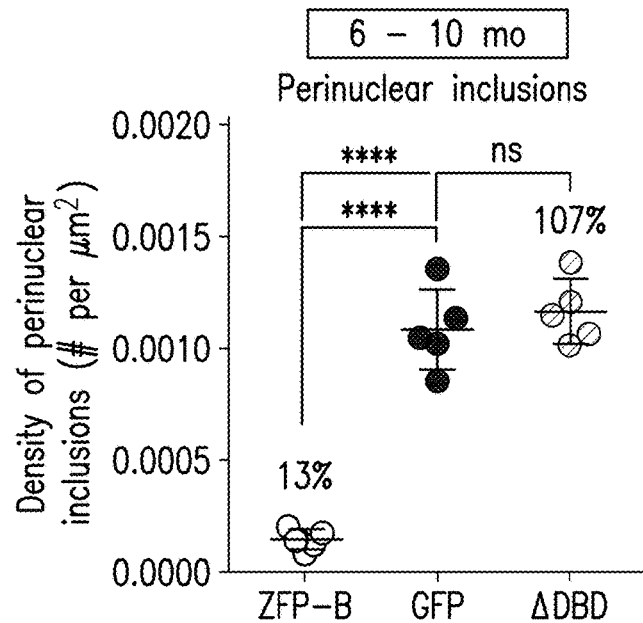
FIGS. 4I and 4J shows data as in 4E and 4F, except for the 6-10 month cohort treated with AAV2/1+2 ZFP-B.T2A.GFP, ΔDBD.T2A.GFP or GFP; n=5; mean±SD.
Figure 4J:
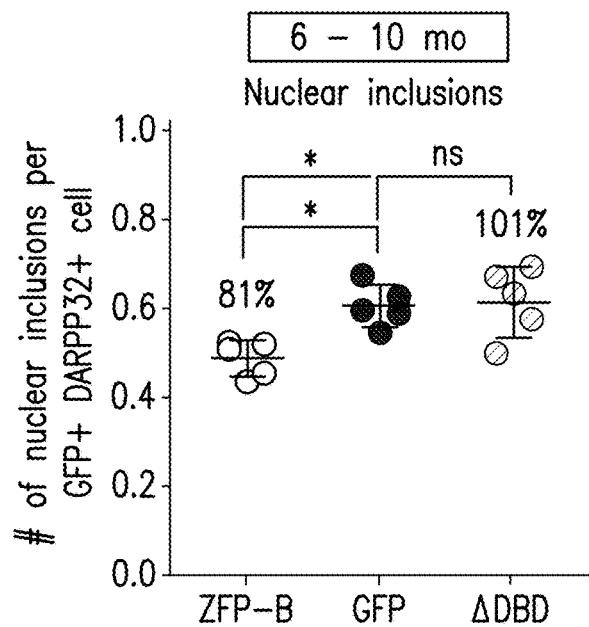
Figure 4K:
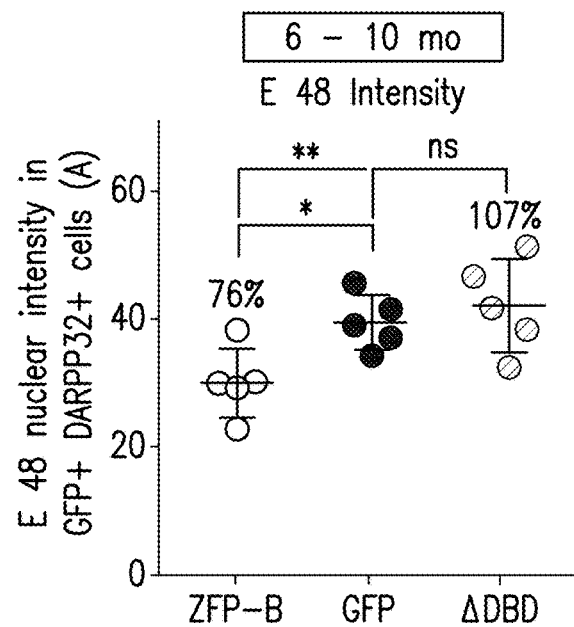
FIG. 4K is as in 4G except for the 6-10 month cohort treated with AAV2/1+2 ZFP-B.T2A.GFP, ΔDBD.T2A.GFP or GFP; n=5; mean±SD.

To assess the impact of a ZFP on mHTT inclusions, we monitored EM48 immunoreactivity in heterozygous zQ175 mice following intrastriatal treatment either prior to (early treatment) or following (late treatment) neuropathological onset (FIG. 4c). For the early treatment cohort, AAV encoding either ZFP-B or GFP was injected into the dorsal striatum of 2-month-old mice and HTT aggregation was assessed at 4 months of age. A self-cleaving T2A-GFP tag was used to label ZFP-expressing cells. In transduced MSNs (DARPP32+GFP+), ZFP-B nearly completely prevented nuclear mHTT aggregation (99.6% reduction, P<0.0001) (FIGS. 4D and 4E; FIG. 14). A significant decrease in the density of perinuclear HTT inclusions (88% reduction; P<0.0001) and total EM48 immunofluorescence (48% reduction; P<0.01) was also observed (FIGS. 4F and 4G). For the late treatment cohort, ZFP-B.T2A.GFP, ΔDBD.T2A.GFP, or GFP vectors to the striatum of 6-month-old heterozygous zQ175 mice, which bear a substantial preexisting burden of HTT aggregates (Mangiarini et al. (1996) *Cell* 87:493-506). Four months after injection, ZFP-B treatment reduced the number of nuclear EM48+ inclusions by 19% (P<0.01, FIGS. 4H and 4I) and perinuclear inclusions by 87% (P<0.0001; FIGS. 4H and 4J) relative to the GFP control group (FIG. 14). EM48 intensity in cells with a nuclear inclusion was also lowered by 24% (P<0.05, FIG. 4k). There was no significant difference between ΔDBD- and GFP-treated mice for any endpoint in these studies.

Together, these results show that an allele-selective ZFP can reduce and potentially block mHTT aggregation both before and after disease onset.

Figure 4L:
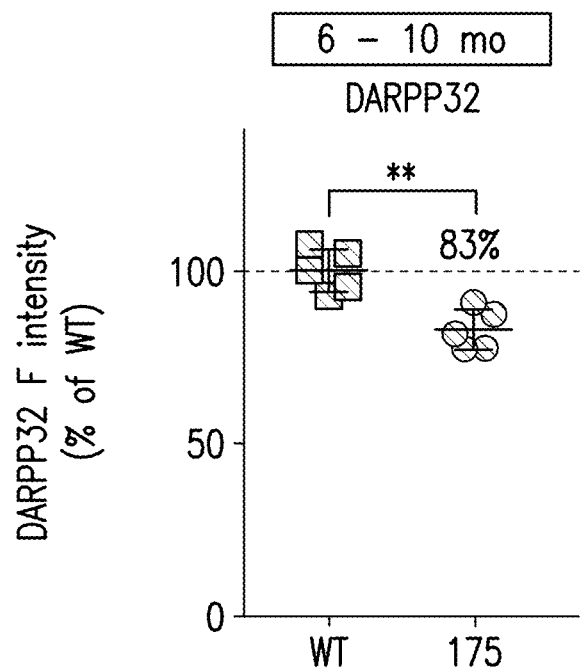
FIG. 4L depicts DARPP32 that was measured by IHC in the striatum of WT and heterozygous zQ175 mice at 10 months of age; n=5; mean±SD.
Figure 4M:
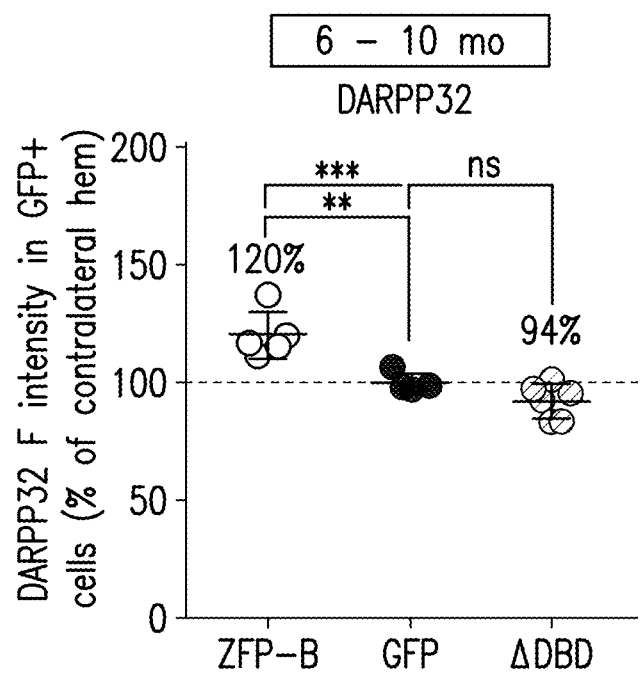
FIG. 4M depicts DARPP32 levels in mouse striata injected with AAV2/1+2 ZFP-B.T2A.GFP, ΔDBD.T2A.GFP or GFP at 6 months of age and analyzed at 10 months of age; n=5; mean±SD.
Figure 4N:
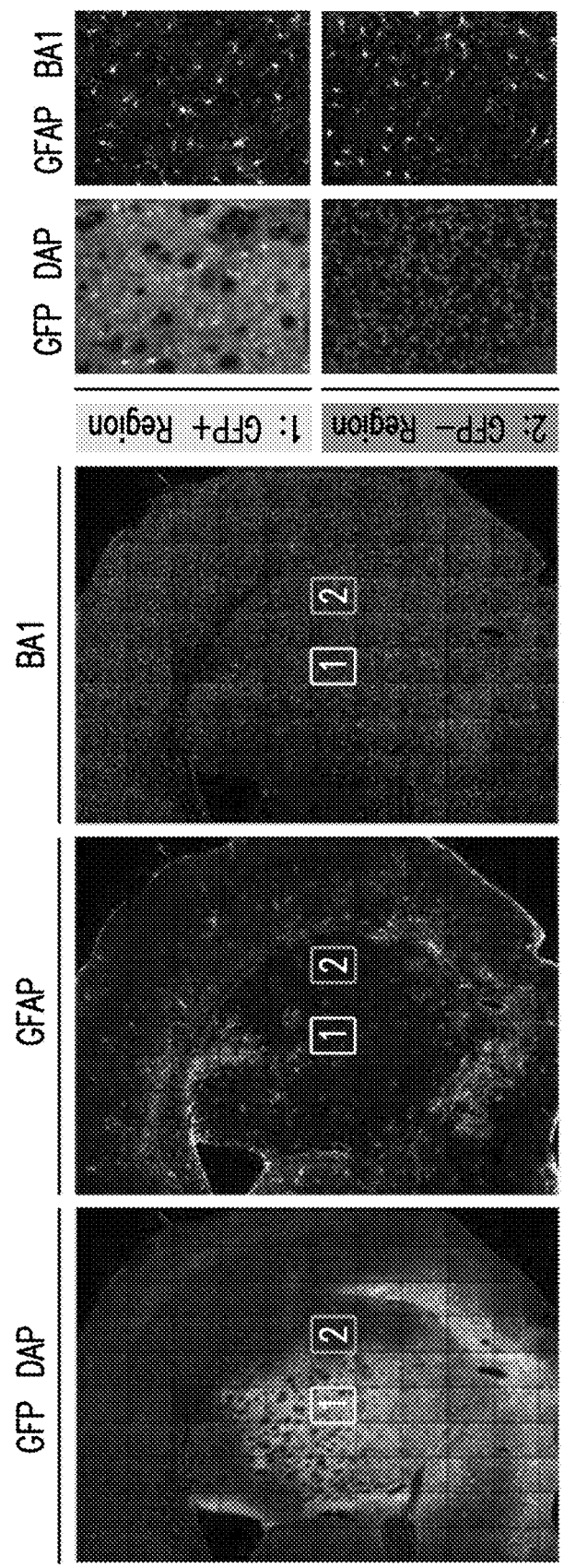
FIG. 4N shows representative images of GFAP and IBA1 immunostaining in heterozygous zQ175 striata injected with AAV2/1+2 encoding ZFP-B.T2A.GFP at 6 months of age and analyzed at 10 months of age for GFP, DAPI, GFAP and IBA1 (color not shown as follows: GFP: green, DAPI: blue, GFAP: red, IBA1: yellow).

We also evaluated the impact of ZFP expression on the health of transduced MSNs in the late treatment cohort by monitoring DARRP32 levels. Compared to age-matched WT mice, 10-month-old zQ175 heterozygotes exhibit a 17% (P<0.01) striatal reduction in DARPP-32 immunoreactivity (FIG. 4L). Consistent with our findings in R6/2 mice, ZFP-B administration to 6-month-old zQ175 mice resulted in a 20% (P<0.01) increase in DARPP32 immunoreactivity at 10 months of age (FIG. 4M). Importantly, the effect was exclusive to ZFP-expressing MSNs, suggesting a protective effect imparted by ZFP expression. To evaluate whether chronic ZFP expression induced a neuro-inflammatory response in vivo, we monitored markers of astrogliosis (GFAP) and microgliosis (Iba1). Besides the transient effects of the injection itself (localized to the needle track), we observed no increase in marker intensity or the number of GFAP+ (FIGS. 4N and 4O) or Iba+ (FIGS. 4N and 4P) cells for any treatment during the time course of these studies. Importantly, there was no effect of GFP expression on these markers (FIG. 15).

The improvements in mHTT aggregation pathology and DARPP32 levels led us to investigate whether a ZFP could also ameliorate important electrophysiological deficits affecting zQ175 indirect pathway projection neurons (iSPNs), which manifest by 4 months of age (PMID: 24991961, reviewed in PMID: 25700146). In these studies, 2- or 4-month-old mice received intrastriatal injections of AAV encoding ZFP-D.T2A.tdTomato or ΔDBD.T2A.tdTomato, and iSPN dendritic excitability was assessed at 6 months of age (FIGS. 4C and 4N; FIG. 15).

Figure 4O:
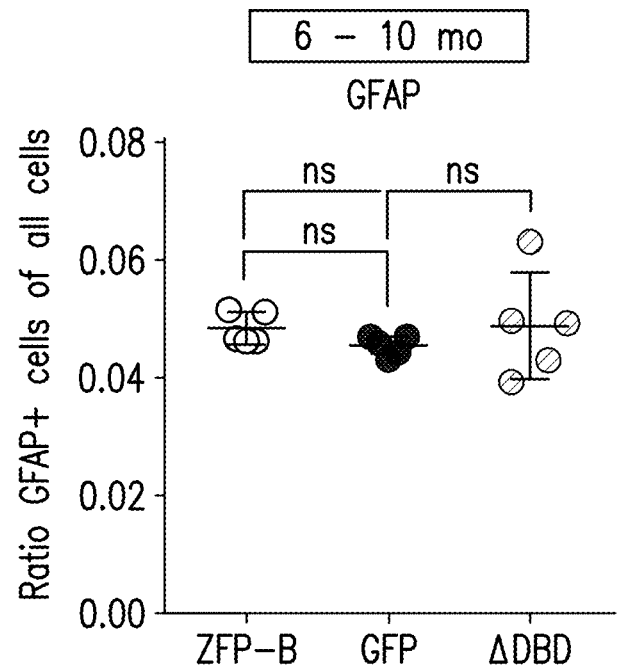
FIGS. 4O and 4P show the quantitation of GFAP+ (o) and IBA+ (p) cells compared to all cells in the striatum of mice treated with AAV2/1+2 ZFP-B.T2A.GFP, ΔDBD.T2A.GFP or GFP at 6 months and analyzed at 10 months. n=5; mean±SD.
Figure 4P:
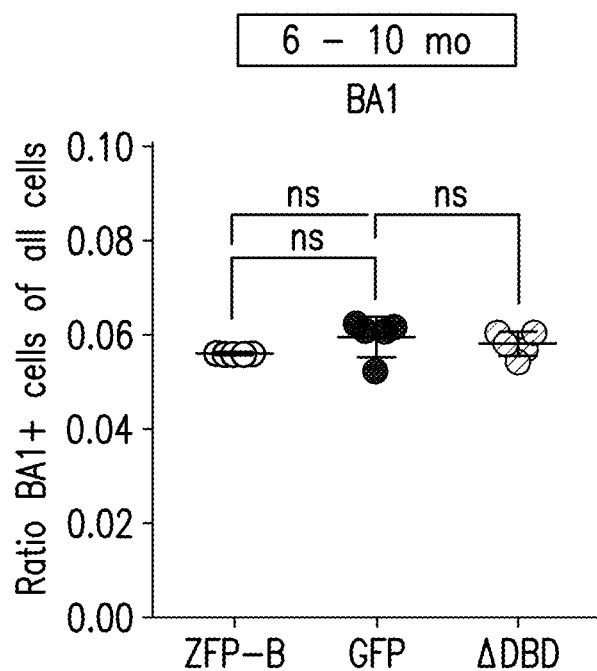
Figure 4Q:
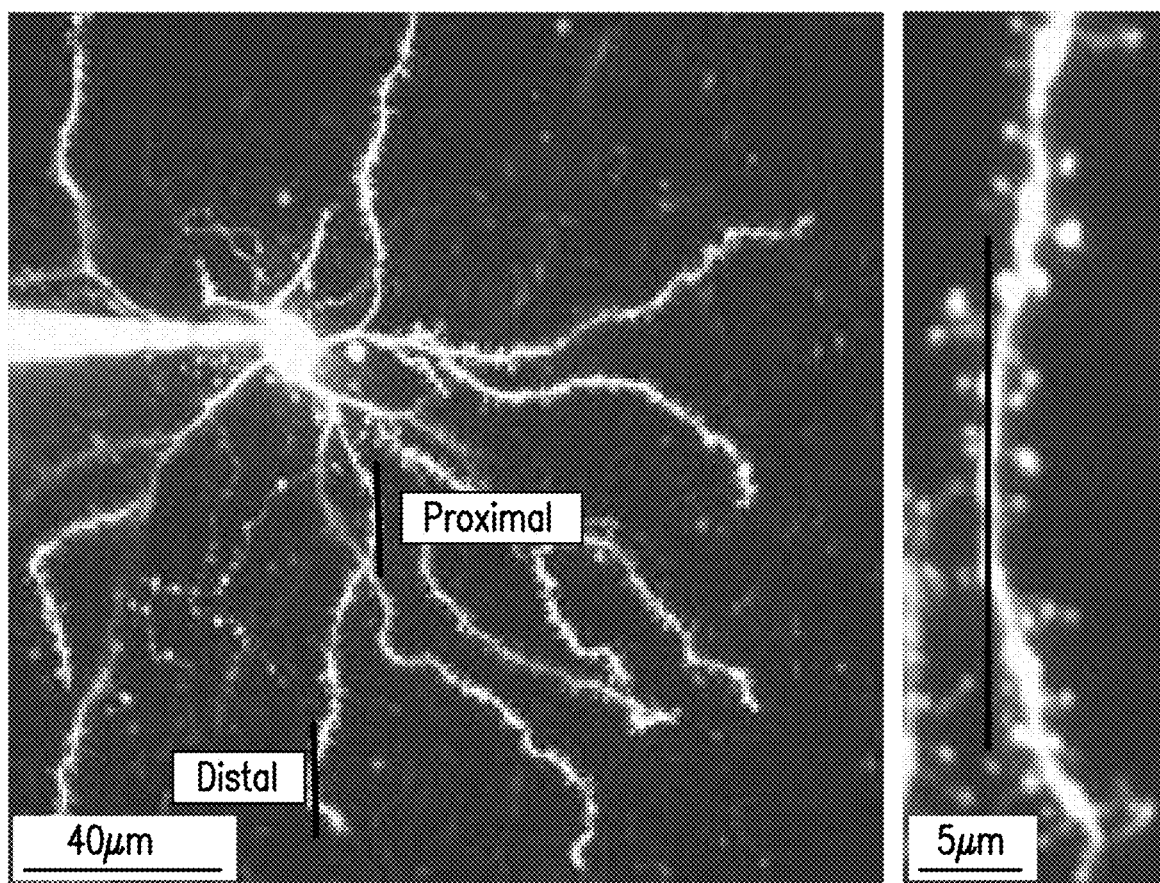
FIG. 4Q shows line scans of bAP-evoked Ca2+ images were taken at proximal and distal locations within the same dendrite and used to calculate the dendritic index.
Figure 4R:
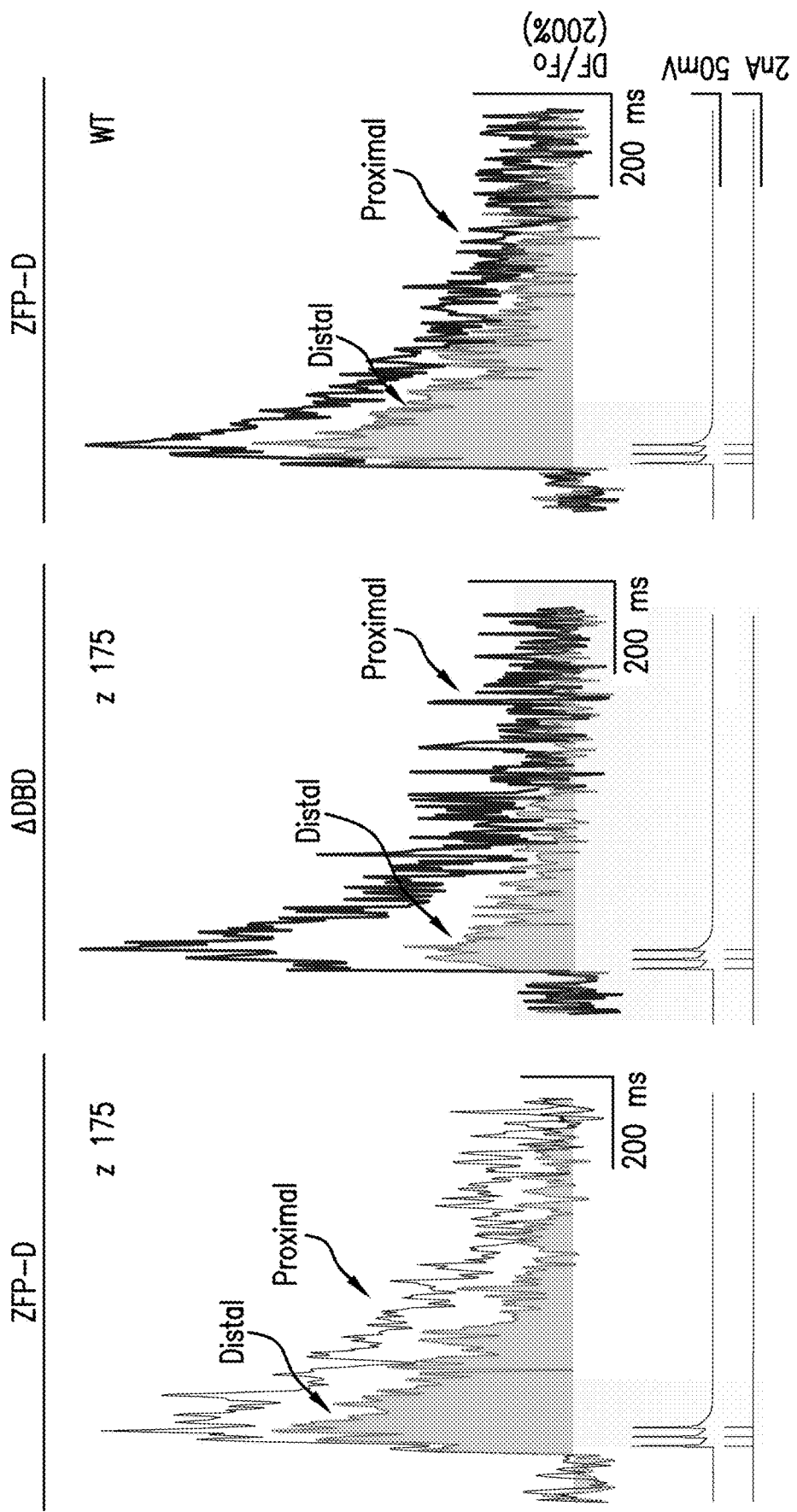
FIG. 4R shows Ca2+ transients from mice injected with AAV2/9 encoding either ZFP-D.T2A.tdTomato (zQ175, left), ΔDBD.T2A.tdTomato zQ175 het (zQ175, middle), or ZFP-D.T2A.tdTomato (WT littermate, right) at 4 months and tested at 6 months.
Figure 4S:
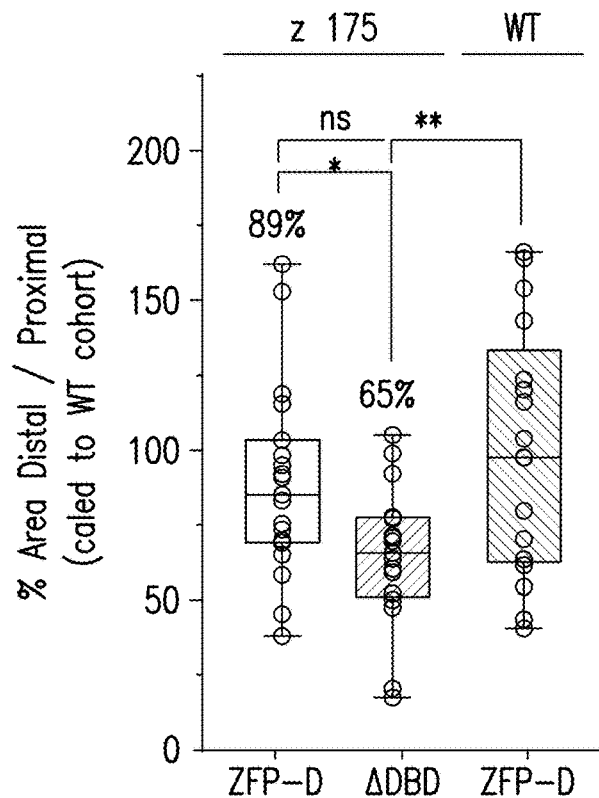
Figure 4T:
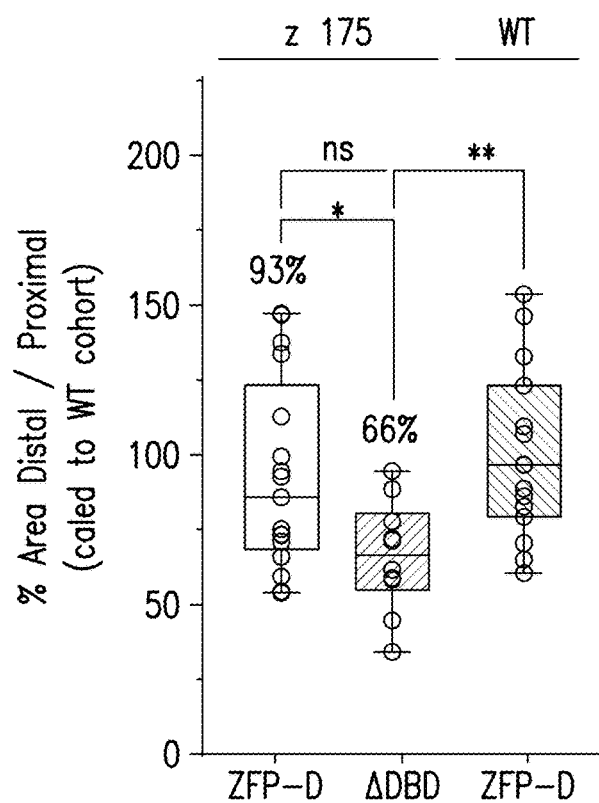

We first confirmed that the degree of mHTT-specific repression by ZFP-D was in line with our previous stereotaxic delivery studies and unchanged in a non-targeted cortical region (data not shown). We then tested dendritic excitability in tdTomato+ iSPNs using a simplified back-propagating action potential (bAP) burst protocol comprised of 3 APs at 50 Hz (FIG. 4O). Relative to control-treated zQ175 iSPNs, which displayed an average 35% suppression of dendritic excitability (P<0.01), the dendritic index of ZFP-D treated zQ175 iSPNs was restored to near wild-type levels for both the 2-month (FIG. 4S, P<0.05) and 4-month cohorts (FIG. 4T, P<0.05). Thus, iSPN electrophysiology deficits in zQ175 mice are both preventable and reversible by a mHTT-targeted ZFP. Moreover, since mHTT repression was restricted to the striatum, our findings are consistent with a regionally autonomous model for the development of dendritic hypoexcitability, rather than a secondary consequence of dysfunctional innervating neurons (Cummings et al. (2009) *J. Neurosci* 29(33):10371-86).

Example 8: Restoration of Translational Biomarkers in ZFP-Treated zQ175 Mice

Our results in R6/2 mice demonstrated that early ZFP treatment can partially restore the expression of genes that are down-regulated in HD, including PDE10A and the D1 and D2 receptors. The importance of monitoring these genes cannot be overstated, since PET imaging studies have shown early, progressive, and profound declines in the levels of PDE10A enzyme and D2-like receptors in HD patients, beginning many years prior to clinical diagnosis (CHDI/Karolinska Institute unpublished results; for review see Niccolini et al. (2018) *J Neurol Neurosurg Psychiatry* PMID:28889093). In analogous studies in heterozygous zQ175 mice (PMID: 27856625), clinical imaging ligands identified early and progressive changes in the orthologous mouse proteins. We therefore explored whether these markers were sensitive to mHTT reduction following ZFP administration using two approaches: in vitro autoradiography (ARG) of striatal brain sections, and longitudinal microPET imaging in live animals.

Figure 5A:
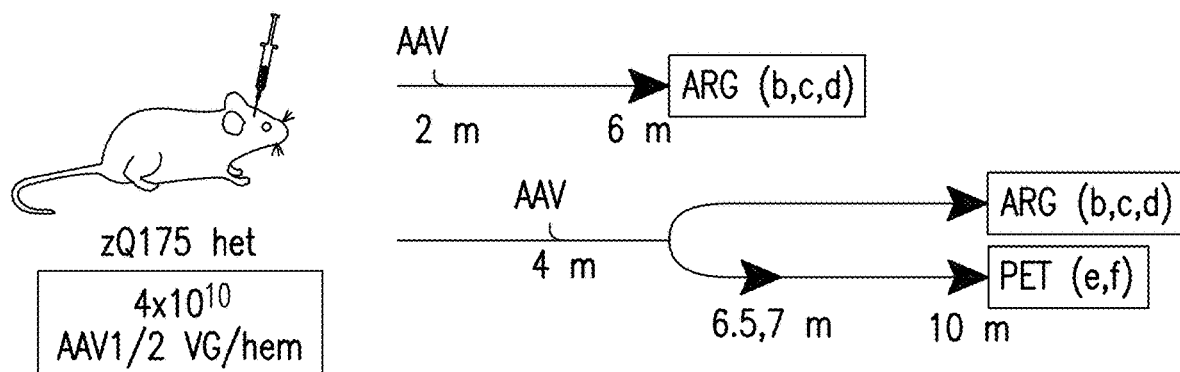
FIGS. 5A through 5F show restoration of imaging markers by ZFP expression in the striatum of Q175 het mice.
Figure 5B:
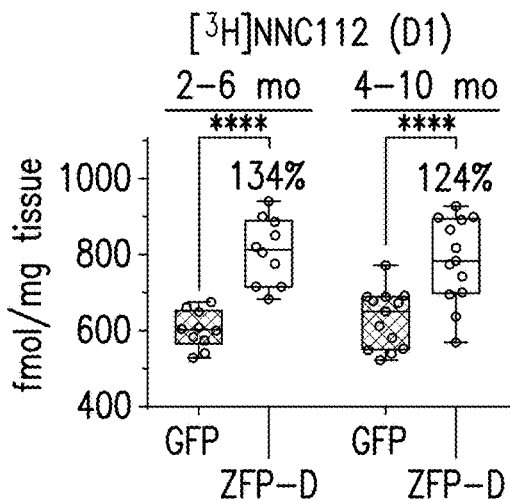
Figure 5C:
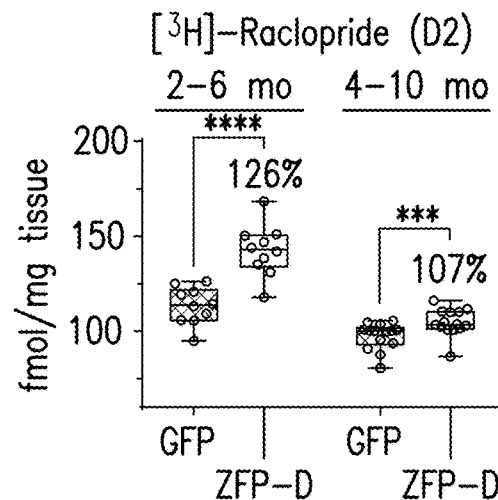
Figure 5D:
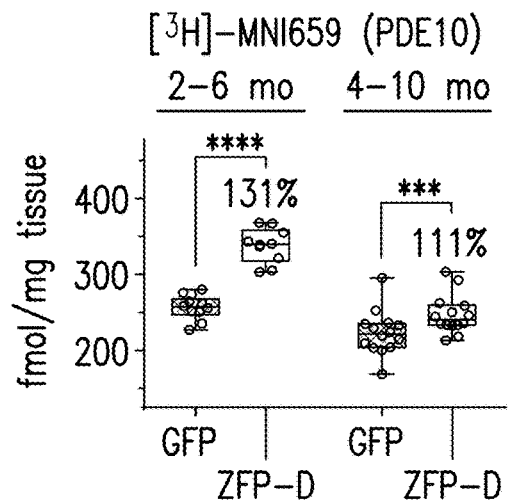

In the first study, 2- or 4-month-old heterozygous zQ175 mice received unilateral intrastriatal injections of AAV encoding either ZFP-D or GFP (FIG. 5A). Expression was evaluated using tritiated ligands for D1-like receptors ([$^3$H] NNC112), D2-like receptors ([$^3$H]raclopride) or PDE10A ([$^3$H]MNI-659). Binding was measured by ARG within a striatum region-of-interest (ROI) delineated by the area showing decreased accumulation of mHTT (assessed by EM48 staining of an adjacent section). In mice treated with ZFP-D, [$^3$H]NNC112 binding in the injected striatum ROI was significantly higher than the binding in the contralateral striatum ROI in both the early 2-6 month (34%, P<0.0001) and late 4-10 month (24%, P<0.0001) cohorts (FIG. 5B). The binding of [$^3$H]raclopride in the injected striatum ROI was also significantly higher than that of the uninjected striatum ROI for the early (26%, P<0.0001) and late (7%, P<0.001) ZFP-treated groups (FIG. 5C). Similarly, [$^3$H] MNI-659 binding in the ZFP-injected striatum ROI was significantly higher in both the early (31%, P<0.0001) and late (11%,P<0.001) cohorts (FIG. 5D).

Together, these data show that an AAV-delivered ZFP repressors can both prevent and restore specific binding for PDE10A enzyme, D1- and D2-like receptors in mice with established disease, with the greatest benefit observed for animals expressing the ZFP prior to symptom onset and decreases in biomarker expression.

Figure 5E:
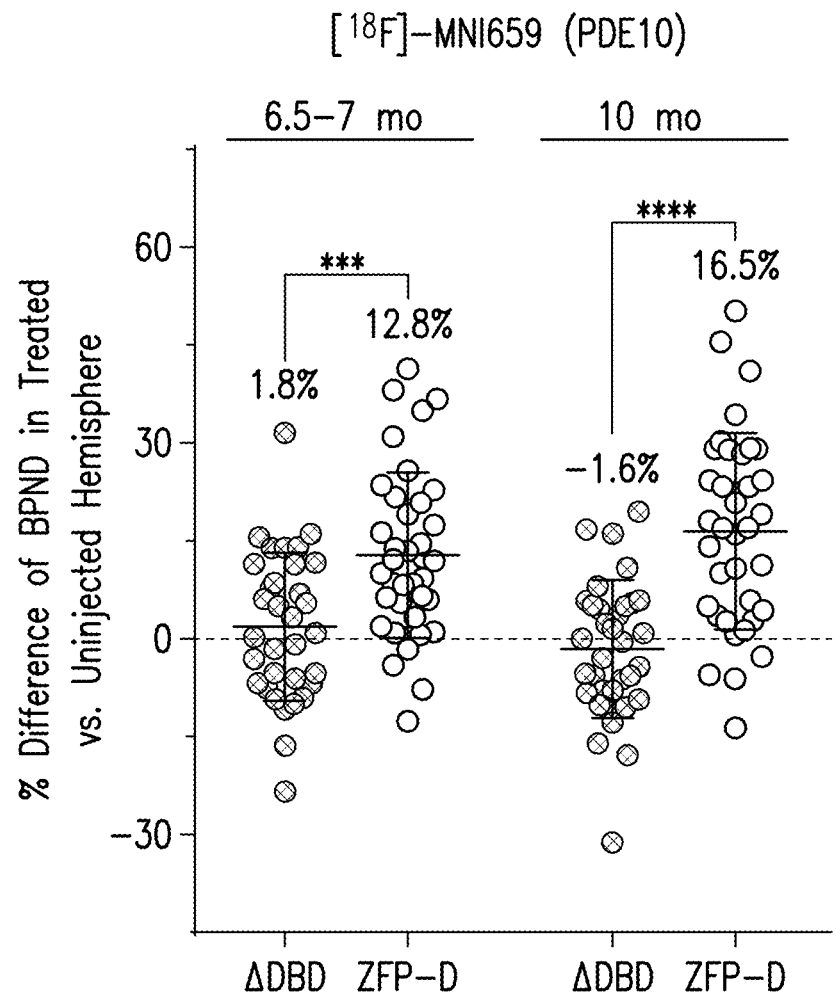
Figure 5F:
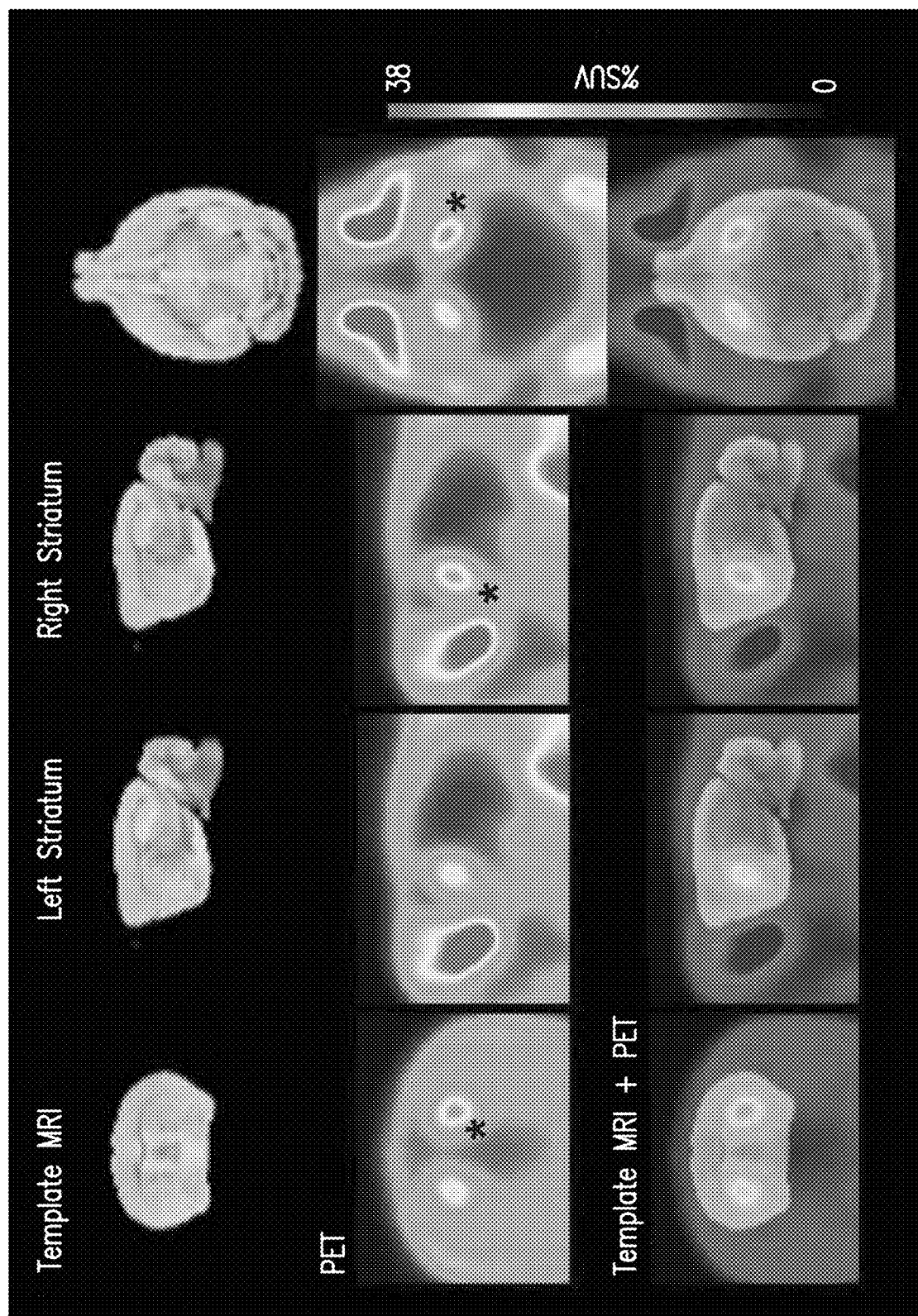

Next, to investigate whether the in vitro changes in D2-like and PDE10 ARG expression could be monitored in live animals, we evaluated the impact of ZFP treatment on [$^{11}$C]raclopride and [$^{18}$F]MNI-659 binding by microPET. We previously showed that both raclopride and MNI-659 binding in the zQ175 striatum progressively decrease between 6 and 9 months of age, from 60% to 56% and 52% to 41%, respectively, between 6 and 9 months of age (PMID 27856625). We therefore injected 4-month-old mice unilaterally with either AAV ZFP-D or ΔDBD and monitored binding longitudinally from 6.5-10 months of age. Consistent with the larger magnitude of the effects obtained using ARG in these mice, [$^{18}$F]MNI-659 BPND for the ZFP-injected versus untreated striatum was significantly increased at both 6.5 (12.8%, P<0.0001) and 10 (16.5%, P<0.001) months of age, whereas there was no statistically significant increase for the ΔDBD cohort at either timepoint (1.9% at 7 months, −1.5% at 10 months; FIGS. 5E and 5F and Table 7). Moreover, when the percent difference in BPND between hemispheres was compared across treatments, the ZFP-D cohort showed significantly elevated BPND compared to GFP mice at both 6.5-7 (11.0%, P<0.001) and 10 (18.1%, P<0.0001) months of age (FIG. 5E). Interestingly, despite seeing a 7% increase in raclopride binding in the 4-10 month ARG cohort, we were unable to detect a significant increase in [$^{11}$C]raclopride BPND for ZFP-D in the microPET studies (Tables 7 and 8).

TABLE 7

Average injected radioactivity levels (Injected RA), injected mass and weight of zQ175 mice imaged with [11C]Raclopride and [18F]MNI-659.

| FIG. | Time point | n | Treatment | Injected RA (MBq) | Injected mass (µg) | Weight (g) |
|---|---|---|---|---|---|---|
| [11C]Raclopride | 6.5-7 M | 41 | ZFP-D | 12.3 ± 0.8 | 0.014 ± 0.019 | 29.3 ± 1.9 |
| [11C]Raclopride | 7 M | 33 | eGFP | 13.1 ± 0.6 | 0.015 ± 0.014 | 29.3 ± 2.3 |
| [11C]Raclopride | 10 M | 35 | ZFP-D | 12.9 ± 0.8 | 0.009 ± 0.004 | 28.2 ± 2.0 |
| [11C]Raclopride | 10 M | 35 | eGFP | 12.6 ± 0.7 | 0.008 ± 0.004 | 28.1 ± 2.6 |
| [18F]MNI-659 | 6.5-7 M | 38 | ZFP-D | 11.7 ± 1.2 | 0.055 ± 0.035 | 28.7 ± 1.7 |
| [18F]MNI-659 | 7 M | 33 | eGFP | 12.8 ± 1.0 | 0.087 ± 0.038 | 29.3 ± 2.3 |
| [18F]MNI-659 | 10 M | 36 | ZFP-D | 12.7 ± 1.5 | 0.13 ± 0.20 | 28.9 ± 2.0 |
| [18F]MNI-659 | 10 M | 33 | eGFP | 12.2 ± 0.6 | 0.061 ± 0.043 | 28.3 ± 2.5 |

TABLE 8

Average % SUV and BPND values of [11C]raclopride or [18F] MNI-659 in striatum of Q175 animals treated with ZFP-D vs control viruses.

| Ligand | Treatment (Left vs. Right Striatum) | Time (mo) | n | % SUV, $BP_{ND}$ | Mean ± SD Left Striatum | Mean ± SD Right Striatum | % Difference Right vs. Left Striatum | Within subject paired t-test |
|---|---|---|---|---|---|---|---|---|
| [$^{18}$F]MNI-659 | Uninjected vs ZFP-D | 4-6.5 | 38 | % SUV $BP_{ND}$ | 23.8 ± 6.6 0.68 ± 0.21 | 25.1 ± 6.5 0.75 ± 0.21 | 0.06 0.13 | **** $p < 0.0001$ **** $p < 0.0001$ |
| [$^{18}$F]MNI-659 | Uninjected vs Control eGFP | 4-7 | 35 | % SUV $BP_{ND}$ | 25.2 ± 16.8 0.66 ± 0.29 | 24.9 ± 17.0 0.66 ± 0.28 | n.s. n.s. | $p > 0.05$ $p > 0.05$ |
| [$^{18}$F]MNI-659 | Uninjected vs ZFP-D | 4-10 | 36 | % SUV $BP_{ND}$ | 21.4 ± 6.9 0.62 ± 0.25 | 23.0 ± 7.3 0.71 ± 0.28 | 0.08 0.17 | *** $p < 0.001$ *** $p < 0.001$ |
| [$^{18}$F]MNI-659 | Uninjected vs Control eGFP | 4-10 | 33 | % SUV $BP_{ND}$ | 19.0 ± 4.8 0.58 ± 0.24 | 18.4 ± 4.9 0.57 ± 0.25 | −3.10 n.s. | **** $p < 0.0001$ $p > 0.05$ |
| [$^{11}$C]Raclopride | Uninjected vs ZFP-D | 4-6.5 | 41 | % SUV $BP_{ND}$ | 98.1 ± 14.4 1.48 ± 0.24 | 98.0 ± 14.0 1.47 ± 0.24 | n.s. n.s. | $p > 0.05$ $p > 0.05$ |
| [$^{11}$C]Raclopride | Uninjected vs Control eGFP | 4-7 | 33 | % SUV $BP_{ND}$ | 90.2 ± 14.2 1.29 ± 0.13 | 88.5 ± 14.5 1.24 ± 0.15 | −0.02 −0.04 | * $p < 0.05$ ** $p < 0.01$ |
| [$^{11}$C]Raclopride | Uninjected vs ZFP-D | 4-10 | 38 | % SUV $BP_{ND}$ | 81.5 ± 14.8 1.16 ± 0.16 | 81.7 ± 16.1 1.15 ± 0.18 | n.s. n.s. | $p > 0.05$ $p > 0.05$ |
| [$^{11}$C]Raclopride | Uninjected vs Control eGFP | 4-10 | 35 | % SUV $BP_{ND}$ | 76.2 ± 14.5 1.17 ± 0.10 | 74.3 ± 14.4 1.13 ± 0.12 | −2.30 −3.90 | **** $p < 0.0001$ *** $p < 0.001$ |

Differences between the left and right striatum were calculated using within subject paired t-test. Each value is expressed as Mean ± SD. n = 33-41 mice/group.

Collectively, our molecular findings in R6/2 and Q175 mice demonstrate that allele-selective ZFP-TFs can prevent and reverse the loss of key markers of disease progression, and that these changes can be monitored in living subjects using a clinical translational biomarker.

Example 9: Assessment of Tolerability and Specificity Following Chronic ZFP-TF Expression In Vivo While we observed no evidence of toxicity for the allele-selective ZFPs in our in vitro or in vivo studies, we sought to more closely examine markers of tolerability and specificity after short- and long-term ZFP treatment in vivo. To evaluate whether chronic ZFP expression results in a neuroinflammatory response or neurodegeneration, we monitored markers of astrogliosis (GFAP), microgliosis (Iba1), and general neuronal viability (NeuN) in both wild-type and zQ175 mice treated with ZFP in both early (2-6 months of age) and late (6-12 months of age) paradigms. Besides the transient effects of the injection itself (localized to the needle track) (FIG. 16A), we observed no increase in marker intensity (FIGS. 16D and 16G), or the number of GFAP+ (FIGS. 4r,s and FIGS. 16E and 16F) or Iba+ (FIGS. 4r,t and FIGS. 16B and 16E) cells for any treatment. Importantly, there was no effect of GFP expression on these markers (FIG. 16). Consistent with an absence of elevated neuroinflammatory markers, we did not detect any reduction in NeuN+ cells or intensity or neuronal number in WT or zQ175 het striata treated with ZFP-B or ZFP-D (FIG. 17). These results indicate that in WT and both pre- and post-disease onset zQ175 mice, long-term striatal expression is generally well-tolerated and does not induce an overt neuroinflammatory response. We further evaluated ZFP-B and ZFP-D in both early (2-6 months of age) and late (6-12 months of age) treatment cohorts of WT and zQ175 het mice following unilateral intrastriatal AAV injections. We observed no BW loss for the duration of the study, and no changes in general activity, spontaneous behavior, grooming, nest building, food and fluid uptake, or body temperature. Histological analysis showed no evidence of brain volumetric changes, no loss of NeuN expression and no elevation in astroglial markers compared to the contralateral hemisphere.

To assess the potential for off-target regulation in our in vivo studies, we first mapped the location of the closest CAG array (length ≥ 6 CAG repeats to minimally account for one ZFP binding site; see methods) to every annotated transcription start site (TSS) in the mouse and human genomes. We considered both perfect CAG arrays, and those that had up 3 mismatches per CAG hexamer to allow for longer, discontiguous repeat tracts. These searches revealed that the mouse genome has a substantially greater CAG content than the human genome (3,472 vs. 1,053 perfect CAG repeats; 32,328 vs. 21,456 imperfect CAG repeats). However, imposing the requirement of 1 kb distance to a TSS revealed that both genomes are similar in terms of total number of genes with TSS-adjacent CAG arrays (150 vs. 176 perfect CAG repeats; 1720 vs. 1872 imperfect CAG repeats). We then performed a bidirectional ortholog analysis whereby each annotated protein coding mouse gene was mapped to the corresponding human ortholog, and vice versa (see methods). Importantly, we found poor CAG conservation between orthologs, with only 15 of the top 100 CAG mouse genes having an ortholog with a TSS-adjacent CAG array of any length in the human ortholog, and just 12 of the top 100 human genes for the converse comparison.

These informatics results were used to guide an in vivo off-target analysis for the ZFPs used in our functional mouse studies. We injected 6 month old wild-type (WT) and zQ175 mice intrastriatally with AAVs encoding either ZFP-B, ZFP-D or ΔDBD in the right hemisphere and PBS in the left hemisphere. Striatal tissue was collected 1 month later for qRT-PCR analysis.

Consistent with the allele-selectivity of these ZFPs, we observed >70% reduction of mutant HTT mRNA levels, but no significant repression of mouse HTT in either genotype. We then examined 12 genes identified in our off-target searches, focusing on those genes with the largest TSS-adjacent CAG repeats in the mouse genome. The panel included genes with and without a TSS-adjacent CAG array in the human ortholog.

Overall, we observed no repression for genes with CAG arrays ≤ 19 CAG (MTUS2, RSLD241, AKT3, KCNA6, ITGA7); the exception being DNAJC12, which was regulated 70% by ZFP-B and 62% by ZFP-D, and lacks a CAG repeat in the mouse ortholog. Examination of the mouse Dnajc12 promoter revealed 12 CAA repeats directly adjacent to the CAG array, which may explain why it was regulated, whereas other similar-length CAG candidates were not. For the examined mouse genes with arrays containing ≥24 CAGs, we observed repression ranging from 38% for ZFP-D on RUNX2 (CAG28 (SEQ ID NO:93), TSS 100 bp) to 79% NAP1L3 (CAG28 (SEQ ID NO:93), TSS 511 bp) reduction for ZFP-B. In most cases, ZFP-D resulted in significantly less off-target repression than ZFP-B despite statistically equivalent zQ175 repression, except in the case of RUNX2 and NAP1L3. Genotype did not appear to substantially alter the pattern or degree of regulation. We also examined whether ZFP-B or ZFP-D treatment resulted in the loss of the neuronal biomarker transcripts DRD1a, DRD2, DARPP32, PDE10a and RBFOX3/NEUN. Consistent with our prior long-term analyses, we found no significant reduction in the levels of these neuronal markers after a 1 month treatment duration. Finally, to investigate the general tolerability and potential for any behavioral deficits imparted by long-term ZFP expression, we conducted two additional studies with large cohorts of mice over extended treatment durations. In the first study, we evaluated the safety of ZFP-B and ZFP-D after unilateral intra-striatal injections at various ages. We injected early (2-6 mo of age) and late (6-12 mo of age) cohorts of WT and zQ175 het mice (n=12 mice per group) with either ZFP-B or ZFP-D. Uninjected age-matched littermates were also included. We observed no body weight loss for the duration of the study (early cohort, 4 months; late cohort, 6 months), and no changes in general activity, spontaneous behavior, grooming, nest building, food and fluid uptake, or body temperature. Consistent with our prior studies, histological analysis showed no evidence of brain volumetric changes, no loss of NeuN expression and no elevation in Iba1 and GFAP as compared to the contralateral side (data not shown), further supporting long-term ZFP tolerability in both the healthy and diseased striatum.

In the second study, a total of 164 6 month old female and male zQ175 heterozygous mice were injected bilaterally with vehicle or AAV encoding either ZFP-D or eGFP and monitored for open field, rotarod, clasping, neurological index measurements, brain MRI and body weight over 9 months (n=22 animals/group for all groups except for the zQ175 het uninjected group, n=15 animals). Uninjected age-matched WT control littermates (n=44) were also included in this study. Overall, we observed no detrimental effects of ZFP-D in zQ175 heterozygous mice in any measure after disease manifestation. zQ175 het mice did not show an obvious clasping phenotype or alterations in spontaneous locomotion in the open field or neurological index deficits. Striatal ZFP treatment did not significantly alter the minor zQ175 het rotarod performance deficit observed at 15 months, body weight changes during disease progression, or affect neurological index scores. Moreover, intra-striatal ZFP-D administration had no impact on zQ175 whole brain, striatal and cortical volume as assessed by MRI.

Taken together, the results of these extensive in vivo studies support the conclusion that the allele-selective ZFPs are well tolerated at the cellular and behavioral levels in the WT and diseased mouse striatum.

In sum, the data demonstrates that ZFP genetic modulators targeting mutant Htt sequences can be used to treat HD in vivo.

CONCLUSION

Our study presents the first direct demonstration of allele-selective transcriptional repression at the native HTT locus in mice. Results from extensive testing in patient-derived cells demonstrate that expression from mHTT alleles with ≥ 38 CAG repeats can be repressed by 79-93%, while expression from normal alleles with ≤ 21 CAG repeats (the longest normal repeat length tested) is repressed by only 0-31%. Thus, allele-selective ZFP-TFs exhibit a remarkable ability to discriminate between 100% of fully penetrant mutant alleles and at least 86% of normal HTT alleles in the HD population (FIG. 1H). Compared to SNP-based allele-selective mHTT-lowering approaches, each limited to a subpopulation of HD patients, CAG-targeted ZFP repressors described in this study have the potential to selectively downregulate expression from the pathogenic allele in a large majority of HD subjects.

Furthermore, we demonstrate robust in vivo repression of mHtt expression by allele-selective ZFPs for exposure durations ranging from 7 weeks to 9 months or more in three different HD mouse models, with a resultant improvement in molecular, histological, electrophysiological and certain behavioral deficits. We also establish sustained ZFP expression and efficacy for >100 days in human HD neurons, as well as the rescue of MSN marker gene expression and electrophysiological deficits of striatal projection neurons in vivo, indicating that chronic expression of a mHTT-selective ZFP in the target brain region and relevant human cell type is well-tolerated and effective in mitigating core disease phenotypes.

The ZFPs that we developed exhibit a high combination of allele selectivity, genome-wide specificity, and long-term sustained repression that is, to our knowledge, unprecedented for synthetic transcription factors. These studies establish new benchmarks for both the performance of such factors as well as their potential applications. The results also raise interesting questions regarding how our development strategy may have contributed to the successful identification of ZFPs with desired properties, particularly as compared to a previous attempt at differential allele repression (Agustin-Pavon et al. (2016) *Mol Neurodegener* 11:64). In this regard, it appears that a key aspect of our work was the recognition that it might be possible to identify poly-CAG targeted ZFP-repressors with a very steep functional dependence on repeat tract length—steeper than possible by simple mass action—by seeking this behavior among a sufficiently diverse panel of candidate designs. It has long been recognized (Pavletich & Pabo (1991) *Science* 252:809-817) that macromolecular systems can offer the capacity for highly cooperative behavior, in which initial binding events facilitate subsequent ones resulting in a concerted all-or-none response. The foremost requirement for such behavior is a means for communication between substrate-bound ligands. ZFP binding to a chromosomal repeat array offers myriad possibilities for such communication, including non-covalent contacts between adjacent DNA-bound fingers (Nekludova & Pabo (1994) *Proc Natl Acad Sci USA* 91:6948-6952), binding-dependent DNA distortion (Mirny (2010) *Proc Natl Acad Sci USA* 107:22534-22539), nucleosome ejection (Iyengar & Farnham (2011) *J Biol Chem* 286:26267-26276), and the potential for avidity effects given the interaction of the KRAB repression domain with large corepressor complexes, components of which form multimers and higher level oligomers (Lupo et al. (2013) *Curr Genomics* 14:268-278; Peng et al. (2000) *J Biol Chem* 275:18000-18010; Hinde et al. (2015) *Sci Rep* 5:12001; Brasher et al. (2000) *EMBO J* 19:1587-1597; Sathasivam et al. (2013) *Proc Natl Acad Sci USA* 110:2366-2370).

These considerations motivated our choices of ZFP architecture (5F- and 6F-proteins comprised of a diversity of fingers, linkers, and targeted poly-CAG frames), design scale (large enough to identify the relatively rare ZFP designs that optimally discriminate alleles), and methodology (independent monitoring of endogenous normal and mutant allele expression in patient cells). With these features in place, a relatively modest screening effort (41 designs) yielded proteins with desired properties. In contrast, the prior study employed just a single reiterated finger and screened far fewer candidates for allelic discrimination (four) using inauthentic contexts such as chimeric episomal reporters and mouse cells (Agustin-Pavon, ibid). That study demonstrated allele-selective mHTT repression, but only in the non-disease relevant context of mouse cells bearing a nonpathogenic allele (CAG 4 (SEQ ID NO:86)) that lacked even a single full-length target. Moreover, the initially identified ZFP was not well tolerated, and required further modifications to the ZFP backbone, KRAB repression domain, and promoter to achieve repression beyond 2 weeks in vivo (Gersbach & Perez-Pinera (2014) *Expert Opin Ther Targets* 18:835-839). We note that in our own testing of these reagents in HD patient cells we observed an inability to discriminate between disease-relevant human HTT alleles (18 (SEQ ID NO:79) vs 45 (SEQ ID NO:80) CAGs). It seems likely that differences in our development strategy compared to the prior study may account for the substantial gap in ZFP performance.

Our findings also provide some insight into possible mechanisms of allele-selective repression. In particular, our observation that the phenomenon is design dependent (FIG. 1D) would appear to disfavor the possibility of indirect communication among bound ZFP-TFs via, for example, propagated distortion of DNA structure or nucleosomal ejection (Mirny, ibid, Iyengar & Farnham, ibid). Moreover, a lack of binding cooperativity seen in gel shift studies using purified components is inconsistent with the occurrence of direct contacts between adjacent bound ZFPs (data not shown). Finally, we note that the KRAB functional domain was required for the observed properties. This leaves the possibility that the allele-selective behavior derives from avidity effects potentially mediated by interaction of the KRAB repression domain with large corepressor complexes.

A key consideration for any therapeutic strategy is the evaluation of specificity and off-target effects. Of particular interest for this approach was the prevalence of the other 1,053 endogenous CAG arrays (length ≥ 6 to account for the approximate DNA footprint of a 6 finger ZFP) in the human genome that, collectively, are adjacent to the promoters of 176 genes). Partially discontiguous arrays (up to 3 mismatches per hexamer) are even more abundant, with 21,456 total sites (all CAG arrays) proximal to 1,872 human genes. While no other human gene has a TSS-adjacent CAG tract as large as the minimum fully-penetrant mHTT allele (CAG40 (SEQ ID NO:91); see FIG. 1H), the potential regulation of certain CAG-adjacent off-target genes could pose a risk for clinical use of this strategy.

To investigate this, we employed global transcriptional profiling in patient neurons and fibroblasts. In contrast to previous CAG-targeted strategies (Gagnon, ibid; Hu, ibid; Yu, ibid; Fiszer, ibid; Lutz, ibid), we selected an unbiased approach to interrogate specificity due to the uncertain influence of promoter context, epigenetic modifications, and potential of our ZFP-TFs to synergize with other factors, any of which could unpredictably affect off-target behavior. We identified ZFPs that exhibited a high degree of genome-wide specificity without performing any optimization for this property. Particularly informative was the apparent architectural influence on specificity for the allele-selective ZFPs. Whereas ZFP-A and ZFP-B had similar on-target behavior for all queried mHTT alleles, they had mutually exclusive off-target profiles in two cellular contexts (FIG. 2G, FIG. 11, FIG. 17). For example, MBD5, a CAG-adjacent gene with a discontiguous CAG tract (CAG19 (SEQ ID NO:92), 0 bp from the TSS), was repressed by ZFP-B, but not ZFP-A (FIGS. 11B and 11C). ZFP-A and ZFP-B target different frames of the CAG tract, are composed of different ZF modules, and employ different linker architectures, suggesting that their off-target properties may be design-dependent and therefore amenable to optimization. Equally paramount to specificity is the efficient targeting of the disease-causing agent(s). While it has long been recognized that the CAG expansion in the HTT gene is causal for HD, the resultant molecular species that potentially drive neurodegeneration continue to be elucidated. For example, an aberrantly spliced Htt isoform containing exon 1 and intron 1 is present in several HD rodent models as well as postmortem HD brains, and may contribute to the formation of pathogenic polyQ-containing N-terminal protein species (Banez-Coronel et al. (2015) *Neuron* 88:667-677). Additionally, a growing number of disease-implicated microsatellite expansions—including the CAG repeat of mHTT—have been shown to undergo antisense transcription as well as repeat associated non-ATG (RAN) translation, yielding neurotoxic dipeptides that accumulate in patient brains (Arber (2017) *EMBO Mol Med* 9:281-284). These HTT isoforms are expected to be resistant to ASO- and RNAi-based strategies that target sequences downstream of exon 1. In contrast, allele-selective ZFP-TFs are expected to reduce production of all sense and antisense mHtt isoforms that contain expanded CAGs, potentially providing an important therapeutic advantage. We note that while other modalities have been developed to target the CAG expansion in exon 1, allele-selective behavior was reported for only narrow dose ranges (2-5 fold) (Pfister et al. (2009) *Current Biology* 19:774-778; Gagnon, ibid; Hu. ibid; Yu, ibid, Fiszer, ibid; Lutz, ibid). Importantly, we show that ZFP-TFs can achieve allele-selective repression over a much wider dose window (at least 100-fold), a critical factor for clinical translatability given current technical difficulties in delivering uniform doses to all cells within a target tissue.

While ZFP-treated R6/2 mice exhibited significant improvements on certain behavioral endpoints (clasping and open field tests), we did not observe a significant treatment effect for other standard HD model endpoints in either R6/2 or zQ175 het mice (e.g., accelerating rotarod or grip strength). An important consideration in this regard is the limited AAV coverage achievable for stereotaxic administration to the mouse brain. In our studies, intraparenchymal injections yielded 30-70% coverage of the mouse striatum, thereby limiting the ability to evaluate the impact of the ZFP on some measures of disease progression, most importantly at the level of behavior. Moreover R6/2 is an aggressive model, and introducing the ZFP at 5 weeks of age (the earliest time point at which stereotaxic injection can be reliably performed) may be too late to affect certain behavioral endpoints. While the involvement of the striatum is critical for motor control, whether striatal selective suppression of mHTT is sufficient to ameliorate these symptoms is unclear given the role of the broader cortico-striatal-thalamocortical loops in motor pattern learning and execution. Additionally, whether the changes in locomotor behavior in HD mice are driven exclusively by striatal mHTT expression is unknown. Clearly other brain regions contribute to spontaneous locomotor control in mice, including the motor-relevant cortical areas, cerebellum and brainstem nuclei, which could also be affected in these models (Capelli et al. (2017) *Nature* 551:373-377; Datson et al. (2017) *PLoS One* 12:e0171127). Therefore, widespread suppression of mHTT might be necessary to rescue these disease phenotypes in HD mouse models. In support of this notion, improvements in spontaneous locomotion and rotarod performance have been reported for alternative approaches (e.g., ASOs or siRNAs) that were shown to distribute more broadly throughout the murine brain, albeit with effects that are typically mild or partially restorative (Stanek et al. (2014) *Human Gene Therapy* 25(5):461-474; Russell et al. (2014) *JAMA Neurol* 71:1520-1528). Given these limitations and the understanding that mHTT is the underlying cause of HD, we primarily focused our analyses on readouts of target engagement, correction of histopathological and electrophysiological deficits, and biomarker improvements, which may represent efficacy readouts that are both more translatable and directly relevant to the goal of delaying and/or reversing neurodegeneration in HD patients.

The autoradiography results using markers for dopamine D1-like and D2-like receptors and PDE10A enzyme showed that lowering mHTT in Q175 heterozygous mice was associated with increased specific binding of [3H]NNC112, [3H]raclopride and [3H]MNI-659, in both the early and later treatment studies (after symptom onset and decline in their expression). The largest difference was observed for D1-like receptors, followed by PDE10A and D2-like receptors, suggesting that the effect of lowering mHTT after symptom onset in mice was more pronounced in direct-pathway striatal neurons, as PDE10 is expressed by both populations of SPNs. The effect of reducing mHTT was also more pronounced in the early treatment study, suggesting that lowering mHTT might produce a larger effect if the intervention is started early. Nonetheless, the treatment initiation at 4 months (with ZFP expression expected within 1-2 weeks of viral transduction in vivo; data not shown) takes place after downregulation of these targets in Q175 heterozygous mice (Monod et al. (1965) *J Mol Biol* 12:88-118), suggesting that ZFP administration can partially restore a pre-existing loss of these proteins. The PDE10A ARG results were confirmed using microPET with [18F]MNI-659, where we show a significant elevation in binding potential even after symptom initiation with a clinically relevant translational endpoint. In contrast, raclopride binding was unchanged in the microPET study, which may reflect methodological differences between D2-like in vitro ARG and in vivo microPET, as well as limited tissue distribution of the viral vectors used to detect a small effect on this marker. Collectively, our findings provide encouraging support for the use of imaging ligands as an early readout of striatal mHTT lowering in human trials (Wilson et al. (2016) *Journal of the Neurological Sciences* 368:243-248; Marks et al. (2016) *Hum Gene Ther* 27:522-527). Additional work is needed to explore markers for other brain regions implicated in HD, such as the cortex, where mHTT lowering is being pursued clinically.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger protein transcription factor (ZFP-TF) repressor comprising a repression domain and a zinc finger protein (ZFP) as follows:

(a) a ZFP designated ZFP-A comprising the amino acid sequence
(SEQ ID NO: 64)
MAPKKKRKVGIHGVPAAMAERPFQCRICMRNFSQSSDLSRHIRTHTGEKP

FACDICGRKFAQWSTRKRHTKIHTGSQKPFQCRICMRNFSQSSDLSRHIR

THTGEKPFACDICGRKFAQWSTRKRHTKIHTGEKPFQCRICMRKFAQSGD

LTRHTKIHLRQKDAARGSGMDAKSLTAWSRTLVTFKDVFVDFTREEWKLL

DTAQQIVYRNVMLENYKNLVSLGYQLTKPDVILRLEKGEEPWLVEREIHQ

ETHPDSETAFEIKSSV;

(b) a ZFP designated ZFP-B comprising the amino acid sequence
(SEQ ID NO: 65)
MAPKKKRKVGIHGVPAAMAERPFQCRICMRNFSRSDNLSEHIRTHTGEKP

FACDICGRKFAKRCNLRCHTKIHTHPRAPIPKPFQCRICMRNFSQSGDLT

RHIRTHTGEKPFACDICGRKFAQSGDLTRHTKIHTPNPHRRTDPSHKPFQ

CRICMRNFSRSDNLSEHIRTHTGEKPFACDICGRKFAKRCNLRCHTKIHL

RQKDAARGSGMDAKSLTAWSRTLVTFKDVFVDFTREEWKLLDTAQQIVYR

NVMLENYKNLVSLGYQLTKPDVILRLEKGEEPWLVEREIHQETHPDSETA

FEIKSSV;

(c) a ZFP designated ZFP-C comprising the amino acid sequence
(SEQ ID NO: 66)
MAPKKKRKVGIHGVPAAMAERPFQCRICMRNFSRSDNLSEHIRTHTGEKP

FACDICGRKFAKRCNLRCHTKIHTGSQKPFQCRICMRNFSRSDNLSEHIR

THTGEKPFACDICGRKFAKRCNLRCHTKIHTGSQKPFQCRICMRNFSRSD

NLSEHIRTHTGEKPFACDICGRKFAKRCNLRCHTKIHLRQKDAARGSGMD

AKSLTAWSRTLVTFKDVFVDFTREEWKLLDTAQQIVYRNVMLENYKNLVS

LGYQLTKPDVILRLEKGEEPWLVEREIHQETHPDSETAFEIKSSV;

and (d) a ZFP designated ZFP-D comprising the amino acid sequence
(SEQ ID NO: 67)
MAPKKKRKVGIHGVPAAMAERPFQCRICMRNFSRSDNLSEHIRTHTGEKP

FACDICGRKFAKRCNLRCHTKIHTHPRAPIPKPFQCRICMRNFSQSSDLS

RHIRTHTGEKPFACDICGRKFAQWSTRKRHTKIHTGEKPFQCRICMRKFA

QSGDLTRHTKIHLRQKDAARGSGMDAKSLTAWSRTLVTFKDVFVDFTREE

WKLLDTAQQIVYRNVMLENYKNLVSLGYQLTKPDVILRLEKGEEPWLVER

EIHQETHPDSETAFEIKSSV.

2. A polynucleotide encoding the ZFP-TF repressor of claim 1.

3. The polynucleotide of claim 2 comprising an mRNA encoding the ZFP-TF.

4. An AAV vector comprising the polynucleotide of claim 2.

5. A pharmaceutical composition comprising the polynucleotide of claim 3.

6. A pharmaceutical composition comprising the AAV vector of claim 4.

7. A cell comprising the ZFP-TF repressor of claim 1.

8. The cell of claim 7, wherein the cell is a neuron or a fibroblast.

9. A method of reducing apoptosis and increasing ATP levels in a neuron from a subject with Huntington's Disease (HD), the method comprising administering the AAV vector of claim 4 the neuron.

10. A method of reducing motor deficits in a subject with Huntington's Disease (HD), the method comprising administering the AAV vector of claim 4 the striatum of the subject.

11. A method of reducing HTT inclusions in a subject with Huntington's Disease (HD), the method comprising administering the AAV vector of claim 4 the striatum of the subject.

12. The method of claim 11, wherein the HTT inclusions are perinuclear or EM48+ inclusions.

13. A method of restoring translational biomarkers in a subject with Huntington's Disease (HD), the method comprising administering the AAV vector of claim 4 the striatum of the subject.

14. The method of claim 13, wherein the biomarkers are PDE10A and/or D1 or D2 receptors.

15. A method of treating and/or preventing Huntington's Disease in a subject in need thereof, the method comprising administering the pharmaceutical composition of claim 5 to the subject in need thereof.

16. A method of treating and/or preventing Huntington's Disease in a subject in need thereof, the method comprising administering the pharmaceutical composition of claim 6 the subject in need thereof.

* * * * *

UNITED STATES PATENT AND TRADEMARK OFFICE
CERTIFICATE OF CORRECTION

PATENT NO. : 11,421,007 B2
APPLICATION NO. : 16/386885
DATED : August 23, 2022
INVENTOR(S) : Steven Froelich et al.

It is certified that error appears in the above-identified patent and that said Letters Patent is hereby corrected as shown below:

In the Claims

Claim 1, Line 25, Column 116 should read:
or

Claim 10, Line 56, Column 116 should read:
administering the AAV vector of claim 4 to the striatum of the Claim 11, Line 60, Column 116 should read:
administering the AAV vector of claim 4 to the striatum of the Claim 13, Line 66, Column 116 should read:
comprising administering the AAV vector of claim 4 to the striatum Claim 16, Line 9, Column 117 should read:
administering the pharmaceutical composition of claim 6 to the Signed and Sealed this
Twenty-eighth Day of February, 2023

Katherine Kelly Vidal
*Director of the United States Patent and Trademark Office*